United States Patent
Zhou et al.

(10) Patent No.: US 7,498,346 B2
(45) Date of Patent: *Mar. 3, 2009

(54) CHEMOKINE RECEPTOR BINDING COMPOUNDS

(75) Inventors: Yuanxi Zhou, Surrey (CA); Gary J. Bridger, Bellingham, WA (US); Renato T. Skerlj, Vancouver (CA); David Bogucki, Surrey (CA); Wen Yang, Aldergrove (CA); Elyse Bourque, Langley (CA); Jonathan Langille, Langley (CA); Tong-Shuang Li, Langley (CA); Markus Metz, Delta (CA)

(73) Assignee: Genzyme Corporation, Cambridge, MA (US)

( * ) Notice: Subject to any disclaimer, the term of this patent is extended or adjusted under 35 U.S.C. 154(b) by 481 days.

This patent is subject to a terminal disclaimer.

(21) Appl. No.: 11/152,589

(22) Filed: Jun. 14, 2005

(65) Prior Publication Data
US 2005/0277668 A1   Dec. 15, 2005

Related U.S. Application Data

(63) Continuation-in-part of application No. 11/012,002, filed on Dec. 13, 2004.

(60) Provisional application No. 60/528,975, filed on Dec. 11, 2003.

(51) Int. Cl.
*A61K 31/4453* (2006.01)
*C07D 211/58* (2006.01)

(52) U.S. Cl. .................. 514/318; 546/194
(58) Field of Classification Search ........... 514/318; 546/194
See application file for complete search history.

(56) References Cited

U.S. PATENT DOCUMENTS

| | | | |
|---|---|---|---|
| 5,021,409 | A | 6/1991 | Murrer |
| 5,583,131 | A | 12/1996 | Bridger |
| 5,698,546 | A | 12/1997 | Bridger |
| 5,817,807 | A | 10/1998 | Bridger |
| 6,001,826 | A | 12/1999 | Murrer |
| 6,159,990 | A | 12/2000 | Lagu et al. |
| 6,319,932 | B1 | 11/2001 | Nerenberg et al. |
| 6,365,583 | B1 | 4/2002 | MacFarland |

FOREIGN PATENT DOCUMENTS

| | | |
|---|---|---|
| EP | 0 747 357 B1 | 1/2002 |
| EP | 1 219 605 A1 | 7/2002 |
| WO | WO-96/40136 | 12/1996 |
| WO | WO-00/56729 | 9/2000 |
| WO | WO-01/25200 | 4/2001 |
| WO | WO-02/22599 | 3/2002 |
| WO | WO-02/22600 | 3/2002 |
| WO | WO-02/34745 | 5/2002 |
| WO | WO-03/042178 | 5/2003 |

OTHER PUBLICATIONS

Abi-Younes et al., Circ. Res. (2000) 86:131-138.
Aiuti et al., J. Exp. Med. (1997) 185:111-120.
Alkhatib et al., Science (1996) 272:1955-1958.
Arai et al., Eur. J. Haematol. (2000) 64:323-332.
Arenburg et al., J. Leukocyte Biol. (1997) 62:554-562.
Balashov et al., PNAS USA (1999) 96:6873-6878.
Blaak et al., Proc. Natl. Acad. Sci. USA (2000) 97:1269-1274.
Blanco et al., Antimircrobial. Agents and Chemother. (2000) 44:51-56.
Bleul et al., J. Exp. Med. (1998) 187:753-762.
Bleul et al., Nature (1996) 382:829-833.
Bradstock et al., Leukemia (2000) 14:882-888.
Bridger et al., Advances in Antiviral Drug Design, vol. 3, E. De Clercq (Ed.), JAI press (1999) pp. 161-229.
Bridger et al., J. Med. Chem. (1999) 42:3971-3981.
Burger et al., Blood (1999) 94:3658-3667.
Carroll et al., Science (1997) 276:273-276.
Cocchi et al., Science (1995) 270:1811-1815.
Connor and Ho, J. Virol. (1994) 68:4400-4408.
Deng et al., Nature (1996) 381:661-666.
Donzella et al., Nature Medicine (1998) 4:72-77.
Dragic et al., Nature (1996) 381:667-673.
Egberink et al., J. Virol. (1999) 73:6346-6352.
Eitner et al., Transplantation (1998) 66:1551-1557.
Fedyk et al., J. Leukocyte Biol. (1999) 66:667-673.
Feng et al., Science (1996) 272:872-877.
Gerard et al., Natl. Immunol. (2001) 2(2):108-115.
Gonzalo et al., J. Immunol. (2000) 165:499-508.
Gupta et al., J. Biolog. Chem. (1998) 7:4282-4287.
Ishii et al., J. Immunol. (1999) 163:3612-3620.
Lataillade et al., Blood (1999) 95:756-768.
Liu et al., Cell (1996) 86:367-377.
Luster, New Eng. J. Med. (1998) 338(7):436-445.
Maekawa et al., Internal Medicine (2000) 39:90-100.
Michael et al., J. Virol. (1998) 72:6040-6047.
Michael et al., Nature Med. (1997) 3:338-340.

(Continued)

*Primary Examiner*—Taofiq A Solola
(74) *Attorney, Agent, or Firm*—Morrison & Foerster LLP

(57) ABSTRACT

The present invention relates to chemokine receptor binding compounds, pharmaceutical compositions and their use. More specifically, the present invention relates to modulators of chemokine receptor activity, preferably modulators of CCR5. These compounds demonstrate protective effects against infection of target cells by a human immunodeficiency virus (HIV).

12 Claims, No Drawings

OTHER PUBLICATIONS

Miedema et al., Immune, Rev. (1994) 140:35.
Moore et al., J. of Invest. Med. (1998) 46:113-120.
Moore et al., Trends Cardiovasc. Med. (1998) 8:51-58.
Murdoch et al., Blood (2000) 95:3032-3043.
Murphy et al., Pharmacol. Rev. (2000) 52(1):145-176.
Nagasawa et al., Nature (1996) 382:635-638.
Nagase et al., J. Immunol. (2000) 164:5935-5943.
Nanki et al., J. Immunol. (2000) 164:5010-5014.
Oberlin et al., Nature (1996) 382:833-835.
Obrien et al., Lancet (1997) 349:1219.
Panzer et al., Transplantation (2004) 78(9):1341-1350.
Peled et al., Blood (2000) 95:3289-3296.
Peled et al., Science (1999) 283:845-848.
Ponath, Exp. Opin. Invest. Drugs (1998) 7:1-18.
Ma et al., Immunity (1999) 10:463-471.
Rana et al., J. Virol. (1997) 71:3219-3227.
Robinson et al., Cancer Res. (2003) 63(23):8360-8365.
Salcedo et al., Am. J. Pathol. (1999) 154:1125-1135.
Samson et al., Nature (1996) 382:722-725.
Schols et al., Anitviral Research (1997) 35:147-156.
Schols et al., J. Exp. Med. (1997) 186:1383-1388.
Schuitemaker et al., J. Virol. (1992) 66:1354-1360.
Seghal et al., J. Surg. Oncol. (1998) 69:99-104.
Simmons et al., J. Virol. (1996) 70:8355-8360.
Simmons et al., J. Virol. (1998) 72:8453-8457.
Szekanecz et al., Seminars in Immunology (2003) 15:15-21.
Tachibana et al., Nature (1998) 393:591-594.
Tan et al., Expert Opin. Investig. Drugs (2003) 12(11):1765-1776.
Tersmette et al., J. Virol. (1988) 62:2026-2032.
Theodorou et al., Lancet (1997) 349:1219-1220.
Viardot et al., Ann. Hematol. (1998) 77:195-197.
Wyatt et al., Science (1998) 280:1884-1888.
Xia et al., J. Neurovirology (1999) 5:32-41.
Yssel et al., Clinical and Experimental Allergy (1998) 28:104-109.
Yun et al., Circulation (2004) 109(7):932-937.
Zhang et al., AIDS Res. Hum. Retroviruses (1997) 13:1357-1366.
Zhang et al., J. Virol. (1998) 72:9307-9312.
Zhang et al., J. Virol. (1999) 73:3443-3448.
Zou et al., Nature (1998) 393:591-594.
International Search Report for PCT/US06/22897, date mailed on Mar. 29, 2007, 4 pages.
Databse CAPLUS on STN, No. 49:17187, accession No. 1955:17187.
International Search Report for PCT/US04/41865, mailed on Oct. 14, 2005, 3 pages.
Mensonides-Harsema et al., J. Med. Chem. (2000) 43;432-439.
Martin et al., J. Med. Chem. (2002) 45:4350-4358.
Non-Final Office Action for U.S. Appl. No. 11/012,002. mailed on Dec. 10, 2007, 24 pages.
Thoma et al., J. Med. Chem. (2004) 47:1939-1955.
Final Office Action for U.S. Appl. No. 11/012,002, mailed on May 21, 2008.
General Chemistry Glossary, "aryl", retrieved online at <http://antoine.frostburg.edu/cgi-bin/senese/searchglossary.cgi?query=aryl&shtml=%2Fchem>, 1 page.
Hawley's Condensed Chemical Dictionary, "aryl", 14th Edition, 2002, online retrieval at Wiley online, 1 page.
Lide, Ed., "Definitions of Scientific Terms" "aryl groups", CRC Handbook of Chemistry and Physics, 88 Edition (Internet Version 2008) <http://www.hbcpnetbase.com>, CRC Press/Taylor and Francis, Boca Raton, FL, Section 2, p. 30.
McNaught and Wilkinson, "Compendium of Chemical Terminology" "aryl group", The Gold Book, Second Edition, Blackwell Science, 1997, 1 page.
Pozharskii et al., Heterocycles in Life and Society Wiley, 1997, pp. 1-6.

CHEMOKINE RECEPTOR BINDING COMPOUNDS

CROSS-REFERENCE

This application is a continuation-in-part of U.S. patent application Ser. No. 11/012,002, filed Dec. 13, 2004, which claims benefit of U.S. provisional patent application 60/528,975 filed Dec. 11, 2003, which are incorporated by reference herein.

TECHNICAL FIELD

This invention generally relates to novel compounds, pharmaceutical compositions and their use. More specifically, these novel compounds may be modulators of chemokine receptor activity, preferably modulators of chemokine receptor CCR5, and may further demonstrate protective effects against infection in target cells by a human immunodeficiency virus (HIV). In another aspect, the compounds in the present invention may be useful in the treatment and prevention of various inflammatory and autoimmune diseases.

BACKGROUND OF THE INVENTION

Approximately 40 human chemokines have been described that function at least in part, by modulating a complex and overlapping set of biological activities important for the movement of lymphoid cells and extravasation and tissue infiltration of leukocytes in response to inciting agents (See, for example: P. Ponath, *Exp. Opin. Invest. Drugs,* 7:1-18, 1998). These chemotactic cytokines, or chemokines, constitute a family of proteins, approximately 8-10 kDa in size, that are released by a wide variety of cells, to attract macrophages, T cells, eosinophils, basophils, and neutrophils to sites of inflammation and also play a role in the maturation of cells of the immune system. Chemokines appear to share a common structural motif that consists of 4 conserved cysteines involved in maintaining tertiary structure. There are two major subfamilies of chemokines: the "CC" or β-chemokines and the "CXC" or α-chemokines, depending on whether the first two cysteines are separated by a single amino acid, i.e., CXC or are adjacent, i.e., CC.

These chemokines bind specifically to cell-surface receptors belonging to the family of G-protein-coupled seven-transmembrane proteins which are referred to as "chemokine receptors", and mediate biological activity through these receptors. The chemokine receptor is classified based upon the chemokine that constitutes the receptor's natural ligand. Chemokine receptors of the β-chemokines are designated "CCR"; while those of the α-chemokines are designated "CXCR." These chemokine receptors include but are not limited to CCR1, CCR2, CCR2A, CCR2B, CCR3, CCR4, CCR5, CCR6, CXCR3 and CXCR4 (see for a complete review, Murphy et al. *Pharmacol. Rev.* 52(1), 145-176 (2000)).

Chemokines are considered to be principal mediators in the initiation and maintenance of inflammation (see *Chemokines in Disease* published by Humana Press (1999), Edited by C. Herbert; Murdoch et al. *Blood* 95, 3032-3043 (2000)). More specifically, chemokines have been found to play an important role in the regulation of endothelial cell function, including proliferation, migration and differentiation during angiogenesis and re-endothelialization after injury (Gupta et al., *J. Biolog. Chem.,* 7:4282-4287, 1998). Both chemokine receptors CXCR4 and CCR5 have been implicated in the etiology of infection by human immunodeficiency virus (HIV).

In most instances, HIV initially binds via its gp120 envelope protein to the CD4 receptor of the target cell. A conformational change appears to take place in the gp120which results in its subsequent binding to a chemokine receptor, such as CCR5 (Wyatt et al., *Science,* 280:1884-1888 (1998)). HIV-1 isolates arising subsequently in the infection bind to the CXCR4 chemokine receptor. The observed binding of another related retrovirus, feline immunodeficiency virus, to a chemokine receptor without needing to bind first to the CD4 receptor, suggests that chemokine receptors may be the primordial obligate receptors for immunodeficiency retroviruses.

Following the initial binding by HIV to CD4, virus-cell fusion results, which is mediated by members of the chemokine receptor family, with different members serving as fusion cofactors for macrophage-tropic (M-tropic) and T cell linetropic (T-tropic) isolates of HIV-1 (Carroll et al., *Science,* 276: 273-276 1997; Feng et al. *Science* 272, 872-877 (1996); Bleul et al. *Nature* 382, 829-833 (1996); Oberlin et al. *Nature* 382, 833-835 (1996); Cocchi et al. *Science* 270, 1811-1815 (1995); Dragic et al. *Nature* 381, 667-673 (1996); Deng et al. *Nature* 381, 661-666 (1996); Alkhatib et al. *Science* 272, 1955-1958, (1996)). During the course of infection within a patient, it appears that a majority of HIV particles shift from the M-tropic to the more aggressive pathogenic T-tropic viral phenotype (Miedema et al., *Immune. Rev.,* 140:35 (1994); Blaak et al. *Proc. Natl. Acad. Sci.* 97, 1269-1274 (2000); Simmonds et al. *J. Virol.* 70, 8355-8360 (1996); Tersmette et al. *J. Virol.* 62, 2026-2032, (1988); Connor, R. I., Ho, D. D. *J. Virol.* 68, 4400-4408 (1994); Schuitemaker et al. *J. Virol.* 66, 1354-1360 (1992)). The M-tropic viral phenotype correlates with the virus' ability to enter the cell following binding of the CCR5 receptor, while the T-tropic viral phenotype correlates with viral entry into the cell following binding and membrane fusion with the CXCR4 receptor. Clinically, observations suggest that patients who possess genetic mutations in the CCR5 or CXCR4 appear resistant or less susceptible to HIV infection (Liu et al. *Cell* 86, 367-377 (1996); Samson et al. *Nature* 382, 722-725 (1996); Michael et al. *Nature Med.* 3, 338-340 (1997); Michael et al. *J. Virol.* 72, 6040-6047 (1998); Obrien et al. *Lancet* 349, 1219 (1997); Zhang et al. *AIDS Res. Hum. Retroviruses* 13, 1357-1366 (1997); Rana et al. *J. Virol.* 71, 3219-3227 (1997); Theodorou et al. *Lancet* 349, 1219-1220 (1997)). Despite the number of chemokine receptors which have been reported to mediate HIV entry into cells, CCR5 and CXCR4 appear to be the only physiologically relevant coreceptors used by a wide variety of primary clinical HIV-1 strains (Zhang et al. *J. Virol.* 72, 9307-9312 (1998); Zhang et al. *J. Virol.* 73, 3443-3448 (1999); Simmonds et al. *J. Virol.* 72, 8453-8457 (1988)). Fusion and entry of T-tropic viruses that use CXCR4 are inhibited by the natural CXC-chemokine stromal cell-derived factor-1 (SDF-1). On the other hand, fusion and entry of M-tropic viruses that use CCR5 are inhibited by the natural CC-chemokines namely, Regulated on Activation Normal T-cell Expressed and Secreted (RANTES or CCL5) and Macrophage Inflammatory proteins (MIP-1 alpha and MIP-1 beta or CCL3 and CCL4, respectively). SDF-1 is known as CXCL12 or Pre B-cell stimulating factor (PBSF).

However, the binding of chemokine receptors to their natural ligands appears to serve a more evolutionary and central role than only as mediators of HIV infection. The binding of the natural ligand, PBSF/SDF-1 to the CXCR4 chemokine receptor provides an important signaling mechanism. CXCR4 or SDF-1 knock-out mice exhibit cerebellar, cardiac and gastrointestinal tract abnormalities and die in utero (Zou et al., *Nature,* 393:591-594 (1998); Tachibana et al., *Nature,*

393:591-594 (1998); Nagasawa et al. *Nature* 382, 635-638 (1996)). CXCR4-deficient mice also display hematopoietic defects (Nagasawa et al. *Nature* 382, 635-638 (1996)). Furthermore, the migration of CXCR4 expressing leukocytes and hematopoietic progenitors to SDF-1 appears to be important for maintaining B-cell lineage and localization of CD34+ progenitor cells in bone marrow (Bleul et al. *J. Exp. Med.* 187, 753-762 (1998); Viardot et al. *Ann. Hematol.* 77, 195-197 (1998); Auiti et al. *J. Exp. Med.* 185, 111-120 (1997); Peled et al. *Science* 283, 845-848 (1999); Qing et al. *Immunity* 10, 463-471 (1999); Lataillade et al. *Blood* 95, 756-768 (1999); Ishii et al. *J. Immunol.* 163, 3612-3620 (1999); Maekawa et al. *Internal Medicine* 39, 90-100 (2000); Fedyk et al. *J. Leukocyte Biol.* 66, 667-673 (1999); Peled et al. *Blood* 95, 3289-3296 (2000)).

The signal provided by SDF-1 on binding to CXCR4 may also play an important role in tumor cell proliferation and regulation of angiogenesis associated with tumor growth (See "*Chemokines and Cancer*" published by Humana Press (1999); Edited by B. J. Rollins; Arenburg et al. *J. Leukocyte Biol.* 62, 554-562 (1997); Moore et al. *J. Invest. Med.* 46, 113-120 (1998); Moore et al. *Trends cardiovasc. Med.* 8, 51-58 (1998); Seghal et al. *J. Surg. Oncol.* 69, 99-104 (1998)). Known angiogenic growth factors VEG-F and bFGF, up-regulated levels of CXCR4 in endothelial cells, and SDF-1 can induce neovascularization in vivo (Salcedo et al. *Am. J. Pathol.* 154, 1125-1135 (1999)). Furthermore, leukemia cells that express CXCR4 migrate and adhere to lymph nodes and bone marrow stromal cells that express SDF-1 (Burger et al. *Blood* 94, 3658-3667 (1999); Arai et al. *Eur. J. Haematol.* 64, 323-332 (2000); Bradstock et al. *Leukemia* 14, 882-888 (2000)).

The binding of SDF-1 to CXCR4 has also been implicated in the pathogenesis of atherosclerosis (Abi-Younes et al. *Circ. Res.* 86, 131-138 (2000)), renal allograft rejection (Eitner et al. *Transplantation* 66, 1551-1557 (1998)), asthma and allergic airway inflammation (Yssel et al. *Clinical and Experimental Allergy* 28, 104-109 (1998); *J. Immunol.* 164, 5935-5943 (2000); Gonzalo et al. *J. Immunol.* 165, 499-508 (2000)), Alzheimer's disease (Xia et al. *J. Neurovirology* 5, 32-41 (1999)) and arthritis (Nanki et al. *J. Immunol.* 164, 5010-5014 (2000)).

Platelets have also been shown to secrete the chemokine RANTES upon activation, and that the presence of RANTES on the endothelium promotes the arrest of monocytes on the inflamed endothelium, an important step in atherogenesis as the conversion of macrophages into foam cells in the subendothelium is a central process in atheroma formation (Tan, et al., *Expert Opin. Investig. Drugs,* 12(11): 1765-1776 (2003)). Hence, the inhibition or prevention of the binding of RANTES, directly or indirectly, to the CCR5 receptor could potentially attenuate the development of atherosclerosis. For example, Met_RANTES has also been shown to inhibit the binding of monocytes to the activated endothelium (Tan, et al., supra).

In attempting to better understand the relationship between chemokines and their receptors, recent experiments to block the fusion, entry and replication of HIV via the CXCR4 chemokine receptor were carried out through the use of monoclonal antibodies or small molecules that appear to suggest a useful therapeutic strategy (Schols et al., *J. Exp. Med.* 186:1383-1388 (1997); Schols et al., *Antiviral Research* 35:147-156 (1997); Bridger et al. *J. Med. Chem.* 42, 3971-3981 (1999); Bridger et al. "Bicyclam Derivatives as HIV Inhibitors" in *Advances in Antiviral Drug Design* Volume 3, p161-229; Published by JAI press (1999); Edited by E. De Clercq). Small molecules, such as bicyclams, appear to specifically bind to CXCR4 and not CCR5 (Donzella et al., *Nature Medicine,* 4:72-77 (1998)). These experiments demonstrated interference with HIV entry and membrane fusion into the target cell in vitro. More recently, bicyclams were also shown to inhibit fusion and replication of Feline Immunodeficiency Virus (FIV) that uses CXCR4 for entry (Egberink et al. *J. Virol.* 73, 6346-6352 (1999)). CCR5 blocking agents include monoclonal antibodies, some which selectively block HIV coreceptor activity but not chemokine binding, and chemokine derivatives, such as truncated versions of RANTES, Met-RANTES, and AOP-RANTES and the viral chemokine KSHV vMIP-II, all which block both chemokine and HIV interaction with CCR5 but are not selective (reviewed by Murphy et al. *Pharmacol. Rev.* 52(1), 145-176 (2000)).

Additional experiments have shown that the bicyclam dose-dependently inhibits binding of 125I-labeled SDF-1 to CXCR4 and the signal transduction (indicated by an increase in intracellular calcium) in response to SDF-1. Thus, the bicyclam also functioned as an antagonist to the signal transduction resulting from the binding of stromal derived factor or SDF-1α, the natural chemokine to CXCR4. Bicyclams also inhibited HIV gp120 (envelope)-induced apoptosis in non-HIV infected cells (Blanco et al. *Antimicrobial Agents and Chemother.* 44, 51-56 (2000)).

Passive immunization with anti-MIP-1 alpha has been shown to delay the onset and reduce the severity of collagen-induced-arthritis (CIA) in mice, where the CIA model is an established murine model representing human rheumatoid arthritis (Szekanecz, Z., et al., *AP, Seminars in Immunology,* 15(2003), p. 15-21). Other studies have also shown that agents that block the CCR5 receptor may provide a rational approach to the treatment of multiple sclerosis. Administration of anti-MIP-1 alpha antiserum has been shown to prevent CNS infiltration by PBMC in mice with experimental allergic encephalomyelitis, a rodent model of multiple sclerosis (Balashov, K. E., et al., *Proc. Natl. Acad. Sci. USA,* Vol. 96 (1999), p. 6873-6878). Other studies involving chronic rejection of transplanted hearts or cardiac allograft vasculopathy (CAV) and acute renal allograft rejection have shown that blocking chemokine receptors such as CCR5 may provide unique therapeutic approaches in the treatment or prevention of such diseases (Yun, J J, et al., *Circulation,* 2004, Vol. 109(7), p. 932-7, Panzer U., et al., Transplantation, 2004, Vol. 78(9), p. 1341-50). For example, antagonism of the chemokine receptors CCR1 and CCR5 with Met-RANTES attenuated CAV development by reducing mononuclear cell recruitment to the transplanted heart. Met-CCL5, an antagonist of CCR1 and CCR5, had been tested and shown to inhibit the growth of breast tumors (Robinson S C. et al, *Cancer Res.,* 2003, Vol. 63(23), p. 8360-5).

Chemokines, as indicated above, play an important role and are implicated in a wide variety of human disease such as in autoimmune disease, allograft rejection, infection, allergies, neoplasia, and vascular abnormalities. In addition to its contributory role in HIV infection, the chemokine receptor CCR5 has been associated with diseases such as the inflammatory demyelinating diseases of the central nervous system, including multiple sclerosis and experimental autoimmune encephalomyelitis, rheumatoid arthritis, intestinal inflammation, allograft rejection, asthma, and cardiovascular disease (reviewed in Gerard et al. *Natl. Immunol.* 2(2), 108-115 (2001) and Luster, A., *N. Eng. J. Med.,* 338 (7), 436-445 (1998)). The CCR5 receptor is expressed on T-lymphocytes, and macrophages and reports of CCR5 on neurons, astrocytes, capillary endothelial cells, epithelium, vascular smooth muscle, and fibroblast have been published. The natural ligands that bind to the CCR5 receptor, in addition to RANTES and MIP-1 alpha/beta, are monocyte chemoattractant protein 2 (MCP-2 or CCL8).

U.S. Pat. Nos. 5,583,131; 5,698,546; 5,817,807; 5,021,409; and 6,001,826 which are incorporated herein in their entirety by reference, disclose cyclic compounds that are active against HIV-1 and HIV-2 in in vitro tests. It was subsequently discovered and further disclosed in PCT WO 02/34745 that these compounds exhibit anti-HIV activity by binding to the chemokine receptor CXCR4 and/or CCR5 expressed on the surface of certain cells of the immune system. This competitive binding thereby protects these target cells from infection by HIV which utilize the CXCR4 receptor for entry. In addition, these compounds antagonize the binding, signaling and chemotactic effects of the natural ligand for CXCR4, the chemokine stromal cell-derived factor 1α (SDF-1). Furthermore, these compounds demonstrate protective effects against HIV infection of target cells by binding in vitro to the CCR5 receptor.

Additionally, U.S. Pat. No. 6,365,583 discloses that these cyclic polyamine antiviral agents described in the above-mentioned patents/patent applications have the effect of enhancing production of white blood cells as well as exhibiting antiviral properties. Thus, these agents are useful for controlling the side-effects of chemotherapy, enhancing the success of bone marrow transplantation, enhancing wound healing and burn treatment, as well as combating bacterial infections in leukemia.

More recently, PCT WO 00/56729, PCT WO 02/22600, PCT WO 02/22599, and PCT WO 02/34745 describe a series of heterocyclic compounds that exhibit anti-HIV activity by binding to the chemokine receptors CXCR4 and CCR5 expressed on the surface of certain cells of the immune system. This competitive binding thereby protects these target cells from infection by HIV which utilize the CXCR4 or CCR5 receptors for entry. In addition, these compounds antagonize the binding, signaling and chemotactic effects of the natural ligand for CXCR4, the chemokine stromal cell-derived factor 1α (SDF-1) and/or the natural ligand for CCR5, the chemokine RANTES.

The chemokine receptor, CXCR4 has been found to be associated with the vascularization of the gastrointestinal tract (Tachibana et al., *Nature*, 393:591-594 (1998)) as well as in hematopoiesis and cerebellar development (Zou et al., *Nature*, 393:591-594 (1998)). Interference with any of these important functions served by the binding of pre-B-cell growth-stimulating factor/stromal derived factor (PBSF/SDF-1) to the CXCR4 chemokine receptor results in lethal deficiencies in vascular development, hematopoiesis and cardiogenesis. Similarly, fetal cerebellar development appears to rely upon the effective functioning of CXCR4 in neuronal cell migration and patterning in the central nervous system. This G-protein-coupled chemokine receptor appears to play an important role in ensuring the necessary patterns of migration of granule cells in the cerebellar anlage.

Herein, we disclose compounds that have unique chemical attributes and that exhibit protective effects against HIV infection of target cells by binding to chemokine receptor CCR5. In addition, these compounds antagonize the binding, signaling and chemotactic effects of the natural ligand for CCR5, the chemokine RANTES.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are hereby incorporated in their entirety by reference herein.

DISCLOSURE OF THE INVENTION

The present invention provides novel compounds that may modulate chemokine receptors and interfere with the binding of the natural ligand thereto. The compounds of the present invention may be useful as agents demonstrating protective effects on target cells from HIV infection. In another aspect, the present invention provides novel compounds that may be useful for the treatment and prevention of inflammatory and autoimmune diseases. Embodiments of the present invention are compounds that may act as antagonists or agonists of chemokine receptors, which may be useful as agents capable of reconstituting the immune system by increasing the level of $CD4^+$ cells; as antagonist agents of apoptosis in immune cells, such as $CD8^+$ cells, and neuronal cells; as antagonist agents of migration of human bone marrow B lineage cells to stromal-derived factor 1, as well as other biological activities related to the ability of these compounds to inhibit the binding of chemokines to their receptors.

More particularly, the present invention relates to novel piperidine derivatives that may bind to chemokine receptors, preferably CCR5 receptors. In one example, the invention is directed to a compound or a pharmaceutically acceptable salt thereof, having the formula

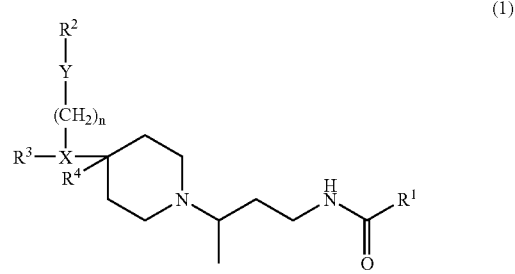

(1)

or a pharmaceutically acceptable salt thereof,
where X is carbon or nitrogen;
Y is oxygen if X is carbon, or a bond if X is nitrogen;
n is 0-1;
$R^1$ is an optionally substituted aryl or heteroaryl;
$R^2$ is an optionally substituted aryl or heteroaryl, or $N=(C_{1-6}\ alkyl)$;
$R^3$ is an optionally substituted aryl, heteroaryl, or a phenyl fused with a 5- or 6-membered heterocyclic ring; and
$R^4$ is hydrogen or alkyl.

In the above formula 1, X may be carbon and Y is oxygen. Alternatively, X may be nitrogen and Y is a bond.

In the above formula 1, $R^1$ may be phenyl, pyrimidinyl, pyridinyl, pyridine N-oxide, thiophenyl, isoxazolyl, or pyrazolyl, each of which is optionally substituted by one or more halogen, alkyl, amine or heteroaryl.

In the above formula 1, $R^2$ may be phenyl, pyridinyl, thiazolyl, furanyl, or thiophenyl, each of which is optionally linked to one or more $C_{1-6}$ alkyl, alkoxy, trifluoromethyl, carboxylalkyl, cyano, or halogen.

In the above formula 1, $R^3$ may be phenyl, pyridinyl, thiazolyl, oxazolyl, pyrimidinyl, indolyl, indolinyl, isoindolinyl, 1,3-benzodioxolyl, 1,4-benzodioxanyl, benzofuranyl, 2,3-dihydroxybenzofuranyl or phthalanyl, each of which is optionally linked to one or more $C_{1-6}$ alkyl, trifluoromethyl, oxotrifluoromethyl, carboxylalkyl, cyano, halogen, sulfanyl, $SO_2R^9$, where $R^9$ is alkyl, amine or amino alkyl, $C(O)R^{10}$, where $R^{10}$ is alkyl, amine, morpholine, $NMe_2$, $N(OMe)Me$, NPh, piperidine, NHMe, piperazine, $NHCH_2C(O)OMe$ or $PhC(O)OH$, $OR^{11}$, where $R^{11}$ is H, alkyl, $(CH_2)_2OMe$, $CH_2C(O)NH_2$, $CH_2C(O)NHNH_2$, $CH_2C(O)OCMe_3$, $CH_2C(O)OMe$, $CH_2C(O)OH$, $PhC(O)OH$, $PhC(O)NH_2$, $SO_2Me$, $C(O)Me$, $C(O)OMe$, $C(O)NEt_2$, $C(O)NMe_2$ or

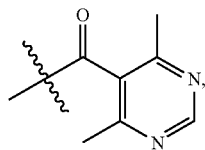

$NHR^{12}$, where $R^{12}$ is H, $C(O)Me$, $C(O)CF_3$, $SO_2Me$, $C(O)NH_2$, $C(O)NMe_2$ or

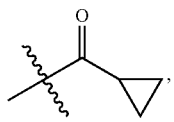

$NO_2$, $CH_2PhC(O)OH$, $SOMe$, $CH_2NHC(O)Me$, morpholine, $CH=CHC(O)OMe$, $CH=CHC(O)OH$,

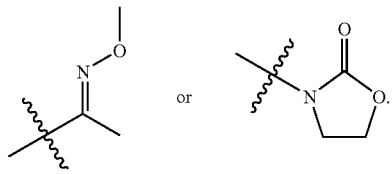

In one aspect, $R^3$ is a phenyl fused with a 5- or 6-membered heterocyclic ring. For example, $R^3$ may be indolyl, benzodioxolyl, dihydrobenzofuranyl, dihydroisobenzofuranyl, benzofuranyl, or dihydrobenzodioxinyl.

In the above formula 1, $R^4$ may be hydrogen or alkyl. In particular examples, $R^4$ is hydrogen.

In another example, the invention is directed to a compound or a pharmaceutically acceptable salt thereof, having the formula:

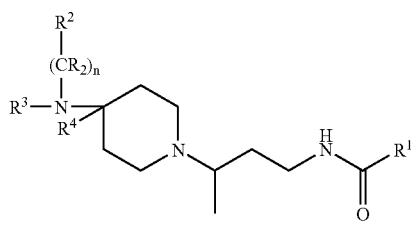

(2)

In the above formula 2, $R^1$ is an optionally substituted aryl or heteroaryl.

In the above formula 2, $R^2$ is an optionally substituted pyridine.

In the above formula, $R^3$ is an optionally substituted aryl, heteroaryl, or a phenyl fused with a cyclic ring.

In the above formula 2, each R and $R^4$ is independently hydrogen or $C_{1-6}$ alkyl, and n is 0 or 1.

The present invention also provides pharmaceutical compositions comprising compounds having Formula 1 or 2, and a pharmaceutically acceptable carrier. Furthermore, the present invention provides methods for treating a CCR5 mediated disease in a cell, tissue or organ, comprising contacting a compound having Formula 1 or 2 with the system, thereby treating a CCR5-mediated disease. The present invention also provides methods for treating a CCR5 mediated disease in a human or animal subject, comprising administering a compound having Formula 1 or 2 with the subject, thereby treating a CCR5-mediated disease.

Examples of CCR5-mediated diseases that may be treated using the compounds of the present invention include but are not limited to HIV, an inflammatory demyelinating disease of the central nervous system, an autoimmune disease, multiple sclerosis, experimental autoimmune encephalomyelitis, psoriatic or rheumatoid arthritis, intestinal inflammation, allograft rejection, asthma, cardiovascular disease, atherosclerosis, allergic disease, allergic rhinitis, dermatitis, conjunctivitis, hypersensitivity lung disease, hypersensitivity pneumonitis, eosinophilic pneumonia, delayed-type hypersensitivity, interstitial lung disease (ILD), idiopathic pulmonary fibrosis, ILD associated with rheumatoid arthritis, systemic lupus erythematosus, ankylosing spondylitis, systemic sclerosis, Sjogren's syndrome, polymyositis, dermatomyositis, systemic anaphylaxis, myastenia gravis, juvenile onset diabetes, glomerulonephritis, autoimmune throiditis, graft rejection, allograft rejection, graft-versus-host disease, inflammatory bowel disease, Crohn's disease, ulcerative colitis, spondyloarthropathy, scleroderma; psoriasis, inflammatory dermatosis, dermatitis, eczema, atopic dermatitis, allergic contact dermatitis, urticaria, vasculitis, eosinphilic myotis, eosiniphilic fasciitis, tumor or cancer.

The compounds of Formula 1 or 2 may form hydrates or solvates, and may be in any stereoisomeric forms and mixtures of stereoisomeric forms thereof. Racemate compounds may be separated into individual isomers using known separation and purification methods. Individual optical isomers and a mixture thereof, are included in the scope of the present invention.

MODES FOR CARRYING OUT THE INVENTION

In one aspect, the invention provides compounds having Formula 1 or 2 described above, which may be chemokine modulators of chemokine receptors.

In more detail, the compounds may bind chemokine receptors and interfere with the binding of the natural ligand thereto, and may demonstrate protective effects on target cells from HIV infection. The compounds may be useful as antagonists or agonists of chemokine receptors, and are thus capable of reconstituting the immune system by increasing the level of CD4+ cells; as antagonist agents of apoptosis in immune cells, such as CD8+ cells, and neuronal cells; as antagonist agents of migration of human bone marrow B lineage cells to stromal-derived factor 1, as well as other biological activities related to the ability of these compounds to inhibit the binding of chemokines to their receptors.

Chemokine antagonists that interfere in the binding of a chemokine to its receptor are useful to reconstitute the immune system by increasing the level of CD4+ cells (Biard-Piechaczyk, et al., *Immunol. Lett.,* 70: 1-3 (1999)); as antagonist agents of apoptosis in immune cells, such as CD8+ cells (Herbin, et al., *Nature* 395: 189-193, (1998)), and as antagonist agents of apoptosis in neuronal cells (Ohagen et al., *J. of*

Virol., 73: 897-906, (1999); and Hesselgesser, et al., Curr. Biol. 8: 595-598, (1998)). Chemokine receptor antagonist agents also inhibit the migration of human bone marrow B lineage cells to stromal-derived factor 1 (See e.g., E. Fedyk, et al., J of Leukocyte Biol., 66:667-783, (1999)).

The invention includes pharmaceutical compositions comprising a therapeutically effective amount of a compound of Formula 1 or 2 along with at least one excipient, and methods of treating diseases of the human body or the bodies of other mammals with such compositions. The term "therapeutically effective amount" means the amount of a compound of Formula 1 or 2 that will elicit the biological or medical response of a cell, tissue, organ, system, animal or human that is being sought by the researcher, veterinarian, medical doctor, or other clinician. The invention provides a method for blocking or interfering with the binding by a chemokine receptor with its natural ligand, comprising contacting of the chemokine receptor with an effective amount of the compound according to Formula 1 or 2. The present invention also provides methods of protecting target cells possessing chemokine receptors, which binding to a pathogenic agent results in disease or pathology, comprising administering to a mammalian subject a pharmaceutical composition comprising a therapeutically effective amount of the compound according to Formula 1 or 2. The invention includes the use of a compound of Formula 1 or 2 in the manufacture of a medicament for the treatment of a disease in which blocking or interfering with binding of a chemokine receptor with its natural ligand is advantageous. The compound is formulated into a composition in an amount corresponding to a therapeutically effective amount of a compound of Formula 1 or 2.

The Invention Compounds

The invention compounds are described generally by Formula 1 or 2. In one embodiment, the compounds of the present invention are of formula 1

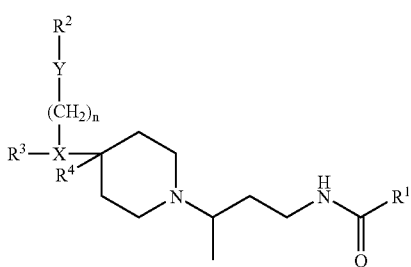

(1)

or a pharmaceutically acceptable salt thereof,
wherein X is carbon or nitrogen;
Y is O, S, SO or $SO_2$ if X is carbon, or a bond if X is nitrogen;
n is 0-3;
$R^1$ is a cyclic or acyclic alkyl or 5- or 6-membered non-aromatic heterocyclic ring, each of which is optionally substituted by one or more of cyclic alkyl, acyclic alkyl, alkene, alkyne, halogen, CN, OH, $NH_2$, $NHR^5$, or $OR^5$; or
phenyl, pyridine, pyridine N-oxide or heteroaryl, each of which is optionally substituted by one or more of cyclic or acyclic alkyl, alkene, alkyne, OH, OMe, $NH_2$, $NH(C_{1-6}$ alkyl), $N(C_{1-6}$ alkyl$)_2$, halogen, CN, $CF_3$, $OCF_3$, $NHC(O)(C_{1-6}$ alkyl), $C(O)(C_{1-6}$ alkyl), $C(O)O(C_{1-6}$ alkyl), $OC(O)(C_{1-6}$ alkyl), $C(O)OH$, $C(O)NH(C_{1-6}$ alkyl), $C(O)N(C_{1-6}$ alkyl$)_2$, $S(C_{1-6}$ alkyl), $SO_nR^6$, NHS $(O)_n(C_{1-6}$ alkyl) where n is 1 or 2; or phenyl, pyridine or pyridine N-oxide, each of which is optionally substituted by one or more of cyclic or acyclic alkyl, alkene, alkyne, halogen, CN, $NH_2$, $NH(C_{1-6}$ alkyl), $N(C_{1-6}$ alkyl$)_2$, $C(O)NH(C_{1-6}$ alkyl), $C(O)N(C_{1-6}$ alkyl$)_2$, or $C(O)O(C_{1-6}$ alkyl); or
an N-linked phenyl, pyridine, pyridine N-oxide or heteroaryl ring, each of which is optionally substituted by one or more of cyclic or acyclic alkyl, alkene, alkyne, halogen, CN, $NH_2$, $NH(C_{1-6}$ alkyl), $N(C_{1-6}$ alkyl$)_2$, $C(O)NH(C_{1-6}$ alkyl), $C(O)N(C_{1-6}$ alkyl$)_2$, or $C(O)O(C_{1-6}$ alkyl);

$R^2$ is phenyl, pyridine or heteroaryl, each of which is optionally substituted by one or more of cyclic or acyclic alkyl, alkene, alkyne, halogen, CN, $NO_2$, OH, $NH_2$, $CF_3$, $CH_2OH$, $C(O)O(C_{1-6}$ alkyl), $OR^7$, or 5- or 6-membered non aromatic heterocyclic ring; or
a $C_{1-6}$ alkyl, alkene or alkyne, $OC(O)(C_{1-6}$ alkyl), $NHC(O)(C_{1-6}$ alkyl), $NHR^8$, or a 5- or 6-membered non aromatic heterocyclic ring;

$R^3$ is phenyl, pyridine, or heteroaryl, each of which is optionally substituted by one or more of cyclic or acyclic alkyl, alkene, alkyne, halogen, CN, CHO, $CF_3$, $OCF_3$, $NO_2$, OH, $NHC(O)(C_{1-6}$ acyclic or $C_{3-6}$ cyclic alkyl), $NHC(O)CF_3$, $NHSO_2(C_{1-6}$ alkyl), $NHC(O)NH_2$, $NHC(O)(C_{1-6}$ alkyl), $C(O)NH_2$, $C(O)NHC_6H_5$, $C(O)C_6H_4C(O)OH$, $C(O)N(OC_{1-6}$ alkyl)$(C_{1-6}$ alkyl), $C(O)NHCH_2C(O)O(C_{1-6}$ alkyl), $C(O)(C_{1-6}$ alkyl), $C(O)O(C_{1-6}$ alkyl), $C(O)(non-aromatic\ heterocylic\ ring)$, $OC(O)(C_{1-6}$ alkyl), $O(C_{1-6}$ alkyl), $O(C_{1-6}$ alkyl$)O(C_{1-6}$ alkyl), $O(C_{1-6}$ alkyl$)C(O)OH$, $OC_6H_4C(O)OH$, $OC_6H_4C(O)NH_2$, $O(C_{1-6}$ alkyl$)C(O)O(C_{1-6}$ alkyl), $O(C_{1-6}$ alkyl$)C(O)NH_2$, $O(C_{1-6}$ alkyl$)C(O)NH_2$, $OSO_2(C_{1-6}$ alkyl), $OC(O)O(C_{1-6}$ alkyl), $OC(O)N(C_{1-6}$ alkyl$)_2$, $OC(O)(heteroaryl)$, COOH, $C(O)NH(C_{1-6}$ alkyl), $C(O)N(C_{1-6}$ alkyl$)_2$, $S(C_{1-6}$ alkyl), CH=NOH, CH=NO$(C_{1-6}$ alkyl), CH=N$(C_{1-6}$ alkyl), $(C_{1-6}$ alkyl)$C$=NOH, $(C_{1-6}$ alkyl)$C$=NO$(C_{1-6}$ alkyl), $(C_{1-6}$ alkyl)$C$=N$(C_{1-6}$ alkyl), $(C_{1-6}$ alkyl)$C_6H_4C(O)OH$, $(C_{1-6}$ alkyl)$NHC(O)(C_{1-6}$ alkyl), CH=CHC(O)O$(C_{1-6}$ alkyl), CH=CHC(O)OH, $SO_nR^6$ where n is 1 or 2; or phenyl, pyridine N-oxide, pyridine or heteroaryl each of which is optionally substituted by one or more of alkyl, alkene, alkyne, halogen, CN, $CF_3$, OH, $NH_2$, $OR^7$, $(C_{1-6}$ alkyl)$R^5$, $(C_{1-6}$ alkene)$R^5$, $(C_{1-6}$ alkyne)$R^5$, or a 5- or 6-membered non aromatic heterocyclic ring;

$R^4$ is hydrogen or $C_{1-6}$ alkyl;

$R^5$ is a $C_{1-6}$ alkyl, phenyl, pyridine, pyridine N-oxide or heteroaryl, each of which is optionally substituted by one or more of $C_{1-6}$ alkyl, OH, OMe, $NH_2$, $NH(C_{1-6}$ alkyl), $N(C_{1-6}$ alkyl$)_2$, halogen, CN, $CF_3$, $OCF_3$, $C(O)NH(C_{1-6}$ alkyl), $C(O)N(C_{1-6}$ alkyl$)_2$, $C(O)O(C_{1-6}$ alkyl), COOH, $SO_nNH(C_{1-6}$ alkyl), or $SON(C_{1-6}$ alkyl) where n is 1 or 2;

$R^6$ is $C_{1-6}$ alkyl, $NH_2$, $NH(C_{1-6}$ alkyl), $N(C_{1-6}$ alkyl$)_2$, or benzyl;

$R^7$ is a cyclic or acyclic alkyl, alkene, alkyne, phenyl, pyridine or heteroaryl, each of which is optionally substituted by one or more of $C_{1-6}$ alkyl, halogen, CN, $NH_2$, $C(O)OH$, $C(O)O(C_{1-6}$ alkyl), OH, $SO_nNH_2$ where n is 1 or 2, $SO_n(C_{1-6}$ alkyl) where n is 1 or 2, $SO_2NH(C_{1-6}$ alkyl), $C(O)NH_2$, $C(O)NH(C_{1-6}$ alkyl), or $C(O)N(C_{1-6}$ alkyl$)_2$; and $R^8$ is a $C_{1-6}$ alkyl, alkene or alkyne, OH, or OMe.

In another embodiment, the compounds of the invention are compounds of formula (2) or or a pharmaceutically acceptable salt thereof:

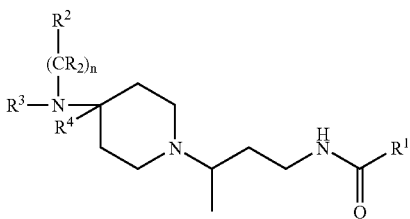

(2)

wherein
- $R^1$ is an optionally substituted aryl or heteroaryl;
- $R^2$ is an optionally substituted pyridine;
- $R^3$ is an optionally substituted aryl, heteroaryl, or a phenyl fused with a cyclic ring;
- R and $R^4$ are independently hydrogen or $C_{1-6}$ alkyl; and
- n is 0 or 1.

The optional substituents for $R^1$, $R^2$, and $R^3$ in formula (2) correspond to those set forth above for groups $R^1$, $R^2$ and $R^3$ respectively in formula (1).

Examples of heteroaryl groups in the above Formula 1-2 include but are not limited to pyridine, quinoline, isoquinoline, imidazole, benzimidazole, benzotriazole, furan, morpholine, benzofuran, dihydrobenzofuran, thiazole, benzothiazole, benzodioxole, benzodioxane, oxazole, isoxazole, benzoxazole, pyrrole, indole, indoline, isoindoline, indazole, pyrrolidine, pyrrolidone, tetrahydroquinoline, tetrahydroisoquinoline, pyrazole, thiophene, isothiazole, triazole, tetrazole, oxadiazole, thiadiazole, benzopyran, pyridazine, pyrimidine, pyrazine, 1,3,5-triazine, cinnoline, tetrahydrocinnoline, quinazoline, tetrahydroquinazoline, quinoxaline, tetrahydroquinoxaline, phthalan or phthalazine.

The present invention also relates to pharmaceutical compositions comprising compounds of Formula 1 or 2, and a pharmaceutically acceptable carrier. Furthermore, the present invention relates to methods for treating a CCR5 mediated disease in a system, comprising contacting a compound of Formula 1 or 2 with a system (e.g., cell, tissue or organ), or in a subject.

Examples of piperidine compounds of the present invention include but are not limited to:

6-Chloro-N-((R)-3-{4-[(4-methoxy-phenyl)-(4-methyl-pyridin-3-ylmethyl)-amino]-piperidin-1-yl}-butyl)-2,4-dimethyl-nicotinamide (1);

4-Cyano-N-((R)-3-{4-[[4-(2-methoxy-ethoxy)-phenyl]-(4-methyl-pyridin-3-ylmethyl)-amino]-piperidin-1-yl}-butyl)-2,6-dimethyl-benzamide (2);

N-((R)-3-{4-[(4-Methoxy-phenyl)-(4-methyl-pyridin-3-ylmethyl)-amino]-piperidin-1-yl}-butyl)-2,6, N',N'-tetramethyl-terephthalamide (3);

6-chloro-N-((R)-3-{4-[(4-methoxy-phenyl)-(4-methyl-pyridin-3-ylmethyl)-amino]-piperidin-1-yl}-butyl)-2,4-dimethyl-1-oxy-nicotinamide (4);

6-Chloro-N-((R)-3-{4-[(4-methoxy-phenyl)-pyridin-3-ylmethyl-amino]-piperidin-1-yl}-butyl)-2,4-dimethyl-nicotinamide (5);

6-Cyano-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide (6);

N'-Isopropyl-N-((R)-3-{4-[(4-methoxy-phenyl)-(4-methyl-pyridin-3-ylmethyl)-amino]-piperidin-1-yl}-butyl)-2,6-dimethyl-terephthalamide (7);

6-cyano-N-((R)-3-{4-[(4-methoxy-phenyl)-(4-methyl-pyridin-3-ylmethyl)-amino]-piperidin-1-yl}-butyl)-2,4-dimethyl-1-oxy-nicotinamide (8);

N-((R)-3-{4-[(4-Carbamoylmethoxy-phenyl)-(4-methyl-pyridin-3-ylmethyl)-amino]-piperidin-1-yl}-butyl)-6-cyano-2,4-dimethyl-nicotinamide (9);

N'-Isopropyl-2,6-dimethyl-N-((R)-3-{4-[(4-methyl-pyridin-3-ylmethyl)-phenyl-amino]-piperidin-1-yl}-butyl)-terephthalamide (10);

6-Fluoro-N-((R)-3-{4-[(4-methoxy-phenyl)-(4-methyl-pyridin-3-ylmethyl)-amino]-piperidin-1-yl}-butyl)-2,4-dimethyl-nicotinamide (11);

6-Chloro-N-((R)-3-{4-[(4-ethoxy-phenyl)-pyridin-3-ylmethyl-amino]-piperidin-1-yl}-butyl)-2,4-dimethyl-nicotinamide (12);

6-Chloro-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide (13);

N-((R)-3-{4-[(4-Ethoxy-phenyl)-(4-methyl-pyridin-3-ylmethyl)-amino]-piperidin-1-yl}-butyl)-6-fluoro-2,4-dimethyl-nicotinamide (14);

6-Chloro-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide (15);

2-Chloro-N-((R)-3-{4-[(4-methoxy-phenyl)-(4-methyl-pyridin-3-ylmethyl)-amino]-piperidin-1-yl}-butyl)-4-methyl-nicotinamide (16);

N-((R)-3-{4-[(4-Difluoromethoxy-phenyl)-pyridin-3-ylmethyl-amino]-piperidin-1-yl}-butyl)-6-fluoro-2,4-dimethyl-nicotinamide (17);

6-Chloro-N-((R)-3-{4-[(6-cyano-pyridin-2-ylmethyl)-(4-methoxy-phenyl)-amino]-piperidin-1-yl}-butyl)-2,4-dimethyl-nicotinamide (18);

2-Chloro-N-((R)-3-{4-[[4-(2-methoxy-ethoxy)-phenyl]-(4-methyl-pyridin-3-ylmethyl)-amino]-piperidin-1-yl}-butyl)-4-methyl-nicotinamide (19);

2-Bromo-N-((R)-3-{4-[(4-methoxy-phenyl)-(4-methyl-pyridin-3-ylmethyl)-amino]-piperidin-1-yl}-butyl)-4-methyl-nicotinamide (20);

2-Chloro-N-((R)-3-{4-[(4-ethoxy-phenyl)-(4-methyl-pyridin-3-ylmethyl)-amino]-piperidin-1-yl}-butyl)-4-methyl-nicotinamide (21);

4-Cyano-N-((R)-3-{4-[(6-cyano-pyridin-2-ylmethyl)-(4-methoxy-phenyl)-amino]-piperidin-1-yl}-butyl)-2,6-dimethyl-benzamide (22);

N-((R)-3-{4-[(6-Cyano-pyridin-2-ylmethyl)-(4-methoxy-phenyl)-amino]-piperidin-1-yl}-butyl)-6-fluoro-2,4-dimethyl-nicotinamide (23);

6-Cyano-N-((R)-3-{4-[(6-cyano-pyridin-2-ylmethyl)-(4-methoxy-phenyl)amino]-piperidin-1-yl}-butyl)-2,4-dimethyl-nicotinamide (24);

2-Chloro-N-((R)-3-{4-[(6-cyano-pyridin-2-ylmethyl)-(4-methoxy-phenyl)-amino]-piperidin-1-yl}-butyl)-4-methyl-nicotinamide (25);

N-(R)-[3-(4-{(6-Cyano-pyridin-2ylmethyl)-[4-(2-methoxy-ethoxy)-phenyl]-amino}-piperidin-1-yl)-butyl]-6-fluoro-2,4-dimethyl-nicotinamide (26);

4,6-Dimethyl-pyrimidine-5-carboxylic acid (3-{4-[(4-methoxy-phenyl)-(5-methyl-pyridin-3-ylmethyl)-amino]-piperidin-1-yl}-butyl)-amide (27);

4,6-Dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide (28);

N-((R)-3-{4-[(4-Methoxy-phenyl)-(4-methyl-pyridin-3-ylmethyl)-amino]-piperidin-1-yl}-butyl)-3,5-dimethyl-isonicotinamide (29);

4,6-Dimethyl-pyrimidine-5-carboxylic acid (R)-(3-{4-[(4-methoxy-phenyl)-pyridin-3-ylmethyl-amino]-piperidin-1-yl}-butyl)-amide (30);

4-[(1-{3-[(2,4-Dimethyl-pyridine-3-carbonyl)-amino]-1-methyl-propyl}-piperidin-4-yl)-(4-methyl-pyridin-3-ylmethyl)-amino]-benzoic acid methyl ester (31);

4,6-Dimethyl-pyrimidine-5-carboxylic acid (R)-(3-{4-[(6-cyano-pyridin-2-ylmethyl)-(4-methoxy-phenyl)-amino]-piperidin-1-yl}-butyl)-amide (32);

N-(3-{4-[(4-Ethyl-phenyl)-(4-methyl-pyridin-3-ylmethyl)-amino]-piperidin-1-yl}-butyl)-2,4-dimethyl-nicotinamide (33);

4,6-Dimethyl-pyrimidine-5-carboxylic acid (3-{4-[(4-ethyl-phenyl)-(4-methyl-pyridin-3-ylmethyl)-amino]-piperidin-1-yl}-butyl)-amide (34);

4-Hydroxy-N-((R)-3-{4-[(4-methoxy-phenyl)-(4-methyl-pyridin-3-ylmethyl)-amino]-piperidin-1-yl}-butyl)-2,6-dimethyl-benzamide (35);

N-((R)-3-{4-[(4-Methoxy-phenyl)-(4-methyl-pyridin-3-ylmethyl)-amino]-piperidin-1-yl}-butyl)-2,6-dimethyl-4-oxazol-2-yl-benzamide (36);

N-((R)-3-{4-[(4-Methoxy-phenyl)-(4-methyl-pyridin-3-ylmethyl)-amino]-piperidin-1-yl}-butyl)-2,6-dimethyl-4-morpholin-4-yl-benzamide (37);

N-((R)-3-{4-[(4-Methoxy-phenyl)-(4-methyl-pyridin-3-ylmethyl)-amino]-piperidin-1-yl}-butyl)-2,6-dimethyl-4-thiazol-2-yl-benzamide (38);

N-((R)-3-{4-[(4-Methoxy-phenyl-1(4-methyl-pyridin-3-ylmethyl)-amino]-piperidin-1-yl}-butyl)-2,6-dimethyl-4-(1H-tetrazol-5-yl)-benzamide (39);

4-Cyano-N-((R)-3-{4-[(4-methoxy-phenyl)-(4-methyl-pyridin-3-ylmethyl)-amino]-piperidin-1-yl}-butyl)-2,6-dimethyl-benzamide (40);

4-(1H-Imidazol-2-yl)-N-((R)-3-{4-[(4-methoxy-phenyl)-(4-methyl-pyridin-3-ylmethyl)-amino]-piperidin-1-yl}-butyl)-2,6-dimethyl-benzamide (41);

N-((R)-3-{4-[(4-Methoxy-phenyl)-(4-methyl-pyridin-3-ylmethyl)-amino]-piperidin-1-yl}-butyl)-2,6-dimethyl-terephthalamide (42);

Dimethyl-carbamic acid 4-[(1-{3-[(2,4-dimethyl-pyridine-3-carbonyl)-amino]-1-methyl-propyl}-piperidin-4-yl)-(4-methyl-pyridin-3-ylmethyl)-amino]-phenyl ester (43);

N-(3-{4-[[4-(2-Methoxy-ethoxy)-phenyl]-(4-methyl-pyridin-3-ylmethyl)-amino]-piperidin-1-yl}-butyl)-2,4-dimethyl-nicotinamide (44);

2,4-Dimethyl-N-(3-{4-[(4-methyl-pyridin-3-ylmethyl)-naphthalen-2-yl-amino]-piperidin-1-yl}-butyl)-nicotinamide (45);

4,6-Dimethyl-pyrimidine-5-carboxylic acid (3-{4-[(4-methyl-pyridin-3-ylmethyl)-naphthalen-2-yl-amino]-piperidin-1-yl}-butyl)-amide (46);

Dimethyl-thiocarbamic acid O-{4-[(1-{3-[(2,4-dimethyl-pyridine-3-carbonyl)-amino]-1-methyl-propyl}-piperidin-4-yl)-(4-methyl-pyridin-3-ylmethyl)-amino]-phenyl}ester (47);

N-((R)-3-{4-[(4-Methoxy-phenyl)-(4-methyl-pyridin-3-ylmethyl)-amino]-piperidin-1-yl}-butyl)-2,6-dimethyl-4-[1,2,4]triazol-4-yl-benzamide (48);

N-((R)-3-{4-[(4-Methoxy-phenyl)-(4-methyl-pyridin-3-ylmethyl)-amino]-piperidin-1-yl}-butyl)-2,6-dimethyl-4-tetrazol-1-yl-benzamide (49);

4-(1H-Imidazol-4-yl)-N-((R)-3-{4-[(4-methoxy-phenyl)-(4-methyl-pyridin-3-ylmethyl)-amino]-piperidin-1-yl}-butyl)-2,6-dimethyl-benzamide (50);

N-((R)-3-{4-[(4-Methoxy-phenyl)-(4-methyl-pyridin-3-ylmethyl)-amino]-piperidin-1-yl}-butyl)-2,6-dimethyl-4-(3-propyl-ureido)-benzamide (51);

4,6-Dimethyl-pyrimidine-5-carboxylic acid [3-(4-{(4-methyl-pyridin-3-ylmethyl)-[4-(pyridin-3-yloxy)-phenyl]-amino}-piperidin-1-yl)-butyl]-amide (52);

4,6-Dimethyl-2-pyridin-4-yl-pyrimidine-5-carboxylic acid (R)-(3-{4-[(4-methoxy-phenyl)-(4-methyl-pyridin-3-ylmethyl)-amino]-piperidin-1-yl}-butyl)-amide (53);

6-Cyano-N-((R)-3-{4-[(4-methoxy-phenyl)-(4-methyl-pyridin-3-ylmethyl)-amino]-piperidin-1-yl}-butyl)-2,4-dimethyl-nicotinamide (54);

2,4-Dimethyl-N-[3-(4-{(4-methyl-pyridin-3-ylmethyl)-[4-(pyridin-3-yloxy)-phenyl]-amino}-piperidin-1-yl)-butyl]-1-oxy-nicotinamide (55);

N-((R)-3-{4-[(4-Methoxy-phenyl)-(4-methyl-pyridin-3-ylmethyl)-amino]-piperidin-1-yl}-butyl)-2,6-dimethyl-4-(1-oxy-pyridin-4-yl)-benzamide (56);

2,4-Dimethyl-N-(3-{4-[(4-methyl-pyridin-3-ylmethyl)-(4-thiophen-2-yl-phenyl)-amino]-piperidin-1-yl}-butyl)-nicotinamide (57);

N-(3-{4-[(4-Acetyl-phenyl)-(4-methyl-pyridin-3-ylmethyl)-amino]-piperidin-1-yl}-butyl)-2,4-dimethyl-nicotinamide (58);

N-(3-{4-[[4-(1-Methoxyimino-ethyl)-phenyl]-(4-methyl-pyridin-3-ylmethyl)-amino]-piperidin-1-yl}-butyl)-2,4-dimethyl-nicotinamide (59);

Dimethyl-carbamic acid 4-((R)-3-{4-[(4-methoxy-phenyl)-(4-methyl-pyridin-3-ylmethyl)-amino]-piperidin-1-yl}-butylcarbamoyl)-3,5-dimethyl-phenyl ester (60);

4-Methoxy-N-((R)-3-{4-[(4-methoxy-phenyl)-(4-methyl-pyridin-3-ylmethyl)-amino]-piperidin-1-yl}-butyl)-2,6-dimethyl-benzamide (61);

4-(2-Hydroxy-ethoxy)-N-((R)-3-{4-[(4-methoxy-phenyl)-(4-methyl-pyridin-3-ylmethyl)-amino]-piperidin-1-yl}-butyl)-2,6-dimethyl-benzamide (62);

N-((R)-3-{4-[(4-Methoxy-phenyl)-(4-methyl-pyridin-3-ylmethyl)-amino]-piperidin-1-yl}-butyl)-2,6-dimethyl-4-(2H-pyrazol-3-yl)-benzamide (63);

6-Imidazol-1-yl-N-((R)-3-{4-[(4-methoxy-phenyl)-(4-methyl-pyridin-3-ylmethyl)-amino]-piperidin-1-yl}-butyl)-2,4-dimethyl-nicotinamide (64);

4-Acetylamino-N-((R)-3-{4-[(4-methoxy-phenyl)-(4-methyl-pyridin-3-ylmethyl)-amino]-piperidin-1-yl}-butyl)-2,6-dimethyl-benzamide (65);

4,6-Dimethyl-[2,4']bipyridinyl-5-carboxylic acid (R)-(3-{4-[(4-methoxy-phenyl)-(4-methyl-pyridin-3-ylmethyl)-amino]-piperidin-1-yl}-butyl)-amide (66);

2-Methoxy-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide (67);

N-((R)-3-{4-[(4-Methoxy-phenyl)-(4-methyl-pyridin-3-ylmethyl)-amino]-piperidin-1-yl}-butyl)-2,4-dimethyl-6-[1,2,4]triazol-1-yl-nicotinamide (68);

4-Aminomethyl-N-((R)-3-{4-[(4-methoxy-phenyl)-(4-methyl-pyridin-3-ylmethyl)-amino]-piperidin-1-yl}-butyl)-2,6-dimethyl-benzamide (69);

N-((R)-3-{4-[(4-Methoxy-phenyl)-(4-methyl-pyridin-3-ylmethyl)-amino]-piperidin-1-yl}-butyl)-2,6, N'-trimethyl-terephthalamide (70);

N'-Ethyl-N-((R)-3-{4-[(4-methoxy-phenyl)-(4-methyl-pyridin-3-ylmethyl)-amino]-piperidin-1-yl}-butyl)-2,6-dimethyl-terephthalamide (71);

N-((R)-3-{4-[(4-Methoxy-phenyl)-(4-methyl-pyridin-3-ylmethyl)-amino]-piperidin-1-yl}-butyl)-3,5-dimethyl-terephthalamic acid methyl ester (72);

N-((R)-3-{4-[(4-Methoxy-phenyl)-(4-methyl-pyridin-3-ylmethyl)-amino]-piperidin-1-yl}-butyl)-2,6-dimethyl-4-ureidomethyl-benzamide (73);

4-(Acetylamino-methyl)-N-((R)-3-{4-[(4-methoxy-phenyl)-(4-methyl-pyridin-3-ylmethyl)-amino]-piperidin-1-yl}-butyl)-2,6-dimethyl-benzamide (74);

4-Hydrazinocarbonyl-N-((R)-3-{4-[(4-methoxy-phenyl)-(4-methyl-pyridin-3-ylmethyl)-amino]-piperidin-1-yl}-butyl)-2,6-dimethyl-benzamide (75);

2-Cyano-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide (76);

4-Cyano-N-((R)-3-{4-[(4-methoxy-phenyl)-pyridin-3-ylmethyl-amino]-piperidin-1-yl}-butyl)-2,6-dimethyl-benzamide (77);

N-((R)-3-{4-[(4-Methoxy-phenyl)-(4-methyl-pyridin-3-ylmethyl)-amino]-piperidin-1-yl}-butyl)-2-methyl-4-pyridin-4-yl-benzamide (78);

2-Cyclopropyl-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide (79);

N'-Hydroxy-N-((R)-3-{4-[(4-methoxy-phenyl)-(4-methyl-pyridin-3-ylmethyl)-amino]-piperidin-1-yl}-butyl)-2,6-dimethyl-terephthalamide (80);

4-Hydroxymethyl-N-((R)-3-{4-[(4-methoxy-phenyl)-(4-methyl-pyridin-3-ylmethyl)-amino]-piperidin-1-yl}-butyl)-2,6-dimethyl-benzamide (81);

N-((R)-3-{4-[(4-Methoxy-phenyl)-(4-methyl-pyridin-3-ylmethyl)-amino]-piperidin-1-yl}-butyl)-2,6-dimethyl-4-(2-methyl-2H-tetrazol-5-yl)-benzamide (82);

3,5-Dimethyl-1-phenyl-1H-pyrazole-4-carboxylic acid (R)-(3-{4-[(4-methoxy-phenyl)-(4-methyl-pyridin-3-ylmethyl)-amino]-piperidin-1-yl}-butyl)-amide (83);

6-Amino-N-((R)-3-{4-[(4-methoxy-phenyl)-(4-methyl-pyridin-3-ylmethyl)-amino]-piperidin-1-yl}-butyl)-2,4-dimethyl-nicotinamide (84);

N'-Methoxy-N-((R)-3-{4-[(4-methoxy-phenyl)-(4-methyl-pyridin-3-ylmethyl)-amino]-piperidin-1-yl}-butyl)-2,6-dimethyl-terephthalamide (85);

N'-Methoxy-N-((R)-3-{4-[(4-methoxy-phenyl)-(4-methyl-pyridin-3-ylmethyl)-amino]-piperidin-1-yl}-butyl)-2,6, N'-trimethyl-terephthalamide (86);

N'-Ethyl-N-((R)-3-{4-[(4-methoxy-phenyl)-(4-methyl-pyridin-3-ylmethyl)-amino]-piperidin-1-yl}-butyl)-2,6,N'-trimethyl-terephthalamide (87);

N-((R)-3-{4-[(4-Methoxy-phenyl)-(4-methyl-pyridin-3-ylmethyl)-amino]-piperidin-1-yl}-butyl)-2,6-dimethyl-4-(pyrrolidine-1-carbonyl)-benzamide (88);

N-((R)-3-{4-[(4-Carbamoylmethoxy-phenyl)-(4-methyl-pyridin-3-ylmethyl)-amino]-piperidin-1-yl}-butyl)-4-cyano-2,6-dimethyl-benzamide (89);

6-Cyano-2,4-dimethyl-N-((R)-3-{4-[(4-methyl-pyridin-3-ylmethyl)-phenyl-amino]-piperidin-1-yl}-butyl)-nicotinamide (90);

N-((R)-3-{4-[(4-Methoxy-phenyl)-(4-methyl-pyridin-3-ylmethyl)-amino]-piperidin-1-yl}-butyl)-2,4-dimethyl-6-pyrimidin-5-yl-nicotinamide (91);

2-Amino-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide (92);

4,6-Dimethyl-pyridine-2,5-dicarboxylic acid 2-dimethylamide 5-[(R)-(3-{4-[(4-methoxy-phenyl)-(4-methyl-pyridin-3-ylmethyl)-amino]-piperidin-1-yl}-butyl)-amide] (93);

4,6-Dimethyl-pyridine-2,5-dicarboxylic acid 5-[(R)-(3-{4-[(4-methoxy-phenyl)-(4-methyl-pyridin-3-ylmethyl)-amino]-piperidin-1-yl}-butyl)-amide] 2-methylamide (94);

4,6-Dimethyl-pyridine-2,5-dicarboxylic acid 2-ethylamide 5-[(R)-(3-{4-[(4-methoxy-phenyl)-(4-methyl-pyridin-3-ylmethyl)-amino]-piperidin-1-yl}-butyl)-amide] (95);

[4-(R)-(3-{4-[(4-Methoxy-phenyl)-(4-methyl-pyridin-3-ylmethyl)-amino]-piperidin-1-yl}-butylcarbamoyl)-3,5-dimethyl-phenyl]-carbamic acid methyl ester (96);

4-Amino-N-((R)-3-{4-[(4-methoxy-phenyl)-(4-methyl-pyridin-3-ylmethyl)-amino]-piperidin-1-yl}-butyl)-2,6-dimethyl-benzamide (97);

4-(3-Ethyl-ureido)-N-((R)-3-{4-[(4-methoxy-phenyl)-(4-methyl-pyridin-3-ylmethyl)-amino]-piperidin-1-yl}-butyl)-2,6-dimethyl-benzamide (98);

4,6-Dimethyl-pyridine-2,5-dicarboxylic acid 2-cyclopropylamide 5-[(R)-(3-{4-[(4-methoxy-phenyl)-(4-methyl-pyridin-3-ylmethyl)-amino]-piperidin-1-yl}-butyl)-amide] (99);

4-Aminooxy-N-((R)-3-{4-[(4-methoxy-phenyl)-(4-methyl-pyridin-3-ylmethyl)-amino]-piperidin-1-yl}-butyl)-2,6-dimethyl-benzamide (100);

6-Cyano-N-((R)-3-{4-[(4-methoxy-phenyl)-pyridin-3-ylmethyl-amino]-piperidin-1-yl}-butyl)-2,4-dimethyl-nicotinamide (101);

6-Cyano-N-((R)-3-{4-[(2,3-dihydro-benzo[1,4]dioxin-6-yl)-(4-methyl-pyridin-3-ylmethyl)-amino]-piperidin-1-yl}-butyl)-2,4-dimethyl-nicotinamide (102);

6-Chloro-N-((R)-3-{4-[(2,3-dihydro-benzo[1,4]dioxin-6-yl)-(4-methyl-pyridin-3-ylmethyl)-amino]-piperidin-1-yl}-butyl)-2,4-dimethyl-nicotinamide (103);

4-Dimethylthiocarbamoyl-N-((R)-3-{4-[(4-methoxy-phenyl)-(4-methyl-pyridin-3-ylmethyl)-amino]-piperidin-1-yl}-butyl)-2,6-dimethyl-benzamide (104);

6-Chloro-N-((R)-3-{4-[(6-chloro-pyridin-3-yl)-(4-methyl-pyridin-3-ylmethyl)-amino]-piperidin-1-yl}-butyl)-2,4-dimethyl-nicotinamide (105);

N'-Cyclopropyl-N-((R)-3-{4-[(4-methoxy-phenyl)-(4-methyl-pyridin-3-ylmethyl)-amino]-piperidin-1-yl}-butyl)-2,6-dimethyl-terephthalamide (106);

N-((R)-3-{4-[(4-Methoxy-phenyl)-(4-methyl-pyridin-3-ylmethyl)-amino]-piperidin-1-yl}-butyl)-2,6-dimethyl-4-(morpholine-4-carbonyl)-benzamide (107);

N-((R)-3-{4-[(4-Methoxy-phenyl)-(4-methyl-pyridin-3-ylmethyl)-amino]-piperidin-1-yl}-butyl)-2,6-dimethyl-N'-propyl-terephthalamide (108);

N'-Butyl-N-((R)-3-{4-[(4-methoxy-phenyl)-(4-methyl-pyridin-3-ylmethyl)-amino]-piperidin-1-yl}-butyl)-2,6-dimethyl-terephthalamide (109);

N'-sec-Butyl-N-((R)-3-{4-[(4-methoxy-phenyl)-(4-methyl-pyridin-3-ylmethyl)-amino]-piperidin-1-yl}-butyl)-2,6-dimethyl-terephthalamide (110);

N-((R)-3-{4-[(4-Methoxy-phenyl)-(4-methyl-pyridin-3-ylmethyl)-amino]-piperidin-1-yl}-butyl)-2,6-dimethyl-N'-(1-methyl-butyl)-terephthalamide (111);

N'-Isobutyl-N-((R)-3-{4-[(4-methoxy-phenyl)-(4-methyl-pyridin-3-ylmethyl)-amino]-piperidin-1-yl}-butyl)-2,6-dimethyl-terephthalamide (112);

N-((R)-3-{4-[(4-Methoxy-phenyl)-(4-methyl-pyridin-3-ylmethyl)-amino]-piperidin-1-yl}-butyl)-2,6-dimethyl-N'-(3-methyl-butyl)-terephthalamide (113);

N'-Allyl-N-((R)-3-{4-[(4-methoxy-phenyl)-(4-methyl-pyridin-3-ylmethyl)-amino]-piperidin-1-yl}-butyl)-2,6-dimethyl-terephthalamide (114);

6-Chloro-2,4-dimethyl-N-{3-[4-(pyridin-3-ylmethyl-quinolin-3-yl-amino)-piperidin-1-yl]-butyl}-nicotinamide (115);

6-Hydroxy-N-((R)-3-{4-[(4-methoxy-phenyl)-(4-methyl-pyridin-3-ylmethyl)-amino]-piperidin-1-yl}-butyl)-2,4-dimethyl-nicotinamide (116);

6-Chloro-N-((R)-3-{4-[(4-fluoro-phenyl)-(4-methyl-pyridin-3-ylmethyl)-amino]-piperidin-1-yl}-butyl)-2,4-dimethyl-nicotinamide (117);

6-Cyano-N-((R)-3-{4-[(4-fluoro-phenyl)-(4-methyl-pyridin-3-ylmethyl)-amino]-piperidin-1-yl}-butyl)-2,4-dimethyl-nicotinamide (118);

6-Cyano-N-((R)-3-{4-[(3,4-dimethoxy-phenyl)-(4-methyl-pyridin-3-ylmethyl)-amino]-piperidin-1-yl}-butyl)-2,4-dimethyl-nicotinamide (119);

6-Chloro-N-((R)-3-{4-[(3,4-dimethoxy-phenyl)-(4-methyl-pyridin-3-ylmethyl)-amino]-piperidin-1-yl}-butyl)-2,4-dimethyl-nicotinamide (120);

4,6-Dimethyl-pyridine-2,5-dicarboxylic acid 2-amide 5-[((R)-3-{4-[(4-methoxy-phenyl)-(4-methyl-pyridin-3-ylmethyl)-amino]-piperidin-1-yl}-butyl)-amide] (121);

N-((R)-3-{4-[(4-Methoxy-phenyl)-(4-methyl-pyridin-3-ylmethyl)-amino]-piperidin-1-yl}-butyl)-2,4-dimethyl-6-(pyrrolidine-1-carbonyl)-nicotinamide (122);

4,6-Dimethyl-pyrimidine-5-carboxylic acid (3-{4-[(6-methoxy-naphthalen-2-yl)-(4-methyl-pyridin-3-ylmethyl)-amino]-piperidin-1-yl}-butyl)-amide (123);

6-Cyano-N-(3-{4-[(6-methoxy-naphthalen-2-yl)-(4-methyl-pyridin-3-ylmethyl)-amino]-piperidin-1-yl}-butyl)-2,4-dimethyl-nicotinamide (124);

6-Chloro-N-((R)-3-{4-[(4-chloro-phenyl)-(4-methyl-pyridin-3-ylmethyl)-amino]-piperidin-1-yl}-butyl)-2,4-dimethyl-nicotinamide (125);

N-((R)-3-{4-[(4-Chloro-phenyl)-(4-methyl-pyridin-3-ylmethyl)-amino]-piperidin-1-yl}-butyl)-6-cyano-2,4-dimethyl-nicotinamide (126);

N-((R)-3-{4-[(4-Methoxy-phenyl)-pyridin-3-ylmethyl-amino]-piperidin-1-yl}-butyl)-2,6-dimethyl-4-(pyrrolidine-1-carbonyl)-benzamide (127);

N'-Isopropyl-N-((R)-3-{4-[(4-methoxy-phenyl)-pyridin-3-ylmethyl-amino]-piperidin-1-yl}-butyl)-2,6-dimethyl-terephthalamide (128);

N-((R)-3-{4-[(4-Methoxy-phenyl)-(4-methyl-pyridin-3-ylmethyl)-amino]-piperidin-1-yl}-butyl)-2,6-dimethyl-3-(pyrrolidine-1-sulfonyl)-benzamide (129);

N-((R)-3-{4-[(4-Carbamoylmethoxy-phenyl)-(4-methyl-pyridin-3-ylmethyl)-amino]-piperidin-1-yl}-butyl)-6-chloro-2,4-dimethyl-nicotinamide (131);

{4-[(1-{(R)-3-[(6-Chloro-2,4-dimethyl-pyridine-3-carbonyl)-amino]-1-methyl-propyl}-piperidin-4-yl)-pyridin-3-ylmethyl-amino]-phenoxy}-acetic acid methyl ester (132);

3-Dimethylsulfamoyl-N-((R)-3-{4-[(4-methoxy-phenyl)-(4-methyl-pyridin-3-ylmethyl)-amino]-piperidin-1-yl}-butyl)-2,6-dimethyl-benzamide (135);

N-((R)-3-{4-[(4-Methoxy-phenyl)-(4-methyl-pyridin-3-ylmethyl)-amino]-piperidin-1-yl}-butyl)-2,4,6-trimethyl-nicotinamide (136);

4-Cyano-N-((R)-3-{4-[(4-methoxy-phenyl)-(4-methyl-pyridin-3-ylmethyl)-amino]-piperidin-1-yl}-butyl)-2-methyl-benzamide (139);

N-((R)-3-{4-[Benzo[1,3]dioxol-5-yl-(4-methyl-pyridin-3-ylmethyl)-amino]-piperidin-1-yl}-butyl)-6-chloro-2,4-dimethyl-nicotinamide (140);

N-((R)-3-{4-[Benzo[1,3]dioxol-5-yl-(4-methyl-pyridin-3-ylmethyl)-amino]-piperidin-1-yl}-butyl)-6-cyano-2,4-dimethyl-nicotinamide (141);

N-((R)-3-{4-[(4-Carbamoylmethoxy-phenyl)-pyridin-3-ylmethyl-amino]-piperidin-1-yl}-butyl)-6-chloro-2,4-dimethyl-nicotinamide (142);

6-Acetyl-N-((R)-3-{4-[(4-methoxy-phenyl)-(4-methyl-pyridin-3-ylmethyl)-amino]-piperidin-1-yl}-butyl)-2,4-dimethyl-nicotinamide (143);

4-Cyano-2,6-dimethyl-N-{(R)-3-[4-(phenyl-pyridin-3-ylmethyl-amino)-piperidin-1-yl]-butyl}-benzamide (144);

6-Chloro-2,4-dimethyl-N-{(R)-3-[4-(phenyl-pyridin-3-ylmethyl-amino)-piperidin-1-yl]-butyl}-nicotinamide (145);

6-Cyano-2,4-dimethyl-N-{(R)-3-[4-(phenyl-pyridin-3-ylmethyl-amino)-piperidin-1-yl]-butyl}-nicotinamide (146);

2,4-Dimethyl-N-((R)-3-{4-[(4-methyl-pyridin-3-ylmethyl)-phenyl-amino]-piperidin-1-yl}-butyl)-6-(pyrrolidine-1-carbonyl)-nicotinamide (147);

4,6-Dimethyl-pyridine-2,5-dicarboxylic acid 2-isopropylamide 5-[(R)-(3-{4-[(4-methyl-pyridin-3-ylmethyl)-phenyl-amino]-piperidin-1-yl}-butyl)-amide] (148);

2,6-Dimethyl-N-((R)-3-{4-[(4-methyl-pyridin-3-ylmethyl)-phenyl-amino]-piperidin-1-yl}-butyl)-4-(pyrrolidine-1-carbonyl)-benzamide (149);

6-Chloro-2,4-dimethyl-N-((R)-3-{4-[(4-methyl-pyridin-3-ylmethyl)-phenyl-amino]-piperidin-1-yl}-butyl)-nicotinamide (150);

4-Cyano-2,6-dimethyl-N-((R)-3-{4-[(4-methyl-pyridin-3-ylmethyl)-phenyl-amino]-piperidin-1-yl}-butyl)-benzamide (151);

{4-[(1-{(R-3-[(6-Cyano-2,4-dimethyl-pyridine-3-carbonyl)-amino]-1-methyl-propyl}-piperidin-4-yl)-pyridin-3-ylmethyl-amino]3-phenoxy}-acetic acid methyl ester (152);

N-((R)-3-{4-[(4-Carbamoylmethoxy-phenyl)-pyridin-3-ylmethyl-amino]-piperidin-1-yl}-butyl)-6-cyano-2,4-dimethyl-nicotinamide (153);

6-Chloro-2,4-dimethyl-N-((R)-3-{4-[(3-methyl-3H-benzoimidazol-5-yl)-(4-methyl-pyridin-3-ylmethyl)-amino]-piperidin-1-yl}-butyl)-nicotinamide (154);

6-Ethoxy-N-((R)-3-{4-[(4-methoxy-phenyl)-(4-methyl-pyridin-3-ylmethyl)-amino]-piperidin-1-yl}-butyl)-2,4-dimethyl-nicotinamide (155);

6-Chloro-N-((R)-3-{4-[(4-ethoxy-phenyl)-(4-methyl-pyridin-3-ylmethyl)-amino]-piperidin-1-yl}-butyl)-2,4-dimethyl-nicotinamide (156);

6-Cyano-N-((R)-3-{4-[(4-ethoxy-phenyl)-(4-methyl-pyridin-3-ylmethyl)-amino]-piperidin-1-yl}-butyl)-2,4-dimethyl-nicotinamide (157);

N-((R)-3-{4-[(4-Methoxy-phenyl)-(4-methyl-pyridin-3-ylmethyl)-amino]-piperidin-1-yl}-butyl)-2,6-dimethyl-3,5-dinitro-benzamide (158);

N-((R)-3-{4-[(4-Acetylamino-phenyl)-(4-methyl-pyridin-3-ylmethyl)-amino]-piperidin-1-yl}-butyl)-6-chloro-2,4-dimethyl-nicotinamide (159);

N-((R)-3-{4-[(4-Methoxy-phenyl)-(4-methyl-pyridin-3-ylmethyl)-amino]-piperidin-1-yl}-butyl)-2-methyl-4-(pyrrolidine-1-carbonyl)-benzamide (160);

N4-Isopropyl-N1-((R)-3-{4-[(4-methoxy-phenyl)-(4-methyl-pyridin-3-ylmethyl)-amino]-piperidin-1-yl}-butyl)-2-methyl-terephthalamide (161);

2,6-Dimethyl-N-{(R)-3-[4-(phenyl-pyridin-3-ylmethyl-amino)-piperidin-1-yl]-butyl}-4-(pyrrolidine-1-carbonyl)-benzamide (162);

N'-Isopropyl-2,6-dimethyl-N-{(R)-3-[4-(phenyl-pyridin-3-ylmethyl-amino)-piperidin-1-yl]-butyl}-terephthalamide (163);

N4-Isopropyl-2-methyl-N1-{(R)-3-[4-(phenyl-pyridin-3-ylmethyl-amino)-piperidin-1-yl]-butyl}-terephthalamide (164);

2-Methyl-N-((R)-3-{4-[(4-methyl-pyridin-3-ylmethyl)-phenyl-amino]-piperidin-1-yl}-butyl)-4-(pyrrolidine-1-carbonyl)-benzamide (165);

N4-Isopropyl-2-methyl-N1-((R)-3-{4-[(4-methyl-pyridin-3-ylmethyl)-phenyl-amino]-piperidin-1-yl}-butyl)-terephthalamide (166);

N-((R)-3-{4-[(4-Methoxy-phenyl)-pyridin-3-ylmethyl-amino]-piperidin-1-yl}-butyl)-2-methyl-4-(pyrrolidine-1-carbonyl)-benzamide (167);

N4-Isopropyl-N1-((R)-3-{4-[(4-methoxy-phenyl)-pyridin-3-ylmethyl-amino]-piperidin-1-yl}-butyl)-2-methyl-terephthalamide (168);

N-((R)-3-{4-[(4-Methoxy-phenyl)-(4-methyl-pyridin-3-ylmethyl)-amino]-piperidin-1-yl}-butyl)-2,6-dimethyl-3-nitro-benzamide (169);

6-Chloro-2,4-dimethyl-N-((R)-3-{4-[(1-methyl-1H-benzoimidazol-5-yl)-(4-methyl-pyridin-3-ylmethyl)-amino]-piperidin-1-yl}-butyl)-nicotinamide (170);

6-Cyano-N-((R)-3-{4-[(4-ethoxy-phenyl)-pyridin-3-ylmethyl-amino]-piperidin-1-yl}-butyl)-2,4-dimethyl-nicotinamide (171);

5-Cyano-N-((R)-3-{4-[(4-methoxy-phenyl)-(4-methyl-pyridin-3-ylmethyl)-amino]-piperidin-1-yl}-butyl)-2-methyl-benzamide (172);

6-Chloro-N-((R)-3-{4-[(4-methoxy-phenyl)-(4-methyl-pyridin-3-ylmethyl)-amino]-piperidin-1-yl}-butyl)-4-methyl-nicotinamide (173);

N-((R)-3-{4-[(4-Ethoxy-phenyl)-pyridin-3-ylmethyl-amino]-piperidin-1-yl}-butyl)-6-fluoro-2,4-dimethyl-nicotinamide (174);

6-Ethynyl-N-((R)-3-{4-[(4-methoxy-phenyl)-(4-methyl-pyridin-3-ylmethyl)-amino]-piperidin-1-yl}-butyl)-2,4-dimethyl-nicotinamide (175);

N-((R)-3-{4-[(4-Methoxy-phenyl)-(4-methyl-pyridin-3-ylmethyl)-amino]-piperidin-1-yl}-butyl)-2,4,6-trimethyl-1-oxy-nicotinamide (176);

6-Chloro-2,4-dimethyl-N-((R)-3-{4-[(4-methyl-pyridin-3-ylmethyl)-pyridin-3-yl-amino]-piperidin-1-yl}-butyl)-nicotinamide (177);

5-Chloro-N-((R)-3-{4-[(4-methoxy-phenyl)-(4-methyl-pyridin-3-ylmethyl)-amino]-piperidin-1-yl}-butyl)-2,4-dimethyl-nicotinamide (178);

3-Cyano-N-((R)-3-{4-[(4-methoxy-phenyl)-(4-methyl-pyridin-3-ylmethyl)-amino]-piperidin-1-yl}-butyl)-2,6-dimethyl-benzamide (179);

3-Amino-N-((R)-3-{4-[(4-methoxy-phenyl)-(4-methyl-pyridin-3-ylmethyl)-amino]-piperidin-1-yl}-butyl)-2,6-dimethyl-benzamide (180);

6-Fluoro-N-((R)-3-{4-[(4-methoxy-phenyl)-pyridin-3-ylmethyl-amino]-piperidin-1-yl}-butyl)-2,4-dimethyl-nicotinamide (181);

N-((R)-3-{4-[(4-Ethoxy-phenyl)-(4-methyl-pyridin-3-ylmethyl)-amino]-piperidin-1-yl}-butyl)-2,4,6-trimethyl-1-oxy-nicotinamide (182);

N-((R)-3-{4-[(3,4-Difluoro-phenyl)-(4-methyl-pyridin-3-ylmethyl)-amino]-piperidin-1-yl}-butyl)-6-fluoro-2,4-dimethyl-nicotinamide (183);

6-Cyano-N-((R)-3-{4-[(3,4-difluoro-phenyl)-(4-methyl-pyridin-3-ylmethyl)-amino]-piperidin-1-yl}-butyl)-2,4-dimethyl-nicotinamide (184);

6-Chloro-N-((R)-3-{4-[(6-methoxy-pyridin-3-yl)-(4-methyl-pyridin-3-ylmethyl)-amino]-piperidin-1-yl}-butyl)-2,4-dimethyl-nicotinamide (185);

6-Fluoro-N-((R)-3-{4-[(3-fluoro-4-methoxy-phenyl)-(4-methyl-pyridin-3-ylmethyl)-amino]-piperidin-1-yl}-butyl)-2,4-dimethyl-nicotinamide (186);

6-Chloro-N-((R)-3-{4-[(3-fluoro-4-methoxy-phenyl)-(4-methyl-pyridin-3-ylmethyl)-amino]-piperidin-1-yl}-butyl)-2,4-dimethyl-nicotinamide (187);

4-Cyano-2,6-dimethyl-N-((R)-3-{4-[(4-methyl-pyridin-3-ylmethyl)-(6-trifluoromethyl-pyridin-3-yl)-amino]-piperidin-1-yl}-butyl)-benzamide (188);

6-Cyano-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide (189);

6-Fluoro-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide (190);

2-Chloro-N-((R)-3-{4-[(4-methoxy-phenyl)-pyridin-3-ylmethyl-amino]-piperidin-1-yl}-butyl)-4-methyl-nicotinamide (191);

6-Fluoro-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide (192);

6-Chloro-5-fluoro-N-((R)-3-{4-[(4-methoxy-phenyl)-pyridin-3-ylmethyl-amino]-piperidin-1-yl}-butyl)-2,4-dimethyl-nicotinamide (193);

N-((R)-3-{4-[(4-Chloro-phenyl)-pyridin-3-ylmethyl-amino]-piperidin-1-yl}-butyl)-6-fluoro-2,4-dimethyl-nicotinamide (194);

6-Chloro-N-(3-{4-[(4-methoxy-phenyl)-pyridin-3-ylmethyl-amino]-piperidin-1-yl}-butyl)-2,4-dimethyl-nicotinamide (195);

6-Chloro-N-(3-{4-[(4-methoxy-phenyl)-(4-methyl-pyridin-3-ylmethyl)-amino]-piperidin-1-yl}-butyl)-2,4-dimethyl-nicotinamide (196);

6-Chloro-N-((R)-3-{4-[(4-methoxy-phenyl)-pyridin-2-ylmethyl-amino]-piperidin-1-yl}-butyl)-2,4-dimethyl-nicotinamide (197);

2-Chloro-4-methyl-N-((R)-3-{4-[(4-methyl-pyridin-3-ylmethyl)-(6-trifluoromethyl-pyridin-3-yl)-amino]-piperidin-1-yl}-butyl)-nicotinamide (198);

N-((R)-3-{4-[(4-Difluoromethoxy-phenyl)-(4-methyl-pyridin-3-ylmethyl)-amino]-piperidin-1-yl}-butyl)-6-fluoro-2,4-dimethyl-nicotinamide (199);

2-Chloro-N-((R)-3-{4-[(3-fluoro-4-methoxy-phenyl)-(4-methyl-pyridin-3-ylmethyl)-amino]-piperidin-1-yl}-butyl)-4-methyl-nicotinamide (200);

2-Chloro-N-((R)-3-{4-[(4-difluoromethoxy-phenyl)-(4-methyl-pyridin-3-ylmethyl)-amino]-piperidin-1-yl}-butyl)-4-methyl-nicotinamide (201);

N-((R)-3-{4-[(4-Methoxy-phenyl)-(4-methyl-pyridin-3-ylmethyl)-amino]-piperidin-1-yl}-butyl)-2,4-dimethyl-6-trifluoromethyl-nicotinamide (202);

N-((R)-3-{4-[(4-Methoxy-phenyl)pyridin-3-ylmethyl-amino]-piperidin-1-yl}-butyl)-2,4-dimethyl-6-trifluoromethyl-nicotinamide (203);

2-Amino-N-((R)-3-{4-[(4-methoxy-phenyl)-(4-methyl-pyridin-3-ylmethyl)-amino]-piperidin-1-yl}-butyl)-4-methyl-nicotinamide (204);

2-Fluoro-N-((R)-3-{4-[(4-methoxy-phenyl)-(4-methyl-pyridin-3-ylmethyl)-amino]-piperidin-1-yl}-butyl)-4-methyl-nicotinamide (205);

6-Chloro-N-((R)-3-{4-[(3,5-difluoro-4-methoxy-phenyl)-(4-methyl-pyridin-3-ylmethyl)-amino]-piperidin-1-yl}-butyl)-2,4-dimethyl-nicotinamide (206);

6-Fluoro-N-((R)-3-{4-[(2-fluoro-4-methoxy-phenyl)-(4-methyl-pyridin-3-ylmethyl)-amino]-piperidin-1-yl}-butyl)-2,4-dimethyl-nicotinamide (209);

6-Chloro-N-((R)-3-{4-[(2-fluoro-4-methoxy-phenyl)-(4-methyl-pyridin-3-ylmethyl)-amino]-piperidin-1-yl}-butyl)-2,4-dimethyl-nicotinamide (208);

2-Chloro-N-((R)-3-{4-[(2-fluoro-4-methoxy-phenyl)-(4-methyl-pyridin-3-ylmethyl)-amino]-piperidin-1-yl}-butyl)-4-methyl-nicotinamide (209);

6-Chloro-N-((R)-3-{4-[(6-fluoro-pyridin-2-ylmethyl)-(4-methoxy-phenyl)-amino]-piperidin-1-yl}-butyl)-2,4-dimethyl-nicotinamide (210);

6-Chloro-N-((R)-3-{4-[(6-chloro-pyridin-2-ylmethyl)-(4-methoxy-phenyl)-amino]-piperidin-1-yl}-butyl)-2,4-dimethyl-nicotinamide (211);

6-Chloro-N-((R)-3-{4-[(5-methoxy-pyridin-2-yl)-(4-methyl-pyridin-3-ylmethyl)-amino]-piperidin-1-yl}-butyl)-2,4-dimethyl-nicotinamide (212);

6-Fluoro-N-((R)-3-{4-[(5-methoxy-pyridin-2-yl)-(4-methyl-pyridin-3-ylmethyl)-amino]-piperidin-1-yl}-butyl)-2,4-dimethyl-nicotinamide (213);

6-Chloro-N-((R)-3-{4-[(4-methoxy-phenyl)-(6-trifluoromethyl-pyridin-2-ylmethyl)-amino]-piperidin-1-yl}-butyl)-2,4-dimethyl-nicotinamide (214);

2-Chloro-N-((R)-3-{4-[(4-methoxy-phenyl)-(4-methyl-pyridin-3-ylmethyl)-amino]-piperidin-1-yl}-butyl)-4-trifluoromethyl-nicotinamide (215);

N-((R)-3-{4-[(4-Methoxy-phenyl)-(4-methyl-pyridin-3-ylmethyl)-amino]-piperidin-1-yl}-butyl)-2-methyl-4-trifluoromethyl-nicotinamide (216);

4-Cyano-N-((R)-3-{4-[(6-cyano-pyridin-2-ylmethyl)-phenyl-amino]-piperidin-1-yl}-butyl)-2,6-dimethyl-benzamide (217);

6-Chloro-N-((S)-3-{4-[(4-methoxy-phenyl)-(4-methyl-pyridin-3-ylmethyl)-amino]-piperidin-1-yl}-butyl)-2,4-dimethyl-nicotinamide (218);

6-Chloro-N-((R)-3-{4-[(4-hydroxy-phenyl)-(4-methyl-pyridin-3-ylmethyl)-amino]-piperidin-1-yl}-butyl)-2,4-dimethyl-nicotinamide (219);

6-Chloro-N-((R)-3-{4-[[6-(2-methoxy-ethoxy)-pyridin-3-yl]-(4-methyl-pyridin-3-ylmethyl)-amino]-piperidin-1-yl}-butyl)-2,4-dimethyl-nicotinamide (220);

6-Fluoro-N-((R)-3-{4-[[6-(2-methoxy-ethoxy)-pyridin-3-yl]-(4-methyl-pyridin-3-ylmethyl)-amino]-piperidin-1-yl}-butyl)-2,4-dimethyl-nicotinamide (221);

6-Chloro-2,4-dimethyl-N-[(R)-3-(4-{(4-methyl-pyridin-3-ylmethyl)-[4-(pyrimidin-2-yloxy)-phenyl]-amino}-piperidin-1-yl)-butyl]-nicotinamide (222);

2-Chloro-N-((R)-3-{4-[[6-(2-methoxy-ethoxy)-pyridin-3-yl]-(4-methyl-pyridin-3-ylmethyl)-amino]-piperidin-1-yl}-butyl)-4-methyl-nicotinamide (223);

6-Chloro-N-[(R)-3-(4-{(6-cyano-pyridin-2-ylmethyl)-[6-(2-methoxy-ethoxy)-pyridin-3-yl]-amino}-piperidin-1-yl)-butyl]-2,4-dimethyl-nicotinamide (224);

2-Chloro-N-[(R)-3-(4-{(6-cyano-pyridin-2-ylmethyl)-[6-(2-methoxy-ethoxy)-pyridin-3-yl]-amino}-piperidin-1-yl)-butyl]-4-methyl-nicotinamide (225);

N-((R)-3-{4-[(6-Cyano-pyridin-2-ylmethyl)-phenyl-amino]-piperidin-1-yl}-butyl)-N'-isopropyl-2,6-dimethyl-terephthalamide (226); and 2,6-Dichloro-N-((R)-3-{4-[(4-methoxy-phenyl)-(4-methyl-pyridin-3-ylmethyl)-amino]-piperidin-1-yl}-butyl)-4-methyl-nicotinamide (227).

The present invention also relates to pharmaceutical compositions comprising a piperidine derivative including but not limited to compounds 1-129; 131-132; 135-136; and 139-227, and a pharmaceutically acceptable carrier. Furthermore, the present invention relates to methods for treating a CCR5 mediated disease in a system, comprising contacting a piperidine derivative, including but not limited to compounds 1-129; 131-132; 135-136; and 139-227, with the system. In one embodiment, the system is a cell or tissue. The present invention also relates to methods for treating a CCR5 mediated disease in a subject, comprising administering a piperidine derivative, including but not limited to compounds 1-129; 131-132; 135-136; and 139-227, to the subject. The subject may be human or an animal.

Moreover, the compounds may be supplied as "pro-drugs" or protected forms, which release the compound after administration to a subject. The terms "administration" and or administering" as used herein should be understood to mean providing a compound of the invention to the subject in need of treatment. For example, the compound may carry a protective group which is split off by hydrolysis in body fluids, e.g., in the bloodstream, thus releasing the active compound or is oxidized or reduced in body fluids to release the compound. A discussion of pro-drugs may be found in "Smith and Williams' Introduction to the Principles of Drug Design," H. J. Smith, Wright, Second Edition, London (1988).

The compounds of the present invention may be administered in the form of pharmaceutically acceptable salts that are non-toxic. The term "pharmaceutically acceptable salt" as used herein means an active ingredient comprising compounds of Formula 1 or 2 used in the form of a salt thereof, particularly where the salt form confers on the active ingredient improved pharmacokinetic properties as compared to the free form of the active ingredient or other previously disclosed salt form. The term "pharmaceutically acceptable salt" encompasses all acceptable salts including but not limited to acetate, lactobionate, benzenesulfonate, laurate, benzoate, malate, bicarbonate, maleate, bisulfate, mandelate, bitartarate, mesylate, borate, methylbromide, bromide, methylnitrite, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutame, stearate, glycollylarsanilate, sulfate, hexylresorcinate, subacetate, hydradamine, succinate, hydrobromide, tannate, hydrochloride, tartrate, hydroxynaphthoate, teoclate, iodide, tosylate, isothionate, triethiodide, lactate, panoate, valerate, and the like.

Pharmaceutically acceptable salts of the compounds of the present invention can be used as a dosage for modifying solubility or hydrolysis characteristics, or can be used in sustained release or pro-drug formulations. Also, pharmaceutically acceptable salts of the compounds of this invention may include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethylamine, diethylamine, piperazine, tris(hydroxymethyl)aminomethane, and tetramethylammonium hydroxide.

All of the compounds of the invention contain at least one chiral center. The invention includes mixtures of stereoisomers, individual stereoisomers, and enantiomeric mixtures, and mixtures of multiple stereoisomers. In short, the compound may be supplied in any desired degree of chiral purity.

Utility and Administration

In one aspect, the invention is directed to compounds of Formula 1 or 2 that may modulate chemokine receptor activity. Chemokine receptors include but are not limited to CCR1, CCR2, CCR3, CCR4, CCR5, CXCR3 and CXCR4.

In one embodiment, the invention provides compounds of Formula 1 or 2 that may demonstrate protective effects on target cells from HIV infection by binding specifically to the chemokine receptor, thus affecting the binding of a natural ligand to the CCR5 and/or CXCR4 of a target cell.

In another embodiment, the compounds of the present invention may be useful as agents which affect chemokine receptors, such as CCR1, CCR2, CCR3, CCR4, CCR5, CXCR3, CXCR4 where such chemokine receptors have been correlated as being important mediators of many inflammatory as well as immunoregulatory diseases.

Other diseases that are also implicated with chemokines as mediators include angiogenesis, and tumorigenesis such as brain, and breast tumors. Thus, a compound that modulates the activity of such chemokine receptors is useful for the treatment or prevention of such diseases.

As used herein, the terms "modulators and/or modulation" encompass antagonist/antagonism, agonist/agonism, partial antagonist/partial antagonism, and or partial agonist/partial agonism, i.e., inhibitors, and activators. The compounds of Formula 1 or 2 described herein may possess biological activity such that they are able to modulate CCR5 chemokine receptor activity and consequent or associated pathogenic processes subsequently mediated by the CCR5 receptor and its natural ligands. In one embodiment, compounds of Formula 1 or 2 demonstrate a protective effect against HIV infection by inhibiting the binding of HIV to a chemokine receptor of a target cell such as CCR5 and/or CXCR4. Such modulation is obtained by a method which comprises contacting a target cell with an effective amount of the compound to inhibit the binding of the virus to the chemokine receptor. As used herein, the terms "modulation and/or modulation" encompass modulating activity in all types and subtypes of CCR5 receptors of a target cell, in any tissues of a particular patient where they are found, and in any cell components comprising those tissues that the target cell may be located.

Compounds that inhibit chemokine receptor activity and function may be used for the treatment of diseases that are associated with inflammation, including but not limited to, inflammatory or allergic diseases such as asthma, allergic rhinitis, hypersensitivity lung diseases, hypersensitivity pneumonitis, eosinophilic pneumonias, delayed-type hypersensitivity, atherosclerosis, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies, insect sting allergies; autoimmune diseases, such as rheumatoid arthritis, psoriatic arthritis, multiple sclerosis, systemic lupus erythematosus, myastenia gravis, juvenile onset diabetes; glomerulonephritis, autoimmune throiditis, graft rejection, including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as dermatitis, eczema, atopic dermatitis, allergic contact dermatitis, urticaria; vasculitis (e.g., necrotizing, cutaneous, and hypersensitivity vasculitis); eosinphilic myotis, eosiniphilic fasciitis; and cancers.

In addition, compounds that activate or promote chemokine receptor function are used for the treatment of diseases associated with immunosuppression, such as in individuals undergoing chemotherapy, radiation therapy, enhanced wound healing and burn treatment, therapy for autoimmune disease or other drug therapy (e.g., corticosteroid therapy) or combination of conventional drugs used in the treatment of autoimmune diseases and graft/transplantation rejection, which causes immunosuppression; or immunosuppression due to congenital deficiency in receptor function or other causes. Compounds that activate or promote chemokine receptor function are also used for the treatment of infectious diseases, such as parasitic diseases, including but not limited to helminth infections, such as nematodes (round worms); Trichuriasis, Enterobiasis, Ascariasis, Hookworm, Strongyloidiasis, Trichinosis, filariasis; trematodes; visceral worms, visceral larva migtrans (e.g., Toxocara), eosinophilic gastroenteritis (e.g., *Anisaki* spp., *Phocanema* ssp.), cutaneous larva migrans (*Ancylostona braziliense, Ancylostoma caninum*); the malaria-causing protozoan *Plasmodium vivax*, Human cytomegalovirus, Herpesvirus saimiri, and Kaposi's sarcoma herpesvirus, also known as human herpesvirus 8, and poxvirus *Moluscum contagiosum*.

Compounds of the present invention may be used in combination with any other active agents or pharmaceutical compositions where such combined therapy is useful to modulate chemokine receptor activity and thereby prevent and treat inflammatory and immunoregulatory diseases.

Furthermore, the compounds may be used in combination with one or more agents useful in the prevention or treatment of HIV. Examples of such agents include:

(1) nucleotide reverse transcriptase inhibitor such as tenofovir disoproxil fumarate; lamivudine/zidovudine; abacavir/lamivudine/zidovudine; emtricitabine; amdoxovir; alovudine; DPC-817; SPD-756; SPD-754; GS7340; ACH-126,443 (beta)-L-F d4C; didanosine, zalcitabine, stavudine, adefovir, adefovir dipivoxil, fozivudine todoxil, etc.;

(2) non-nucleotide reverse transcriptase inhibitor (including an agent having anti-oxidation activity such as immunocal, oltipraz, etc.) such as nevirapine, delavirdine, efavirenz, loviride, immunocal, oltipraz, TMC-125; DPC-083; capravarine; calanolide A; SJ-3366 series, etc.;

(3) protease inhibitors such as saquinavir, lopinavir/ritonavir, atazanavir, fosamprenavir, tipranavir, TMC-114, DPC-684, indinavir, nelfinavir, amprenavir, palinavir, lasinavir, etc.;

(4) entry inhibitors such as T-20; T-1249; PRO-542; PRO-140; TNX-355; BMS-806 series; and 5-Helix;

(5) CCR5-receptor inhibitors such as Sch-C (or SCH351125); Sch-D (or SCH350634); TAK779; UK 427,857 and TAK 449; or CXCR4-receptor inhibitors such as T22, T134, T140, 18 amino acid analogs of polyphemusin II, ALX40-4C, ALK40-4C, AMD3100 and AMD070;

(6) Integrase inhibitors such as L-870,810; GW-810781 (S-1360); and (7) Budding inhibitors such as PA-344; and PA-457.

Combinations of compounds of the present invention with HIV agents are not limited to the above examples, but include the combination with any agent useful for the treatment of HIV. Combinations the compounds of the invention and other HIV agents may be administered separately or in conjunction. The administration of one agent may be prior to, concurrent to, or subsequent to the administration of other agent(s).

The compounds according to the present invention may be administered by oral, intramuscular, intraperitoneal, intravenous, intracisternal injection or infusion, subcutaneous injection, transdermal or transmucosal administration or by implant. They may also be administered by inhalation spray, nasal, vaginal, rectal, sublingual, or topical routes and may be formulated, alone or together, in suitable dosage unit formulations containing conventional non-toxic pharmaceutically acceptable carriers, adjuvants and vehicles appropriate for each route of administration.

The compounds of the invention may be used to treat animals, including mice, rats, horses, cattle, sheep, dogs, cats, and monkeys. However, compounds of the invention can also be used in other species, such as avian species (e.g., chickens). The compounds of the invention may also be effective for use in humans. The term "subject" or alternatively referred to herein as "patient" is intended to be referred to an animal, preferably a mammal, most preferably a human, who has been the object of treatment, observation or experiment. However, the compounds, methods and pharmaceutical compositions of the present invention may be used in the treatment of animals.

The invention also relates to a pharmaceutical composition comprising a pharmaceutically acceptable carrier or diluent and an effective amount of compound of Formula 1 or 2. The compounds may be administered alone or as a mixture with a pharmaceutically acceptable carrier (e.g., solid formulations such as tablets, capsules, granules, powders, etc.; liquid formulations such as syrups, injections, etc.). The compounds may be administered orally or non-orally. Examples of non-oral formulations include injections. drops, suppositories, pessaryies.

In the treatment or prevention of conditions which require chemokine receptor modulation, an appropriate dosage level will generally be about 0.01 to 500 mg per kg subject body weight per day, and can be administered in singe or multiple doses. Preferably, the dosage level will be about 0.1 to about 250 mg/kg per day. It will be understood that the specific dose level and frequency of dosage for any particular patient may be varied and will depend upon a variety of factors including the activity of the specific compound used, the metabolic stability and length of action of that compound, the age, body weight, general health, sex, diet, mode and time of administration, rate of excretion, drug combination, the severity of the particular condition, and the patient undergoing therapy.

In another aspect of the present invention, a compound of Formula 1 or 2 may be used in screening assays for compounds which modulate the activity of chemokine receptors, preferably CCR5 receptors. The ability of a test compound to inhibit gp120 and CD4/CCR5-dependent cell-cell fusion may be measured using a cell fusion assay known in the art.

The compounds of Formula 1 or 2 as disclosed herein may be useful for isolating receptor mutants, which can then be made into screening tools for the discovery of even more potent compounds, following procedures described herein and procedures known in the art. The compounds of Formula 1 or 2 may also be useful in establishing or characterizing the binding sites of other ligands, including compounds other than those of Formula 1 or 2 to chemokine receptors, e.g., by competitive inhibition. The compounds of the present invention may also be useful for the evaluation of putative specific modulators of various chemokine receptors. As appreciated in the art, thorough evaluation of specific agonists and antagonists of the above chemokine receptors has been hampered by the lack of availability of non-peptidyl (metabolically resistant) compounds with high binding affinity for these receptors. Thus, the compounds of this invention are commercial products to be sold for these purposes.

Illustrative examples of compounds having formula (1) and formula (2) are shown in the Examples. The present invention also encompasses other compounds having formula (1) and formula (2), wherein the optional substituents in $R^1$, $R^2$ and $R^3$ are independently selected from the substituents exemplified in the Examples. Thus, the present invention is not limited to the specific combination of substituents described in various embodiments below.

Experimental

General Procedures for the preparation of many of the compounds and intermediates are described in Bridger, et al., International Patent Application No. PCT/US2004/041865.

General Procedure A: Reductive Amination with $NaBH(OAc)_3$

To a stirred solution of the amine (1 equivalent) in $CH_2Cl_2$ (concentration ~0.2M) at room temperature were added the carbonyl compound (1-2 equivalents), glacial AcOH (0-2 equivalents) and sodium triacetoxyborohydride ($NaBH(OAc)_3$) (~1.5-3 equivalents) and the resultant solution was stirred at room temperature. In a standard workup, the reaction mixture was poured into either saturated aqueous $NaHCO_3$ or 1N NaOH. The phases were separated and the aqueous extracted with $CH_2Cl_2$. The combined organic extracts were dried ($Na_2SO_4$ or $MgSO_4$), filtered and concentrated under reduced pressure. The crude material was purified by flash column chromatography on silica gel or by recrystallization.

General Procedure B: Boc Deprotection with TFA

The Boc-protected amine was dissolved in $CH_2Cl_2$ (~4 mL/mmol) and trifluoroacetic acid (TFA) (~2 mL/mmol) was added. The mixture was stirred at room temperature for 0.5-5 h. In a standard work-up, the mixture was neutralized with saturated aqueous $NaHCO_3$ or 1N NaOH and the aqueous extracted with $CH_2Cl_2$. The combined extracts were dried ($Na_2SO_4$ or $MgSO_4$), filtered and concentrated under reduced pressure. The crude material was used in the next reaction as is or was purified by flash column chromatography on silica gel.

General Procedure C: EDCI Coupling

To a stirred solution of a primary or secondary amine (1 equivalent), a carboxylic acid (1.1-2.0 equivalents), 1-hydroxy-benzotriazole hydrate (HOBT) (1.1-2.0 equivalents) and DIPEA (DIPEA) or N-methylmorpholine (NMM) (1.5-3 equivalents) in $CH_2Cl_2$ or DMF (concentration ~0.05-1.5M) was added 1-[3-(dimethylamino)propyl]-3-ethylcarbodiimide hydrochloride (EDCI) (1.1-2.0 equivalents). The solution was stirred at room temperature for 1-3 days and concentrated in vacuo. In a standard work-up, the mixture was diluted with $CH_2Cl_2$ or EtOAc and washed consecutively with saturated aqueous $NaHCO_3$ and brine. The organic layer was dried ($Na_2SO_4$ or $MgSO_4$), filtered and concentrated under reduced pressure. The crude material was purified by flash column chromatography or by radial chromatography on silica gel.

General Procedure D: Coupling with an Acid Chloride

To a stirred suspension of a carboxylic acid (2 equivalents) in $CH_2Cl_2$ (concentration ~0.1-0.2M) were added DMF (1-5 drops) followed by oxalyl chloride (6 equivalents) and the resultant mixture was stirred at room temperature for 1-2 h. The mixture was concentrated under reduced pressure and the acid chloride was dried in vacuo for 10-45 minutes. To the acid chloride was added a solution of the amine (1 equivalent) and $Et_3N$ (1.5-2 equivalents) in THF (concentration ~0.1-0.2M) and the mixture was stirred at room temperature for 1-18 h. In a standard work-up, the mixture was diluted with $CH_2Cl_2$ or EtOAc and washed consecutively with saturated aqueous $NaHCO_3$ and brine. The organic layer was dried ($Na_2SO_4$ or $MgSO_4$), filtered and concentrated under reduced pressure. The crude material was purified by flash column chromatography or by radial chromatography on silica gel.

General Procedure E: N-Alkylation with Benzyl Halides

To a solution of the amine (1 equivalent), the benzyl halide (1-2 equivalents) in $CH_3CN$ (concentration ~0.1-0.3M) was added DIPEA and the mixture was stirred at 50-90° C. for 2-72 h. In a standard work-up, the reaction was cooled to room temperature, concentrated under reduced pressure, diluted with $CH_2Cl_2$ and washed with either saturated aqueous $NaHCO_3$ or brine. The aqueous was extracted with $CH_2Cl_2$ and the combined organic extracts were dried ($Na_2SO_4$ or $MgSO_4$), filtered and concentrated under reduced pressure. The crude material was purified by flash column chromatography on silica gel.

General Procedure F: Hydrogenation of Nitrile with Raney Nickel

The nitrile (1 equivalent) was dissolved in $NH_3$ saturated MeOH (concentration ~0.05-0.2M), treated with Raney nickel (excess), and placed under 45 psi $H_2$ on a Parr shaker for 1-8 h. In a standard work-up the mixture was diluted with MeOH and filtered through celite. The cake was washed with MeOH and the combined filtrate was concentrated under reduced pressure. The crude material was purified by flash column chromatography on silica gel.

Intermediates

The preparation of various intermediates used in preparing the present compounds is described below. The intermediates (R)-3-(4-oxo-piperidin-1-yl)-butyronitrile, (R)-3-[4-(4-methoxy-phenylamino)-piperidin-1-yl]-butyronitrile and [1-((R)-3-amino-1-methyl-propyl)-piperidin-4-yl]-(4-methoxy-phenyl)-(4-methyl-pyridin-3-ylmethyl)-amine, were prepared as described in Bridger et al., International Patent Application No. PCT/US2004/041865.

6-Chloro-2,4-dimethyl-nicotinic acid. To a solution of 2,4-dimethyl-nicotinic acid ethyl ester (1.79 g, 10.0 mmol) in $CH_2Cl_2$ (50 mL) was added 3-chloroperoxybenzoic acid (77% max., 4.48 g, 20.0 mmol). The mixture was stirred at room temperature for 2 days, and then concentrated under reduced pressure. The residual solid was purified by flash column chromatography on silica gel (EtOAc) to afford 2,4-dimethyl-1-oxy-nicotinic acid ethyl ester as a white solid (1.95 g, 100%). $^1$H NMR (CDCl$_3$) δ 1.41 (t, 3H, J=7.2 Hz), 2.30 (s, 3H), 2.49 (s, 3H), 4.44 (q, 2H, J=7.2 Hz), 7.00 (d, 1H, J=6.6 Hz), 8.19 (d, 1H, J=6.6 Hz).

A solution of 2,4-dimethyl-1-oxy-nicotinic acid ethyl ester (1.95 g, 10.0 mmol) in POCl$_3$ (8 mL) was heated at reflux for 2 h. After cooled to room temperature the reaction mixture was poured to ice (~20 mL) and neutralized with saturated $Na_2CO_3$. The aqueous mixture was extracted with $CH_2Cl_2$ (4×20 mL), and the combined extract was dried ($Na_2SO_4$). After filtration the solvent was removed under vacuum, and the residue was purified by flash column chromatography on silica gel ($CH_2Cl_2$) to afford 6-chloro-2,4-dimethyl-nicotinic acid ethyl ester as a pale yellow liquid (0.945 g, 44%). $^1$H NMR (CDCl$_3$) δ 1.40 (t, 3H, J=7.2 Hz), 2.32 (s, 3H), 2.53 (s, 3H), 4.41 (q, 2H, J=7.2 Hz), 7.05 (s, 1H).

To a solution of 6-chloro-2,4-dimethyl-nicotinic acid ethyl ester (0.200 g, 0.930 mmol) in EtOH (1 mL) was added 4N NaOH (1 mL), and the mixture was heated at 90° C. for 1 h. After the mixture was cooled to room temperature EtOH was removed and the aqueous residue was acidified with 4N HCl to afford a white precipitate. The precipitate (0.152 g, 88%) was collected by filtration and dried under vacuum to give 6-chloro-2,4-dimethyl-nicotinic acid as a white solid. $^1$H NMR (CD$_3$OD) δ 2.37 (s, 3H), 2.51 (s, 3H), 7.23 (s, 1H).

6-Cyano-2,4-dimethyl-nicotinic acid. To a solution of 2,4-dimethyl-1-oxy-nicotinic acid (0.700 g, 3.56 mmol in dry DMF (10 mL) was added $(CH_3)_2NCOCl$ (0.766 g, 7.13 mmol) and then TMSCN (1.06 g, 10.7 mmol). The mixture was stirred at 70° C. overnight, and then concentrated to dryness under reduced pressure. The residual solid was purified by flash column chromatography on silica gel (1:4, MeOH/EtOAc) to afford a brown solid (0.520 g, 82%). $^1$H NMR (CD$_3$OD) δ 2.39 (s, 3H), 2.56 (s, 3H), 7.57 (s, 1H).

6-fluoro-2,4-dimethyl-nicotinic acid. To a suspension of 2-amino-5-bromo-4,6-dimethylpyridine (4.02 g, 20.0 mmol) in HBF$_4$ (48% in water, 15 mL) cooled in an ice bath was added a solution of NaNO$_2$ (1.73 g, 25.0 mmol) in water (5 mL). The reaction mixture turned clear, and 10 min later a precipitate was formed. The precipitate was collected by filtration, dried under vacuum and added to hot heptane (100 mL) pre-heated at 90° C. After heated at 90° C. for 2 h the mixture was cooled to room temperature and filtered. The filtrate was concentrated under vacuum to afford 3-bromo-2,4-dimethyl-6-fluoropyridine as a pale yellow solid (1.45 g, 36%). $^1$H NMR (CDCl$_3$): δ 2.43 (s, 3H), 2.61 (s, 3H), 6.66 (d, 1H, J=3.0 Hz). $^{19}$F NMR (CDCl$_3$): δ 3.24.

To a solution of 3-bromo-2,4-dimethyl-6-fluoropyridine (1.45 g, 7.10 mmol) in anhydrous Et$_2$O (25 mL) at −78° C. was added t-BuLi (1.7M in pentane, 8.8 mL, 15 mmol) dropwise. After addition the mixture was stirred at −78° C. for 10 min, and CO$_2$ was introduced. After 10 min the cooling bath was removed, and the bubbling of CO$_2$ was continued until the mixture was warmed to 0° C. Water (30 mL) was then added and Et$_2$O was removed. The aqueous layer was washed CH$_2$Cl$_2$ (2×30 mL) and acidified with 6N HCl, resulting in precipitation of a pale brown solid (0.87 g, 73%) which was collected by filtration and dried under vacuum. $^1$H NMR (CD$_3$OD): δ 2.38 (s, 3H), 2.46 (s, 3H), 6.69 (s, 1H). $^{19}$F NMR (CD$_3$OD): δ 0.63.

EXAMPLE 1

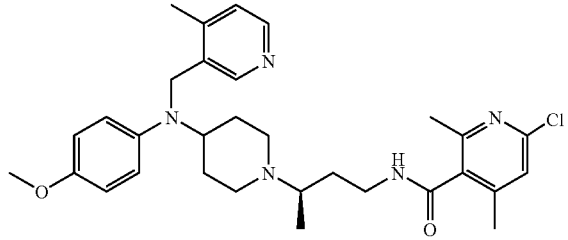

Preparation of 6-Chloro-N-((R)-3-{4-[(4-methoxy-phenyl)-(4-methyl-pyridin-3-ylmethyl)-amino]-piperidin-1-yl}-butyl)-2,4-dimethyl-nicotinamide To a solution of [1-((R)-3-amino-1-methyl-propyl)-piperidin-4-yl]-(4-methoxy-phenyl)-(4-methyl-pyridin-3-ylmethyl)-amine (63 mg, 0.17 mmol) in DMF (1.5 mL) was added 6-chloro-2,4-dimethyl-nicotinic acid (40 mg, 0.22 mmol), HOBT (31 mg, 0.23 mmol), EDCI (44 mg, 0.23 mmol) and DIPEA (85 μL, 0.50 mmol). After the mixture was stirred at room temperature overnight brine (5 mL) was added, and the mixture was extracted with CH$_2$Cl$_2$ (2×5 mL). The organic extracts were combined and dried (Na$_2$SO$_4$). After filtration the solvent was removed under vacuum, and the residue was purified by flash chromatography on a silica gel column (20:1:0.1, CH$_2$Cl$_2$/MeOH/NH$_4$OH) to afford the title compound as a white solid (72 mg, 80%). $^1$H NMR (CDCl$_3$) δ 0.98 (d, 3H, J=6.6 Hz), 1.00 (m, 1H), 1.19 (m, 1H), 1.54 (m, 1H), 1.71 (m, 1H), 1.80 (br d, 2H, J=12.6 Hz), 2.11 (t, 1H, J=11.2 Hz), 2.29 (s, 3H), 2.35 (s, 3H), 2.48 (t, 1H, J=11.2 Hz), 2.51 (s, 3H), 2.65-2.85 (m, 3H), 3.15-3.45 (m, 2H), 3.72 (s, 3H), 3.78 (m, 1H), 3.97 (s, 2H), 6.62-6.78 (m, 4H), 6.98 (s, 1H), 7.02 (d, 1H, J=4.8 Hz), 8.05 (br. S, 1H), 8.25 (s, 1H), 8.28 (d, 1H, J=5.1 Hz). $^{13}$C NMR (CDCl$_3$) δ 13.74, 19.16, 19.22, 22.51, 30.07, 31.01, 31.72, 40.04, 44.27, 47.85, 52.20, 55.93, 59.41, 60.20, 114.75 (2C), 120.74 (2C), 122.85, 125.47, 132.90, 133.43, 142.69, 145.73, 147.66, 148.42, 149.78, 150.59, 154.22, 155.58, 167.68. ES-MS m/z 550 (M+H). Anal. Calcd. For C$_{31}$H$_{40}$N$_5$ClO$_2$.0.7CH$_2$Cl$_2$: C, 62.46; H, 6.85; N, 11.49. Found: C, 62.68; H, 6.89; N, 11.73.

EXAMPLE 2

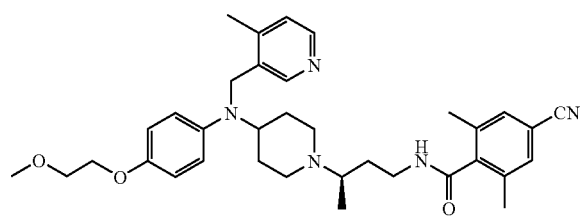

Preparation of 4-Cyano-N-((R)-3-{4-[[4-(2-methoxy-ethoxy)-phenyl]-(4-methyl-pyridin-3-ylmethyl)-amino]-piperidin-1-yl}-butyl)-2,6-dimethyl-benzamide To a solution of 4-nitrophenol (2.16 g, 15.5 mmol) in DMF (8 mL) was added 2-bromoethyl methyl ether (1.9 mL, 20.2 mmol) and K$_2$CO$_3$ (4.08 g, 29.6 mmol) and the reaction stirred at 60° C. for 3 h then at 80° C. for 2 h. The mixture was cooled and diluted with H$_2$O (30 mL) and EtOAc (40 mL) and the aqueous layer extracted again with EtOAc (1×25 mL). The combined organic extracts were washed with brine (2×20 mL), dried (Na$_2$SO$_4$) and concentrated to afford the desired ether (3.05 g) as a white solid.

The 4-nitrophenol (3.05 g), MeOH (30 mL), 10% Pd on activated carbon, (304 mg) were combined in a hydrogenation vessel and the reaction mixture was shaken on a Parr hydrogenator for 1 h at 40 psi of hydrogen. The mixture was filtered through celite, the cake washed with MeOH and the solvent from the eluent removed in vacuo to afford the desired aniline (1.75 g, 68% 2 step) as a brown oil: $^1$H NMR (CDCl$_3$) δ 3.44 (s, 3H), 3.70-3.73 (m, 2H), 4.03-4.06 (m, 2H), 6.64 (d, 2H, J=9 Hz), 6.78 (d, 2H, J=9 Hz).

Following General Procedure A: To a solution of (R)-3-(4-oxo-piperidin-1-yl)-butyronitrile (492 mg, 2.95 mmol) and 4-(2-methoxy-ethoxy)-phenylamine (492 mg, 2.95 mmol) in CH$_2$Cl$_2$ (12 mL) and glacial AcOH (14 drops) was added NaBH(OAc)$_3$ (758 mg, 3.58 mmol) and the reaction stirred at room temperature overnight. Purification of the crude product by column chromatography on silica gel (CH$_2$Cl$_2$/MeOH, 96:4) gave the desired aniline (R)-3-{4-[4-(2-methoxy-ethoxy)-phenylamino-piperidin-1-yl}-butyronitrile (0.72 g, 94%) as an orange oil.

Following General Procedure D: To a stirred suspension of a 4-methylnicotinic acid (452 mg, 2.60 mmol) in CH$_2$Cl$_2$ (5 mL) were added DMF (0.2 mL) followed by oxalyl chloride (0.70 mL, 8.02 mmol) and the resultant mixture was stirred at room temperature for 1.5 h. To the acid chloride was added a solution of the aniline from above (0.72 g, 2.27 mmol) and DIPEA (1.5 mL, 8.63 mmol) in THF (10 mL) and the mixture stirred at 60° C. overnight. The crude material was purified by flash column chromatography on silica gel (CH$_2$Cl$_2$/MeOH, 96:4 then 92:8) to afford the desired amide as a brown foam (0.39 g, 39%).

To a solution of the nitrile from above (0.39 g, 0.89 mmol) in THF (10 mL) was added a solution of borane-THF in THF (1.0 M, 7.2 mL, 7.2 mmol) and the reaction stirred for 2 d. The reaction was cooled and carefully quenched with 6N HCl (8 mL) and heated to 65° C. for 2 h. The mixture was neutralized to pH>12 with 10N NaOH and diluted with CH$_2$Cl$_2$ (20 mL). The aqueous layer was extracted with CH$_2$Cl$_2$ (2×10 mL) and the combined organic extracts were dried (Na$_2$SO$_4$) and purified by column chromatography on silica gel (CH$_2$Cl$_2$/MeOH/NH$_4$OH, 96:4:0 then 88:10:2) to give [1-((R)-3-amino-1-methyl-propyl)-piperidin-4-yl]-[4-(2-methoxy-ethoxy)-phenyl]-(4-methyl-pyridin-3-ylmethyl)-amine (0.35 g, 92%) as a clear oil.

Following General Procedure C: To a solution of the amine from above (96 mg, 0.225 mmol) and 4-cyano-2,6-dimethyl-benzoic acid (47 mg, 0.27 mmol) in CH$_2$Cl$_2$ (5 mL) was added DIPEA (0.1 mL, 0.58 mmol), HOBT (58 mg, 0.43 mmol) and EDCI (80 mg, 0.42 mmol) and the reaction stirred overnight. Purification of the crude product by column chromatography on silica gel (CH$_2$Cl$_2$/MeOH, 96:4 then 92:8) gave the title compound (66 mg, 68%) as a white foam: $^1$H NMR (CDCl$_3$) δ 0.99 (d, 3H, J=6.3 Hz), 1.19-1.25 (m, 2H), 1.55-1.59 (m, 1H), 1.74-1.84 (m, 3H), 2.10-2.17 (m, 1H), 2.30 (s, 3H), 2.32 (s, 6H), 2.48-2.54 (m, 1H), 2.70-2.81 (m, 3H), 3.25-3.42 (m, 2H), 3.42 (s, 3H), 3.69 (br t, 2H, J=5.1 Hz), 3.71-3.76 (m, 1H), 3.97 (s, 2H), 4.02 (br t, 2H, J=5.1 Hz), 6.61 (d, 2H, J=9 Hz), 6.78 (d, 2H, J=9 Hz), 7.04 (d, 1H, J=4.8 Hz), 7.26 (s, 2H), 7.83 (br s, 1H), 8.23 (s, 1H), 8.29 (d, 1H, J=4.8 Hz). $^{13}$C NMR (CDCl$_3$) δ 12.50, 17.83, 18.10, 28.76, 29.49, 30.75, 38.19, 43.26, 46.65, 50.63, 57.50, 58.26, 58.46, 66.79, 70.24, 111.25, 114.44, 114.71, 117.50, 118.61, 124.21, 129.92, 132.22, 134.80, 141.68, 144.00, 147.06, 148.10, 151.89, 167.20. ES-MS m/z 584 (M+H). Anal. Calcd. for C$_{35}$H$_{45}$N$_5$O$_3$.0.3H$_2$O.0.3CH$_2$Cl$_2$: C, 68.98; H, 7.58; N, 11.39. Found: C, 69.21; H, 7.62; N, 11.37.

EXAMPLE 3

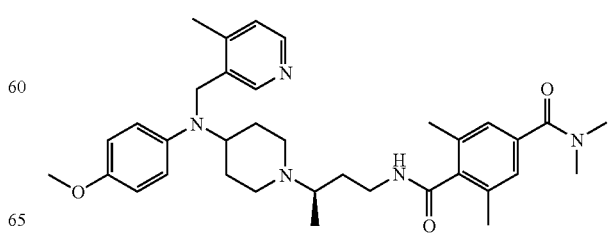

Preparation of N-((R)-3-{4-[(4-Methoxy-phenyl)-(4-methyl-pyridin-3-ylmethyl)-amino]-piperidin-1-yl}-butyl)-2,6, N',N'-tetramethyl-terephthalamide (R)-[1-(3-Amino-1-methyl-propyl)-piperidin-4-yl]-(4-methoxy-phenyl)-(4-methyl-pyridin-3-ylmethyl)-amine (1.00 g, 2.62 mmol), EDCI (0.55 g, 2.88 mmol) and HOBT (0.39 g, 2.88 mmol) were combined in DMF (5 mL) to give a pale yellow solution. To this solution was added 4-cyano-2, 6-dimethyl-benzoic acid (0.50 g, 2.88 mmol) followed by DIPEA (1.14 mL, 6.55 mmol) and the resulting mixture was stirred at 25° C. for 16 h. Standard workup according to General Procedure C gave the crude product as a tan oil. Purification by column chromatography on silica gel ($CH_2Cl_2$:MeOH:$NH_4OH$, 96:3:1, v/v/v) afforded 4-cyano-N-((R)-3-{4-[(4-methoxy-phenyl)-(4-methyl-pyridin-3-ylmethyl)-amino]-piperidin-1-yl}-butyl)-2,6-dimethyl-benzamide (0.77 g, 54%) as a white foam. $^1$H NMR ($CDCl_3$) δ 0.98-1.04 (d+m, 4H), 1.22 (m, 1H), 1.54 (m, 1H), 1.73-1.82 (m, 3H), 2.16 (t, 1H), 2.33 (s, 3H), 2.36 (s, 3H), 2.40 (m, 1H), 2.52 (m, 1H), 2.69-2.88 (m, 3H), 3.21 (m, 1H), 3.33 (m, 1H), 3.73 (s, 3H), 3.77 (m, 1H), 3.96 (s, 2H), 6.63 (d, 2H, J=9.0 Hz), 6.73 (d, 2H, J=9.0 Hz), 7.05 (d, 1H, J=6.0 Hz), 7.27 (s, 2H), 7.84 (br s, 1H), 8.25 (s, 1H), 8.31 (d, 1H, J=6.0 Hz).

To a solution of the above compound (0.61 g, 1.13 mmol) in EtOH (15 mL) was added 3N NaOH (5 mL) and the resulting colourless solution was stirred at 100° C. for 18 h. The EtOH was removed in vacuo and the pH adjusted to ~5 before dry loading onto silica gel. Purification by column chromatography on silica gel ($CH_2Cl_2$:MeOH:$NH_4OH$, 82:15:3, v/v/v) afforded N-((R)-3-{4-[(4-methoxy-phenyl)-(4-methyl-pyridin-3-ylmethyl)-amino]-piperidin-1-yl}-butyl)-3,5-dimethyl-terephthalamic acid (0.58 g, 92%) as a white solid. $^1$H NMR ($CDCl_3$) δ 1.26 (d, 3H, J=6.0 Hz), 1.72 (m, 1H), 1.92-2.02 (m, 3H), 2.21 (s, 3H), 2.24 (s, 3H), 2.25 (m, 2H), 2.41 (m, 1H), 2.63 (m, 1H), 2.81 (m, 1H), 3.23 (m, 2H), 3.41-3.49 (m, 4H), 3.68 (s, 3H), 3.75 (m, 1H), 6.71 (m, 4H), 7.01 (d, 1H, J=3.0 Hz), 7.23 (s, 2H), 8.00 (br s, 1H), 8.28 (s, 1H), 8.30 (d, 1H, J=6.0 Hz).

N-((R)-3-{4-[(4-Methoxy-phenyl)-(4-methyl-pyridin-3-ylmethyl)-amino]-piperidin-1-yl}-butyl)-3,5-dimethyl-terephthalamic acid (0.070 g, 0.12 mmol), EDCI (0.026 g, 0.13 mmol) and HOBT (0.019 g, 0.13 mmol) were combined in DMF (5 mL) to give a pale yellow solution. To this solution was added dimethylamine (2M in THF) (94 μL, 0.18 mmol) followed by DIPEA (33 μL, 0.18 mmol) and the resulting mixture was stirred at 25° C. for 16 h. Standard workup according to General Procedure C gave the crude product as a tan oil. Purification by column chromatography on silica gel ($CH_2Cl_2$:MeOH:$NH_4OH$, 93:5:2, v/v/v) afforded N-((R)-3-{4-[(4-methoxy-phenyl)-(4-methyl-pyridin-3-ylmethyl)-amino]-piperidin-1-yl}-butyl)-2,6, N',N'-tetramethyl-terephthalamide (0.028 g, 38%) as a white foam. $^1$H NMR ($CDCl_3$) δ 0.99 (d, 3H, J=6.0 Hz), 1.26 (m, 1H), 1.37 (m, 1H), 1.62 (m, 2H), 1.78-1.85 (m, 3H), 2.14 (br t, 1H), 2.33 (s+m, 8H), 2.47 (br t, 1H), 2.74 (m, 3H), 2.94 (s, 3H), 3.06 (s, 3H), 3.32-3.46 (m, 2H), 3.66 (m, 1H), 3.72 (s, 3H), 4.10 (s, 2H), 6.66 (d, 2H, J=9.0 Hz), 6.73 (d, 2H, J=9.0 Hz), 6.93 (br t, 1H), 7.02 (d, 1H, J=3.0 Hz), 7.05 (s, 2H), 8.29 (s, 1H), 8.31 (d, 1H, J=6.0 Hz). $^{13}$C NMR ($CDCl_3$) δ 13.8, 19.2, 19.6, 29.9, 30.7, 32.8, 39.0, 39.9, 44.8, 47.6, 51.8, 56.0, 58.8, 58.9, 114.8, 119.4, 125.3, 126.4, 133.8, 134.8, 143.0, 145.4, 148.3, 149.6. ES-MS m/z 586 (M+H), 608 (M+Na). Anal. Calcd. for $C_{35}H_{47}N_5O_3$.0.2 $CH_2Cl_2$: C, 70.14; H, 7.93; N, 11.62. Found: C, 70.06; H, 8.03; N, 11.54.

EXAMPLE 4

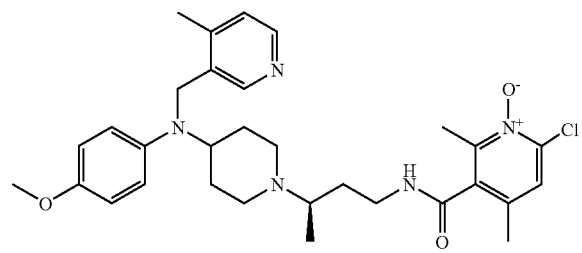

Preparation of 6-chloro-N-((R)-3-{4-[(4-methoxy-phenyl)-(4-methyl-pyridin-3-ylmethyl)-amino]-piperidin-1-yl}-butyl)-2,4-dimethyl-1-oxy-nicotinamide To a suspension of 6-chloro-2,4-dimethyl-nicotinic acid (1.20 g, 6.47 mmol) in $CH_2Cl_2$ (250 mL) was added 3-chloroperoxybenzoic acid (77% max., 7.90 g, 31.2 mmol). The mixture was stirred at room temperature overnight, and then concentrated under reduced pressure. The residual solid was purified by flash column chromatography on silica gel (5:2, $CH_2Cl_2$/MeOH) to afford 6-chloro-2,4-dimethyl-1-oxy-nicotinic acid as a white solid (0.530 g, 41%). $^1$H NMR ($CD_3OD$) δ 2.37 (s, 3H), 2.56 (s, 3H), 7.56 (s, 1H).

To a solution of [1-((R)-3-amino-1-methyl-propyl)-piperidin-4-yl]-(4-methoxy-phenyl)-(4-methyl-pyridin-3-ylmethyl)-amine (0.620 g, 1.62 mmol) in DMF (8 mL) was added 6-chloro-2,4-dimethyl-1-oxy-nicotinic acid (0.375 g, 1.86 mmol), HOBT (0.328 g, 2.43 mmol), EDCI (0.468 g, 2.43 mmol) and DIPEA (0.335 g, 2.60 mmol). After the mixture was stirred at room temperature overnight water (20 mL) was added, and the mixture was extracted with $CH_2Cl_2$ (4×20 mL). The organic extracts were combined and dried ($Na_2SO_4$). After filtration the solvent was removed under vacuum, and the residue was purified by flash column chromatography on silica gel (7:100, $CH_2Cl_2$/MeOH) to afford the title compound as an off-white solid (0.425 g, 46%). $^1$H NMR ($CDCl_3$) δ 1.01 (d, 3H, J=6.6 Hz), 1.25-1.50 (m, 2H), 1.50-1.88 (m, 4H), 2.15-2.20 (m, 1H), 2.29 (s, 3H), 2.33 (s, 3H), 2.42 (s, 3H), 2.45-2.50 (m, 1H), 2.75-2.85 (m, 3H), 3.25-3.35 (m, 1H), 3.40-3.48 (m, 1H), 3.55-3.65 (m, 1H), 3.73 (s, 3H), 4.14 (s, 2H), 6.66-6.76 (m, 4H), 7.02 (d, 1H, J=5.1 Hz), 8.23 (br. s, 1H), 8.28-8.30 (m, 3H). $^{13}$C NMR ($CDCl_3$) δ 13.83, 16.30, 18.80, 18.88, 29.96, 30.40, 32.58, 38.74, 45.15, 47.93, 51.20, 55.79, 58.11, 58.70, 114.62, 119.63, 125.22, 125.58, 133.51, 134.57, 135.20, 140.88, 142.77, 145.25, 147.33, 148.15, 149.27, 153.63, 165.06. ES-MS m/z 566 (M+H). Anal. Calcd. for $C_{31}H_{40}N_5ClO_3$.0.7$CH_2Cl_2$: C, 60.86; H, 6.67; N, 11.19; Cl, 13.60. Found: C, 60.83; H, 6.69; N, 10.98; Cl, 13.79.

EXAMPLE 5

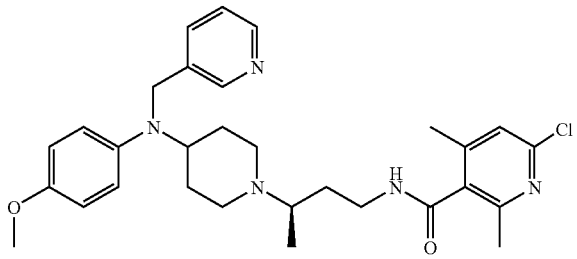

Preparation of 6-Chloro-N-((R)-3-{4-[(4-methoxy-phenyl)-pyridin-3-ylmethyl-amino]-piperidin-1-yl}-butyl)-2,4-dimethyl-nicotinamide Nicotinic acid (492 mg, 4 mmol) was suspended in DCM (40 mL) and cooled to 0° C. DMF (12 µL, 0.05 eq.) was added, followed by drop-wise addition of oxalyl chloride (1.4 mL, 4 eq.). The mixture was stirred at 0° C. for 15 min, then warmed to room temperature and stirred for 2 h. All volatiles were removed by rotary evaporation, and the residue was placed under high vacuum for 30 min at room temperature.

The residue was suspended in THF (30 mL) and cooled to 0° C. A solution of (R)-3-[4-(4-methoxy-phenylamino)-piperidin-1-yl]-butyronitrile (1.09 g, 1 eq.) and DIPEA (1.5 mL, 2 eq.) in THF (10 mL) was added drop-wise and the mixture was stirred at 0° C. for 30 min. The reaction was quenched with saturated NaHCO$_3$ (50 mL) and extracted with DCM (150 mL in 3 extracts). The organic layer was washed once with saturated NaHCO$_3$ (20 mL), dried with Na$_2$SO$_4$ and filtered through a silica plug (35 mL glass frit, 1 cm). The plug was washed with 50 mL 5:1 Et$_2$O-MeOH, and the filtrate was concentrated. The residue was purified by flash chromatography on 150 mL silica using 10:1 Et$_2$O-MeOH as the eluent to give N-[(R)-1-(2-cyano-1-methyl-ethyl)piperidin-4-yl]-N-(4-methoxy-phenyl)-nicotinamide (1.23 g, 81%) as light brown thick oil. $^1$H NMR (δ, CDCl$_3$): 8.44 (1H, s), 8.39 (1H, d, J=4.8 Hz), 7.53 (1 H, d, J=7.5 Hz), 7.08 (1 H, dd, J=7.5, 4.8 Hz), 6.90 (2 H, d, J=8.7 Hz), 6.72 (2 H, d, J=8.7 Hz), 4.69 (1 H, t, br, J=12.9 Hz), 3.73 (3 H, s, and an overlapping 1 H, m), 3.05-2.95 (1 H, m), 2.95-2.75 (2 H, dd, J=20, 11), 2.53-2.25 (4 H, m), 1.96-1.80 (3 H, m), 1.50 (2 H, qd, J=11.4, 2.4 Hz), 1.77(3 H, d, J=6.9 Hz), 1.01 (2 H, d, J=6.3 Hz).

N-[(R)-1-(2-Cyano-1-methyl-ethyl)-piperidin-4-yl]-N-(4-methoxy-phenyl)-nicotinamide (1.23 g, 3.25 mmol) was dissolved in THF (15 mL) and cooled to 0° C. BH$_3$-THF complex (1 M, 20 mL, 6 eq.) was added in one portion and the mixture was heated at 70° C. overnight. Additional BH$_3$-THF (6.5 mL, 2 eq.) was added and heating was continued for 2 h. The mixture was cooled to 0° C. and was carefully quenched with MeOH (10 mL). The mixture was stirred at room temperature for 10 min, and then was concentrated by rotary evaporation. The residue was taken up in HCl (6 M, 20 mL) and heated at 80° C. for 1.5 h. The mixture was cooled to 0° C. and the pH was adjusted to ≧10 with 4N NaOH. The mixture was extracted with DCM, and the organic was dried with Na$_2$SO$_4$. The residue was purified with flash chromatography on 150 mL silica using 10:1:1% DCM-MeOH—NH$_4$OH as the eluent to give (R)-[1-(3-amino-1-methyl-propyl)-piperidin-4-yl]-(4-methoxy-phenyl)-pyridin-3-ylmethyl-amine (0.78 g, 65%) as yellow thick oil. $^1$H NMR (δ, CDCl$_3$): 8.54 (1 H, d, J=1.5 Hz), 8.44 (1 H, dd, J=4.8, 1.5 Hz), 7.58 (1 H, d, J=7.8), 7.18 (1 H, dd, J=7.8, 4.8 Hz), 6.8-6.65 (4 H, m), 4.38 (2 H, s), 3.72 (3 H, s), 3.52-3.40 (1H, m), 2.90-2.62 (5 H, m), 2.43 (1 H, t, J=10.8 Hz), 2.19 (1 H, t, J=11.1 Hz), 1.9-1.5 (8 H, m), 1.46-1.32 (1 H, m), 0.96 (3 H, d, J=6.3 Hz).

(R)-[1-(3-Amino-1-methyl-propyl)-piperidin-4-yl]-(4-methoxy-phenyl)-pyridin-3-ylmethyl-amine (0.78 g, 2.12 mmol) was dissolved in DCM (10 mL). 6-Chloro-2,4-dimethyl-nicotinic acid (474 mg, 1.2 eq.), HOBT (430 mg, 1.5 eq.), DIPEA (760 µL, 2 eq.), and EDCI (612 mg, 1.5 eq.) were added sequentially. The mixture was stirred at room temperature for 6 h, and then quenched with saturated NaHCO$_3$ (20 mL). The pH of the equilibrated aqueous was adjusted to 8 with 1N HCl, and the mixture was extracted with DCM (200 mL in 5 extracts). The combined organic was dried (Na$_2$SO$_4$) and concentrated. The residue was purified with flash chromatography on 150 mL silica using a gradient of 5%→10% MeOH in EtOAc containing 1% NH$_4$OH as the eluent to give 6-chloro-N-((R)-3-{4-[(4-methoxy-phenyl)-pyridin-3-ylmethyl-amino]-piperidin-1-yl}-butyl)-2,4-dimethyl-nicotinamide (0.88 g, 77%) as light brown foam. $^1$H NMR (δ, CDCl$_3$): 8.66 (1 H, d, br, J=5.7 Hz), 8.51 (1 H, s), 8.44 (1 H, d, J=4.8 Hz), 7.61 (1 H, d, J=8.1 Hz), 7.20 (1 H, dd, J=7.8, 4.8 Hz), 7.01 (1 H, s), 6.73 (2 H, d, J=9.0 Hz), 6.62 (2 H, d, J=9.0 Hz), 3.88 (2 H, s, an overlapping 1H, m), 3.71 (3 H, s), 3.33 (2 H, pentet, J=13.5 Hz), 2.80 (3 H, m), 2.51 (3 H, s, an overlapping 1 H, m), 2.30 (3 H, s), 2.12 (1 H, t, J=11.4 Hz), 1.82-1.66 (3 H, m), 1.60-1.46 (1 H, m), 1.11 (1 H, qd, J=12.3, 3.6 Hz), 0.99 (3 H, d, J=6.6 Hz), 0.92 (1 H, qd, J=12.0, 3.0 Hz); $^{13}$C NMR (δ, CDCl$_3$): 167.2, 155.4, 152.9, 150.2, 148.9, 148.1, 147.5, 142.5, 135.7, 134.8, 123.3, 122.5, 117.8, 114.6, 60.5, 58.1, 55.6, 52.1, 47.5, 43.6, 40.1, 30.7, 29.4, 22.1, 18.8, 13.4; ES-MS m/z 536.5 (M+1). Anal. Calcd. for (C$_{30}$H$_{38}$N$_5$ClO$_2$) 0.2(H$_2$O): C, 66.76; H, 7.17; N, 12.98; Cl, 6.57. Found: C, 66.80; H, 7.00; N, 12.86; Cl, 6.55.

EXAMPLE 6

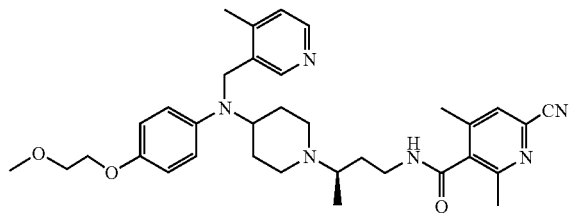

Preparation of 6-Cyano-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide Following General Procedure C: To a solution of [1-((R)-3-amino-1-methyl-propyl)-piperidin-4-yl]-[4-(2-methoxy-ethoxy)-phenyl]-(4-methyl-pyridin-3-ylmethyl)-amine (180 mg, 0.42 mmol) and 2,4-dimethyl-1-oxy-nicotinic acid (97 mg, 0.27 mmol) in DMF (2.5 mL) was added DIPEA (0.2 mL, 1.15 mmol), HOBT (76 mg, 0.56 mmol) and EDCI (130 mg, 0.68 mmol) and the reaction stirred overnight. Purification of the crude product by column chromatography on silica gel (CH$_2$Cl$_2$/MeOH/NH$_4$OH, 96:4:0 then 88:10:2) gave the desired N-oxide amide (224 mg, 93%) as a pale yellow oil.

To a solution of the N-oxide from above (224 mg, 0.38 mmol) in CH$_2$Cl$_2$ (5 mL) was added TMSCN (0.10 mL, 0.75 mmol) followed by N,N-dimethylcarbamyl chloride (0.05 mL, 0.54 mmol) and the reaction stirred at room temperature for 2 d. The mixture was diluted with CH$_2$Cl$_2$ (20 mL) and saturated aqueous NaHCO$_3$ (25 mL) and the aqueous layer re-extracted with CH$_2$Cl$_2$ (2×5 mL). The combined organic extracts were dried (Na$_2$SO$_4$), concentrated and purified by column chromatography on silica gel ((CH$_2$Cl$_2$/MeOH/NH$_4$OH, 96:4:0 then 88:10:2) followed by radial chromatography on silica gel (CH$_2$Cl$_2$/MeOH/NH$_4$OH, 50:1:1) to afford the title compound (41 mg, 25%) as an orange oil: $^1$H NMR (CDCl$_3$) δ 0.97-1.23 (m, 2H), 0.98 (d, 3H, J=6.6 Hz), 1.52-1.58 (m, 1H), 1.68-1.82 (m, 3H), 2.09-2.19 (m, 1H), 2.31 (s, 3H), 2.33 (s, 3H), 2.44-2.57 (m, 1H), 2.54 (s, 3H), 2.68-2.81 (m, 3H), 3.20-3.38 (m, 2H), 3.41 (s, 3H), 3.69 (br t, 2H, J=5.1 Hz), 3.70-3.74 (m, 1H), 3.99 (s, 2H), 4.02 (br t, 2H, J=5.1 Hz), 6.60 (d, 2H, J=9 Hz), 6.76 (d, 2H, J=9 Hz), 7.03 (d, 1H, J=4.8 Hz), 7.29 (s, 1H), 8.18 (br s, 2H), 8.26 (d, 1H, J=4.8 Hz). $^{13}$C NMR (CDCl$_3$) δ 13.78, 19.13, 22.68, 30.27, 31.02, 31.75, 39.86, 44.38, 48.14, 51.99, 58.74, 59.55, 59.86, 68.09, 71.53, 115.73, 117.34, 120.18, 125.55, 127.78, 132.95, 133.41, 137.00, 142.82, 145.55, 145.83, 148.39, 149.40, 153.30, 156.99, 166.85. ES-MS m/z 607 (M+Na). Anal. Calcd. for C$_{34}$H$_{44}$N$_6$O$_3$.0.2H$_2$O.0.3CH$_2$Cl$_2$: C, 67.11; H, 7.39; N, 13.69. Found: C, 66.91; H, 7.34; N, 13.74.

EXAMPLE 7

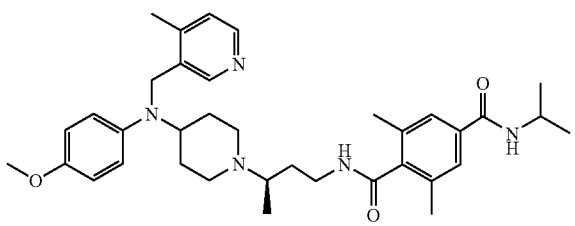

Preparation of N'-Isopropyl-N-((R)-3-{4-[(4-methoxy-phenyl)-(4-methyl-pyridin-3-ylmethyl)-amino]-piperidin-1-yl}-butyl)-2,6-dimethyl-terephthalamide N-((R)-3-{4-[(4-Methoxy-phenyl)-(4-methyl-pyridin-3-ylmethyl)-amino]-piperidin-1-yl}-butyl)-3,5-dimethyl-terephthalamic acid (0.050 g, 0.09 mmol), EDCI (0.019 g, 0.10 mmol) and HOBT (0.013 g, 0.10 mmol) were combined in DMF (5 mL) to give a pale yellow solution. To this solution was added isopropylamine (8 μL, 0.10 mmol) followed by DIPEA (19 μL, 0.11 mmol) and the resulting mixture was stirred at 25° C. for 16 h. Standard workup according to General Procedure C gave the crude product as a tan oil. Purification by column chromatography on silica gel (CH$_2$Cl$_2$:MeOH:NH$_4$OH, 93:5:2, v/v/v) afforded N'-isopropyl-N-((R)-3-{4-[(4-methoxy-phenyl)-(4-methyl-pyridin-3-ylmethyl)-amino]-piperidin-1-yl}-butyl)-2,6-dimethyl-terephthalamide (0.046 g, 86%) as a white foam. $^1$H NMR (CDCl$_3$) δ 0.97 (d+m, 4H), 1.18 (d+m, 7H), 1.55 (m, 1H), 1.72 (m, 3H), 2.08 (br t, 1H), 2.26 (s, 6H), 2.30 (s, 3H), 2.42 (br t, 1H), 2.67-2.81 (m, 3H), 3.14 (m, 1H), 3.31 (m, 1H), 3.72 (s, 3H), 3.78 (m, 1H), 3.99 (s, 2H), 4.23 (m, 1H), 6.57 (d, 1H, J=6.0 Hz), 6.68 (d, 2H, J=9.0 Hz), 6.73 (d, 2H, J=9.0 Hz), 7.00 (d, 1H, J=3.0 Hz), 7.45 (s, 2H), 7.83 (s, 1H), 8.29 (s, 1H), 8.31 (d, 1H, J=6.0 Hz). $^{13}$C NMR (CDCl$_3$) δ 13.7, 19.0, 19.6, 23.1, 29.7, 30.4, 31.3, 39.6, 42.2, 44.2, 47.7, 49.2, 51.9, 55.9, 59.6, 60.0, 114.8, 118.2, 121.4, 125.3, 126.5, 134.0, 134.8, 135.1, 141.2, 143.3, 145.2, 148.1, 149.4, 154.5, 166.5, 169.8. ES-MS m/z 600 (M+H). Anal. Calcd. for C$_{36}$H$_{49}$N$_5$O$_3$.0.1 CH$_2$Cl$_2$: C, 71.28; H, 8.15; N, 11.51. Found: C, 71.26; H, 8.18; N, 11.41.

EXAMPLE 8

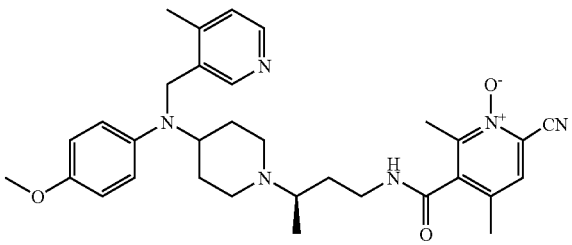

Preparation of 6-cyano-N-((R)-3-{4-[(4-methoxy-phenyl)-(4-methyl-pyridin-3-ylmethyl)-amino]-piperidin-1-yl}-butyl)-2,4-dimethyl-1-oxy-nicotinamide To a suspension of 6-cyano-2,4-dimethyl-nicotinic acid (0.690 g, 3.88 mmol) in dry CH$_2$Cl$_2$ (40 mL) at 0° C. was added H$_2$O$_2$-urea (1.37 g, 14.5 mmol) and trifluoroacetic anhydride (2.45 g, 11.6 mmol). The mixture was warmed to room temperature, and stirred overnight. The reaction mixture was then concentrated under reduced pressure, and the residual solid was purified by flash column chromatography on silica gel (3:1, EtOAc/MeOH) to afford 6-cyano-2,4-dimethyl-1-oxy-nicotinic acid as a pale yellow solid (0.700 g, 93%). $^1$H NMR (CD$_3$OD) δ 2.38 (s, 3H), 2.50 (s, 3H), 7.81 (s, 1H).

To a solution of [1-((R)-3-amino-1-methyl-propyl)-piperidin-4-yl]-(4-methoxy-phenyl)-(4-methyl-pyridin-3-ylmethyl)-amine (0.960 g, 2.51 mmol) in DMF (15 mL) was added 6-cyano-2,4-dimethyl-1-oxy-nicotinic acid (0.700 g, 3.61 mmol), HOBT (0.540 g, 4.00 mmol), EDCI (0.768 g, 4.00 mmol) and DIPEA (0.645 g, 5.00 mmol). After the mixture was stirred at room temperature for 20 h saturated aqueous NaHCO$_3$ solution (20 mL) was added, and the mixture was extracted with CH$_2$Cl$_2$ (3×40 mL). The organic extracts were combined and dried (Na$_2$SO$_4$). After filtration the solvent was removed under vacuum, and the residue was purified by flash chromatography on a silica gel column (7:100, CH$_2$Cl$_2$/MeOH) to afford the title compound as a yellow solid (0.769 g, 55%). $^1$H NMR (CDCl$_3$) δ 1.00 (d, 3H, J=6.3 Hz), 1.20-1.45 (m, 2H), 1.55-1.90 (m, 4H), 2.11-2.20 (m, 1H), 2.31 (s, 3H), 2.33 (s, 3H), 2.41 (s, 3H), 2.43-2.50 (m, 1H), 2.72-2.84 (m, 3H), 3.19-3.28 (m, 1H), 3.40-3.50 (m, 1H), 3.62-3.72 (m, 1H), 3.74 (s, 3H), 4.13 (s, 2H), 6.64-6.78 (m, 4H), 7.04 (d, 1H, J=4.8 Hz), 8.13 (br. s, 1H), 8.26-8.30 (m, 3H). $^{13}$C NMR (CDCl$_3$) δ 13.66, 15.34, 18.61, 18.91, 30.17, 30.64, 32.20, 39.04, 44.70, 48.36, 51.38, 55.82, 58.38, 58.69, 111.83, 114.63, 120.34, 124.42, 125.33, 129.88, 134.57, 139.64, 142.59, 145.43, 147.34, 148.16, 149.25, 153.97, 164.21. ES-MS m/z 557 (M+H). Anal. Calcd. for $C_{32}H_{40}N_6O_3 \cdot 0.4CH_2Cl_2$: C, 65.88; H, 6.96; N, 14.23. Found: C, 66.08; H, 7.07; N, 13.92.

EXAMPLE 9

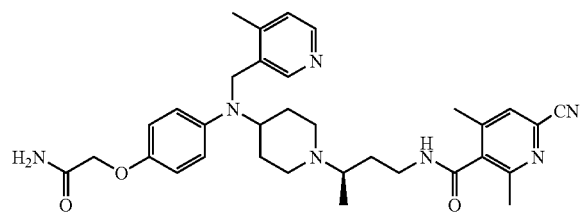

Preparation of N-((R)-3-{4-[(4-Carbamoylmethoxy-phenyl)-(4-methyl-pyridin-3-ylmethyl)-amino]-piperidin-1-yl}-butyl)-6-cyano-2,4-dimethyl-nicotinamide To a solution of 4-nitrophenol (1.69 g, 12.1 mmol) in DMF (8 mL) was added methyl bromoacetate (1.50 mL, 15.8 mmol) and $K_2CO_3$ (3.40 g, 24.6 mmol) and the reaction stirred at 60° C. overnight. The mixture was cooled and diluted with $H_2O$ (30 mL) and EtOAc (40 mL) and the aqueous layer extracted again with EtOAc (1×25 mL). The combined organic extracts were washed with brine (2×20 mL), dried ($Na_2SO_4$) and concentrated to afford the desired ester (2.66 g) as a red solid.

The 4-nitrophenol from above (2.66 g), MeOH (25 mL), 10% Pd on activated carbon, (367 mg) were combined in a hydrogenation vessel and the reaction mixture was shaken on a Parr hydrogenator for 1 h at 40 psi of hydrogen. The mixture was filtered through celite, the cake washed with MeOH and the solvent from the eluent removed in vacuo to afford the title compound (2.18 g, 99% 2 step) as a red solid: $^1$H NMR (CDCl$_3$) δ 3.47 (br s, 2H), 3.79 (s, 3H), 4.56 (s, 2H), 6.63 (d, 2H, J=9 Hz), 6.77 (d, 2H, J=9 Hz).

Following General Procedure A: To a solution of [(R)-3-(4-oxo-piperidin-1-yl)-butyl]-carbamic acid tert-butyl ester (0.79 g, 2.93 mmol) and (4-Amino-phenoxy)-acetic acid methyl ester (568 mg, 3.14 mmol) in $CH_2Cl_2$ (125 mL) and glacial AcOH (11 drops) was NaBH(OAc)$_3$ (904 mg, 4.26 mmol) and the reaction stirred at room temperature for 4.5 h. Purification of the crude product by column chromatography on silica gel ($CH_2Cl_2$/MeOH/NH$_4$OH, 96:4:0 then 90:8:2) gave the desired Boc-protected aniline (1.09 g, 86%) as a clear oil.

Following General Procedure A: To a solution of a 4-methyl-3-pyridinecarboxaldehyde (0.28 g, 2.31 mmol) in 1,2-dichloroethane (10 mL) at 60° C. was added NaBH(OAc)$_3$ (680 mg, 3.21 mmol) and the reaction stirred at 60° C. overnight. Another portion of the pyridinecarboxaldehyde (0.27 g, 2.23 mmol) in 1,2-dichloroethane (5 mL) was added followed by more NaBH(OAc)$_3$ (604 mg, 2.85 mmol) and the mixture stirred again at 60° C. for 4 h. The crude material was purified by flash column chromatography on silica gel ($CH_2Cl_2$/MeOH, 96:4 then 9:1) to afford the desired amine as an orange oil (672 mg, 50%).

Following General Procedure B: The Boc-protected amine was dissolved in $CH_2Cl_2$ (1.5 mL) and TFA (1.5 mL) was added. The mixture was stirred at room temperature for 1 h and the resultant crude amine (240 mg) used in the next reaction.

Following General Procedure C: To a solution of the amine from above (147 mg, 0.33 mmol) and 2,4-dimethyl-6-cyanonicotinic acid (60 mg, 0.34 mmol) in DMF (2 mL) was added DIPEA (0.1 mL, 0.58 mmol), HOBT (55 mg, 0.41 mmol) and EDCI (90 mg, 0.47 mmol) and the reaction stirred overnight. Purification of the crude product by column chromatography on silica gel ($CH_2Cl_2$/MeOH/NH$_4$OH, 96:4:0 then 9:1 then 88:10:2) gave the desired amide (79 mg, 20% 2 steps) as a clear oil.

A solution of the methyl ester from above (79 mg, 0.13 mmol) in NH$_3$(g) saturated MeOH (5 mL) was stirred at room temperature overnight. The reaction was concentrated and purified by radial chromatography on silica gel ($CH_2Cl_2$/MeOH/NH$_4$OH, 50:1:1) to afford the title compound (21 mg, 27%) as a white foam: $^1$H NMR (CDCl$_3$) δ 0.94-1.02 (m, 1H), 1.01 (d, 3H, J=6.6 Hz), 1.15-1.24 (m, 1H), 1.54-1.61 (m, 1H), 1.70-1.92 (m, 3H), 2.12-2.20 (m, 1H), 2.34 (s, 3H), 2.36 (s, 3H), 2.48-2.55 (m, 1H), 2.55 (s, 3H), 2.71-2.85 (m, 3H), 3.28-3.39 (m, 2H), 3.73-3.81 (m, 1H), 4.03 (s, 2H), 4.40 (s, 2H), 5.69 (br s, 1H), 6.54-6.62 (br s, 1H), 6.61 (d, 2H, J=9 Hz), 6.75 (d, 2H, J=9 Hz), 7.07 (d, 1H, J=4.8 Hz), 7.31 (s, 1H), 8.01-8.05 (m, 1H), 8.22 (s, 1H), 8.31 (d, 1H, J=4.8 Hz). $^{13}$C NMR (CDCl$_3$) δ 13.77, 19.12, 22.69, 28.87, 30.04, 30.81, 31.80, 39.79, 44.44, 47.61, 52.07, 58.31, 59:86, 68.17, 115.86, 117.36, 119.20, 125.63, 127.78, 132.96, 133.13, 136.95, 143.76, 145.44, 145.90, 148.52, 149.05, 151.27, 156.98, 166.85, 171.68. ES-MS m/z 584 (M+H). Anal. Calcd. for $C_{33}H_{41}N_7O_3 \cdot 0.5H_2O \cdot 0.1CH_2Cl_2$: C, 66.12; H, 7.07; N, 16.31. Found: C, 65.73; H, 7.03; N, 16.18.

EXAMPLE 10

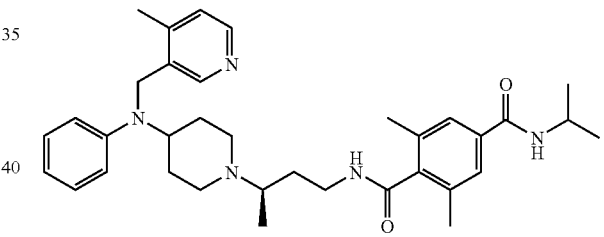

Preparation of N'-Isopropyl-2,6-dimethyl-N-((R)-3-{4-[(4-methyl-pyridin-3-ylmethyl)-phenyl-amino]-piperidin-1-yl}-butyl)-terephthalamide To a stirred solution of aniline (2.61 mL, 25.65 mmol) in $CH_2Cl_2$ (75 mL) at room temperature were added (R)-3-(4-oxo-piperidin-1-yl)-butyronitrile (5.00 g, 30.08 mmol), glacial AcOH (1.64 mL, 28.65 mmol) and NaBH(OAc)$_3$ (8.50 g, 40.11 mmol) and the resultant solution was stirred at room temperature for 16 h. The reaction mixture was then poured into saturated aqueous NaHCO$_3$ (50 mL). The phases were separated and the aqueous layer was extracted with $CH_2Cl_2$ (3×50 mL). The combined organic extracts were dried (Na$_2$SO$_4$), filtered and concentrated under reduced pressure. The crude material was purified by flash column chromatography on silica gel (94:5:1, $CH_2Cl_2$/MeOH/NH$_4$OH) to generate (R)-3-(4-phenylamino-piperidin-1-yl)-butyronitrile as a off-white solid (5.68 g, 78%). $^1$H-NMR (CDCl$_3$) δ 1.21 (d, 3H, J=7 Hz), 1.44 (m, 2H), 2.08 (m, 2H), 2.34 (m, 2H), 2.39 (m, 2H), 2.81 (m, 2H), 3.07 (sext, 1H, J=7 Hz), 3.28 (m, 1H), 3.47 (br s, 1H), 6.59 (m, 2H), 6.68 (m, 1H), 7.16 (m, 2H).

To a stirred suspension of a 4-methylnicotinic acid (3.49 g, 20.1 mmol) in $CH_2Cl_2$ (90 mL) were added DMF (13 drops)

followed by oxalyl chloride (5.36 mL, 61.4 mmol) and the resultant mixture was stirred at room temperature for 1.5 h. The mixture was concentrated and the acid chloride was dried in vacuo for 45 minutes. To the acid chloride was added a solution of (R)-3-(4-phenylamino-piperidin-1-yl)-butyronitrile (3.91 g, 16.1 mmol) and DIPEA (3.36 mL, 19.3 mmol) in THF (90 mL) and the mixture was stirred at 50° C. for 16 h. The mixture was concentrated and then diluted with CH$_2$Cl$_2$ (30 mL) and 30 mL saturated aqueous NaHCO$_3$. The phases were separated and the aqueous layer was extracted with CH$_2$Cl$_2$ (3×40 mL). The organic layer was dried (Na$_2$SO$_4$), filtered and concentrated under reduced pressure. The crude material was purified by flash column chromatography on silica gel (97:2:1, CH$_2$Cl$_2$/MeOH/NH$_4$OH) to generate (R)-N-[1-(2-cyano-1-methyl-ethyl)-piperidin-4-yl]-4-methyl-N-phenyl-nicotinamide as a yellow oil (3.85 g, 66%). $^1$H-NMR (CDCl$_3$) δ 1.17 (d, 3H, J=7 Hz), 1.51 (m, 2H), 1.97 (br d, 2H), 2.35 (s, 3H), 2.46 (m, 3H), 2.84 (m, 2H), 3.01 (sext, 1H, J=7 Hz), 4.77 (m, 1H), 6.92 (d, 1H, J=6 Hz), 6.99 (m, 2H), 7.18 (m, 3H), 8.17 (m, 2H).

To a solution of (R)-N-[1-(2-cyano-1-methyl-ethyl)-piperidin-4-yl]-4-methyl-N-phenyl-nicotinamide (3.85 g, 10.62 mmol) in THF (150 mL) was added a solution of borane-THF in THF (1.0 M, 63.72 mL, 63.7 mmol) and the reaction was refluxed for 16 h. The reaction was cooled and carefully quenched with 6N HCl (150 mL) and heated to 65° C. for 2 h. The mixture was cooled and concentrated to remove the THF. The remaining aqueous solution was neutralized to pH>12 with 10N NaOH and diluted with CH$_2$Cl$_2$ (100 mL). The two phases were separated and the aqueous layer was extracted with CH$_2$Cl$_2$ (4×100 mL). The combined organic extracts were dried (Na$_2$SO$_4$) and purified by column chromatography on silica gel (83:15:2, CH$_2$C$_2$/MeOH/NH$_4$OH) to give [1-((R)-3-amino-1-methyl-propyl)-piperidin-4-yl]-(4-methyl-pyridin-3-ylmethyl)-phenyl-amine as a yellow oil (2.97 g, 79%). $^1$H-NMR (CDCl$_3$) δ 0.97 (d, 3H, J=6 Hz), 1.43 (m, 4H), 1.64 (m, 4H), 1.90 (m, 2H), 2.26 (dt, 1H, J=2 Hz, 11 Hz), 2.34 (s, 3H), 2.45 (dt, 1H, J=2 Hz, 11 Hz), 2.77 (m, 5H), 3.76 (m, 1H), 4.39 (s, 2H), 6.65 (m, 2H), 6.71 (m, 1H), 7.07 (d, 1H, J=5 Hz), 7.17 (m, 2H), 8.36 (d, 1H, J=5 Hz), 8.38 (s, 1H).

[1-((R)-3-Amino-1-methyl-propyl)-piperidin-4-yl]-(4-methyl-pyridin-3-ylmethyl)-phenyl-amine (200.0 mg, 0.57 mmol), EDCI (120.0 mg, 0.62 mmol) and HOBT (84.3 mg, 0.62 mmol) were combined in DMF (25 mL) to give a pale yellow solution. To this solution was added 4-cyano-2,6-dimethyl-benzoic acid (109.3 mg, 0.62 mmol) followed by DIPEA (119.0 μL, 0.68 mmol) and the resulting mixture was stirred at room temperature for 16 h. Standard workup according to General Procedure C gave the crude product as a tan oil. Purification by column chromatography on silica gel (97:2:1, CH$_2$Cl$_2$/MeOH/NH$_4$OH) afforded 4-cyano-2,6-dimethyl-N-((R)-3-{4-[(4-methyl-pyridin-3-ylmethyl)-phenyl-amino]-piperidin-1-yl}-butyl)-benzamide as an off-white foam (209.0 mg, 72%). $^1$H NMR (CDCl$_3$) δ 1.02 (d, 3H, J=6 Hz), 1.04 (m, 1H), 1.30 (m, 1H), 1.59 (m, 1H), 1.64 (s, 2H), 1.76 (m, 1H), 1.86 (m, 2H), 2.21 (t, 1H, J=11 Hz), 2.32 (s, 6H), 2.55 (t, 1H, J=11 Hz), 2.78 (m, 3H), 2.87 (s, 2H), 2.95 (s, 3H), 3.35 (m, 1H), 3.64 (m, 1H), 3.78 (sext, 1H, J=6 Hz), 4.07 (s, 2H), 6.59 (d, 2H, J=9 Hz), 6.73 (t, 1H, J=8 Hz), 7.14 (m, 3H), 7.50 (m, 1H), 8.01 (s, 1H), 8.28 (s, 1H), 8.35 (d, 1H, J=5 Hz).

To a solution of 4-cyano-2,6-dimethyl-N-((R)-3-{4-[(4-methyl-pyridin-3-ylmethyl)-phenyl-amino]-piperidin-1-yl}-butyl)-benzamide (0.21 g, 0.41 mmol) in EtOH (10 mL) was added 3N NaOH (5 mL) and the resulting colourless solution was stirred at 100° C. for 18 h. The EtOH was removed in vacuo and the pH adjusted to ~5 before dry loading onto silica gel. Purification by column chromatography on silica gel (8:1:1, CH$_3$CN/MeOH/NH$_4$OH) afforded 3,5-dimethyl-N-((R)-3-{4-[(4-methyl-pyridin-3-ylmethyl)-phenyl-amino]-piperidin-1-yl}-butyl)-terephthalamic acid (0.23 g, 100%) as a white solid. $^1$H NMR (CD$_3$OD) δ 1.43 (d, 3H, J=8 Hz), 1.91 (m, 1H), 2.14 (m, 3H), 2.22 (m, 1H), 2.32 (s, 6H), 2.41 (s, 2H), 3.34 (s, 5H), 3.45 (m, 4H), 3.53 (m, 1H), 4.20 (m, 1H), 4.48 (s, 2H), 6.79 (m, 3H), 7.19 (m, 3H), 7.66 (m, 2H), 8.23 (m, 2H).

3,5-Dimethyl-N-((R)-3-{4-[(4-methyl-pyridin-3-ylmethyl)-phenyl-amino]-piperidin-1-yl}-butyl)-terephthalamic acid (50.0 mg, 0.09 mmol), EDCI (19.9 mg, 0.10 mmol) and HOBT (14.1 mg, 0.10 mmol) were combined in DMF (4 mL) to give a pale yellow solution. To this solution was added isopropylamine (8.9 μL, 0.10 mmol) followed by DIPEA (19.7 μL, 0.11 mmol) and the resulting mixture was stirred at room temperature for 16 h. Standard workup according to General Procedure C gave the crude product as a tan oil. Purification by preparative TLC (91:8:1, CH$_2$Cl$_2$/MeOH/NH$_4$OH) afforded N'-isopropyl-2,6-dimethyl-N-((R)-3-{4-[(4-methyl-pyridin-3-ylmethyl)-phenyl-amino]-piperidin-1-yl}-butyl)-terephthalamide as a white foam (10.1 mg, 19%). $^1$H NMR (CDCl$_3$) δ 1.02 (br s, 3H), 1.22 (d, 6H, J=7 Hz), 1.83 (m, 3H), 2.22 (m, 1H), 2.29 (s, 3H), 2.34 (s, 6H), 2.55 (m, 1H), 2.80 (m, 4H), 3.38 (m, 1H), 3.62 (m, 1H), 3.76 (m, 1H), 4.10 (s, 2H), 4.23 (sext, 1H, J=6 Hz), 6.04 (d, 1H, J=7 Hz), 6.59 (d, 2H, J=8 Hz), 6.72 (t, 1H, J=7 Hz), 7.05 (d, 1H, J=5 Hz), 7.16 (t, 2H, J=8 Hz), 7.34 (br s, 1H), 7.39 (s, 2H), 8.27 (s, 1H), 8.33 (d, 1H, J=5 Hz). ES-MS m/z 570 (M+H), 593 (M+Na). Anal. Calcd. For C$_{35}$H$_{47}$N$_5$O$_2$: C, 73.78; H, 8.31; N, 12.29.

EXAMPLE 11

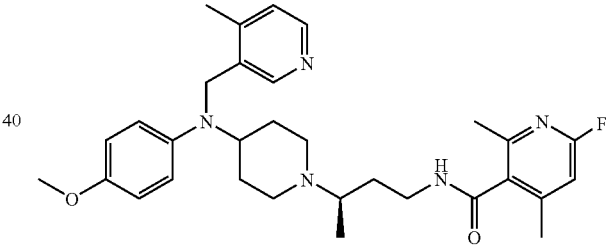

Preparation of 6-Fluoro-N-((R)-3-{4-[(4-methoxy-phenyl)-(4-methyl-pyridin-3-ylmethyl)-amino]-piperidin-1-yl}-butyl)-2,4-dimethyl-nicotinamide To a solution of [1-((R)-3-amino-1-methyl-propyl)-piperidin-4-yl]-(4-methoxy-phenyl)-(4-methyl-pyridin-3-ylmethyl)-amine (41 mg, 0.11 mmol) in DMF (0.5 mL) was added 6-fluoro-2,4-dimethyl-nicotinic acid (27 mg, 0.16 mmol), HOBT (20 mg, 0.15 mmol), EDCI (29 mg, 0.15 mmol) and DIPEA (55 μL, 0.32 mmol). After the mixture was stirred at room temperature overnight brine (5 mL) was added, and the mixture was extracted with CH$_2$Cl$_2$ (2×5 mL). The organic extracts were combined and dried (Na$_2$SO$_4$). After filtration the solvent was removed under vacuum, and the residue was purified by flash chromatography on a silica gel column (50:1:0.1, CH$_2$Cl$_2$/MeOH/NH$_4$OH) to afford the title compound as a white solid (40 mg, 67%). $^1$H NMR (CDCl$_3$) δ 0.99 (d, 3H, J=6.6 Hz), 1.00 (m, 1H), 1.19 (m, 1H), 1.54 (m, 1H), 1.72 (m, 1H), 1.82 (br d, 2H, J=12.6 Hz), 2.12 (t, 1H, J=10.5 Hz), 2.32 (s, 3H), 2.34 (s, 3H), 2.47 (s, 3H), 2.48 (t, 1H, J=12.6 Hz), 2.65-2.85 (m, 3H), 3.15-3.45 (m, 2H), 3.72 (s, 3H), 3.82 (m, 1H), 3.96 (s, 2H), 6.51 (s, 1H), 6.60-6.76 (m, 4H), 7.03 (d, 1H, J=4.8 Hz), 8.08 (br. S, 1H), 8.25 (s, 1H), 8.29 (d, 1H, J=4.8 Hz). $^{13}$C NMR (CDCl$_3$) δ 13.81, 19.08, 19.50, 22.26, 30.09, 30.90, 31.82, 39.89, 44.46, 47.79, 52.05, 55.92, 59.16, 59.94, 107.62 (d, 1C, J=146 Hz), 114.75 (2C), 120.21 (2C), 125.48, 132.05, 133.47, 142.68, 145.64, 148.27, 149.45, 150.58 (d, 1C, J=32 Hz), 153.08 (d, 1C, J=48 Hz), 162.64 (d, 1C, J=949 Hz), 162.88, 167.92. ES-MS m/z 533 (M+H). Anal. Calcd. For C$_{31}$H$_{40}$N$_5$FO$_2$.0.2CH$_2$Cl$_2$: C, 68.05; H, 7.39; N, 12.72. Found: C, 68.26; H, 7.78; N, 13.08.

EXAMPLE 12

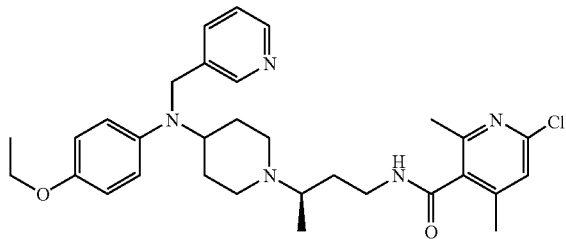

Preparation of 6-Chloro-N-((R)-3-{4-[(4-ethoxy-phenyl)-pyridin-3-ylmethyl-amino]-piperidin-1-yl}-butyl)-2,4-dimethyl-nicotinamide Following General Procedure A, a solution of 4-ethoxyaniline (0.48 g, 3.5 mmol) and (R)-3-(4-oxo-piperidin-1-yl) butyronitrile (0.49 g, 3.0 mmol) in CH$_2$Cl$_2$ (10 mL), was treated with glacial AcOH (3 drops) and NaBH(OAc)$_3$ (0.93 g, 4.4 mmol), stirring for 16 h at room temperature. Saturated aqueous NaHCO$_3$ solution (15 mL) and 1N NaOH (2 mL) was added and the phases were separated and the aqueous extracted with CH$_2$Cl$_2$ (2×15 mL). The combined organic extracts were dried (Na$_2$SO$_4$), filtered and concentrated under reduced pressure. The crude material was then purified by flash column chromatography on silica gel (1:1 EtOAc/CH$_2$Cl$_2$) to afford (R)-3-[4-(4-ethoxy-phenylamino)-piperidin-1-yl]-butyronitrile as a pale brown solid (90%). $^1$H NMR (CDCl$_3$) δ 1.20 (d, 3H, J=6.6 Hz), 1.37 (t, 2H, J=7.2 Hz), 1.39 (m, 2H), 2.05 (br d, 2H), 2.36 (m, 3H), 2.47 (m, 1H), 2.81 (m, 2H), 3.07 (sex, 1H, J=7.2 Hz), 3.28 (m, 2H), 3.96 (q, 2H, J=7.5 Hz), 6.55 (d, 2H, J=9.0 Hz), 6.76 (d, 2H, J=9.0 Hz).

A solution of the above nitrile (0.18 g, 0.63 mmol) and nicotinoyl chloride hydrochloride (0.45 g, 2.5 mmol) in THF (6 mL) was then treated with DIPEA (0.55 mL, 3.2 mmol) and stirred at 80° C. for 16 h. The reaction was cooled to room temperature, concentrated under reduced pressure, diluted with CH$_2$Cl$_2$ (10 mL) and washed with brine solution (2×10 mL). The combined organic extracts were then dried (Na$_2$SO$_4$), filtered and concentrated and the crude material purified by flash column chromatography on silica gel (25:1:0.1 CH$_2$Cl$_2$/MeOH/NH$_4$OH) to afford N-[(R)-1-(2-cyano-1-methyl-ethyl)-piperidin-4-yl]-N-(4-ethoxy-phenyl)-nicotinamide impure with nicotinyl chloride (88%).

The above mixture (0.22 g) in THF (5 mL) was treated with borane-THF complex (1N in THF, 5 mL, 5.6 mmol) at 70° C. for 16 h. Afterwards, the mixture was concentrated and MeOH (3 mL) and 6N HCl (3 mL) were added (to decomplex the boron) at 70° C. for 1 h. The solution was cooled to room temperature, and basisified to pH=10 with 10 N NaOH. The aqueous phase was then extracted with CH$_2$Cl$_2$ (3×15 mL), the combined organic phases dried (Na$_2$SO$_4$), filtered and concentrated under reduced pressure. The residue was purified by flash column chromatography on silica gel (25:1:0.1 CH$_2$Cl$_2$/MeOH/NH$_4$OH) to afford [1-((R)-3-amino-1-methyl-propyl)-piperidin-4-yl]-(4-ethoxy-phenyl)-pyridin-3-ylmethyl-amine as a colourless oil (120 mg, 57% over 2 steps). $^1$H NMR (CDCl$_3$) δ 0.95 (d, 3H, J=6.6 Hz), 1.39 (t, 2H, J=7.2 Hz), 1.35-1.70 (m, 4H), 1.84 (br d, 2H), 2.20 (t, 1H, J=11.6 Hz), 2.43 (t, 1H, J=11.3 Hz), 2.65-2.85 (m, 5H), 3.47 (m, 1H), 3.94 (q, 2H, J=7.5 Hz), 4.37 (s, 2H), 6.72 (m, 4H), 7.18 (m, 1H), 7.57 (d, 1H, J=6.0 Hz), 8.43 (d, 1H, J=3.3 Hz), 8.53 (s, 1H).

To a solution of the above compound (41 mg, 0.11 mmol) in DMF (0.5 mL) was added 6-chloro-2,4-dimethyl-nicotinic acid (30 mg, 0.16 mmol), HOBT (20 mg, 0.15 mmol), EDCI (29 mg, 0.15 mmol) and DIPEA (55 μL, 0.32 mmol). After the mixture was stirred at room temperature overnight brine (5 mL) was added, and the mixture was extracted with CH$_2$Cl$_2$ (2×5 mL). The organic extracts were combined and dried (Na$_2$SO$_4$). After filtration the solvent was removed under vacuum, and the residue was purified by flash chromatography on a silica gel column (50:1:0.1, CH$_2$Cl$_2$/MeOH/NH$_4$OH) to afford the title compound as a white solid (39 mg, 63%). $^1$H NMR (CDCl$_3$) δ 0.90 (m, 1H), 0.98 (d, 3H, J=6.6 Hz), 1.10 (m, 1H), 1.35 (t, 3H, J=7.2 Hz), 1.54 (m, 1H), 1.74 (m, 1H), 1.77 (br d, 2H, J=12.6 Hz), 2.12 (t, 1H, J=11.2 Hz), 2.30 (s, 3H), 2.51 (s, 3H), 2.52 (t, 1H, J=11.2 Hz), 2.65-2.90 (m, 3H), 3.23-3.43 (m, 2H), 3.85 (m, 1H), 3.88 (s, 2H), 3.92 (q, 2H, J=7.2 Hz), 6.60 (d, 2H, J=9.3 Hz), 6.74 (d, 2H, J=9.3 Hz), 7.00 (s, 1H), 7.20 (m, 1H), 7.61 (d, 1H, J=7.8 Hz), 8.44 (d, 1H, J=4.5 Hz), 8.51 (br s, 1H), 8.69 (br d, 1H). $^{13}$C NMR (CDCl$_3$) δ 13.79, 15.35, 19.14, 22.47, 29.79, 31.07, 31.16, 40.41, 44.03, 47.87, 52.41, 58.41, 60.72, 64.23, 115.70 (2C), 118.09 (2C), 122.83, 123.69, 133.16, 135.21, 136.22, 142.81, 147.84, 148.41, 149.21, 150.55, 152.57, 155.71, 167.54. ES-MS m/z 550 (M+H). Anal. Calcd. for C$_{31}$H$_{40}$N$_5$ClO$_2$.0.3CH$_2$Cl$_2$: C, 65.31; H, 7.11; N, 12.17. Found: C, 65.30; H, 7.30; N, 12.29.

EXAMPLE 13

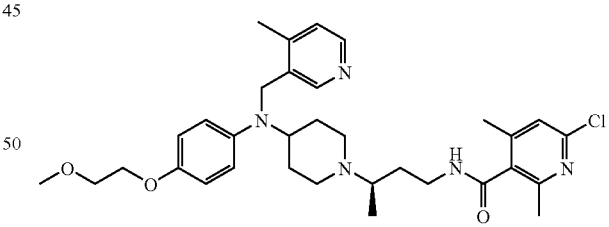

Preparation of 6-Chloro-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide Following General Procedure C: To a solution of [1-((R)-3-amino-1-methyl-propyl)-piperidin-4-yl]-[4-(2-methoxy-ethoxy)-phenyl]-(4-methyl-pyridin-3-ylmethyl)-amine (130 mg, 0.31 mmol) and 2,4-dimethyl-6-chloronicotinic acid (68 mg, 0.31 mmol) in DMF (4 mL) was added DIPEA (0.8 mL), HOBT (75 mg, 0.56 mmol) and EDCI (89 mg, 0.46 mmol) and the reaction stirred overnight. Purification of the crude product by column chromatography on silica gel (CH$_2$Cl$_2$/MeOH/NH$_4$OH,) gave 42 mg (23%) of the title compound as a white solid: $^1$H NMR (CDCl$_3$) δ 1.02 (d, 3H, J=6 Hz) 1.07-1.32 (m, 2H), 1.53-1.61 (m, 1H), 1.83-1.91 (m, 3H), 2.29 (s, 3H), 2.34 (s, 3H), 2.48 (s, 3H, 2.76-2.91 (m, 3H), 3.26-3.39 (m, 3H), 3.43 (s, 3H), 3.68-3.71 (m, 2H), 3.73-3.82 (m, 1H), 4.01-4.04 (m, 4H), 6.64 (d, 2H, J=9 Hz), 6.76 (d, 2H, J=9 Hz), 6.98 (s, 1H), 7.03 (d, 1H, J=6 Hz), 7.97 (br s, 1H), 8.26 (s, 1H), 8.29 (d, 1H, J=6 Hz). $^{13}$C NMR (CDCl$_3$) δ 13.60, 19.19, 22.52, 29.68, 30.58, 31.80, 39.70, 44.36, 47.79, 59.57, 60.04, 68.06, 71.53, 115.72, 120.29, 122.88, 125.50, 148.34, 149.57. ES-MS m/z 594 (M+H). Anal. Calcd. for C$_{33}$H$_{44}$N$_5$ClO$_3$.0.2CH$_2$Cl$_2$: C, 65.24; H, 7.32; N, 11.46. Found: C, 64.88; H, 7.36; N, 11.54.

EXAMPLE 14

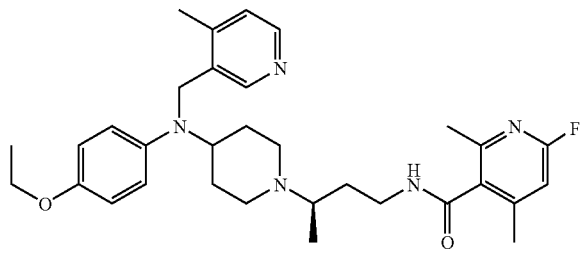

Preparation of N-((R)-3-{4-[(4-Ethoxy-phenyl)-(4-methyl-pyridin-3-ylmethyl)-amino]-piperidin-1-yl}-butyl)-6-fluoro-2,4-dimethyl-nicotinamide 4-Methyl-nicotinic acid hydrochloride (0.83 g, 4.8 mmol) was suspended in CH$_2$Cl$_2$ (25 mL) with DMF (6 drops). Oxalyl chloride (2.5 mL, 28.8 mmol) was added and the mixture stirred at room temperature for 2 h. The homogenous solution was then concentrated and dried in vacuo. To the solid was added THF (12.5 mL) and a solution of (R)-3-[4-(4-ethoxy-phenylamino)-piperidin-1-yl]-butyronitrile (0.69 g, 2.4 mmol) in THF (12.5 mL). The mixture was treated with Et$_3$N (1.0 mL, 7.2 mmol) and heated to reflux, stirring for 16 h. The reaction was cooled to room temperature, concentrated under reduced pressure, diluted with CH$_2$Cl$_2$ (100 mL) and washed with brine solution (100 mL). The aqueous phase was back-extracted with CH$_2$Cl$_2$ (100 mL) and the combined organic phases rewashed with brine (200 mL). The organic phase was dried (Na$_2$SO$_4$), filtered and concentrated and the crude material purified by flash column chromatography on silica gel (10:1 Et$_2$O/MeOH to afford N-[(R)-1-(2-cyano-1-methyl-ethyl)-piperidin-4-yl]-N-(4-ethoxy-phenyl)-4-methyl-nicotinamide contaminated with nicotinyl chloride byproduct (24%).

The above mixture (0.24 g) in THF (6 mL) was treated with borane-THF complex (1N in THF, 5.9 mL, 5.9 mmol) at 70° C. for 16 h. Afterwards, the mixture was concentrated and MeOH (3 mL) and 6N HCl (3 mL) were added (to decomplex the boron) at 70° C. for 1 h. The solution was cooled to room temperature, and basisified to pH=10 with 10N NaOH. The aqueous phase was then extracted with CH$_2$Cl$_2$ (3×15 mL), the combined organic phases dried (Na$_2$SO$_4$), filtered and concentrated under reduced pressure. The crude material was purified by flash column chromatography on silica gel (20:1:0.1 CH$_2$Cl$_2$MeOH/NH$_4$OH) to afford [1-((R)-3-amino-1-methyl-propyl)-piperidin-4-yl]-(4-ethoxy-phenyl)-(4-methyl-pyridin-3-ylmethyl)-amine as a colourless oil (86 mg, 37% over 2 steps). $^1$H NMR (CDCl$_3$) δ 0.95 (d, 3H, J=6.6 Hz), 1.37 (t, 2H, J=7.2 Hz), 1.38 (m, 1H), 1.60 (m, 3H), 1.88 (br d, 2H), 2.19 (t, 1H, J=11.6 Hz), 2.34 (s, 3H), 2.43 (t, 1H, J=11.3 Hz), 2.65-2.85 (m, 5H), 3.41 (m, 1H), 3.94 (q, 2H, J=7.5 Hz), 4.28 (s, 2H), 6.72 (m, 4H), 7.03 (d, 1H, J=5.9 Hz), 8.32 (d, 1H, J=4.3 Hz), 8.37 (s, 1H).

To a solution of the above compound (38 mg, 0.10 mmol) in DMF (0.5 mL) was added 6-fluoro-2,4-dimethyl-nicotinic acid (24 mg, 0.14 mmol), HOBT (18 mg, 0.13 mmol), EDCI (26 mg, 0.13 mmol) and DIPEA (50 µL, 0.29 mmol). After the mixture was stirred at room temperature overnight brine (5 mL) was added, and the mixture was extracted with CH$_2$Cl$_2$ (2×5 mL). The organic extracts were combined and dried (Na$_2$SO$_4$). After filtration the solvent was removed under vacuum, and the residue was purified by flash chromatography on a silica gel column (20:1:0.1, CH$_2$Cl$_2$/MeOH/NH$_4$OH) to afford the title compound as a white solid (36 mg, 68%). $^1$H NMR (CDCl$_3$) δ 0.99 (d, 3H, J=6.6 Hz), 1.00 (m, 1H), 1.19 (m, 1H), 1.35 (t, 3H, J=7.2 Hz), 1.54 (br, 1H), 1.73 (br, 1H), 1.80 (br d, 2H, J=12.6 Hz), 2.12 (t, 1H, J=11.2 Hz), 2.32 (s, 3H), 2.34 (s, 3H), 2.47 (s, 3H), 2.48 (t, 1H, J=11.2 Hz), 2.65-2.85 (m, 3H), 3.27 (m, 2H), 3.80 (m, 1H), 3.92 (q, 2H, J=7.2 Hz), 3.96 (s, 2H), 6.51 (s, 1H), 6.61 (d, 2H, J=9.6 Hz), 6.71 (d, 2H, J=9.0 Hz), 7.03 (br d, 1H, J=4.8 Hz), 8.07 (br. s, 1H), 8.26 (s, 1H), 8.29 (d, 1H, J=5.1 Hz). $^{13}$C NMR (CDCl$_3$) δ 13.78, 15.35, 19.10, 19.53, 22.30, 30.02, 30.86, 31.76, 39.95, 44.41, 47.81, 52.14, 59.06, 60.12, 64.15, 107.66 (d, 1C, J=146 Hz), 115.48 (2C), 120.20 (2C), 125.47, 131.97, 133.46, 142.60, 145.61, 148.32, 149.51, 150.55 (d, 1C, J=32 Hz), 153.39, 153.98 (d, 1C, J=61 Hz), 162.68 (d, 1C, J=949 Hz), 167.93. ES-MS m/z 548 (M+H). Anal. Calcd. for C$_{32}$H$_{42}$N$_5$FO$_2$.0.2CH$_2$Cl$_2$: C, 68.49; H, 7.57; N. 12.40. Found: C, 68.50; H, 7.69; N, 12.35.

EXAMPLE 15

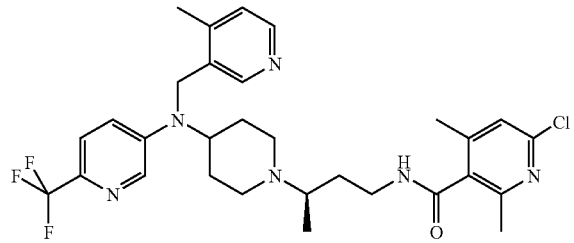

Preparation of 6-Chloro-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide To a stirred solution of 3-amino-6-(trifluoromethyl)pyridine (1.48 g, 9.13 mmol) in CH$_2$Cl$_2$ (20 mL) at room temperature were added (R)-3-(4-oxo-piperidin-1-yl)-butyronitrile (1.59 g, 9.59 mmol), glacial AcOH (0.52 mL, 9.13 mmol) and NaBH(OAc)$_3$ (2.71 g, 12.78 mmol) and the resultant solution was stirred at room temperature for 16 h. The reaction mixture was then poured into saturated aqueous NaHCO$_3$ (20 mL). The phases were separated and the aqueous layer was extracted with CH$_2$Cl$_2$ (3×50 mL). The combined organic extracts were dried (Na$_2$SO$_4$), filtered and concentrated under reduced pressure. The crude material was purified by flash column chromatography on silica gel (95:4:1, CH$_2$Cl$_2$/MeOH/NH$_4$OH) to generate (R)-3-[4-(6-trifluoromethyl-pyridin-3-ylamino)-piperidin-1-yl]-butyronitrile as an off-white solid (1.94 g, 68%). $^1$H-NMR (CDCl$_3$) δ 1.19 (d, 3H, J=8 Hz), 1.50 (m, 2H), 1.63 (s, 1H), 2.07 (m, 2H), 2.43 (m, 4H), 2.82 (m, 2H), 3.08 (sext, 1H, J=7 Hz), 3.32 (m, 1H), 4.01 (d, 1H, J=8 Hz), 6.86 (dd, 1H, J=3 Hz, 9 Hz), 7.43 (d, 1H, J=9 Hz), 8.02 (d, 1H, J=3 Hz).

To a stirred suspension of a 4-methylnicotinic acid (1.14 g, 6.58 mmol) in CH$_2$Cl$_2$ (20 mL) were added DMF (4 drops) followed by oxalyl chloride (1.72 mL, 19.74 mmol) and the resultant mixture was stirred at room temperature for 1.5 h. The mixture was concentrated and the acid chloride was dried in vacuo for 45 minutes. To the acid chloride was added a solution of (R)-3-[4-(6-trifluoromethyl-pyridin-3-ylamino)-piperidin-1-yl]-butyronitrile (1.37 g, 4.39 mmol) and 3,5-lutidine (1.50 mL, 13.16 mmol) in toluene (40 mL) and the mixture was stirred at reflux for 16 h. The mixture was concentrated in vacuo and then diluted with CH$_2$Cl$_2$ (30 mL) and 30 mL saturated aqueous NaHCO$_3$. The phases were separated and the aqueous layer was extracted with CH$_2$Cl$_2$ (3×40 mL). The organic layer was dried (Na$_2$SO$_4$), filtered and concentrated under reduced pressure. The crude material was purified by flash column chromatography on silica gel (97:2:1, Et$_2$O/MeOH/NH$_4$OH) to generate (R)-N-[1-(2-cyano-1-methyl-ethyl)-piperidin-4-yl]-4-methyl-N-(6-trifluoromethyl-pyridin-3-yl)-nicotinamide as a yellow oil (0.620 g, 33%). $^1$H-NMR (CDCl$_3$) δ 1.16 (d, 3H, J=6 Hz), 1.23 (m, 1H), 1.45 (m, 2H), 1.98 (m, 2H), 2.37 (m, 7H), 2.87 (m, 2H), 3.01 (m, 1H), 4.73 (m, 1H), 7.03 (m, 1H), 7.60 (m, 2H), 8.18 (m, 1H), 8.29 (m, 1H), 8.34 (m, 1H).

To a solution of (R)-N-[1-(2-cyano-1-methyl-ethyl)-piperidin-4-yl]-4-methyl-N-(6-trifluoromethyl-pyridin-3-yl)-nicotinamide (0.62 g, 1.44 mmol) in THF (25 mL) was added a solution of borane-THF in THF (1.0 M, 8.62 mL, 8.62 mmol) and the reaction was refluxed for 16 h. The reaction was cooled and carefully quenched with 9N HCl (14 mL) and heated to 65° C. for 2 h. The mixture was cooled and concentrated to remove the THF. The remaining aqueous solution was neutralized to pH>13 with 10N NaOH and diluted with CH$_2$Cl$_2$ (50 mL). The two phases were separated and the aqueous layer was extracted with CH$_2$Cl$_2$ (4×50 mL). The combined organic extracts were dried (Na$_2$SO$_4$) and purified by column chromatography on silica gel (92:7:1, CH$_2$Cl$_2$/MeOH/NH$_4$OH) to afford [1-((R)-3-amino-1-methyl-propyl)-piperidin-4-yl]-(4-methyl-pyridin-3-ylmethyl)-(6-trifluoromethyl-pyridin-3-yl)-amine as a pale yellow oil (0.355 g, 58%). $^1$H-NMR (CDCl$_3$) δ 0.98 (d, 3H, J=7 Hz), 1.41 (m, 2H), 1.51 (m, 2H), 1.68 (m, 4H), 1.91 (m, 2H), 2.72 (dt, 1H, J=2 Hz, 12 Hz), 2.35 (s, 3H), 2.51 (dt, 1H, J=2 Hz, 11 Hz), 2.72 (m, 3H), 2.86 (m, 2H), 3.84 (m, 1H), 4.46 (s, 2H), 6.90 (dd, 1H, J=3 Hz, 9 Hz), 7.11 (d, 1H, J=5 Hz), 7.42 (d, 1H, J=9 Hz), 8.08 (d, 1H, J=3 Hz), 8.24 (s, 1H), 8.39 (d, 1H, J=5 Hz).

[1-((R)-3-Amino-1-methyl-propyl)-piperidin-4-yl]-(4-methyl-pyridin-3-ylmethyl)-(6-trifluoromethyl-pyridin-3-yl)-amine (72.9 mg, 0.17 mmol), EDCI (36.4 mg, 0.19 mmol) and HOBT (25.7 mg, 0.19 mmol) were combined in DMF (5 mL) to give a pale yellow solution. To this solution was added 6-chloro-2,4-dimethyl-nicotinic acid hydrochloride salt (42.2 mg, 0.19 mmol) followed by DIPEA (66.3 μL, 0.38 mmol) and the resulting mixture was stirred at room temperature for 16 h. Standard workup according to General Procedure C gave the crude product as a tan oil. Purification by preparative TLC (91:8:1, CH$_2$Cl$_2$/MeOH/NH$_4$OH) afforded 6-chloro-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide as a white foam (61.1 mg, 60%). $^1$H NMR (CDCl$_3$) δ 1.03 (d, 3H, J=5 Hz), 1.23 (m, 1H), 1.40 (m, 1H), 1.65 (m, 3H), 1.76 (m, 1H), 1.91 (d, 2H, J=11 Hz), 2.24 (m, 1H), 2.30 (s, 3H), 2.41 (s, 3H), 2.51 (s, 3H), 2.61 (m, 1H), 2.85 (m, 3H), 3.40 (m 1H), 3.48 (s, 1H), 3.74 (m, 2H), 4.25 (s, 2H), 6.84 (dd, 1H, J=3 Hz, 9 Hz), 6.99 (s, 1H), 7.13 (d, 1H, J=5 Hz), 7.41 (m, 2H), 8.05 (d, 1H, J=3 Hz), 8.17 (s, 1H), 8.38 (d, 1H, J=5 Hz). ES-MS m/z 589 (M+H), 612 (M+Na). Anal. Calcd. For C$_{30}$H$_{36}$ClF$_3$N$_6$O: C, 61.17; H, 6.16; Cl, 6.02; F, 9.67; N, 14.27.

EXAMPLE 16

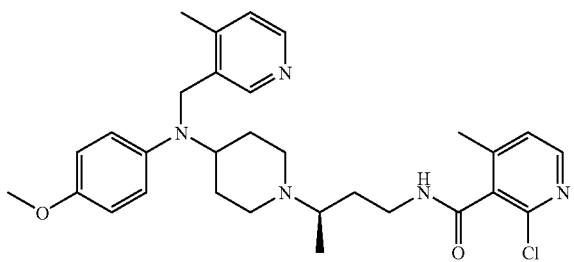

Preparation of 2-Chloro-N-((R)-3-{4-[(4-methoxy-phenyl)-(4-methyl-pyridin-3-ylmethyl)-amino]-piperidin-1-yl}-butyl)-4-methyl-nicotinamide To a solution of 3-bromo-2-chloro-4-picoline (0.65 g, 3.14 mmol) in Et$_2$O (30 mL) cooled to −78° C. was added t-BuLi (1.7M in hexanes) (3.9 mL, 6.59 mmol) to give an orange solution. The solution was stirred at −78° C. for 2 h and then CO$_2$ was bubbled through the solution for 20 minutes at −78° C. and then 30 minutes at 0° C. prior to quenching with water (10 mL) to give a biphasic system. The Et$_2$O was removed in vacuo and the aqueous mixture was dry loaded onto silica gel. Purification by column chromatography on silica gel (MeCN:MeOH:NH$_4$OH, 8:1:1, v/v/v) afforded 2-chloro-4-methyl-nicotinic acid (0.39 g, 72%) as a white crystalline solid. $^1$H NMR (CD$_3$OD) δ 2.39 (s, 3H), 7.23 (d, 1H, J=5.1 Hz), 8.12 (d, 1H, J=5.1 Hz).

(R)-[1-(3-Amino-1-methyl-propyl)-piperidin-4-yl]-(4-methoxy-phenyl)-(4-methyl-pyridin-3-ylmethyl)-amine (0.077 g, 0.20 mmol), EDCI (0.043 g, 0.22 mmol) and HOBT (0.030 g, 0.22 mmol) were combined in DMF (5 mL) to give a pale yellow solution. To this solution was added 2-chloro-4-methyl-nicotinic acid (0.038 g, 0.22 mmol) followed by DIPEA (42 μL, 0.24 mmol) and the resulting mixture was stirred at 25° C. for 16 h. Standard workup according to General Procedure C gave the crude product as a tan oil. Purification by column chromatography on silica gel (Et$_2$O:MeOH:NH$_4$OH, 90:8:2, v/v/v) afforded 2-chloro-N-((R)-3-{4-[(4-methoxy-phenyl)-(4-methyl-pyridin-3-ylmethyl)-amino]-piperidin-1-yl}-butyl)-4-methyl-nicotinamide (0.062 g, 57%) as a white foam. $^1$H NMR (CDCl$_3$) δ 0.98 (d, 3H, J=6.0 Hz), 1.06 (m, 1H), 1.22 (m, 1H), 1.57 (m, 2H), 1.81 (m, 3H), 2.11 (br t, 1H), 2.36 (s, 6H), 2.53 (br t, 1H), 2.75-2.88 (m, 3H), 3.20-3.33 (m, 2H), 3.71 (s, 3H), 3.82 (m, 1H), 3.90 (m, 2H), 6.63 (d, 2H, J=9.0 Hz), 6.71 (d, 2H, J=9.0 Hz), 6.96 (d, 1H, J=6.0 Hz), 7.03 (d, 1H, J=6.0 Hz), 7.98 (d, 1H, J=6.0 Hz), 8.25 (s, 1H), 8.30 (d, 1H, J=3.0 Hz), 8.42 (br s, 1H). $^{13}$C NMR (CDCl$_3$) δ 13.3, 18.9, 19.1, 29.6, 30.4, 30.9, 39.9, 43.8, 47.0, 51.9, 55.5, 59.2, 60.0, 114.4, 119.9, 124.2, 125.1, 148.0, 149.0, 149.3. ES-MS m/z 536 (M+H), 558 (M+Na). Anal.

Calcd. for $C_{30}H_{38}N_5O_2Cl.0.2$ $CH_2Cl_2$: C, 65.58; H, 7.00; N, 12.66. Found: C, 65.64; H, 7.15; N, 12.79.

EXAMPLE 17

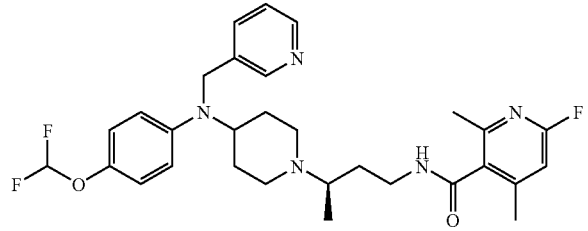

Preparation of N-((R)-3-{4-[(4-Difluoromethoxy-phenyl)-pyridin-3-ylmethyl-amino]-piperidin-1-yl}-butyl)-6-fluoro-2,4-dimethyl-nicotinamide Following General Procedure A, a solution of 4-difluoromethoxyaniline (0.50 g, 3.1 mmol) and (R)-3-(4-oxo-piperidin-1-yl)-butyronitrile (0.44 g, 2.6 mmol) in $CH_2Cl_2$ (10 mL), was treated with glacial AcOH (3 drops) and NaBH$(OAc)_3$ (0.83 g, 3.9 mmol), stirring for 16 h at room temperature. Saturated aqueous $NaHCO_3$ solution (15 mL) and 1N NaOH (2 mL) was added and the phases were separated and the aqueous extracted with $CH_2Cl_2$ (2×15 mL). The combined organic extracts were dried ($Na_2SO_4$), filtered and concentrated under reduced pressure. The crude material was then purified by flash column chromatography on silica gel (1:1 EtOAc/$CH_2Cl_2$) to afford (R)-3-[4-(4-difluoromethoxy-phenylamino)-piperidin-1-yl]-butyronitrile as a white solid (0.61 g, 76%). $^1$H NMR (CDCl$_3$) δ 1.20 (d, 3H, J=6.6 Hz), 1.43 (m, 2H), 2.06 (br d, 2H), 2.36 (m, 3H), 2.52 (m, 1H), 2.82 (m, 2H), 3.07 (sex, 1H, J=7.2 Hz), 3.24 (m, 1H), 6.36 (t, 1H, J=75 Hz), 6.54 (d, 2H, J=9.0 Hz), 6.95 (d, 2H, J=9.0 Hz).

A solution of the above nitrile (0.20 g, 0.65 mmol) and nicotinoyl chloride hydrochloride (0.46 g, 2.6 mmol) in THF (6 mL) was then treated with DIPEA (0.56 mL, 3.2 mmol) and stirred at 80° C. for 16 h. The reaction was cooled to room temperature, concentrated under reduced pressure, diluted with $CH_2Cl_2$ (10 mL) and washed with brine solution (2×10 mL). The combined organic extracts were then dried ($Na_2SO_4$), filtered and concentrated and the crude material purified by flash column chromatography on silica gel (50:1:0.1 $CH_2Cl_2$/MeOH/NH$_4$OH) to afford N-[(R)-1-(2-cyano-1-methyl-ethyl)-piperidin-4-yl]-N-(4-difluoromethoxy-phenyl)-nicotinamide as a pale yellow oil (104 mg, 39%).

The above compound (104 mg, 0.25 mmol) was dissolved in THF (5 mL) and treated with borane-THF complex (1N in THF, 2.5 mL, 2.5 mmol) at 70° C. for 16 h. Afterwards, the mixture was concentrated and MeOH (1 mL) and 6N HCl (1 mL) were added (to decomplex the boron) at 70° C. for 1 h. The solution was cooled to room temperature, and basisified to pH=10 with 10N NaOH. The aqueous phase was then extracted with $CH_2Cl_2$ (3×10 mL), the combined organic phases dried ($Na_2SO_4$), filtered and concentrated under reduced pressure. The residue was purified by flash column chromatography on silica gel (15:1:0.1 $CH_2Cl_2$/MeOH/NH$_4$OH) to afford [1-((R)-3-amino-1-methyl-propyl)-piperidin-4-yl]-(4-difluoromethoxy-phenyl)-pyridin-3-ylmethyl-amine as a colourless oil (45 mg, 45%). $^1$H NMR (CDCl$_3$) δ 0.97 (d, 3H, J=6.6 Hz), 1.41 (m, 1H), 1.65 (m, 3H), 1.84 (br d, 2H), 2.23 (t, 1H, J=11.6 Hz), 2.47 (t, 1H, J=11.3 Hz), 2.65-2.85 (m, 5H), 3.66 (m, 1H), 4.46 (s, 2H), 6.36 (t, 1H, J=75 Hz), 6.63 (d, 2H, J=9.0 Hz), 6.95 (d, 2H, J=9.0 Hz), 7.22 (m, 1H), 7.54 (d, 1H, J=6.0 Hz), 8.46 (d, 1H, J=3.3 Hz), 8.53 (s, 1H).

To a solution of the above compound (50 mg, 0.12 mmol) in DMF (0.5 mL) was added 6-fluoro-2,4-dimethyl-nicotinic acid hydrochloride (38 mg, 0.19 mmol), HOBT (23 mg, 0.17 mmol), EDCI (33 mg, 0.17 mmol) and DIPEA (100 µL, 0.62 mmol). After the mixture was stirred at room temperature overnight brine (5 mL) was added, and the mixture was extracted with $CH_2Cl_2$ (2×5 mL). The organic extracts were combined and dried ($Na_2SO_4$). After filtration the solvent was removed under vacuum, and the residue was purified by flash chromatography on a silica gel column (20:1, $CH_2Cl_2$/MeOH) to afford the title compound as a white solid (38 mg, 55%). $^1$H NMR (CDCl$_3$) 67 0.99 (d, 3H, J=6.6 Hz), 1.00 (m, 1H), 1.17 (m, 1H), 1.57 (m, 1H), 1.74 (br, 1H), 1.78 (br d, 2H, J=12.6 Hz), 2.18 (t, 1H, J=11.2 Hz), 2.34 (s, 3H), 2.48 (s, 3H), 2.58 (t, 1H, J=11.2 Hz), 2.70-2.95 (m, 3H), 3.30 (m, 1H), 3.57 (m, 1H), 3.86 (m, 1H), 3.92 (s, 2H), 6.35 (t, 1H, J=75 Hz), 6.54 (s, 1H), 6.61 (d, 2H, J=9.6 Hz), 6.91 (d, 2H, J=9.0 Hz), 7.24 (m, 1H), 7.58 (d, 1H, J=7.8 Hz), 8.48 (br, 2H), 8.54 (br, 1H). $^{13}$C NMR (CDCl$_3$) δ 13.81, 19.51, 22.27, 29.58, 30.81, 31.26, 40.35, 44.04, 47.09, 52.41, 53.85, 57.17, 60.67, 107.70 (d, 1C, J=146 Hz), 113.29, 115.18 (2C), 116.73 (t, 1C, J=1030 Hz), 121.64 (2C), 123.84, 132.23, 134.69, 135.41, 142.95, 146.52, 148.67 (2C), 150.84 (d, 1C, J=32 Hz), 154.09 (d, 1C, J=61 Hz), 162.70 (d, 1C, J=949 Hz), 167.72. ES-MS m/z 556 (M+H). Anal. Calcd. for $C_{30}H_{36}N_5F_3O_2.0.1CH_2Cl_2$: C, 64.09; H, 6.47; N, 12.41. Found: C, 63.94; H, 6.54; N, 12.33.

EXAMPLE 18

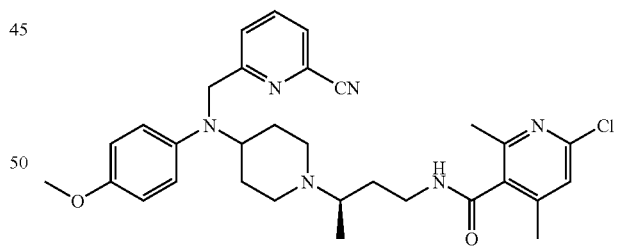

Preparation of 6-Chloro-N-((R)-3-{4-[(6-cyano-pyridin-2-ylmethyl)-(4-methoxy-phenyl)-amino]-piperidin-1-yl}-butyl)-2,4-dimethyl-nicotinamide Using General Procedure C, (R)-[1-(3-amino-1-methyl-propyl)-piperidin-4-yl]-(4-methoxy-phenyl)-amine (1.86 g, 6.71 mmol), 6-chloro-2,4-dimethyl-nicotinic acid (1.64 g, 7.39 mmol), EDCI (1.54 g, 8.05 mmol), HOBT (1.09 g, 8.05 mmol) and DIPEA (2.92 mL, 16.78 mmol) were combined in CH$_2$Cl$_2$ (67 mL) for 18.5 h. The reaction was quenched with a saturated NaHCO$_3$ solution (20 mL) and the phases were separated. The aqueous layer was extracted with CH$_2$Cl$_2$ (4×60 mL). The combined organic layers were dried (Na$_2$SO$_4$) and concentrated in vacuo to afford a yellow foamy solid. Purification by flash chromatography on silica gel using CH$_2$Cl$_2$/MeOH/NH$_4$OH (195:4:1) gave 6-chloro-N-(R)-{3-[4-(4-methoxy-phenylamino)-piperidin-1-yl]-butyl}-2,4-dimethyl-nicotinamide (2.94 g, 98%) as a yellow solid. $^1$H NMR (CDCl$_3$) δ 0.45-0.57 (m, 1H), 0.66-0.78 (m, 1H), 0.99 (d, J=6.5 Hz, 3H), 1.47-1.56 (m, 1H), 1.68-1.82 (m, 1H), 1.85-1.94 (m, 2H), 2.11 (dt, J=11.4, 2.2 Hz, 1H), 2.31 (s, 3H), 2.53 (s, 3H), 2.61-2.70 (m, 2H), 2.74-2.88 (m, 2H), 2.98-3.08 (m, 1H), 3.23-3.33 (m, 1H), 3.73 (s, 3H), 3.81-3.91 (m, 1H), 6.52 (d, J=8.8 Hz, 2H), 6.75 (d, J=8.8 Hz, 2H), 7.05 (s, 1H), 9.06 (bs, 1H).

2-Methyl-6-cyanopyridine (0.17 g, 1.4 mmol), NBS (0.18 g, 1.0 mmol) and benzoyl peroxide (35 mg, 0.14 mmol) were dissolved in CCl$_4$ (5 mL) and stirred at 70° C. for 16 h. Another 0.5 eq. of NBS and 0.2 eq. of initiator were then added, and the reaction stirred with heat for 64 more h. The mixture was then cooled and concentrated and the crude material purified by flash column chromatography using silica gel (10:1 hexanes/EtOAc). This gave a pale yellow liquid of approximately 1:1 starting, material to brominated product that was carried forward in the next reaction (111 mg, 55%).

The material isolated from above and 6-chloro-N-(R)-{3-[4-(4-methoxy-phenylamino)-piperidin-1-yl]-butyl}-2,4-dimethyl-nicotinamide (62 mg, 0.14 mmol) were dissolved in CH$_3$CN (0.7 mL), and treated with DIPEA (35 μL, 0.18 mmol) for 16 h at room temperature. Brine (5 mL) was added, and the mixture was extracted with CH$_2$Cl$_2$ (2×5 mL). The organic extracts were combined and dried (Na$_2$SO$_4$). After filtration the solvent was removed under vacuum, and the residue was purified by flash chromatography on a silica gel column (NH$_3$/Et$_2$O) to afford the title compound as a white solid (27 mg, 34%). $^1$H NMR (CDCl$_3$) δ 0.98 (d, 3H, J=6.6 Hz), 1.00 (m, 1H), 1.15 (m, 1H), 1.54 (m, 1H), 1.73 (m, 3H), 2.11 (t, 1H, J=11.2 Hz), 2.35 (s, 3H), 2.50 (s, 3H), 2.51 (t, 1H, J=11.2 Hz), 2.72 (br, 1H), 2.84 (m, 2H), 3.30 (m, 2H), 3.72 (s, 3H), 3.80 (m, 1H), 4.03 (s, 2H), 6.66 (d, 2H, J=9.0 Hz), 6.75 (d, 2H, J=9.0 Hz), 7.12 (s, 1H), 7.50 (m, 2H), 7.70 (t, 1H, J=7.8 Hz), 8.40 (br, 1H). $^{13}$C NMR (CDCl$_3$) δ 13.77, 19.21, 22.46, 29.99, 31.12, 31.39, 40.30, 43.97, 52.41 (2C), 55.99, 59.15, 60.51, 115.02 (2C), 117.85, 118.64 (2C), 123.35, 123.47, 125.62, 126.95, 129.06, 133.31, 137.77, 142.71, 147.66, 148.42, 150.43, 155.53, 163.77, 167.65. ES-MS m/z 561 (M+H). Anal. Calcd. for C$_{31}$H$_{37}$N$_6$ClO$_2$.0.2CH$_2$Cl$_2$: C, 64.82; H, 6.52; N, 14.54. Found: C, 65.14; H, 6.64; N, 14.28.

EXAMPLE 19

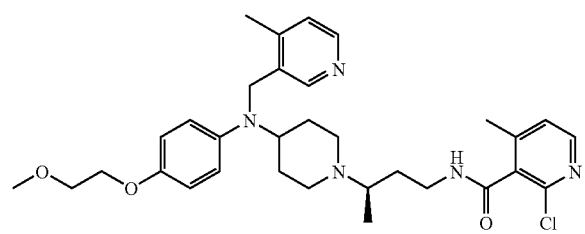

Preparation of 2-Chloro-N-((R)-3-{4-[[4-(2-methoxy-ethoxy)-phenyl]-(4-methyl-pyridin-3-ylmethyl)-amino]-piperidin-1-yl}-butyl)-4-methyl-nicotinamide (R)-[1-(3-Amino-1-methyl-propyl)-piperidin-4-yl]-[4-(2-methoxy-ethoxy)-phenyl]-(4-methyl-pyridin-3-ylmethyl)-amine (0.065 g, 0.15 mmol), EDCI (0.033 g, 0.17 mmol) and HOBT (0.023 g, 0.17 mmol) were combined in DMF (5 mL) to give a pale yellow solution. To this solution was added 2-chloro-4-methyl-nicotinic acid (0.029 g, 0.17 mmol) followed by DIPEA (54 μL, 0.31 mmol) and the resulting mixture was stirred at 25° C. for 16 h. Standard workup according to General Procedure C gave the crude product as a tan oil. Purification by column chromatography on silica gel (Et$_2$O: MeOH:NH$_4$OH, 88:10:2, v/v/v) afforded 2-chloro-N-((R)-3-{4-[[4-(2-methoxy-ethoxy)-phenyl]-(4-methyl-pyridin-3-ylmethyl)-amino]-piperidin-1-yl}-butyl)-4-methyl-nicotinamide (0.068 g, 76%) as a white foam. $^1$H NMR (CDCl$_3$) δ 0.98 (d, 3H, J=6.0 Hz), 1.06 (m, 1H), 1.25 (m, 1H), 1.58 (m, 2H), 1.82 (m, 3H), 2.11 (br t, 1H), 2.35 (s, 6H), 2.50 (br t, 1H), 2.75-2.89 (m, 3H), 3.21-3.33 (m, 2H), 3.42 (s, 3H), 3.69 (t, 2H, J=4.5 Hz), 3.82 (m, 1H), 3.90 (m, 3H), 4.01 (t, 2H, J=4.5 Hz), 6.59 (d, 2H, J=9.0 Hz), 6.72 (d, 2H, J=9.0 Hz), 6.96 (d, 1H, J=6.0 Hz), 7.03 (d, 1H, J=6.0 Hz), 7.99 (d, 1H, J=6.0 Hz), 8.25 (s, 1H), 8.30 (d, 1H, J=3.0 Hz), 8.38 (br s, 1H). ES-MS m/z 580 (M+H). Anal. Calcd. for C$_{32}$H$_{42}$N$_5$O$_3$Cl.0.4 CH$_2$Cl$_2$: C, 63.37; H, 7.02; N, 11.40. Found: C, 63.28; H, 7.16; N, 11.60.

EXAMPLE 20

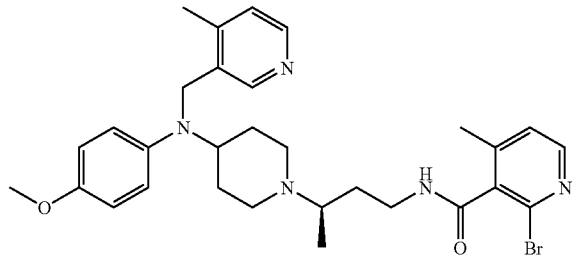

Preparation of 2-Bromo-N-((R)-3-{4-[(4-methoxy-phenyl)-(4-methyl-pyridin-3-ylmethyl)-amino]-piperidin-1-yl}-butyl)-4-methyl-nicotinamide Bromine (1.9 mL, 37.0 mmol) was added dropwise to a slurry of 2-amino-4-picoline (4.00 g, 37.0 mmol) in fuming sulfuric acid (20 mL) at 0° C. The resulting red/brown mixture was stirred at reflux for 2 h and then poured into ~200 g ice to give a yellow slurry. 10N NaOH was added slowly to the mixture until pH ~12 and then the mixture was extracted with CH$_2$Cl$_2$ (3×50 mL), dried (Na$_2$SO$_4$), filtered and concentrated in vacuo to yield 3,5-dibromo-4-methyl-pyridin-2-ylamine (5.35 g, 54%) as a pale orange solid. $^1$H NMR (CDCl$_3$) δ 2.51 (s, 3H), 4.94 (br s, 2H), 8.05 (s, 1H).

To a solution of 3,5-dibromo-4-methyl-pyridin-2-ylamine (3.38 g, 12.7 mmol) in THF (60 mL) cooled to −78° C. was added n-BuLi (1.9M in pentane) (13.4 mL, 25.4 mmol) to give an orange solution. The solution was stirred at −78° C. for 1 h and then quenched with water (10 mL). The pH of the mixture was adjusted to ~12 with 10N NaOH and then extracted with $CH_2Cl_2$ (3×30 mL), dried ($Na_2SO_4$), filtered and concentrated in vacuo to give an orange oil. Purification by column chromatography on silica gel ($Et_2O$) afforded 3-bromo-4-methyl-pyridin-2-ylamine (1.68 g, 71%) as a pale yellow solid. $^1$H NMR ($CDCl_3$) δ 2.32 (s, 3H), 5.00 (br s, 2H), 6.52 (d, 1H, J=6.0 Hz), 7.84 (d, 1H, J=6.0 Hz).

Bromine (0.35 mL, 6.8 mmol) was added dropwise to a solution of 3-bromo-4-methyl-pyridin-2-ylamine (0.44 g, 2.4 mmol) in 48% HBr (3 mL) at −10° C. to give an orange slurry. After 5 minutes $NaNO_2$ (0.47 g, 6.8 mmol), dissolved in water (1.5 mL), was added dropwise over 5 minutes. The dark brown mixture was slowly warmed to 10° C. over 3.5 h and then cooled to 0° C. and quenched with 10N NaOH until pH~12. The resulting orange slurry was extracted with $CH_2Cl_2$ (3×50 mL), dried ($Na_2SO_4$), filtered and concentrated in vacuo to give an orange/brown solid. Purification by column chromatography on silica gel (Hexanes:$Et_2O$, 7:3, v/v) yielded 2,3-dibromo-4-methyl-pyridine (0.28 g, 47%) as a pale yellow solid. $^1$H NMR ($CDCl_3$) δ 2.48 (s, 3H), 7.11 (d, 1H, J=6.0 Hz), 8.16 (d, 1H, J=6.0 Hz).

To a solution of 2,3-dibromo-4-methyl-pyridine (0.28 g, 1.12 mmol) in $Et_2O$ (20 mL) cooled to −78° C. was added t-BuLi (1.7M in hexanes) (1.0 mL, 1.68 mmol) to give an orange solution. The solution was stirred at −78° C. for 2 h and then $CO_2$ was bubbled through the solution for 20 minutes at −78° C. and then 30 minutes at r.t. prior to quenching with water (10 mL) to give a biphasic system. The $Et_2O$ was removed in vacuo and the aqueous mixture was dry loaded onto silica gel. Purification by column chromatography on silica gel (MeCN:MeOH:$NH_4OH$, 7:2:1, v/v/v) afforded 2-bromo-4-methyl-nicotinic acid (0.135 g, 56%) as a white crystalline solid. $^1$H NMR ($CD_3OD$) δ 2.38 (s, 3H), 7.23 (d, 1H, J=5.1 Hz), 8.06 (d, 1H, J=5.1 Hz).

(R)-[1-(3-Amino-1-methyl-propyl)-piperidin-4-yl]-(4-methoxy-phenyl)-(4-methyl-pyridin-3-ylmethyl)-amine (0.070 g, 0.18 mmol), EDCI (0.039 g, 0.20 mmol) and HOBT (0.027 g, 0.20 mmol) were combined in DMF (5 mL) to give a pale yellow solution. To this solution was added 2-bromo-4-methyl-nicotinic acid (0.043 g, 0.20 mmol) followed by DIPEA (38 μL, 0.22 mmol) and the resulting mixture was stirred at 25° C. for 16 h. Standard workup according to General Procedure C gave the crude product as a tan oil. Purification by column chromatography on silica gel ($Et_2O$: MeOH:$NH_4OH$, 89:10:1, v/v/v) afforded 2-bromo-N-((R)-3-{4-[(4-methoxy-phenyl)-(4-methyl-pyridin-3-ylmethyl)-amino]-piperidin-1-yl}-butyl)-4-methyl-nicotinamide (0.040 g, 38%) as a white foam. $^1$H NMR ($CDCl_3$) δ 0.98 (d+m, 4H,), 1.07 (m, 1H), 1.57 (m, 2H), 1.84 (m, 3H), 2.13 (br t, 1H), 2.36 (s, 6H), 2.53 (br t, 1H), 2.75-2.88 (m, 3H), 3.24-3.33 (m, 2H), 3.71 (s, 3H), 3.82 (m, 1H), 3.88 (m, 2H), 6.61 (d, 2H, J=9.0 Hz), 6.69 (d, 2H, J=9.0 Hz), 6.97 (d, 1H, J=6.0 Hz), 7.03 (d, 1H, J=6.0 Hz), 7.94 (d, 1H, J=6.0 Hz), 8.25 (s, 1H), 8.30 (d, 1H, J=6.0 Hz), 8.52 (br s, 1H). $^{13}$C NMR ($CDCl_3$) δ. ES-MS m/z 582 (M+H), 604 (M+Na). Anal. Calcd. for $C_{30}H_{38}N_5O_2Br.0.25CH_2Cl_2$: C, 60.37; H, 6.45; N, 11.64. Found: C, 60.34; H, 6.47; N, 11.52.

EXAMPLE 21

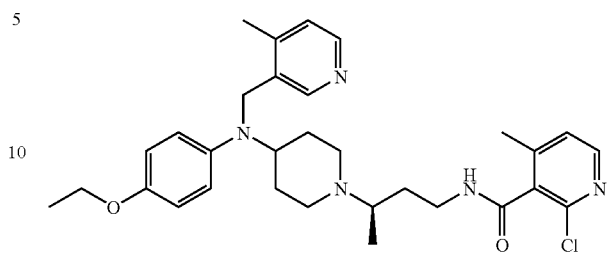

Preparation of 2-Chloro-N-((R)-3-{4-[(4-ethoxy-phenyl)-(4-methyl-pyridin-3-ylmethyl)-amino]-piperidin-1-yl}-butyl)-4-methyl-nicotinamide

[1-((R)-3-Amino-1-methyl-propyl)-piperidin-4-yl]-(4-ethoxy-phenyl)-(4-methyl-pyridin-3-ylmethyl)-amine (58.0 mg, 0.15 mmol), EDCI (30.9 mg, 0.16 mmol) and HOBT (21.8 mg, 0.16 mmol) were combined in DMF (5 mL) to give a pale yellow solution. To this solution was added 2-chloro-4-methyl-nicotinic acid (27.5 mg, 0.16 mmol) followed by DIPEA (30.6 μL, 0.18 mmol) and the resulting mixture was stirred at room temperature for 16 h. Standard workup according to General Procedure C gave the crude product as a tan oil. Purification by preparative TLC (91:8:1, $CH_2Cl_2$/MeOH/$NH_4OH$) afforded 2-chloro-N-((R)-3-{4-[(4-ethoxy-phenyl)-(4-methyl-pyridin-3-ylmethyl)-amino]-piperidin-1-yl}-butyl)-4-methyl-nicotinamide as a white foam (49.2 mg, 61%). $^1$H NMR ($CDCl_3$) δ 1.02 (d, 3H, J=5 Hz), 1.25 (s, 1H), 1.35 (t, 4H, J=5 Hz), 1.58 (m, 1H), 1.84 (m, 4H), 2.15 (m, 1H), 2.35 (s, 6H), 2.54 (m, 1H), 2.86 (m, 3H), 3.31 (m, 2H), 3.78 (m, 1H), 3.93 (m, 4H), 6.66 (dd, 4H, J=9 Hz, 24 Hz), 7.00 (dd, 2H, J=6 Hz, 18 Hz), 8.01 (d, 1H, J=6 Hz), 8.35 (m, 2H). ES-MS m/z 550 (M+H). Anal. Calcd. For $C_{31}H_{40}ClN_5O_2$: C, 67.68; H, 7.33; Cl, 6.44; N, 12.73.

EXAMPLE 22

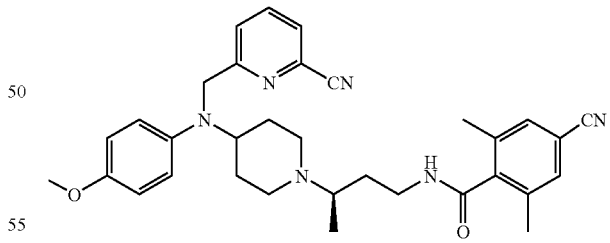

Preparation of 4-Cyano-N-((R)-3-{4-[(6-cyano-pyridin-2-ylmethyl)-(4-methoxy-phenyl)-amino]1-piperidin-1-yl}-butyl)-2,6-dimethyl-benzamide (R)-3-[4-(4-Methoxy-phenylamino)-piperidin-1-yl]-butyronitrile (0.53 g, 1.94 mmol) was dissolved in $NH_3$ saturated MeOH (15 mL), treated with Raney nickel (excess), and placed under 45 psi H$_2$ on a Parr shaker for 8 h. In a standard work-up the mixture was diluted with MeOH and filtered through celite. The cake was washed with MeOH and the combined filtrate was concentrated to give crude (R)-[1-(3-amino-1-methyl-propyl)-piperidin-4-yl]-(4-methoxy-phenyl)-amine as a pale yellow oil (0.54 g, quant.). TLC analysis and $^1$H NMR confirmed the crude product to be pure with no further purification required. $^1$H NMR (CDCl$_3$) δ 0.98 (d, 3H, J=6.0 Hz), 1.36 (m, 5H), 1.71 (m, 2H), 2.03 (d, 2H, J=12.0 Hz), 2.23 (br t, 1H), 2.42 (br t, 1H), 2.49-2.71 (m, 4H), 3.17 (m, 2H), 3.76 (s, 3H), 6.57 (d, 2H, J=9.0 Hz), 6.75 (d, 2H, J=9.0 Hz).

To a solution of the above amine (0.54 g, 1.94 mmol) in CH$_2$Cl$_2$ (20 mL) was added Boc$_2$O (0.53 g, 2.39 mmol) and Et$_3$N (0.54 mL, 3.82 mmol) and the resulting solution stirred at room temperature for 16 h. Standard basic workup gave the crude product as a brown oil. Purification by column chromatography on silica gel (CH$_2$Cl$_2$:MeOH:NH$_4$OH, 94:5:1, v/v/v) afforded pure (R)-{3-[4-(4-methoxy-phenylamino)-piperidin-1-yl]-butyl}-carbamic acid tert-butyl ester as a yellow oil (0.68 g, 95%). $^1$H NMR (CDCl$_3$) δ 0.96 (d, 3H, J=6.0 Hz), 1.36 (m, 3H), 1.44 (s+m, 10H), 1.67 (m, 1H), 2.05 (d, 2H, J=12.0 Hz), 2.19 (br t, 1H), 2.51 (br t, 1H), 2.69-2.82 (m, 3H), 3.07-3.17 (m, 3H), 3.32 (m, 1H), 3.74 (s, 3H), 6.57 (d, 2H, J=9.0 Hz), 6.75 (d, 2H, J=9.0 Hz).

Using General Procedure E, (R)-{3-[4-(4-methoxy-phenylamino)-piperidin-1-yl]-butyl}-carbamic acid tert-butyl ester (0.681 g, 1.81 mmol), 6-bromomethyl-pyridine-2-carbonitrile (0.535 g, 2.71 mmol) and DIPEA (630 μL, 3.62 mmol) in CH$_3$CN (20 mL) at 55° C. for 16 h gave the crude product as a pale brown oil. Purification by column chromatography on silica gel (CH$_2$Cl$_2$:MeOH:, 95:5, v/v) afforded (R)-(3-{4-[(6-cyano-pyridin-2-ylmethyl)-(4-methoxy-phenyl)-amino]-piperidin-1-yl}-butyl)-carbamic acid tert-butyl ester (0.696 g, 78%) as a yellow crystalline solid. $^1$H NMR (CDCl$_3$) δ 0.95 (d, 3H, J=6.0 Hz), 1.40 (s+m, 11H), 1.65 (m, 4H), 1.86 (m, 2H), 2.13 (br t, 1H), 2.54 (br t, 1H), 2.73-2.86 (m, 3H), 3.06 (m, 1H), 3.31 (m, 1H), 3.54 (m, 1H), 3.73 (s, 3H), 4.50 (s, 2H), 6.06 (br s, 1H), 6.68 (d, 2H, J=9.0 Hz), 6.76 (d, 2H, J=9.0 Hz), 7.52 (d, 1H, J=6.0 Hz), 7.54 (d, 1H, J=6.0 Hz), 7.70 (t, 1H, J=6.0 Hz).

(R)-(3-{4-[(6-Cyano-pyridin-2-ylmethyl)-(4-methoxy-phenyl)-amino]-piperidin-1-yl}-butyl)-carbamic acid tert-butyl ester (0.070 g, 0.14 mmol) was dissolved in a 3:1 mixture of CH$_2$Cl$_2$ and TFA and the mixture was stirred at room temperature for 1 h. The solvent was removed in vacuo and the resulting brown oil dried in vacuo (high vacuum system) for 2 h. The resulting amine, EDCI (0.030 g, 0.0.16 mmol) and HOBT (0.021 g, 0.16 mmol) were combined in DMF (5 mL) to give a pale yellow solution. To this solution was added 4-cyano-2,6-dimethyl-benzoic acid (0.027 g, 0.16 mmol) followed by DIPEA (163 μL, 0.94 mmol) and the resulting mixture was stirred at 25° C. for 16 h. Standard workup according to General Procedure C gave the crude product as a tan oil. Purification by column chromatography on silica gel (Et$_2$O:MeOH:NH$_4$OH, 90:8:2, v/v/v) afforded 4-cyano-N-((R)-3-{4-[(6-cyano-pyridin-2-ylmethyl)-(4-methoxy-phenyl)-amino]-piperidin-1-yl}-butyl)-2,6-dimethyl-benzamide (0.043 g, 55%) as a white foam. $^1$H NMR (CDCl$_3$) δ 0.90 (m, 1H), 0.98 (d, 3H, J=6.0 Hz), 1.09 (m, 1H), 1.53 (m, 1H), 1.73 (m, 3H), 2.10 (br t, 1H), 2.37 (s, 6H), 2.51 (br t, 1H), 2.69 (m, 1H), 2.81-2.85 (m, 2H), 3.30-3.37 (m, 2H), 3.72 (s, 3H), 3.84 (m, 1H), 3.92 (s, 2H), 6.63 (d, 2H, J=9.0 Hz), 6.75 (d, 2H, J=9.0 Hz), 7.37 (s, 2H), 7.42 (d, 1H, J=6.0 Hz), 7.53 (d, 1H, J=9.0 Hz), 7.69 (t, 1H, J=9.0 Hz), 8.48 (br s, 1H). ES-MS m/z 551 (M+H), 573 (M+Na). Anal. Calcd. for C$_{33}$H$_{38}$N$_6$O$_2$.0.1 CH$_2$Cl$_2$: C, 71.10; H, 6.89; N, 15.03. Found: C, 71.17; H, 7.01; N, 15.00.

EXAMPLE 23

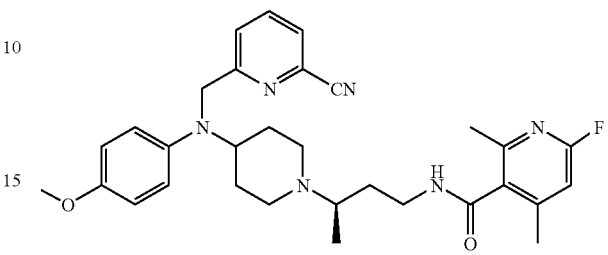

Preparation of N-((R)-3-{4-[(6-Cyano-pyridin-2-ylmethyl)-(4-methoxy-phenyl)-amino]-piperidin-1-yl}-butyl)-6-fluoro-2,4-dimethyl-nicotinamide (R)-(3-{4-[(6-Cyano-pyridin-2-ylmethyl)-(4-methoxy-phenyl)-amino]-piperidin-1-yl}-butyl)-carbamic acid tert-butyl ester (0.070 g, 0.14 mmol) was dissolved in a 3:1 mixture of CH$_2$Cl$_2$ and TFA and the mixture was stirred at room temperature for 1 h. The solvent was removed in vacuo and the resulting brown oil dried in vacuo (high vacuum system) for 2 h. The resulting amine, EDCI (0.030 g, 0.0.16 mmol) and HOBT (0.021 g, 0.16 mmol) were combined in DMF (5 mL) to give a pale yellow solution. To this solution was added 6-fluoro-2,4-dimethyl-nicotinic acid hydrochloride (0.032 g, 0.16 mmol) followed by DIPEA (163 μL, 0.94 mmol) and the resulting mixture was stirred at 25° C. for 16 h. Standard workup according to General Procedure C gave the crude product as a tan oil. Purification by column chromatography on silica gel (Et$_2$O:MeOH:NH$_4$OH, 90:8:2, v/v/v) afforded N-((R)-3-{4-[(6-cyano-pyridin-2-ylmethyl)-(4-methoxy-phenyl)-amino]-piperidin-1-yl}-butyl)-6-fluoro-2,4-dimethyl-nicotinamide (0.058 g, 75%) as a white foam. $^1$H NMR (CDCl$_3$) δ 0.97 (m, 1H), 0.99 (d, 3H, J=6.0 Hz), 1.16 (m, 1H), 1.53 (m, 1H), 1.76 (m, 3H), 2.14 (br t, 1H), 2.37 (s, 3H), 2.47 (s, 3H), 2.53 (br t, 1H), 2.71 (m, 1H), 2.81-2.85 (m, 2H), 3.32-3.36 (m, 2H), 3.72 (s, 3H), 3.81 (m, 1H), 4.02 (s, 2H), 6.64 (m, 3H), 6.74 (d, 2H, J=9.0 Hz), 7.46 (d, 1H, J=6.0 Hz), 7.53 (d, 1H, J=9.0 Hz), 7.69 (t, 1H, J=9.0 Hz), 8.33 (br s, 1H). ES-MS m/z 545 (M+H), 567 (M+Na). Anal. Calcd. for C$_{31}$H$_{37}$N$_6$O$_2$F.0.15 CH$_2$Cl$_2$: C, 67.12; H, 6.74; N, 15.08. Found: C, 67.16; H, 6.85; N, 15.06.

EXAMPLE 24

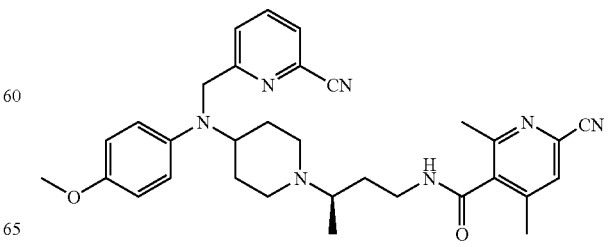

Preparation of 6-Cyano-N-((R)-3-{4-[(6-cyano-pyridin-2-ylmethyl)-(4-methoxy-phenyl)-amino]-piperidin-1-yl}-butyl-2,4-dimethyl-nicotinamide (R)-(3-{4-[(6-Cyano-pyridin-2-ylmethyl)-(4-methoxyphenyl)-amino]-piperidin-1-yl}-butyl)-carbamic acid tert-butyl ester (0.070 g, 0.14 mmol) was dissolved in a 3:1 mixture of $CH_2Cl_2$ and TFA and the mixture was stirred at room temperature for 1 h. The solvent was removed in vacuo and the resulting brown oil dried in vacuo (high vacuum system) for 2 h. The resulting amine, EDCI (0.030 g, 0.16 mmol) and HOBT (0.021 g, 0.16 mmol) were combined in DMF (5 mL) to give a pale yellow solution. To this solution was added 6-cyano-2,4-dimethyl-nicotinic acid hydrochloride (0.033 g, 0.16 mmol) followed by DIPEA (163 µL, 0.94 mmol) and the resulting mixture was stirred at 25° C. for 16 h. Standard workup according to General Procedure C gave the crude product as a tan oil. Purification by column chromatography on silica gel ($Et_2O$:MeOH:$NH_4OH$, 90:8:2, v/v/v) afforded 6-cyano-N-((R)-3-{4-[(6-cyano-pyridin-2-ylmethyl)-(4-methoxy-phenyl)-amino]-piperidin-1-yl}-butyl)-2,4-dimethyl-nicotinamide (0.041 g, 52%) as a white foam. $^1$H NMR ($CDCl_3$) δ 0.89 (m, 1H), 0.99 (d, 3H, J=6.0 Hz), 1.08 (m, 1H), 1.53 (m, 1H), 1.74 (m, 3H), 2.11 (br t, 1H), 2.41 (s, 3H), 2.51 (br t, 1H), 2.57 (s, 3H), 2.72 (m, 1H), 2.84 (m, 2H), 3.29-3.38 (m, 2H), 3.73 (s, 3H), 3.84 (m, 1H), 3.97 (s, 2H), 6.65 (d, 2H, J=9.0 Hz), 6.77 (d, 2H, J=9.0 Hz), 7.46 (d, 1H, J=6.0 Hz), 7.52 (s, 1H), 7.53 (d, 1H, J=9.0 Hz), 7.73 (t, 1H, J=9.0 Hz), 8.56 (br s, 1H). ES-MS m/z 552 (M+H), 574 (M+Na). Anal. Calcd. for $C_{32}H_{37}N_7O_2 \cdot 0.2$ $CH_2Cl_2$: C, 68.01; H, 6.63; N, 17.24. Found: C, 67.79; H, 6.69; N, 17.11.

EXAMPLE 25

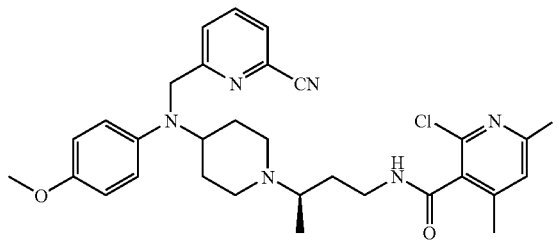

Preparation of 2-Chloro-N-((R)-3-{4-[(6-cyano-pyridin-2-ylmethyl)-(4-methoxy-phenyl)-amino]-piperidin-1-yl}-butyl)-4-methyl-nicotinamide (R)-(3-{4-[(6-Cyano-pyridin-2-ylmethyl)-(4-methoxyphenyl)-amino]-piperidin-1-yl}-butyl)-carbamic acid tert-butyl ester (0.070 g, 0.14 mmol) was dissolved in a 3:1 mixture of $CH_2Cl_2$ and TFA and the mixture was stirred at room temperature for 1 h. The solvent was removed in vacuo and the resulting brown oil dried in vacuo (high vacuum system) for 2 h. The resulting amine, EDCI (0.030 g, 0.0.16 mmol) and HOBT (0.021 g, 0.16 mmol) were combined in DMF (5 mL) to give a pale yellow solution. To this solution was added 2-chloro-4-methyl-nicotinic acid (0.027 g, 0.16 mmol) followed by DIPEA (163 µL, 0.94 mmol) and the resulting mixture was stirred at 25° C. for 16 h. Standard workup according to General Procedure C gave the crude product as a tan oil. Purification by column chromatography on silica gel ($Et_2O$:MeOH:$NH_4OH$, 90:8:2, v/v/v) afforded 2-chloro-N-((R)-3-{4-[(6-cyano-pyridin-2-ylmethyl)-(4-methoxy-phenyl)-amino]-piperidin-1-yl}-butyl)-4-methyl-nicotinamide (0.027 g, 35%) as a white foam. $^1$H NMR ($CDCl_3$) δ 0.94 (m, 1H), 1.00 (d, 3H, J=6.0 Hz), 1.20 (m, 1H), 1.53 (m, 1H), 1.77 (m, 3H), 2.14 (br t, 1H), 2.41 (s, 3H), 2.54 (br t, 1H), 2.80-2.96 (m, 3H), 3.33-3.47 (m, 2H), 3.71 (s, 3H), 3.88 (s+m, 3H), 6.61 (d, 2H, J=9.0 Hz), 6.72 (d, 2H, J=9.0 Hz), 7.16 (d, 1H, J=4.5 Hz), 7.43 (d, 1H, J=9.0 Hz), 7.54 (d, 1H, J=9.0 Hz), 7.67 (t, 1H, J=9.0 Hz), 8.14 (d, 1H, J=4.5 Hz), 8.77 (br s, 1H). ES-MS m/z 547 (M+H), 569 (M+Na). Anal. Calcd. for $C_{30}H_{35}N_6O_2Cl \cdot 0.2$ $CH_2Cl_2$: C, 64.30; H, 6.33; N, 14.90. Found: C, 64.10; H, 6.39; N, 14.74.

EXAMPLE 26

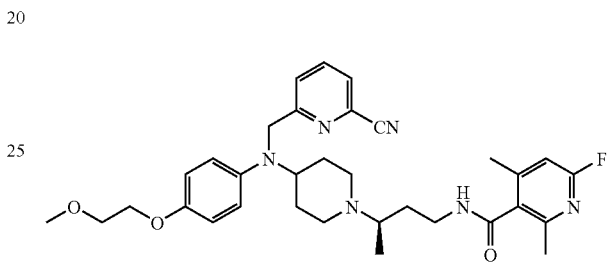

Preparation of N-(R)-[3-(4-{(6-Cyano-pyridin-2ylmethyl)-[4-(2-methoxy-ethoxy)-phenyl]-amino}-piperidin-1-yl)-butyl]-6-fluoro-2,4-dimethyl-nicotinamide Using General Procedure F with (R)-3-{4-[4-(2-methoxy-ethoxy)-phenylamino-piperidin-1-yl}-butyronitrile (872 mg, 2.75 mmol) the corresponding amine was obtained (422 mg, 48%). Using General Procedure C with the amine (138 mg, 0.427 mmol) and 6-fluoro-2,4-dimethyl-nicotinic acid (80 mg, 0.470 mmol), gave 6-fluoro-N-(R)-(3-{4-[4-(2-methoxy-ethoxy)-phenylamino]-piperidin-1-yl}-butyl)-2,4-dimethyl-nicotinamide (154 mg, 74%). Using General Procedure E, the above substrate (154 mg, 0.315 mmol) was alkylated with 6-bromomethyl-pyridine-2-carbonitrile (68 mg, 0.346 mmol) to give after workup and purification the title compound (92 mg, 50%) as a yellow foam. $^1$H NMR ($CDCl_3$) δ 0.98 (d, 3H, J=6.6 Hz), 0.97-1.20 (m, 2H), 1.51-1.58 (m, 1H), 1.68-1.77 (m, 3H), 2.08-2.16 (m, 1H), 2.38 (s, 3H), 2.47 (s, 3H), 2.47-2.56 (m, 1H), 2.71-2.87 (m, 3H), 3.30-3.39 (m, 2H), 3.42 (s, 3H), 3.67-3.70 (m, 2H), 3.76-3.82 (m, 1H), 4.00-4.03 (m, 4H), 6.61-6.79 (m, 5H), 7.44 (d, 1H, J=7.8 Hz), 7.52 (d, 1H, J=7.2 Hz), 7.69 (dd, 1H, J=7.8, 7.2 Hz), 8.34 (br s, 1H). $^3$C NMR ($CDCl_3$) δ 13.78, 19.50, 22.18, 29.97, 30.95, 31.51, 40.14, 44.08, 52.26, 58.72, 59.52, 60.23, 68.09, 71.50, 107.86, 108.35, 115.95, 117.92, 125.43, 126.97, 132.11, 133.20, 137.85, 142.94, 150.50, 150.60, 152.54, 153.77, 153.98, 161.06, 163.62, 164.23, 167.93. ES-MS m/z 589 (M+H). Anal. Calcd. for $C_{33}H_{41}FN_6O_3 \cdot 0.6$ $H_2O$: C, 66.11; H, 7.09; N, 14.02. Found: C, 66.15; H, 6.91; N, 13.88.

EXAMPLE 27

The following compounds were prepared following the general procedures exemplified above.

| Ex. # | Structure/Name | Characterization Data |
|---|---|---|
| 27 | 4,6-Dimethyl-pyrimidine-5-carboxylic acid (3-{4-[(4-methoxy-phenyl)-(5-methyl-pyridin-3-ylmethyl)-amino]-piperidin-1-yl}-butyl)-amide | $^1$H NMR(CDCl$_3$) δ 1.34-1.49(m, 2H), 1.86-1.95 (m, 2H), 2.21(s, 3H), 2.72-2.85(m, 2H), 3.06-3.16 (m, 2H), 3.73(s, 3H), 4.78-4.89(m, 1H), 6.73(d, 2H, J=8.4 Hz), 6.91(d, 2H, J=8.4 Hz), 7.42(s, 1H), 8.16-8.24(m, 2H). |
| 28 | 4,6-Dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.92-1.05(m, 4H), 1.10-1.25(m, 2H), 1.52-1.50(m, 1H), 1.69-1.90(m, 5H), 2.11(t, J=11.0 Hz, 1H), 2.35(s, 3H), 2.46-2.53(m, 7H), 2.71-2.84(m, 3H), 3.18-3.38(m, 2H), 3.71(s, 3H), 3.75-3.83(m, 1H), 3.91(s, 2H), 6.60-6.64(m, 2H), 6.68-6.72(m, 2H), 7.03(d, J=5.0 Hz, 1H), 8.24-8.29(m, 3H), 8.78(s, 1H); $^{13}$C NMR(CDCl$_3$) δ 13.77, 19.19, 22.34, 30.03, 30.91, 31.47, 40.19, 44.25, 47.75, 52.19, 55.93, 59.28, 60.27, 114.76, 120.50, 125.48, 131.08, 133.35, 142.58, 145.67, 148.42, 149.62, 154.15, 157.88, 163.32, 166.84; ES-MS m/z 517(M+H). Anal Calcd. For C$_{30}$H$_{40}$N$_6$O$_2$ 0.3(H2O): C, 69.02; H, 7.84; N, 16.10. Found: C, 68.63; H, 7.97; N, 16.00. |
| 29 | N-((R)-3-{4-[(4-Methoxy-phenyl)-(4-methyl-oyridin-3-ylmethyl)-amino]-piperidin-1-yl}-butyl)-3,5-dimethyl-isonicotinamide | $^1$H NMR(CDCl$_3$) δ 0.91-1.21(m, 2H), 0.98(d, 3H, J=6.6 Hz), 1.49-1.60(m, 1H), 1.68-1.85(m, 3H), 2.07-2.17(m, 1H), 2.23, 2.25(s, 6H), 2.33(s, 3H), 2.45-2.55(m, 1H), 2.68-2.89(m, 3H), 3.19-3.38 (m, 2H), 3.70(s, 3H), 3.75-3.87(m, 1H), 3.90(s, 2H), 6.57-6.63(m, 2H), 6.68-6.74(m, 2H), 7.04(d, 1H, J=4.8 Hz), 8.07(hr s, 1H), 8.21-8.33(m, 4H). ES-MS m/z 516(M+H). |
| 30 | 4,6-Dimethyl-pyrimidine-5-carboxylic acid (R)-(3-{4-[(4-methoxy-phenyl)-pyridin-3-ylmethyl-amino]-piperidin-1-yl}-butyl)-amide | $^1$H NMR(CDCl$_3$) δ 0.84-1.17(m, 2H), 1.00(d, 3H, J=6.6 Hz), 1.50-1.65(m, 1H), 1.68-1.83(m, 3H), 2.07-2.18(m, 1H), 2.42-2.58(m, 1H), 2.52(s, 6H) 2.69-2.90(m, 3H), 3.22-3.40(m, 2H), 3.71(s, 3H), 3.83(s, 2H), 3.84-3.92(m, 1H), 6.62(d, 2H, J=9.0 Hz), 6.72(d, 2H, J=8.7 Hz), 7.20(dd, 1H, J=7.8, 4.8 Hz), 7.56(d, 1H, J=8.1 Hz), 8.45(d, 1H, J=4.5 Hz), 8.50(s, 1H), 8.69(br s, 1H), 8.84 (s, 1H). $^{13}$C NMR(CDCl$_3$) δ 13.39, 21.93, 29.48, 30.62, 30.74, 40.10, 43.63, 47.88, 51.99, 55.59, 58.39, 60.31, 114.54, 118.41, 123.28, 130.85, 134.79, 135.58, 142.40, 148.11, 148.90, 153.13, 157.56, 163.02, 166.35. ES-MS m/z 503(M+H). Anal. Calcd. for C$_{29}$H$_{38}$N$_6$O$_2$•1.1H$_2$O: C, 66.67; H, 7.75; N, 16.09. Found: C, 66.72; H, 7.86; N, 16.28. |

| Ex. # | Structure/Name | Characterization Data |
|---|---|---|
| 31 | 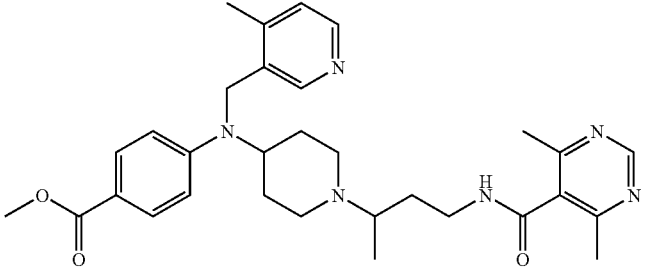<br>4-[1-{3-[(2,4-Dimethyl-pyridine-3-carbonyl)-amino]-1-methyl-propyl}-piperidin-4-yl)-(4-methyl-pyridin-3-ylmethyl)-amino]-benzoic acid methyl ester | $^1$H NMR(CDCl$_3$) δ 1.03(d, 3H, J=6.6 Hz), 1.08-1.37(m, 2H), 1.53-1.63(m, 1H), 1.72-1.91(m, 3H), 2.25(td, 1H, J=11.5, 1.8 Hz), 2.29(s, 3H), 2.39(s, 3H), 2.53(s, 3H), 2.60(td, 1H, J=11.5, 1.8 Hz), 2.74-2.92(m, 3H), 3.32-3.42(m, 1H), 3.73-3.84(m, 2H), 3.82(s, 3H), 4.12(s, 2H), 6.51 (d, 2H, J=9.2 Hz), 6.84(d, 1H, J=5.1 Hz), 7.12 (d, 1H, J=5.0 Hz), 7.63(br. s, 1H), 7.81(d, 2H, J=9.2 Hz), 8.17(s, 1H), 8.19(d, 1H, J=5.1 Hz), 8.37(d, 1H, J=5.0 Hz). $^{13}$C NMR(CDCl$_3$) δ 13.41, 18.58, 18.64, 22.21, 29.24, 30.12, 31.71, 38.99, 44.00, 44.74, 51.45, 51.49, 55.94, 59.12, 111.61, 118.11, 122.38, 125.01, 131.31, 131.69, 133.46, 143.73, 144.04, 147.27, 148.14, 148.57, 151.59, 153.96, 167.01, 168.16. ES-MS m/z 544 (M + H)$^+$. Anal. Calcd. for C$_{32}$H$_{41}$N$_5$O$_3$•0.6CH$_2$Cl$_2$: C, 65.84; H, 7.15;N, 11.78. Found: C, 66.15; H, 7.36; N, 11.83. |
| 32 | 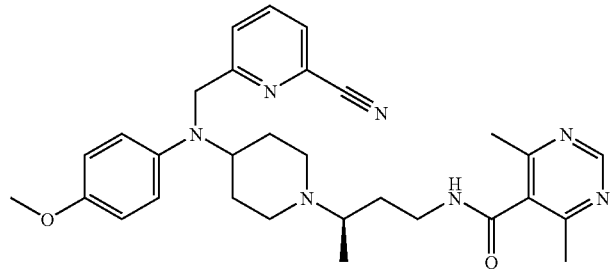<br>4,6-Dimethyl-pyrimidine-5-carboxylic acid (R)-(3-{4-[(6-cyano-pyridin-2-ylmethyl)-(4-methoxy-phenyl)-amino]-piperidin-1-yl}-butyl)-amide | $^1$H NMR(CDCl$_3$) δ 1.01(3H, d, J=6.6 Hz), 1.18-1.25(1H, m), 1.55-1.61(1 H, m), 1.77(5H, brs), 2.15(1H, t, J=11.3 Hz), 2.52(6H, s), 2.75-2.88(3H, m), 3.32-3.40(2H, m), 3.72(3H, s), 3.77-3.84(1H, m), 4.05((2H, s), 6.67(2H, d, J=9.0 Hz), 6.74(2H, d, J=9.0 Hz), 7.47(1H, d, J=8.1 Hz), 7.53(1H, d, J=7.2 Hz), 7.69(1H, d, J=7.8 Hz), 8.33(1H, brs), 8.90(1H, s). $^{13}$C NMR(CDCl$_3$) δ 13.74, 22.34, 30.05, 30.96, 31.48, 40.08, 44.11, 52.27, 52.52, 55.93, 59.44, 60.20, 114.95, 117.78, 119.18, 125.45, 127.00, 131.05, 133.32, 137.73, 142.53, 153.78, 158.18, 163.36, 163.50, 166.89. ES-MS m/z 528.5(M+H)$^+$. Anal. Calc. for (C30H37N7O2) 0.2(CH2Cl2) 0.2(C6H14): C 67.12, H 7.21, N 17.45; Found: C 66.89, H 7.10, N 17.10. |
| 33 | 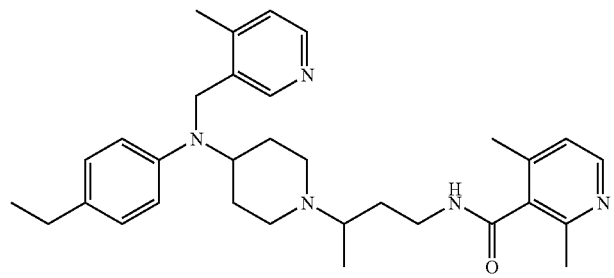<br>N-(3-{4-[(4-Ethyl-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98-1.29(m, 2H), 1.01(d, 3H, J=6.6 Hz), 1.15(t, 3H, J=7.5 Hz), 1.52-1.61 (m, 1H), 1.70-1.88(m, 3H), 2.18(td, 1H, J=11.9, 2.0 Hz), 2.29(s, 3H), 2.37(s, 3H), 2.50(q, 2H, J=7.5 Hz), 2.50-2.59(m, 1H), 2.54(s, 3H), 2.71-2.90 (m, 3H), 3.28-3.38(m, 1H), 3.55(tt, 1H, J=11.3, 3.6 Hz), 3.78-3.89(m, 1H), 3.93(s, 2H), 6.51(d, 2H, J=8.5 Hz), 6.81(d, 1H, J=5.4 Hz), 6.97(d, 2H, J=8.5 Hz), 7.07(d, 1H, J=5.1 Hz), 7.99(br. s, 1H), 8.13(d, 1H, J=5.4 Hz), 8.29(s, 1H), 8.34 (d, 1H, J=5.1 Hz). $^{13}$C NMR (CDCl$_3$) δ 13.34, 15.67, 18.61, 18.65, 22.19, 27.60, 29.20, 30.13, 31.42, 39.26, 43.99, 45.40, 51.78, 56.96, 59.53, 114.60, 122.30, 124.84, 128.37, 133.07, 133.51, 133.60, 143.60, 144.27, 146.31, 147.75, 148.24, 148.54, 153.96, 168.12. ES-MS m/z 514(M+H)$^+$. Anal. Calcd. for C$_{32}$H$_{43}$N$_5$O•0.3CH$_2$Cl$_2$: C, 71.95; H, 8.15; N, 12.99. Found: C, 72.08; 11, 8.23; N, 12.98. |
| 34 | 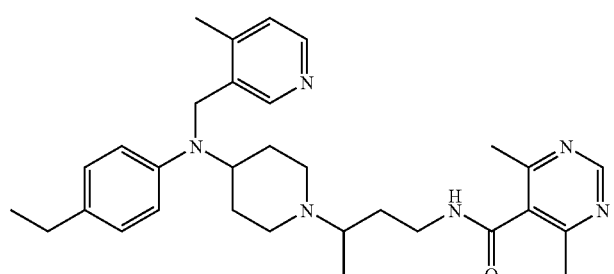<br>4,6-Dimethyl-pyrimidine-5-carboxylic acid (3-{4-[(4-ethyl-phenyl)-(4-methyl-pyridin-3-ylmethyl)-amino]-piperidin-1-yl}-butyl)-amide | $^1$H NMR(CDCl$_3$) δ 0.97-1.26(m, 2H), 1.02(d, 3H, J=6.6 Hz), 1.16(t, 3H, J=7.5 Hz), 1.52-1.62 (m, 1H), 1.72-1.91(m, 3H), 2.15-2.23(m, 1H), 2.39(s, 3H), 2.50(s, 6H), 2.47-2.60(m, 3H), 2.70-2.89(m, 3H), 3.30-3.40(m, 1H), 3.51-3.61(m, 1H), 3.75-3.86(m, 1H), 3.99(s, 2H), 6.52(d, 2H, J=8.6 Hz), 6.97(d, 2H, J=8.6 Hz), 7.07(d, 1H, J=4.8 Hz), 8.11(br. s, 1H), 8.29(s, 1H), 8.33(d, 1H, J=4.8 Hz), 8.77(s, 1H). $^{13}$C NMR(CDCl$_3$) δ 13.38, 15.67, 18.59, 21.84, 27.61, 29.28, 30.21, 31.30, 39.34, 44.01, 45.65, 51.68, 56.77, 59.34, 114.68, 124.88, 128.41, 130.59, 132.98, 133.76, 144.37, 146.22, 147.74, 148.14, 157.31, 162.81, 166.37. ES-MS m/z 515(M+H)$^+$. Anal. Calcd. for C$_{31}$H$_{42}$N$_6$O•0.2CH$_2$Cl$_2$: C, 70.48; H, 8.04; N, 15.81. Found: C, 70.29; H, 8.14; N, 15.53. |

| Ex. # | Structure/Name | Characterization Data |
|---|---|---|
| 35 | 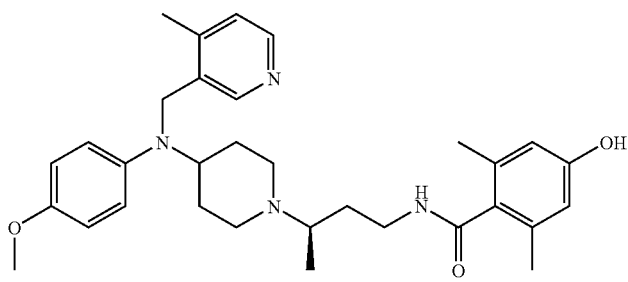

4-Hydroxy-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.98(d, 3H, J=6 Hz), 1.05-1.26(m, 3H), 1.47-1.55(m, 1H), 1.67-1.75(m, 3H), 2.08-2.16(m, 1H), 2.21(s, 6H), 2.24(s, 3H), 2.28-2.46(m, 1H), 2.71-2.83(m, 3H), 3.05-3.28 (m, 2H), 3.70(s, 3H), 3.71-3.74(m, 1H), 4.00(s, 2H), 6.45(s, 2H), 6.69-6.76(m, 4H), 7.00(d, 1H, J=5.1 Hz), 8.22(d, 1H, J=5.1 Hz), 8.29(br s, 1H), 8.40(s, 1H). ES-MS , m/z 531(M+H). |
| 36 | 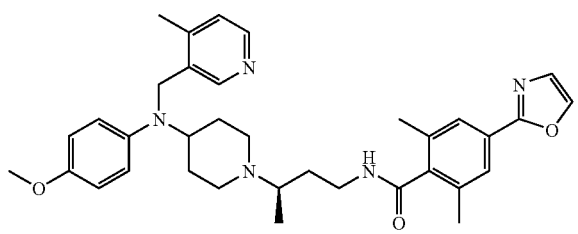

N-((R)-3-{4-[(4-Methoxy-phenyl)-(4-methyl-pyridin-3-ylmethyl)-amino]-piperidin-1-yl}-butyl)-2,6-dimethyl-4-oxazol-2-yl-benzamide | $^1$H NMR(CDCl$_3$) δ 0.98(d, 3H, J=6.6 Hz), 1.10 (m, 1H), 1.25(m, 1H), 1.54(m, 1H), 1.73(m, 3H), 2.08(t, 1H, J=11.2 Hz), 2.16(s, 3H), 2.40(s, 3H), 2.46(t, 1H, J=11.2 Hz), 2.65-2.90(m, 3H), 3.15 (m, 1H), 3.32(m, 1H), 3.68(s, 3H), 3.75(s, 2H), 3.86(m, 1H), 6.58(d, 2H, J=9.0 Hz), 6.68(d, 2H, J=9.0 Hz), 6.86(d, 1H, J=5.1 Hz), 7.14(s, 1H), 7.58(s, 1H), 7.68(s, 2H), 8.09(s, 1H), 8.15(br, 1H), 8.20(d, 1H, J=4.8 Hz). $^{13}$C NMR(CDCl$_3$) δ 13.78, 18.98, 19.58(2C), 29.74, 30.55, 31.78, 39.80, 44.38, 46.96, 52.14, 55.85, 60.18, 60.32, 114.58(2C), 120.98(2C), 125.38, 125.56(2C), 127.53, 128.71, 133.30, 135.31(2C), 139.04, 140.62, 142.87, 145.65, 148.04, 149.71, 154.15, 161.58, 169.68. ES-MS m/z 582(M+H). Anal. Calcd. for C$_{35}$H$_{43}$N$_5$O$_3$•0.3CH$_2$Cl$_2$: C, 69.82; H, 7.24; N, 11.53. Found: C, 70.11; H, 7.33; N, 11.44 |
| 37 | 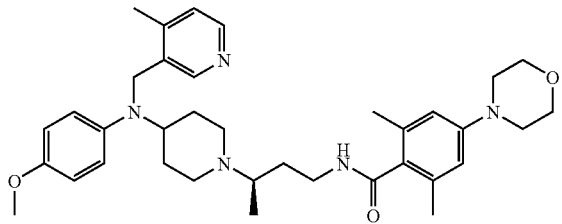

N-((R)-3-{4-[(4-Methoxy-phenyl)-(4-methyl-pyridin-3-ylmethyl)-amino]-piperidin-1-yl}-butyl)-2,6-dimethyl-4-morpholin-4-yl-benzamide | $^1$H NMR(CDCl$_3$) δ 0.99(d, 3H, J=6 Hz), 1.09-1.25(m, 3H), 1.76-1.82(m, 7H), 2.20-2.25(m, 1H), 2.28(s, 6H), 2.30(s, 3H), 2.67-2.85(m, 4H), 3.15-3.28(m, 2H), 3.70(s, 3H), 3.71-3.76(m, 5H), 3.99(s, 2H), 5.40(br s, 1H), 6.49(s, 2H), 6.66(d, 2H, J=9 Hz), 6.72(d, 2H, J=9 Hz), 7.00(d, 1H, J=5.1 Hz), 8.27(br m, 2H). ES-MS m/z 600 (M+H). |
| 38 | 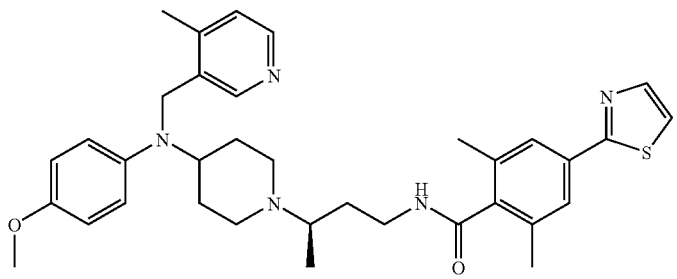

N-((R)-3-{4-[(4-Methoxy-phenyl)-(4-methyl-pyridin-3-ylmethyl)-amino]-piperidin-1-yl}-butyl)-2,6-dimethyl-4-thiazol-2-yl-benzamide | $^1$H NMR(CDCl$_3$) δ 0.98(d, 3H, J=6.0 Hz), 1.06 (m, 1H), 1.23(m, 1H), 1.57(m, 1H), 1.81(m, 3H), 2.17(br t, 1H), 2.40(s, 6H), 2.46(br t, 1H), 2.74-2.87(m, 3H), 3.16(m, 1H), 3.31(m, 1H), 3.68(s, 3H), 3.78(s, 2H), 3.85(m, 1H), 6.58(d, 2H, J= 9.0 Hz), 6.64(d, 2H, J=9.0 Hz), 6.83(d, 1H, J= 6.0 Hz), 7.25(s, 1H), 7.61(s, 2H), 7.78(d, 1H, J= 3.0 Hz), 8.08(s+br s, 2H), 8.16(d, 1H, J=6.0 Hz). $^{13}$C NMR(CDCl$_3$) δ 13.7, 19.0, 19.6, 29.7, 30.7, 31.8, 39.9, 44.3, 46.9, 52.3, 55.9, 60.4, 114.6, 119.4, 121.0, 125.3, 125.8, 133.3, 135.5, 142.9, 143.9, 148.2, 149.9. ES-MS m/z 597(M+H), 619 (M+Na). Anal. Calcd. for C$_{35}$H$_{42}$N$_5$O$_2$S•09 CH$_2$Cl$_2$: C, 64.05; H, 6.56; N, 10.40. Found: C, 63.97; H, 6.82; N, 10.41. |

| Ex. # | Structure/Name | Characterization Data |
|---|---|---|
| 39 | 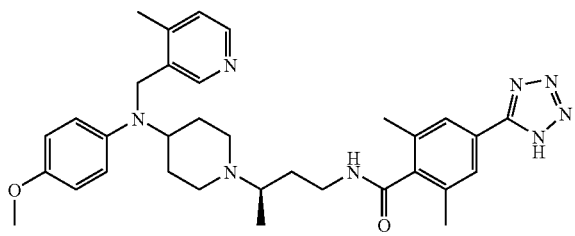<br>N-((R)-3-{4-[(4-Methoxy-phenyl)-(4-methyl-pyridin-3-ylmethyl)-amino]-piperidin-1-yl}-butyl)-2,6-dimethyl-4-(1H-tetrazol-5-yl)-benzamide | $^1$H NMR(CDCl$_3$) δ 0.85(m, 2H), 1.22(s, 1H), 1.43(d, 3H, J=9 Hz), 1.56(s, iR), 1.94(s+m, 7H), 2.17(m, 3H), 2.37(s, 3H), 2.66(br t, 1H), 3.21(br s, 2H), 3.44(s+m, 4H), 3.68(s, 3H), 3.86 (br q+m, 2H), 4.04(m, 1H), 4.46(br s, 2H), 6.74 (m, 4H), 7.06(m, 1H), 7.18(m, 2H), 8.19(br s, 2H). $^{13}$C NMR(CDCl$_3$) δ 12.4, 19.1, 19.4, 26.8, 33.0, 36.3, 56.0, 59.1, 114.2, 115.2, 125.6, 128.1, 134.0. ES-MS m/z 583(M+H). Anal. Calcd. For C$_{33}$H$_{42}$N$_8$O$_2$•3.5 CH$_3$OH: C, 63.09; H, 8.12; N, 16.13. Found: C, 63.30; H, 7.94; N, 15.68. |
| 40 | 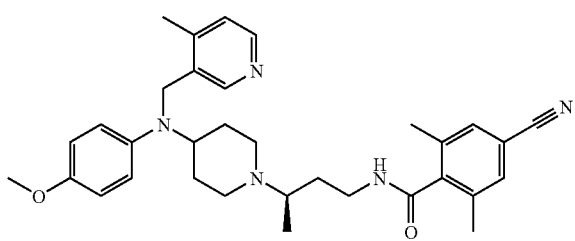<br>4-Cyano-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.99(d, 3H, J=9 Hz), 1.05(m, 2H), 1.25(m, 1H), 1.66(m, 8H), 2.12(t, 1H, J=12H), 2.30(s, 3H), 2.33(s, 6H), 2.48(t, 3H, J=12H), 2.80(m, 3H), 3.21(m, 1H), 3.24(m, 1H), 3.73(s, 3H), 3.76(m, 1H), 3.96(s, 2H), 6.64(dd, 4H, J=3 Hz, 9 Hz), 7.05(d, 1H, J=6 Hz), 7.27(s, 1H), 7.85(br s, 1H), 8.25(s, 1 Hz), 8.31(d, 1H, J=6 Hz). $^{13}$C NMR(CDCl$_3$) δ 13.7, 19.1, 19.4, 30.2, 31.0 31.9, 39.8, 44.4, 48.1, 52.1, 56.0, 59.1, 60.1, 112.6, 114.8, 118.7, 120.6, 125.5, 131.2, 133.4, 136.1, 142.7, 145.4, 148.5, 149.7, 168.4. ES-MS m/z 540(M+H). Anal. Calcd. For C$_{33}$H$_{41}$N$_5$O$_2$•0.8 CH$_2$Cl$_2$: C, 66.81; H, 7.07; N, 11.53. Found: C, 66.98; H, 7.11;N, 11.42. |
| 41 | 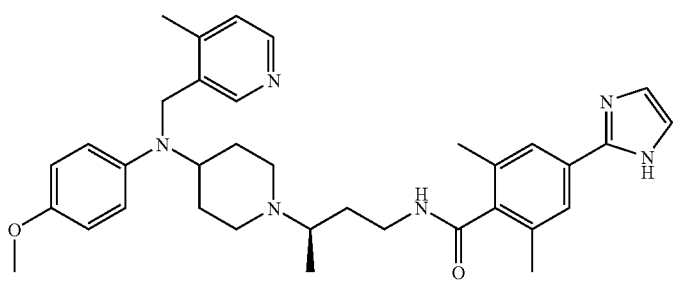<br>4-(1H-Imidazol-2-yl)-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d, 3H, J=6.0 Hz), 1.09 (m, 1H), 1.23(m, 1H), 1.53(m, 1H), 1.69(m, 3H), 2.07(s+m, 7H), 2.17(s, 3H), 2.33-2.49(m, 2H), 2.67-2.79(m, 3H), 3.09(m, 1H), 3.28(m, 1H), 3.67(s, 3H), 3.69(m, 1H), 3.99(s, 2H), 6.59-6.64 (m, 4H), 6.94(d, 1H, J=6.0 Hz), 7.25(s, 1H), 7.37(s, 2H), 8.27(d, 1H, J=6.0 Hz), 8.31(s, 1H), 8.44(br s, 1H). $^{13}$C NMR(CDCl$_3$) δ 13.9, 18.9, 19.4, 30.8, 31.4, 31.8, 39.7, 44.5, 49.2, 51.6, 55.9, 59.9, 60.2, 114.7, 122.1, 125.0, 125.4, 129.3, 130.8, 134.4, 134.5, 138.0, 143.3, 145.4, 147.1, 147.6, 149.1, 154.7, 170.6. ES-MS m/z 580 (M+H), 602(M+Na). Anal. Calcd. for C$_{35}$H$_{43}$N$_6$O$_2$•<br>0.4 CH$_2$Cl$_2$: C, 69.28; H, 7.19; N, 13.69. Found: C, 69.49; H, 7.53; N, 13.78. |
| 42 | 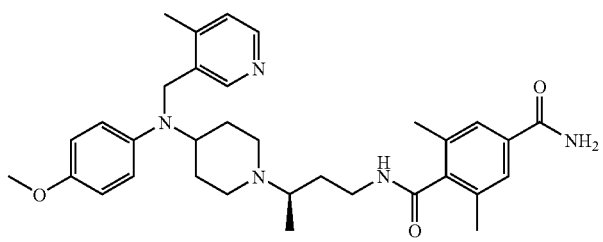<br>N-((R)-3-{4-[(4-Methoxy-phenyl)-(4-methyl-pyridin-3-ylmethyl)-amino]-piperidin-1-yl}-butyl)-2,6-dimethyl-terephthalamide | $^1$H NMR(CD$_3$OD) δ 1.08(d, 3H, J=7 Hz), 1.58 (m, 3H), 1.88(m, 3H), 2.34(s, 6H), 2.42(s, 3H), 2.89(m, 3H), 3.58(m, 4H), 3.69(s, 3H), 4.25(s, 2H), 6.76(dd, 4H, J=9 Hz, 16 Hz), 7.17(d, 1H, J=5 Hz), 7.57(s, 2H), 8.16(s, 1H), 8.17(d, 1H, J=5 Hz). $^{13}$C NMR(CD$_3$OD) δ 14.6, 19.3, 19.7, 31.1, 31.4, 33.6, 39.3, 47.4, 51.5, 56.3, 59.2, 60.9, 115.7, 122.8, 127.1, 128.2, 135.4, 136.2, 142.6, 143.9, 148.3, 148.9, 149.9, 156.1, 172.0, 172.6. ES-MS m/z 558(M+H). Anal. Calcd. For C$_{33}$H$_{43}$N$_5$O$_3$•0.3 CH$_2$Cl$_2$: C, 68.58; H, 7.53; N, 12.01. Found: C, 68.45; H, 7.77; N, 11.92. |

| Ex. # | Structure/Name | Characterization Data |
|---|---|---|
| 43 | 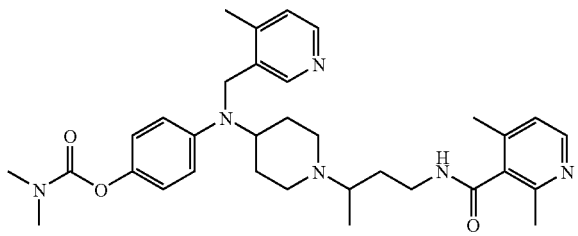<br>Dimethyl-carbamic acid 4-[(1-{3-[(2,4-dimethyl-pyridine-3-carbonyl)-amino]-1-methyl-propyl}-piperidin-4-yl)-(4-methyl-pyridin-3-ylmethyl)-amino]-phenyl ester | $^1$H NMR(CDCl$_3$) δ 1.06(3H, brs), 1.50-1.90(8H, m), 2.30(3H, s), 2.32(3H, s), 2.36(3H, s), 2.97 (3H, s), 3.05(3H, s), 2.75-3.75(6H, m), 3.98(2H, s), 6.56(2H, d, J=8.7 Hz), 6.85(1H, d, J=6.6 Hz), 6.87(2H, d, J=9.0 Hz), 7.07(1H, d, J=4.8 Hz), 7.90(1H, brs), 8.15(1H, d, J=4.2 Hz), 8.28(1H, s), 8.34(1H, d, J=4.8 Hz). $^{13}$C NMR(CDCl$_3$) δ 13.26, 18.81, 22.36, 31.52, 36.39, 36.67, 44.08, 45.79, 51.96, 59.77, 115.63, 122.31, 122.51, 125.08, 132.85, 133.25, 143.59, 143.81, 144.68, 145.90, 148.07, 148.35, 148.78, 154.10, 155.46, 156.99. ES-MS m/z 573.5(M+H)$^+$. |
| 44 | 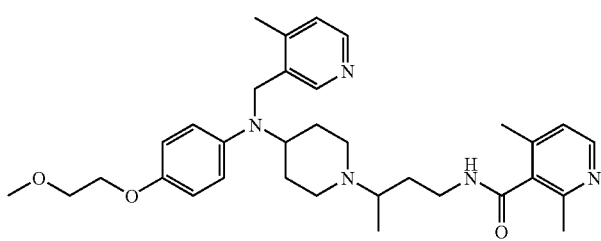<br>N-(3-{4-[[4-(2-Methoxy-ethoxy)-phenyl]-(4-methyl-pyridin-3-ylmethyl)-amino]-piperidin-1-yl}-butyl)-2,4-dimethyl-nicotinamide | $^1$H NMR(CDCl$_3$) δ 0.99(3H, d, J=6.6 Hz), 1.17-1.25(2H, m), 1.52-1.58(1 H, m), 1.70-1.81(3H, m), 2.12(1H, t, J=11.0 Hz), 2.30(3H, s), 2.34(3H, s), 2.40-2.51(1 H, m), 2.54(3H, s), 2.72-2.86(3H, m), 3.23-3.36(2H, m), 3.42(3H, s), 3.68(2H, t, J=4.7 Hz), 3.80-3.92(1H, m), 3.86(2H, t, J= 4.8 Hz), 6.59(2H, d, J=9.0 Hz), 6.73(2H, d, J=8.7 Hz), 6.83(1H, d, J=4.8 Hz), 7.03(1H, d, J=4.8 Hz), 8.11(1H, brs), 8.13(1H, d, J=4.8 Hz), 8.26 (1H, s), 8.30(1H, d, J=4.8 Hz). $^{13}$C NMR(CDCl$_3$) δ 13.74, 19.15, 19.25, 22.70, 29.86, 30.73, 31.66, 40.04, 44.26, 47.10, 52.29, 59.34, 59.56, 60.37, 68.06, 71.53, 115.71, 119.63, 122.82, 125.44, 133.48, 134.02, 143.05, 144.11, 145.47, 148.38, 149.15, 149.58, 152.96, 154.50, 168.62. ES-MS m/z 560.5(M+H)$^+$. |
| 45 | 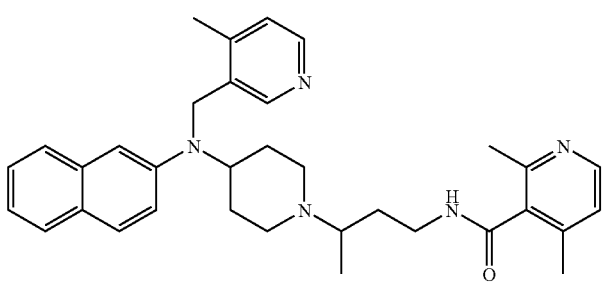<br>2,4-Dimethyl-N-(3-{4-[(4-methyl-pyridin-3-ylmethyl)-naphthalen-2-yl-amino]-piperidin-1-yl}-butyl)-nicotinamide | $^1$H NMR(CDCl$_3$) δ 1.04(d, 3H, J=7.0 Hz), 1.09-1.38(m, 2H), 1.511.98(m, 4H), 2.16-2.69(m, 2H), 2.30(s, 3H), 2.43(s, 3H), 2.52(s, 3H), 2.74-2.96 (m, 3H), 3.28-3.46(m, 1H), 3.68-3.90(m, 1H), 4.08(s, 2H), 6.75-6.88(m, 2H), 6.93(dd, 1H, 2.2, 9.1 Hz), 7.10(d, 1H, J=4.8 Hz), 7.18-7.35 (m, 2H), 7.54(d, 1H, J=8.4 Hz), 7.63(t, 2H, J= 8.8 Hz), 7.87-7.98(m, 1H), 8.13(d, 1H, J=5.4 Hz), 8.30-8.37(m, 2H). $^{13}$C NMR(CDCl$_3$) δ 13.83, 19.17, 19.26, 22.74, 29.68, 30.62, 31.93, 39.75, 44.49, 45.67, 52.34, 57.70, 60.11, 109.31, 117.79, 122.85, 123.03, 125.47, 126.66, 127.72, 129.37, 133.27, 133.97, 135.03, 144.18, 144.89, 146.56, 148.46, 148.68, 149.12, 154.49, 168.68. ES-MS m/z 536(M+H). Anal. Calcd. For C$_{34}$H$_{41}$N$_5$O.0.6H$_2$O.0.1CH$_2$Cl$_2$: C, 73.79; H, 7.69; N, 12.62. Found: C, 73.78; H, 7.61;N, 12.71. |
| 46 | 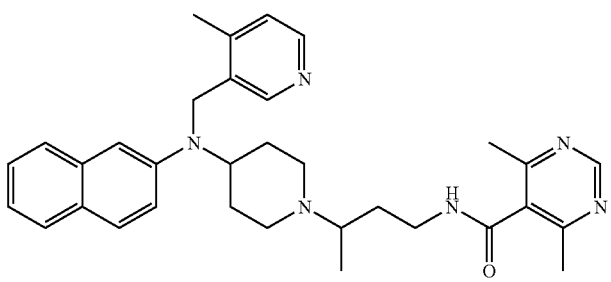<br>4,6-Dimethyl-pyrimidine-5-carboxylic acid (3-{4-[(4-methyl-pyridin-3-ylmethyl)-naphthalen-2-yl-amino]-piperidin-1-yl}-butyl-amide | $^1$H NMR(CDCl$_3$) δ 1.05(d, 3H, J=6.6 Hz), 1.06-1.40(m, 2H), 1.551.95(m, 4H), 2.20-2.30(m, 1H), 2.44(s, 3H), 2.52(s, 6H), 2.58-2.63(m, 1H), 2.77-2.92(m, 3H), 3.30-3.45(m, 1H), 3.70-3.85(m, 2H), 4.14(s, 2H), 6.23(d, 1H, J=2.2 Hz), 6.94 (dd, 1H, J=2.3, 9.0 Hz), 7.10(d, 1H, J=4.8 Hz), 7.18-7.37(m, 2H), 7.54(d, 1H, J=8.2 Hz), 7.63 (t, 2H, J=8.8 Hz), 7.94-8.05(m, 1H), 8.32-8.38 (m, 2H), 8.77(s, 1H). $^{13}$C NMR(CDCl$_3$) δ 13.84, 19.19, 22.39, 29.85, 30.83, 31.75, 40.03, 44.41, 45.83, 52.39, 57.59, 60.08, 109.43, 117.77, 123.07, 125.47, 126.67, 127.74, 129.42, 133.09, 135.03, 146.49, 148.56, 148.71, 157.91, 163.38. ES-MS m/z 537(M+H). Anal. Calcd. For C$_{33}$H$_{40}$N$_6$O.0.6H$_2$O.0.5CH$_2$Cl$_2$: C, 71.86; H, 7.55; N, 15.21. Found: C, 71.87; H, 7.47; N, 15.19. |

| Ex. # | Structure/Name | Characterization Data |
|---|---|---|
| 47 | 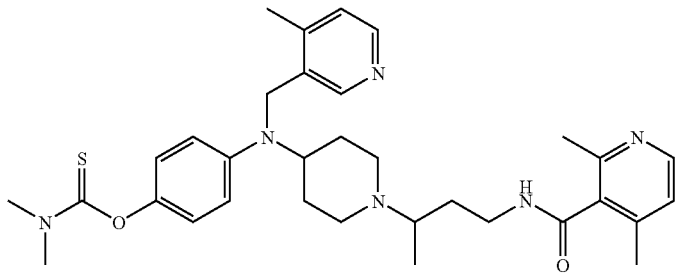<br>Dimethyl-thiocarbamic acid O-{4-[(1-{3-[(2,4-dimethyl-pyridine-3-carbonyl)-amino]-1-methyl-propyl}-piperidin-4-yl)-(4-methyl-pyridin-3-ylmethyl)-amino]-phenyl} ester | $^1$H NMR(CDCl$_3$) δ 1.02(3H, d, J=6.6 Hz), 1.50-2.23(8H, m), 2.30(3H, s), 2.37(3H, s), 2.54(3H, s), 3.29(3H, s), 3.43(3H, s), 2.75-3.85(6H, m), 3.99 (2H, s), 6.53(2H, d, J=9.3 Hz), 6.82(2H, d, J=9.3 Hz), 6.84(1H, d, J=4.8 Hz), 7.09(1H, d, J=4.8 Hz), 7.89(1H, brs), 8.15(1H, d, J=5.4 Hz), 8.28(1H, s), 8.35(1H, d, J=4.8 Hz). $^{13}$C NMR (CDCl$_3$) δ 13.61, 19.18, 19.20, 22.79, 31.99, 39.00, 43.65, 46.08, 52.32, 60.14, 114.43, 122.94, 123.61, 125.48, 133.19, 134.53, 140.30, 143.81, 144.21, 146.10, 146.69, 148.47, 149.20, 154.48, 155.95, 156.99. ES-MS m/z 589.5(M+H)$^+$. |
| 48 | 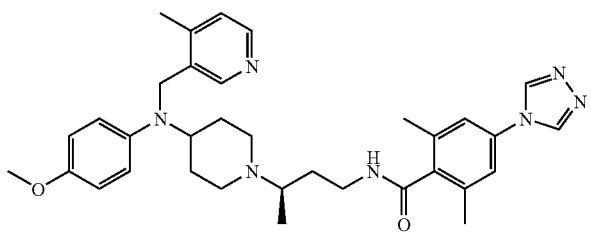<br>N-((R)-3-{4-[(4-Methoxy-phenyl)-(4-methyl-pyridin-3-ylmethyl)-amino]-piperidin-1-yl}-butyl)-2,6-dimethyl-4-[1,2,4]triazol-4-yl-benzamide | $^1$H NMR(CDCl$_3$) δ 0.98(d, 3H, J=6.6 Hz), 1.10 (m, 1H), 1.24(m, 1H), 1.58(m, 1H), 1.78(m, 3H), 2.13(t, 1H, J=11.2 Hz), 2.17(s, 3H), 2.40(s, 3H), 2.48(t, 1H, J=11.2 Hz), 2.65-2.90(m, 3H), 3.21 (m, 1H), 3.40(m, 1H), 3.71(s, 3H), 3.75(m, 1H), 4.01(s, 2H), 6.60-6.70(m, 4H), 6.95(d, 2H, J= 4.8 Hz), 7.04(s, 2H), 8.28(s, 1H), 8.29(d, 2H, J= 5.4 Hz), 8.37(s, 2H). $^{13}$C NMR(CDCl$_3$) δ 13.87, 18.93, 19.73(2C), 30.33, 30.90, 32.50, 39.27, 44.80, 48.28, 51.68, 55.95, 59.14, 59.24, 114.75 (2C), 120.48(2C), 120.63(2C), 125.40, 133.68, 133.75, 137.62(2C), 139.39, 141.26, 142.96, 145.12, 148.37, 149.40, 154.13, 168.84. ES-MS m/z 582(M+H)$^+$. Anal. Calcd. for C$_{34}$H$_{43}$N$_7$O$_2$•0.4CH$_2$Cl$_2$: C, 67.10; H, 7.17; N, 15.92. Found: C, 67.05; H, 7.25;N, 16.03. |
| 49 | 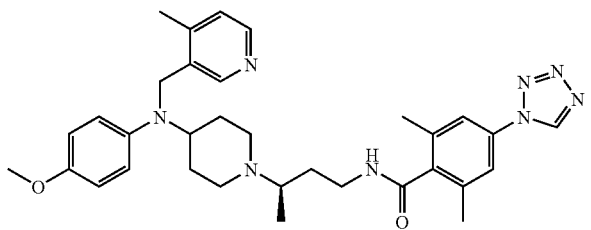<br>N-((R)-3-{4-[(4-Methoxy-phenyl)-(4-methyl-pyridin-3-ylmethyl)-amino]-piperidin-1-yl}-butyl)-2,6-dimethyl-4-tetrazol-1-yl-benzamide | $^1$H NMR(CDCl$_3$) δ 0.99(d, 3H, J=6.6 Hz), 1.10 (m, 1H), 1.24(m, 1H), 1.58(m, 1H), 1.78(m, 3H), 2.11(t, 1H, J=11.2 Hz), 2.15(s, 3H), 2.43(s, 3H), 2.48(t, 1H, J=11.2 Hz), 2.65-2.90(m, 3H), 3.15 (m, 1H), 3.37(m, 1H), 3.70(s, 3H), 3.85(m, 1H), 3.91(s, 2H), 6.55-6.70(m, 4H), 6.88(d, 2H, J= 5.1 Hz), 7.40(s, 2H), 8.00(br, 1H), 8.23(s, 1H), 8.24(d, 2H, J=6.0 Hz), 8.91(s, 1H). $^{13}$C NMR (CDCl$_3$) δ 13.84, 18.93, 19.74(2C), 30.30, 30.97, 32.08, 39.64, 44.49, 48.06, 51.89, 55.92, 59.55, 59.73, 114.69(2C), 119.73(2C), 120.93(2C), 125.38, 133.61, 133.63, 137.43(2C), 140.26, 140.66, 142.90, 145.23, 148.23, 149.38, 154.27, 168.70. ES-MS m/z 583(M+H). Anal. Calcd. for C$_{33}$H$_{42}$N$_8$O$_2$•0.3CH$_2$Cl$_2$: C, 65.76; H, 7.06; N, 18.42. Found: C, 65.93; H, 7.13; N, 18.55. |
| 50 | 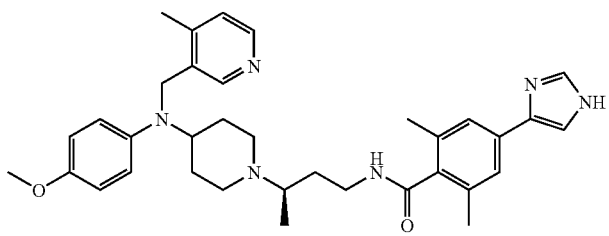<br>4-(1H-Imidazol-4-yl)-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d, 3H, J=6.6 Hz), 1.02-1.30(m, 2H), 1.45-1.55(m, 1H), 1.70-1.80(m, 3H), 2.0.2-2.10(m, 1H), 2.16(s, 3H), 2.28(s, 6H), 2.39-2.43(m, 1H), 2.69-2.84(m, 3H), 3.04-3.12 (m, 1H), 3.25-3.33(m, 1H), 3.66(s, 3H), 3.75-3.80 (m, 3H), 6.55-6.70(m, 4H), 6.86(d, 1H, J=4.8 Hz), 7.00(br. s, 1H), 7.31(s, 2H), 7.45(s, 1H), 8.08(br. s, 1H), 8.15(d, 1H, J=4.8 Hz), 8.37(br. s, 1H). $^{13}$C NMR(CDCl$_3$) δ 13.60, 18.87, 19.40, 29.79, 30.62, 31.43, 39.73, 44.08, 47.46, 51.92, 55.64, 60.10, 60.63, 114.36, 121.67, 123.84, 125.25, 133.78, 134.56, 135.88, 136.72, 142.92, 145.77, 147.39, 149.22, 154.27, 170.56. ES-MS m/z 581(M+H). Anal. Calcd. for C$_{35}$H$_{44}$N$_6$O•0.5CH$_2$Cl$_2$: C, 68.42; H, 7.28; N, 13.48. Found: C, 68.67; H, 7.39; N, 13.54. |

| Ex. # | Structure/Name | Characterization Data |
|---|---|---|
| 51 | 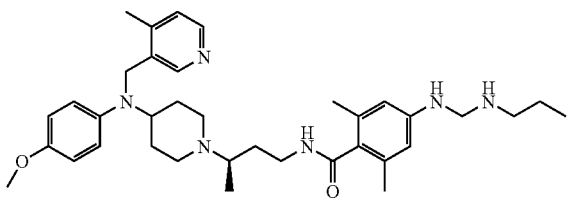<br>N-((R)-3-{4-[(4-Methoxy-phenyl)-(4-methyl-pyridin-3-ylmethyl)-amino]-piperidin-1-yl}-butyl)-2,6-dimethyl-4-(3-propyl-ureido)-benzamide | $^1$H NMR(CDCl$_3$) δ 0.87(t, 3H, J=6 Hz), 0.96(d, 3H, J=6 Hz), 1.05-1.26(m, 2H), 1.42-1.51(m, 3H), 1.69-1.75(m, 3H), 2.02-2.13(m, 2H), 2.16(s, 6H), 2.24(s, 3H), 2.20-2.42(m, 1H), 2.71-2.83(m, 3H), 3.08-3.28(m, 3H), 3.70(s, 3H), 3.71-3.73(m, 1H), 3.96(s, 2H), 5.49(br m, 1H), 6.70-6.74(m, 4H), 6.77(s, 2H), 6.99(d, 1H, J=5.1 Hz), 7.45(s, 1H), 8.06(br m, 1H), 8.25(d, 1H, J=5.1 Hz), 8.34(s, 1H). ES-MS m/z 615(M+H). |
| 52 | 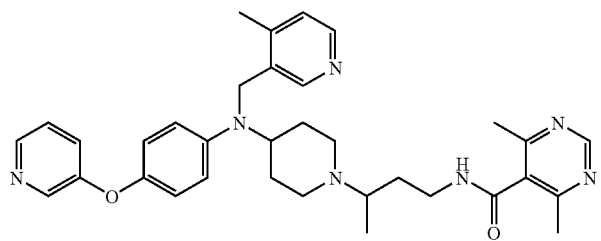<br>4,6-Dimethyl-pyrimidine-5-carboxylic acid [3-(4-{(4-methyl-pyridin-3-ylmethyl)-[4-(pyridin-3-yloxy)-phenyl]-amino}-piperidin-1-yl)-butyl]-amide | $^1$H NMR(CDCl$_3$) δ 1.02(d, 3H, J=6.6 Hz), 1.05-1.26(m, 2H), 1.54-1.60(m, 1H), 1.74-1.90(m, 3H), 2.16-2.23(m, 1H), 2.39(s, 3H), 2.48-2.59(m, 1H), 2.50(s, 6H), 2.74-2.89(m, 3H), 3.34-3.38(m, 1H), 3.50-3.58(m, 1H), 3.74-3.81(m, 1H), 4.02(s, 2H), 6.57(d, 2H, J=9 Hz), 6.84(d, 2H, J=9 Hz), 7.08(d, 1H, J=5.1 Hz), 7.16-7.19(m, 1H), 7.16 (s, 1H), 8.09(br s, 1H), 8.25(dd, 1H, J=3.9, 2.1 Hz), 8.28(s, 1H), 8.31-8.33(m, 1H), 8.33(d, 1H, J=4.8 Hz), 8.78(s, 1H). $^{13}$C NMR(CDCl$_3$) δ 13.84, 19.07, 22.35, 29.84, 30.74, 31.86, 39.86, 44.44, 46.33, 52.15, 57.68, 59.85, 116.58, 121.07, 121.30, 124.26, 125.49, 131.08, 132.96, 140.70, 143.69, 144.99, 145.74, 147.83, 148.49, 148.59, 155.51, 157.82, 163.34, 166.85. ES-MS m/z 580 (M+H). Anal. Calcd. for C$_{34}$H$_{41}$N$_7$O$_2$•0.8H$_2$O•0.3CH$_2$Cl$_2$: C, 66.49; H, 7.03; N, 15.82. Found: C, 66.23; H, 6.88; N, 16.16. |
| 53 | 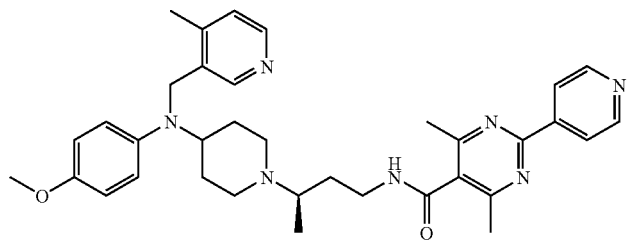<br>4,6-Dimethyl-2-pyridin-4-yl-pyrimidine-5-carboxylic aicd (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 1.00(d, 3H, J=6.6 Hz), 0.99-1.25(m, 2H), 1.54-1.60(m, 1H), 1.73-1.83(m, 3H), 2.08-2.15(m, 1H), 2.10(s, 3H), 2.49-2.57(m, 1H), 2.60(s, 6H), 2.76-2.86(m, 3H), 3.12-3.19(m, 1H), 3.30-3.40(m, 1H), 3.68(s, 31-I), 3.79(s, 2H), 3.79-3.90(m, 1H), 6.53-6.65(m, 411), 6.79(d, 1H, J=4.8 Hz), 8.11(s, 1H), 8.17-8.19(m, 3H), 8.33 (br s, 1H), 8.65-8.67(m, 2H). $^{13}$C NMR(CDCl$_3$) δ 15.13, 15.39, 20.59, 24.13, 31.05, 31.70, 32.50, 33.33, 34.70, 41.64, 44.72, 45.93, 49.09, 53.68, 55.42, 57.45, 59.77, 61.39, 61.59, 116.21, 116.59, 122.70, 123.96, 126.90, 131.68, 134.80, 144.25, 146.30, 147.10, 149.88, 150.63, 151.24, 152.19, 155.93, 163.02, 165.62, 168.70. ES-MS m/z 594 (M+H). Anal. Calcd. for C$_{35}$H$_{43}$N$_7$O$_2$•0.2 H2O•0.2 CH$_2$Cl$_2$: C, 68.62; H, 7.20; N, 15.91. Found: C, 68.65; H, 7.20; N, 15.87. |
| 54 | 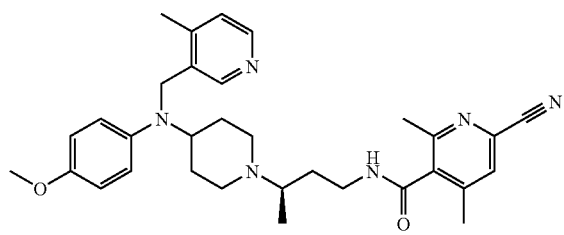<br>6-Cyano-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.95-1.18(m, 5H), 1.52-1.60 (m, 1H), 1.65-1.90(m, 3H), 2.09-2.17(m, 1H), 2.32(s, 3H), 2.34(s, 3H), 2.45-2.50(m, 1H), 2.55 (s, 3H), 2.69-2.82(m, 3H), 3.16-3.26(m, 1H), 3.32-3.38(m, 1H), 3.73(s, 3H), 3.73-3.80(m, 1H), 3.99(s, 2H), 6.62-6.75(m, 4H), 7.04(d, 1H, J= 4.8 Hz), 7.30(s, 1H), 8.10-8.22(m, 2H), 8.27(d, 1H, J=4.8 Hz). $^{13}$C NMR(CDCl$_3$) δ 13.56, 18.91, 22.46, 30.01, 30.71, 31.57, 39.55, 44.21, 48.01, 51.71, 55.74, 58.65, 59.54, 114.59, 117.13, 120.28, 125.35, 127.56, 132.68, 133.24, 136.79, 142.37, 145.43, 145.60, 148.12, 149.16, 153.99, 156.78, 166.66. ES-MS m/z 541(M+H). Anal. Calcd. for C$_{32}$H$_{40}$N$_6$O$_2$•0.4CH$_2$Cl$_2$: C, 67.67; H, 7.16; N, 14.62. Found: C, 67.54; H, 7.28; N, 14.47. |

| Ex. # | Structure/Name | Characterization Data |
|---|---|---|
| 55 | 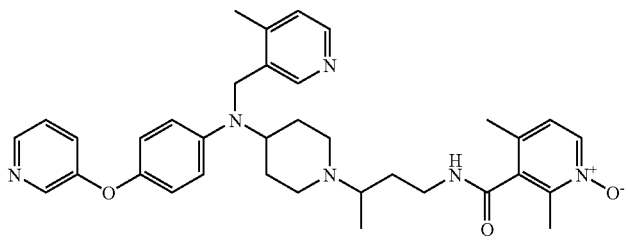<br>2,4-Dimethyl-N-[3-(4-{(4-methyl-pyridin-3-ylmethyl)-[4-(pyridin-3-yloxy)-phenyl]-amino}-piperidin-1-yl)-butyl]-1-oxy-nicotinamide | $^1$H NMR(CDCl$_3$) δ 1.03(d, 3H, J=6.6 Hz), 1.41-1.66(m, 3H), 1.81-1.92(m, 3H), 2.15-2.20(m, 1H), 2.25(s, 3H), 2.29(s, 3H), 2.35(s, 3H), 2.47-2.57(m, 1H), 2.79-2.89(m, 3H), 3.40-3.46(m, 1H), 3.56-3.64(m, 2H), 4.25(s, 2H), 6.63(d, 2H, J=9 Hz), 6.81(d, 1H, J=6.6 Hz), 6.86(d, 2H, J=9 Hz), 7.07(d, 1H, J=4.8 Hz), 7.14-7.18(m, 1H), 7.16(s, 1H), 7.80(d, 1H, J=6.6 Hz), 8.24(dd, 1H, J=3.9, 2.1 Hz), 8.32-8.34(m, 2H), 8.33(s, 1H), 8.52(br t, 1H). $^{13}$C NMR(CDCl$_3$) δ 13.99, 15.38, 18.67, 18.99, 30.10, 30.52, 33.10, 38.88, 45.28, 46.63, 51.51, 57.62, 58.27, 116.21, 121.13, 124.20, 124.27, 125.24, 125.45, 133.28, 135.04, 137.32, 138.09, 140.65, 143.66, 144.87, 145.89, 146.06, 147.55, 148.43, 148.56, 155.59, 165.84. ES-MS m/z 595(M+H). Anal. Calcd. for C$_{35}$H$_{42}$N$_6$O$_3$F$_3$•4H$_2$O•0.6CH$_2$Cl$_2$: C, 65.49; H, 6.79; N, 12.87. Found: C, 65.64; H, 6.79; N, 12.99. |
| 56 | 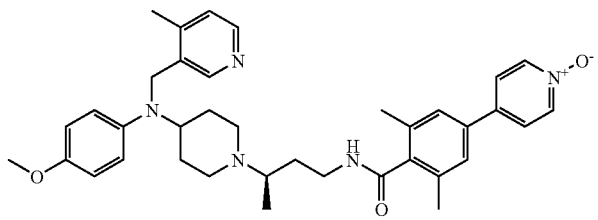<br>N-((R)-3-{4-[(4-Methoxy-phenyl)-(4-methyl-pyridin-3-ylmethyl)-amino]-piperidin-1-yl}-butyl)-2,6-dimethyl-4-(1-oxy-pyridin-4-yl)-benzamide | $^1$H NMR(CDCl$_3$) δ 0.99(d, 3H, J=6.6 Hz), 1.12-1.38(m, 2H), 1.54-1.62(m, 1H), 1.72-1.82(m, 4H), 2.15(s, 3H), 2.35-2.50(m, 1H), 2.40(s, 6H), 2.73-2.87(m, 3H), 3.17-3.21(m~ 1H), 3.34-3.40(m, 1H), 3.69(s, 3H), 3.69-3.87(m, 1H), 3.87(s, 2H), 6.58-6.70(m, 4H), 6.88(d, 1H, J=5.1 Hz), 7.27-7.29(m, 2H), 7.98-8.01(br s, 1H), 8.05-8.08(m, 2H), 8.23-8.26(m, 2H). $^{13}$C NMR(CDCl$_3$) δ 13.83, 19.06, 19.80, 29.87, 30.69, 32.10, 39.67, 44.53, 47.12, 52.07, 55.89, 59.90, 60.17, 114.65, 120.83, 123.60, 125.32, 125.55, 133.46, 135.90, 136.13, 137.95, 139.51, 139.67, 142.90, 145.16, 148.36, 149.87, 154.20, 169.56. ES-MS m/z 609 (M+H). Anal. Calcd. for C$_{37}$H$_{45}$N$_5$O$_3$: C, 62.34; H, 6.53; N, 9.42. Found: C, 62.68; H, 6.58; N, 9.30. |
| 57 | 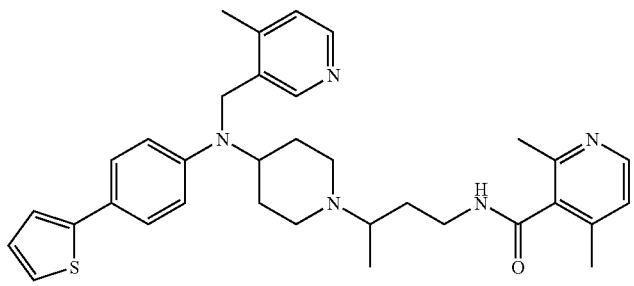<br>2,4-Dimethyl-N-(3-{4-[(4-methyl-pyridin-3-ylmethyl)-(4-thiophen-2-yl-phenyl)-amino]-piperidin-1-yl}-butyl)-nicotinamide | $^1$H NMR(CDCl$_3$) δ 1.03(d, 3H, J=6.6 Hz), 1.04-1.34(m, 2H), 1.50-1.92(m, 4H), 2.15-2.35(m, 1H), 2.30(s, 3H), 2.40(s, 3H), 2.49-2.67(m, 1H), 2.55(s, 3H), 2.73-2.94(m, 3H), 3.28-3.43(m, 1H), 3.60-3.88(m, 2H), 4.03(s, 2H), 6.56(d, 2H, J=8.8 Hz), 6.83(d, 1H, J=4.8 Hz), 7.00(dd, 1H, J=1.0, 3.8 Hz), 7.06-7.16(m, 3H), 7.38(d, 2H, J=8.8 Hz), 7.84(br s, 1H), 8.15(d, 1H, J=4.7 Hz), 8.28(s, 1H), 8.37(d, 1H, J=4.2 Hz). $^{13}$C NMR (CDCl$_3$) δ 13.79, 19.18, 22.74, 30.66, 31.94, 44.39, 45.48, 52.37, 57.02, 60.13, 114.33, 121.60, 122.86, 123.47, 125.45, 127.44, 128.22, 148.38, 148.51, 149.14. ES-MS m/z 568(M+H). Anal. Calcd. For C$_{34}$H$_{41}$N$_5$OS•0.9CH$_4$OH: C, 70.22; H, 7.54; N, 11.72. Found: C, 70.09; H, 7.20; N, 11.94. |
| 58 | 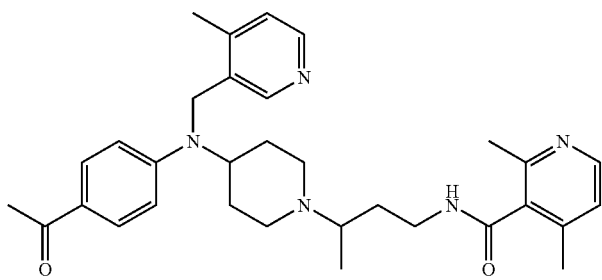<br>N-(3-{4-[(4-Acetyl-phenyl)-(4-methyl-pyridin-3-ylmethyl)-amino]-piperidin-1-yl}-butyl)-2,4-dimethyl-nicotinamide | $^1$H NMR(CDCl$_3$) δ 1.04(d, 3H, J=6.5 Hz), 1.08-1.42(m, 2H), 1.53-1.96(m, 4H), 2.19-2.35(m, 1H), 2.30(s, 3H), 2.41(s, 3H), 2.47(s, 3H), 2.54(s, 3H), 2.56-2.69(m, 1H), 2.73-2.94(m, 3H), 3.30-3.45(m, 1H), 3.72-3.89(m, 2H), 4.15(s, 2H), 6.52(d, 2H, J=9.1 Hz), 6.85(d, 1H, J=4.7 Hz), 7.13(d, 1H, J=4.8 Hz), 7.58(br s, 1H), 7.78(d, 2H, J=9.3 Hz), 8.17(s, 1H), 8.19(d, 1H, J=5.4 Hz), 8.39(d, 1H, J=5.3 Hz). $^{13}$C NMR(CDCl$_3$) δ 13.86, 19.12, 22.76, 26.41, 29.78, 30.69, 32.13, 39.66, 44.35, 45.16, 52.14, 56.50, 59.88, 112.06, 122.89, 125.53, 131.03, 132.01, 144.25, 144.53, 147.79, 148.79, 149.16, 152.17, 154.49. ES-MS m/z 528(M+H). Anal. Calcd. For C$_{32}$H$_{41}$N$_5$O$_2$•0.7H$_2$NO: C, 69.60; H, 8.12; N, 14.46. Found: C, 69.56; H, 7.88; N, 14.42. |

| Ex. # | Structure/Name | Characterization Data |
|---|---|---|
| 59 | 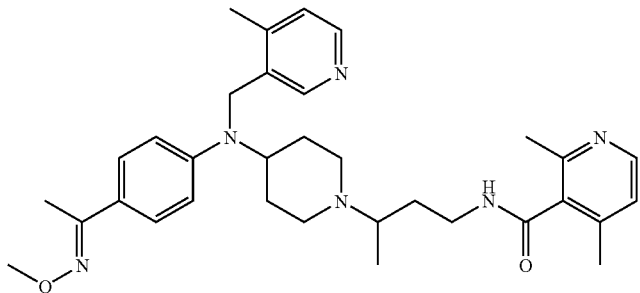

N-(3-{4-[[4-(1-Methoxyimino-ethyl)-phenyl]-(4-methyl-pyridin-3-ylmethyl)-amino]-piperidin-1-yl}-butyl)-2,4-diemthyl-nicotinamide | $^1$H NMR(CDCl$_3$) δ 0.96-1.37(m, 3H), 1.03(d, 3H, J=6.5 Hz), 1.58-1.92(m, 3H), 2.08-2.24(m, 1H), 2.13(s, 3H), 2.30(s, 3H), 2.39(s, 3H), 2.49-2.67 (m, 1H), 2.54(s, 3H), 2.71-2.94(m, 3H), 3.29-3.42(m, 1H), 3.63-3.76(m, 1H), 3.77-3.90(m, 1H), 3.93(s, 3H), 4.02(s, 2H), 6.52(d, 2H, J=9.3 Hz), 6.82 (d, 1H, J=5.4 Hz), 7.09(d, 1H, J=4.9 Hz), 7.43(d, 2H, J=8.7 Hz), 7.81(br s, 1H), 8.14 (d, 1H, J=5.3 Hz), 8.23(s, 1H), 8.35(d, 1H, J=4.8 Hz). $^{13}$C NMR(CDCl$_3$) δ 13.82, 19.16, 29.72, 30.69, 31.93, 39.85, 44.34, 45.21, 52.35, 53.83, 56.88, 60.15, 113.55, 122.85, 125.41, 127.52, 148.32, 148.52, 149.14. ES-MS m/z 557(M+H). Anal. Calcd. For C$_{33}$H$_{44}$N$_6$O$_2$•0.7H$_2$O: C, 69.54; H, 8.04; N, 14.75. Found: C, 69.59; H, 7.90; N, 14.50 |
| 60 | 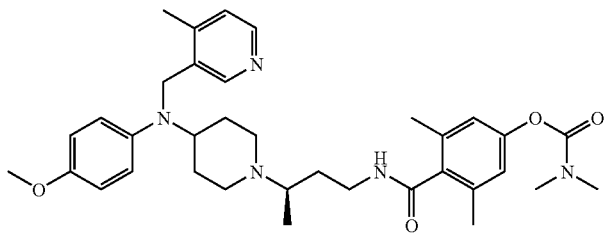

Dimethyl-carbamic acid 4-((R)-3-{4-[(4-methoxy-phenyl)-(4-methyl-pyridin-3-ylmethyl)-amino]-piperidin-1-yl}-butylcarbamoyl)-3,5-dimethyl-phenyl ester | $^1$H NMR(CDCl$_3$) δ 0.98(d, 3H, J=6 Hz), 1.25(m, 3H), 1.59(m, 3H), 1.72(m, 1H), 1.82(m, 2H), 2.13(t, 1H, J=10 Hz), 2.30(s, 6H), 2.33(s, 4H), 2.46(t, 2H, J=11Hz), 2.75(m, 4H), 2.99(d, 6H, J=11 Hz), 3.28(m, 2H), 3.66(t, 1H, J=6 Hz), 3.71 (s, 3H), 4.07(s, 2H), 6.70(m, 4H), 6.78(m, 2H), 7.01 (m, 2H), 8.29(m, 2H). $^{13}$C NMR(CDCl$_3$) δ 13.8, 19.1, 19.7, 29.8, 30.6, 32.7, 36.8, 37.0, 39.0, 44.8, 47.5, 51.9, 55.9, 59.0, 59.6, 114.7, 118.1, 120.1, 121.0, 125.3, 133.8, 135.7, 136.0, 143.1, 145.5, 148.3, 149.7, 151.6, 153.8, 155.1, 170.1. ES-MS m/z 602(M+H), 625(M+Na). Anal. Calcd. For C$_{35}$H$_{47}$N$_5$O$_4$•0.6 CH$_2$Cl$_2$: C, 69.86; 11, 7.87; N, 11.64. Found: C, 65.53; H, 7.52; N, 10.67. |
| 61 | 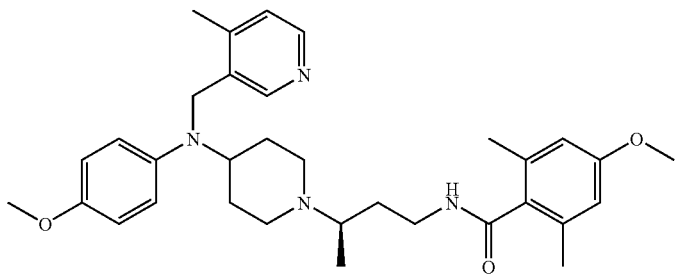

4-Methoxy-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.89(m, 1H), 0.97(d, 3H, J=6 Hz), 1.16(m, 1H), 1.32(m, 2H), 1.55(m, 4H), 1.76(m, 3H), 2.09(t, 1H, J=12 Hz), 2.30(s, 9H), 3.52(s, 3H), 3.71(s, 3H), 3.78(m, 2H), 3.87(s, 2H), 6.48(s, 2H), 6.68(m, 4H), 7.00(d, 1H, J=6 Hz), 7.76(br s, 1H), 8.29(m, 2H). $^{13}$C NMR (CDCl$_3$) δ 13.8, 19.2, 19.9, 29.6, 30.6, 32.1, 39.8, 44.4, 46.8, 52.3, 55.9, 60.2, 60.3, 113.0, 114.7, 118.2, 120.5, 125.4, 129.2, 131.3, 131.7, 133.6, 136.1, 143.0, 145.6, 148.3, 149.9, 154.0, 159.6, 170.5. ES-MS m/z 545(M+H), 568 (M+Na). Anal. Calcd. For C$_{33}$H$_{44}$N$_4$O$_3$•0.3 CH$_2$Cl$_2$: C, 72.76; H, 8.14;N, 0.28. Found: C, 70.22; H, 8.07; N, 9.56. |
| 62 | 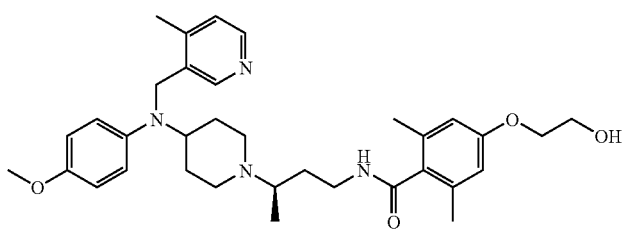

4-(2-Hydroxy-ethoxy)-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d, 3H, J=6 Hz), 1.08(m, 1H), 1.26(m, 2H), 1.54(m, 1H), 1.73(m, 4H), 2.04(t, 1H, J=11 Hz), 2.28(s, 3H), 2.31(s, 6H), 2.46(t, 2H, J=11Hz), 2.71(m, 1H), 2.83(m, 2H), 3.09(m, 1H), 3.26(br t, 1H), 3.69(s, 3H), 3.85(m, 7H), 6.47(s, 2H), 6.68(s, 4H), 6.97(d, 1H, J=6 Hz), 8.26(m, 3H). $^{13}$C NMR(CDCl$_3$) δ 13.7, 19.3, 19.9, 29.7, 30.8, 31.7, 40.2, 44.0, 47.1, 52.4, 55.8, 60.8, 61.4, 61.7, 70.0, 113.8, 114.5, 122.5, 125.5, 133.6, 136.1, 142.9, 146.0, 147.8, 150.3, 158.9, 170.4. ES-MS m/z 575. Anal. Calcd. For C$_{34}$H$_{46}$N$_4$O$_4$•1.0 CH$_2$Cl$_2$: C, 71.05; H, 8.07; N, 9.75. Found: C, 63.97; 11, 7.23; N, 8.60. |

| Ex. # | Structure/Name | Characterization Data |
|---|---|---|
| 63 | 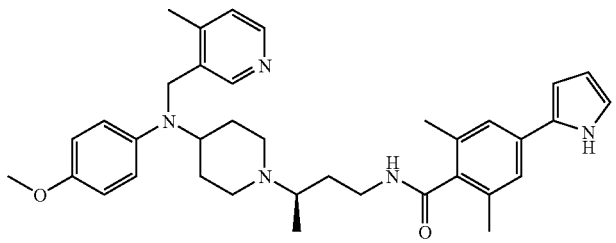<br>N-((R)-3-{4-[(4-Methoxy-phenyl)-(4-methyl-pyridin-3-ylmethyl)-amino]-piperidin-1-yl}-butyl)-2,6-dimethyl-4-(2H-pyrazol-3-yl)-benzamide | $^1$H NMR(CDCl$_3$) δ 0.97(d, 3H, J=6.6 Hz), 1.08 (m, 1H), 1.24(m, 1H), 1.54(m, 1H), 1.78(m, 3H), 2.07(t, 1H, J=11.2 Hz), 2.17(s, 3H), 2.33(s, 3H), 2.45(t, 1H, J=11.2 Hz), 2.65-2.90(m, 3H), 3.08 (m, 1H), 3.33(m, 1H), 3.68(s, 3H), 3.85(m, 1H), 3.85(s, 2H), 6.45(d, 1H, J=5.1 Hz), 6.64(s, 4H), 6.89(d, 1H, J=5.1 Hz), 7.40(s, 2H), 7.48(s, 1H), 8.19(br, 1H), 8.24(d, 1H, J=4.5 Hz). $^{13}$C NMR (CDCl$_3$) δ 13.64, 19.09, 19.65(2C), 29.85, 30.75, 32.05, 39.73, 44.31, 47.60, 52.14, 55.86, 60.05, 60.76, 102.66, 114.56(2C), 121.96(2C), 124.94 (2C), 125.47, 132.59, 133.76(2C), 134.81, 138.10, 143.03(2C), 145.95, 147.79, 149.87, 154.48, 170.44. ES-MS m/z 581(M+H). Anal. Calcd. for C$_{35}$H$_{44}$N$_6$O$_2$•0.9CH$_2$Cl$_2$: C, 65.61; H, 7.02; N, 12.79. Found: C, 65.77; H, 7.11; N, 12.92. |
| 64 | 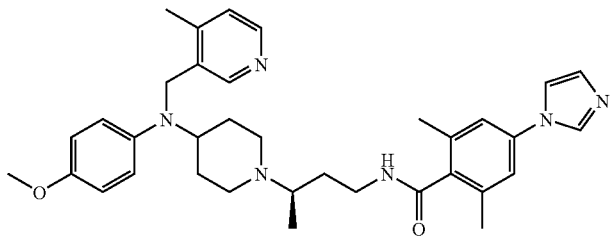<br>6-Imidazol-1-yl-N-((R)-3-{4-[(4-methoxy-phenyl)-(4-methoxy-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 1.10 (m, 1H), 1.24(m, 1H), 1.58(m, 1H), 1.78(m, 3H), 2.13(t, 1H, J=11.2 Hz), 2.13(s, 3H), 2.38(s, 3H), 2.49(t, 1H, J=11.2 Hz), 2.54(s, 3H), 2.65-2.90 (m, 3H), 3.20(m, 1H), 3.37(m, 1H), 3.69(s, 3H), 3.80(m, 1H), 3.90(s, 2H), 6.55-6.70(m, 4H), 6.89 (d, 2H, J=4.8 Hz), 6.95(s, 2H), 7.12(s, 1H), 7.50 (t, 1H, J=1.2 Hz), 8.07(br, 1H), 8.20(s, 1H), 8.23 (s, 1H), 8.24(d, 2H, J=5.4 Hz). $^{13}$C NMR (CDCl$_3$) δ 13.85, 18.85, 19.63, 22.65, 30.21, 30.91, 32.15, 39.66, 44.60, 47.87, 51.90, 55.94, 59.34, 59.61, 110.56, 114.74(2C), 116.34, 120.50(2C), 125.40, 130.79, 132.56, 133.47, 135.15, 142.84, 145.33, 147.94, 148.09, 148.31, 149.41, 154.13, 155.06, 168.01. ES-MS m/z 582(M+H). Anal. Calcd. for C$_{34}$H$_{43}$N$_7$O$_2$•0.8CH$_2$Cl$_2$: C, 64.33; H, 6.92; N, 15.09. Found: C, 64.46; H, 7.01; N, 15.10 |
| 65 | 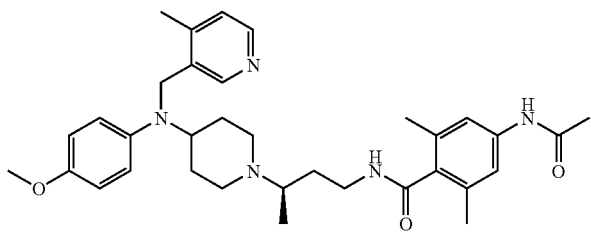<br>4-Acetylamino-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.95(d, 3H, J=6.0 Hz), 1.05-1.09(m, 1H), 1.60(s, 3H), 1.70-1.72(m, 3H), 2.01 (s, 3H), 2.23(s, 2H), 2.30(s, 6H), 2.48(m, 1H), 2.77(m, 1H), 2.80(m, 2H), 3.01(m, 1H), 3.27(m, 1H), 3.72(s, 3H), 3.84(m, 1H), 3.89(s, 2H), 6.71 (s, 4H), 6.98(d, 1H, J=6.0 Hz), 7.21(s, 1H), 7.91 (s, 1H), 8.28(d, 1H, J=6.0 Hz), 8.39(s, 2H). $^{13}$C NMR(CDCl$_3$) δ 13.75, 19.08, 19.74, 24.84, 30.43, 31.26, 31.53, 40.05, 43.98, 48.41, 52.11, 55.87, 60.49, 60.79, 114.58, 118.84, 123.28, 125.47, 134.16, 134.62, 135.23, 138.79, 143.11, 145.78, 147.84, 150.02, 155.06, 168.97, 170.36. ES-MS m/z 572(M+H). Anal. Calcd. for C$_{34}$H$_{45}$N$_5$O$_3$•0.37CH$_2$Cl$_2$: C, 68.44; H, 7.64; N, 11.61. Found: C, 68.09; H, 7.77; N, 11.62. |
| 66 | 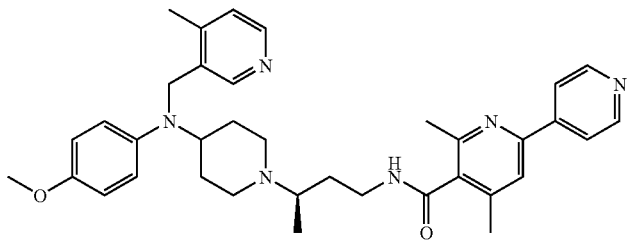<br>4,5-Dimethyl-[2,4']bypyridinyl-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.99(d, 3H, J=6.6 Hz), 0.98-1.26(m, 2H), 1.54-1.60(m, 1H), 1.73-1.83(m, 3H), 2.08-2.15(m, 1H), 2.09(s, 3H), 2.41(s, 3H), 2.49-2.60(m, 1H), 2.64(s, 3H), 2.72-2.87(m, 3H), 3.14-3.22(m, 1H), 3.30-3.40(m, 1H), 3.68(s, 3H), 3.79(s, 2H), 3.79-3.90(m, 1H), 6.54-6.66(m, 4H), 6.79(d, 1H, J=5.1 Hz), 7.43(s, 1H), 7.74-7.77(m, 2H), 8.11(s, 1H), 8.15(s, 1H), 8.20(d, 1H, J=5.1 Hz, 3H), 8.61-8.63(m, 2H). $^{13}$C NMR(CDCl$_3$) δ 13.78, 19.00, 19.49, 22.95, 29.97, 30.82, 31.84, 39.94, 44.34, 47.25, 52.15, 55.87, 59.90, 60.08, 114.63, 119.85, 120.87, 121.26, 125.31, 133.31, 134.05, 142.77, 145.28, 145.39, 146.03, 148.30, 149.65, 150.65, 153.77, 154.21, 155.22, 168.46. ES-MS m/z 593(M+H). Anal. Calcd. for C$_{36}$H$_{44}$N$_6$O$_2$•0.4 H$_2$O•0.7 CH$_2$Cl$_2$: C, 66.84; H, 7.06; N, 12.74. Found: C, 66.79; H, 6.86; N, 12.83. |

| Ex. # | Structure/Name | Characterization Data |
|---|---|---|
| 67 | 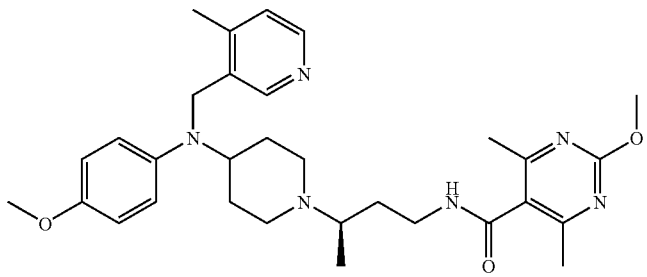<br>2-Methoxy-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.98(d, 3H, J=6.6 Hz), 1.06-1.33(m, 2H), 1.52-1.60(m, 1H), 1.69-1.86(m, 3H), 2.08-2.15(m, 1H), 2.34(s, 3H), 2.44(s, 3H), 2.44-2.60(m, 1H), 2.71-2.86(m, 3H), 3.18-3.35 (m, 2H), 3.71(s, 3H), 3.80(s, 3H), 3.79-3.90(m, 1H), 3.97(s, 2H), 6.54-6.73(m, 4H), 7.01(d, 1H, J=4.5 Hz), 7.43(s, 1H), 7.94(br s, 1H), 8.27-8.29 (m, 2H). $^{13}$C NMR(CDCl$_3$) δ 13.77, 19.14, 22.45, 30.00, 30.83, 31.87, 40.00, 44.40, 47.47, 52.10, 54.97, 55.90, 58.20, 59.80, 59.93, 114.72, 118.01, 120.82, 125.22, 125.47, 133.41, 142.77, 145.86, 148.32, 149.77, 154.21, 164.55, 166.40, 167.64. ES-MS m/z 569(M+Na). Anal. Calcd. for C$_{31}$H$_{42}$N$_6$O$_3$·1.0 H$_2$O: C, 66.79; H, 7.81; N, 15.07. Found: C, 66.68; H, 7.68; N, 15.08. |
| 68 | 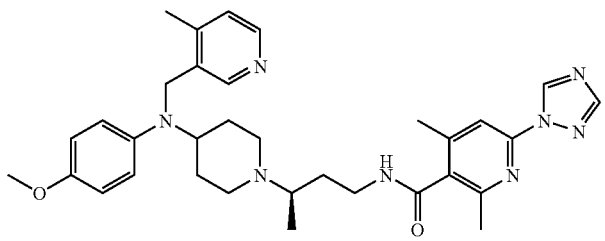<br>N-((R)-3-{4-[(4-Methoxy-phenyl)-(4-methyl-pyridin-3-ylmethyl)-amino]-piperidin-1-yl}-butyl)-2,4-dimethyl-6-[1,2,4]triazol-1-yl-nicotinamide | $^1$H NMR(CDCl$_3$) δ 0.99(d, 3H, J=6.6 Hz), 1.07 (m, 1H), 1.22(m, 1H), 1.58(m, 1H), 1.78(m, 3H), 2.11(t, 1H, J=11.2 Hz), 2.15(s, 3H), 2.41(s, 3H), 2.48(t, 1H, J=11.2 Hz), 2.56(s, 3H), 2.65-2.90 (m, 3H), 3.17(m, 1H), 3.35(m, 1H), 3.70(s, 3H), 3.83(m, 1H), 3.83(s, 2H), 6.50-6.75(m, 4H), 6.88 (d, 2H, J=5.1 Hz), 7.58(s, 1H), 8.01(s, 1H), 8.12 (br, 1H), 8.14(s, 1H), 8.23(d, 2H, J=4.8 Hz), 9.04(s, 1H). $^{13}$C NMR(CDCl$_3$) δ 13.77, 18.86, 19.67, 22.55, 30.11, 30.90, 31.79, 40.01, 44.32, 47.69, 52.11, 55.88, 59.79, 60.10, 111.43, 114.64 (2C), 120.66, 121.16(2C), 125.35, 133.19, 133.49, 141.80, 142.69, 145.39, 148.35, 148.50, 149.67, 153.09, 154.37, 154.60, 167.84. ES-MS m/z 583 (M+H). Anal. Calcd. for C$_{33}$H$_{42}$N$_8$O$_2$·0.3 CH$_2$Cl$_2$: C, 65.76; H, 7.06; N, 18.42. Found: C, 66.04; H, 7.10; N, 18.52. |
| 69 | 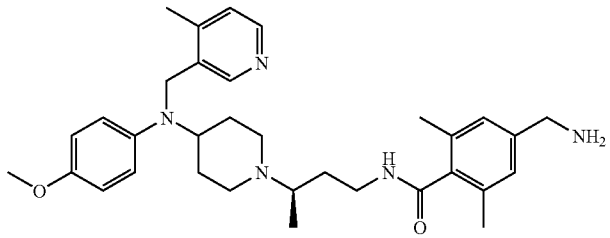<br>4-Aminomethyl-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.97(d, 3H, J=6.0 Hz), 1.25 (m, 1H), 1.33(m, 1H), 1.54(m, 1H), 1.78(m, 3H), 2.10(br t, 1H), 2.27(s, 3H), 2.31(s, 6H), 2.45(br t, 1H), 2.71-2.81(m, 3H), 3.22(m, 1H), 3.32(m, 1H), 3.55(s, 2H), 3.70(s, 3H), 3.75(m, 1H), 3.90 (s, 2H), 6.64(d, 2H, J=6.0 Hz), 6.68(d, 2H, J= 6.0 Hz), 6.90(s, 1H), 7.00(d, 1H, J=6.0 Hz), 7.51 (br s, 1H), 8.27(s, 1H), 8.28(d, 1H, J=6.0 Hz). $^{13}$C NMR(CDCl$_3$) δ 13.8, 19.2, 19.6, 29.7, 30.5, 32.3, 39.4, 44.5, 46.3, 47.1, 52.0, 55.9, 59.7, 60.1, 114.7, 118.2, 120.6, 125.4, 126.4, 133.6, 134.7, 137.3, 143.0, 143.8, 145.5, 148.4, 149.9, 154.0, 170.5. ES-MS m/z 544(M+H), 566(M+Na). Anal. Calcd. for C$_{33}$H$_{45}$N$_6$O$_2$·0.65 CH$_2$Cl$_2$: C, 67.48; H, 7.79; N, 11.69. Found: C, 67.52; H, 7.84; N, 11.66. |
| 70 | 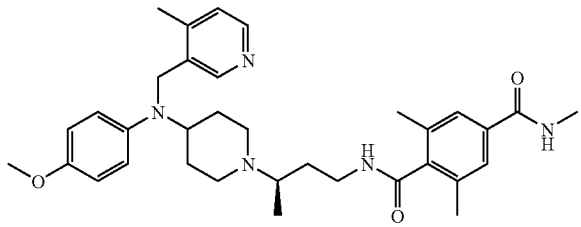<br>N-((R)-3-{4-[(4-Methoxy-phenyl)-(4-methyl-pyridin-3-ylmethyl)-amino]-piperidin-1-yl}-butyl)-2,6,N'-trimethyl-terephthalamide | $^1$H NMR(CDCl$_3$) δ 0.97(d+m, 4H), 1.16(m, 1H), 1.52(m, 1H), 1.73(m, 3H), 2.07(br t, 1H), 2.24(s, 3H), 2.33(s, 6H), 2.46(br t, 1H), 2.69(m, 1H), 2.80(m, 2H), 2.89(d, 3H, J=6.0 Hz), 3.10(m, 1H), 3.30(m, 1H), 3.72(s, 3H), 3.86(m, 1H), 3.92 (s, 2H), 6.64-6.73(m, 5H), 7.00(d, 1H, J= 6.0 Hz), 7.46(s, 2H), 8.05(br s, 1H), 8.30(m, 2H). $^{13}$C NMR(CDCl$_3$) δ 13.7, 19.0, 19.6, 27.1, 30.5, 31.4, 31.7, 39.9, 44.0, 48.8, 52.1, 55.9, 60.2, 60.4, 114.7, 122.1, 125.4, 126.5, 134.0, 134.9, 143.3, 145.3, 148.1, 149.6. ES-MS m/z 572(M+H), 594 (M+Na). Anal. Calcd. for C$_{34}$H$_{45}$N$_5$O$_3$·0.2 CH$_2$Cl$_2$: C, 69.77; H, 7.77; N, 11.90. Found: C, 69.74; H, 7.83; N, 11.97. |

| Ex. # | Structure/Name | Characterization Data |
|---|---|---|
| 71 | 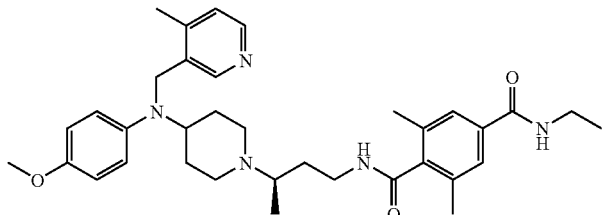<br>N'-Ethyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.97(d+m, 4H), 1.16(t +m, 4H), 1.56(m, 1H), 1.73(m, 3H), 2.09(br t, 1H), 2.25(s, 3H), 2.33(s, 6H), 2.44(br t, 1H), 2.69(m, 1H), 2.80(m, 2H), 3.12(m, 1H), 3.30(m, 1H), 3.43(m, 2H), 3.72(s, 3H), 3.82(m, 1H), 3.95(s, 2H), 6.64-6.73(m, 5H), 7.00(d, 1H, J=6.0 Hz), 7.47(s, 2H), 7.98(br s, 1H), 8.30(m, 2H). $^{13}$C NMR(CDCl$_3$) δ 13.7, 15.2, 19.0, 19.6, 30.5, 31.4, 31.8, 35.2, 39.8, 44.1, 48.9, 52.0, 55.9, 59.9, 60.2, 114.7, 121.8, 125.3, 126.5, 134.0, 134.8, 1349, 141.3, 143.3, 145.3, 148.0, 149.5, 154.6, 167.1, 169.7. ES-MS m/z 586(M+H), 608(M+Na). Anal. Calcd. for C$_{35}$H$_{47}$N$_5$O$_3$•0.15 CH$_2$Cl$_2$: C, 70.54; H, 7.97; N, 11.70. Found: C, 70.43; H, 8.04; N, 11.65. |
| 72 | 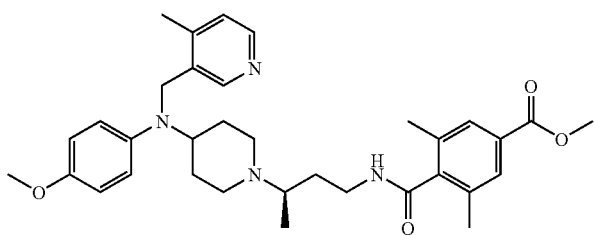<br>N-((R)-3-{4-[(4-Methoxy-phenyl)-(4-methyl-pyridin-3-ylmethyl)-amino]-piperidin-1-yl}-butyl)-3,5-dimethyl-terephthalamic acid methyl ester | $^1$H NMR(CDCl$_3$) δ 0.97(d, 3H, J=6.0 Hz), 1.02 (m, 1H), 1.13(m, 1H), 1.56(m, 1H), 1.77(m, 3H), 2.08(br t, 1H), 2.25(s, 3H), 2.37(s, 6H), 2.46(br t, 1H), 2.72(m, 1H), 2.83(m, 2H), 3.15(m, 1H), 3.32(m, 1H), 3.70(s, 3H), 3.76(s, 5H), 3.88(m, 1H), 6.61(d, 2H, J=7.5 Hz), 6.67(d, 2H, J= 7.5 Hz), 6.98(d, 1H, J=6.0 Hz), 7.67(s, 2H), 8.05(br s, 1H), 8.18(s, 1H), 8.26(d, 1H, J=3.0 Hz). $^{13}$C NMR(CDCl$_3$) δ 13.7, 19.1, 19.5, 29.8, 30.7, 31.7, 39.9, 44.2, 47.1, 52.3, 52.5, 55.9, 60.4, 114.6, 121.2, 125.4, 128.9, 130.2, 133.3, 134.9, 142.8, 145.7, 148.4, 150.1, 154.3, 169.5. ES-MS m/z 573 (M+H), 595(M+Na). Anal. Calcd. for C$_{34}$H$_{44}$N$_4$O$_4$• 0.3 CH$_2$Cl$_2$: C, 68.87; H, 7.51; N, 9.37. Found: C, 68.81; H, 7.55; N, 9.36. |
| 73 | 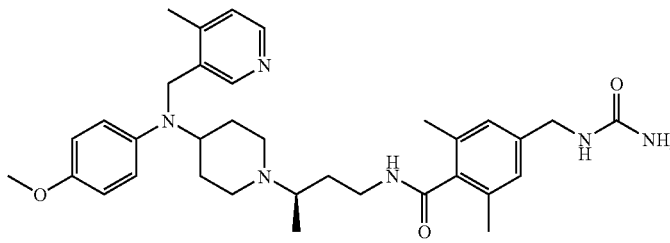<br>N-((R)-3-{4-[(4-Methoxy-phenyl)-(4-methyl-pyridin-3-ylmethyl)-amino]-piperidin-1-yl}-butyl)-2,6-dimethyl-4-ureidomethyl-benzamide | $^1$H NMR(CDCl$_3$) δ 0.98(d, 3H, J=6.0 Hz), 1.07 (m, 1H), 1.28(m, 1H), 1.53(m, 1H), 1.75(m, 3H), 2.10(br t, 1H), 2.25(s, 3H), 2.26(s, 6H), 2.46(br t, 1H), 2.71-2.81(m, 3H), 3.12(m, 1H), 3.29(m, 1H), 3.71(s, 3H), 3.74(m, 1H), 3.97(s, 2H), 4.07 (d, 2H, J=6.0 Hz), 4.69(s, 2H), 6.64-6.72(m, 4H), 6.84(s, 2H), 7.00(d, 1H, J=6.0 Hz), 7.98(br s, 1H), 8.26(d, 1H, J=3.0 Hz), 8.29(s, 1H). $^{13}$C NMR(CDCl$_3$) δ 13.7, 19.1, 19.6, 31.9, 43.9, 48.1, 51.9, 55.9, 60.2, 114.6, 122.3, 125.6, 126.4, 134.6, 140.2, 142.8, 145.6, 148.0, 149.8, 159.3. ES-MS m/z 587(M+H). Anal. Calcd. for C$_{34}$H$_{46}$N$_6$O$_3$•0.25 CH$_2$Cl$_2$: C, 67.66; H, 7.71; N, 13.82. Found: C, 67.73; H, 7.82; N, 13.76. |
| 74 | 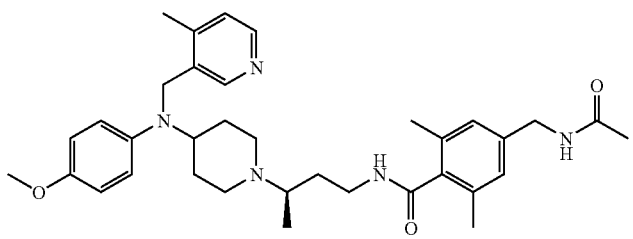<br>4-(Acetylamino-methyl)-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.97(d, 3H, J=6.0 Hz), 1.08 (m, 1H), 1.26(m, 1H), 1.53(m, 1H), 1.75(m, 3H), 1.96(s, 3H), 2.08(brt, 1H), 2.26(s, 3H), 2.31(s, 6H), 2.45(brt, 1H), 2.69-2.83(m, 3H), 3.12(m, 1H), 3.29(m, 1H), 3.72(s, 3H), 3.81(m, 1H), 3.96 (s, 2H), 4.21(d, 2H, J=6.0 Hz), 6.38(br t, 1H), 6.65-6.73(m, 4H), 6.91(s, 2H), 7.01(d, 1H, J=6.0 Hz), 7.75(br s, 1H), 8.28(m, 2H). $^{13}$C NMR (CDCl$_3$) δ 13.7, 19.1, 19.6, 31.3, 32.1, 39.7, 43.3, 48.2, 52.1, 60.1, 114.6, 121.9, 125.4, 126.9, 148.1, 149.8. ES-MS m/z 586(M+H), 608(M+Na). Anal. Calcd. for C$_{35}$H$_{47}$N$_5$O$_3$•0.25 CH$_2$Cl$_2$: C, 69.75; H, 7.89; N, 11.54. Found: C, 69.83; H, 8.08; N, 11.43. |

| Ex. # | Structure/Name | Characterization Data |
|---|---|---|
| 75 | 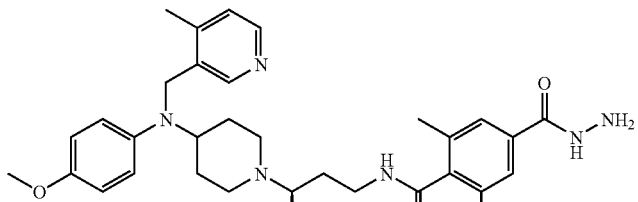<br>4-Hydrazinocarbonyl-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.90(d+m, 4H), 1.16(m, 1H), 1.57(m, 1H), 1.72(m, 3H), 2.10(br t, 1H), 2.24(s, 3H), 2.33(s, 6H), 2.45(br t, 1H), 2.69-2.83(m, 3H), 3.06(m, 1H), 3.31(m, 1H), 3.72(s, 3H), 3.96 (m, 3H), 6.66-6.73(m, 4H), 7.00(d, 1H, J= 6.0 Hz), 7.46(s, 2H), 8.28(s, 1H), 8.32(d+m, 3H). $^{13}$C NMR(CDCl$_3$) δ 13.7, 19.1, 19.6, 31.5, 49.1, 52.1, 55.9, 60.5, 114.7, 122.8, 125.4, 126.5, 132.9, 135.0, 148.0, 149.6. ES-MS m/z 573(M+H). Anal. Calcd. for C$_{33}$H$_{44}$N$_6$O$_3$•0.4 CH$_2$Cl$_2$: C, 66.12; H, 7.44; N, 13.85. Found: C, 66.27; H, 7.51; N, 13.55. |
| 76 | 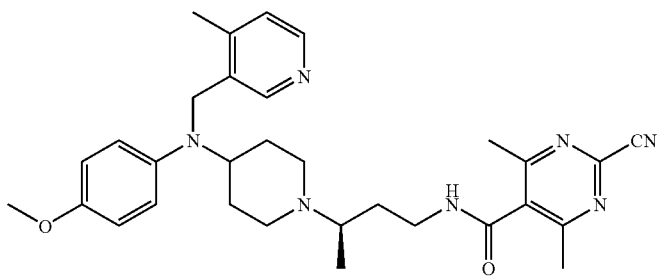<br>2-Cyano-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.99(d, 3H, J=6.6 Hz), 0.92-1.16(m, 2H), 1.54-1.60(m, 1H), 1.69-1.86(m, 3H), 2.08-2.16(m, 1H), 2.36(s, 3H), 2.46-2.53(m, 1H), 2.53(s, 3H), 2.72-2.82(m, 3H), 3.15-3.37(m, 2H), 3.74(s, 3H), 3.74-3.81(m, 1H), 4.01(s, 2H), 6.62-6.76(m, 4H), 7.05(d, 1H, J=4.5 Hz), 8.21(s, 1H), 8.28(d, 1H, J=4.5 Hz), 8.35(br s, 1H). $^{13}$C NMR(CDCl$_3$) δ 13.81, 19.13, 22.25, 30.39, 31.05, 31.84, 39.81, 44.49, 48.41, 51.87, 53.86, 55.96, 58.89, 59.50, 114.82, 115.87, 120.69, 125.62, 132.97, 133.52, 142.48, 143.77, 145.87, 148.20, 149.28, 154.32, 165.30, 165.40. ES-MS m/z 543 (M+H). Anal. Calcd. for C$_{31}$H$_{39}$N$_7$O$_2$•0.1 H$_2$O•0.2 CH$_2$Cl$_2$: C, 66.86; H, 7.12; N, 17.49. Found: C, 66.68; H, 7.08; N, 17.52. |
| 77 | 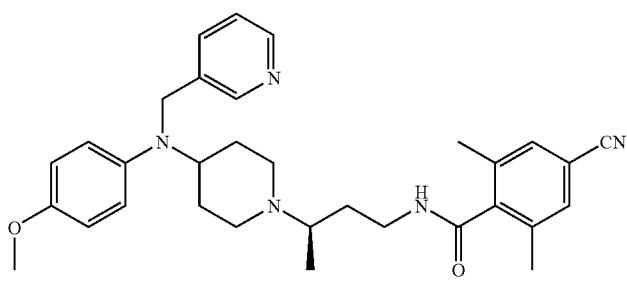<br>4-Cyano-N-((R)-3-{4-[(4-methoxy-phenyl)-pyridin-3-ylmethyl-amino]-piperidin-1-yl}-butyl)-2,6-dimethyl-benzamide | $^1$H NMR(CDCl$_3$) δ 0.95-1.05(m, 1H), 0.99(d, 3H, J=6 Hz), 1.54-1.85(m, 4H), 2.09-2.13(m, 1H), 2.35(s, 6H), 2.47-2.54(m, 1H), 2.70-2.87(m, 3H), 3.30-3.37(m, 3H), 3.71(s, 3H), 3.73-3.84(m, 1H), 3.83(s, 2H), 6.62(d, 2H, J=9 Hz), 6.73(d, 2H, J=9 Hz), 7.20-7.29(m, 3H), 7.52(d, 1H, J= 5.1 Hz), 8.44(br m, 3H). ES-MS m/z 615(M+H). |
| 78 | 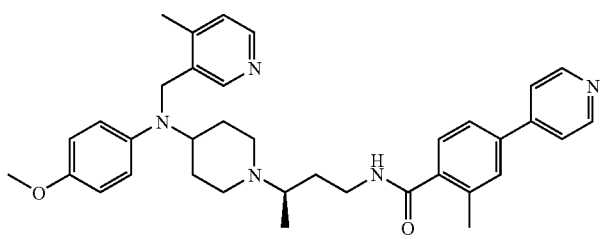<br>N-((R)-3-{4-[(4-Methoxy-phenyl)-(4-methyl-pyridin-3-ylmethyl)-amino]-piperidin-1-yl}-butyl)-2-methyl-4-pyridin-4-yl-benzamide | $^1$H NMR(CDCl$_3$) δ 1.01(d, 3H, J=6.5 Hz), 1.39-1.48(m, 1H), 1.52-1.63(m, 1H), 1.75-1.89(m, 4H), 2.04(s, 3H), 2.09-2.19(m, 1H), 2.42-2.52(m, 1H), 2.53(s, 3H), 2.75-2.93(m, 3H), 3.22-3.41(m, 2H), 3.69(s, 3H), 3.72-3.82(m, 1H), 4.08(m, 1H), 6.60(d, 2H, J=9.2 Hz), 6.68(d, 2H, J=9.2 Hz), 6.83(d, 1H, J=4.8 Hz), 7.37(d, 2H, J=6.1 Hz), 7.42(s, 1H), 7.46(d, 2H, J=4.0 Hz), 7.75(s, br, 1H), 8.23(d, 2H, J=4.8 Hz), 8.61(d, 2H, J= 6.1 Hz); $^{13}$C NMR(CDCl$_3$) δ 13.79, 18.93, 20.38, 30.02, 30.75, 32.14, 39.97, 44.55, 47.37, 52.18, 55.92, 59.59, 60.04, 114.74(2), 120.09(2), 121.74(2), 124.43, 125.29, 127.90, 129.83, 133.43, 137.53, 142.92, 145.09, 148.38, 149.60, 150.73(2), 169.70; ES-MS m/z 578(M+H). |

| Ex. # | Structure/Name | Characterization Data |
|---|---|---|
| 79 | 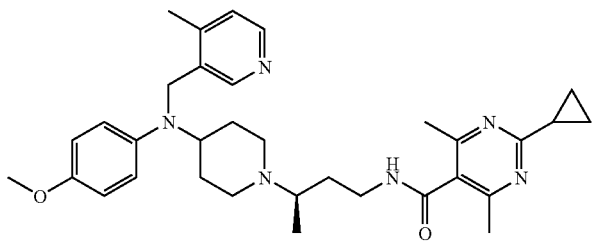<br>2-Cyclopropyl-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.85-0.91(m, 2H), 0.98(d, 3H, J=6.6 Hz), 0.96-1.12(m, 4H), 1.23-1.43(m, 2H), 1.57-1.63(m, 1H), 1.73-1.84(m, 3H), 2.01-2.14(m, 2H), 2.35(s, 3H), 2.43(s, 6H), 2.70-2.84 (m, 2H), 3.20-3.40(m, 2H), 3.72(s, 3H), 3.72-3.80 (m, 1H), 3.96(s, 2H), 6.63-6.75(m, 4H), 7.01(d, 1H, J=5.1 Hz), 7.85-7.86(m, 1H), 8.26-8.29(m, 2H). $^{13}$C NMR(CDCl$_3$) δ 10.91, 13.72, 18.40, 19.23, 22.37, 29.95, 30.08, 30.86, 31.92, 39.90, 44.36, 47.60, 52.12, 52.49, 53.82, 55.91, 59.73, 59.91, 114.71, 114.99, 117.98, 120.85, 125.44, 127.72, 133.49, 142.81, 145.78, 148.38, 149.87, 154.23, 162.96, 167.86. ES-MS m/z 579(M+Na). Anal. Calcd. for C$_{33}$H$_{44}$N$_6$O$_2$•0.4 C$_4$H$_{10}$O•0.3 H$_2$O: C, 70.22; 11, 8.28; N, 14.20. Found: C, 69.95; H, 7.90; N, 13.85. |
| 80 | 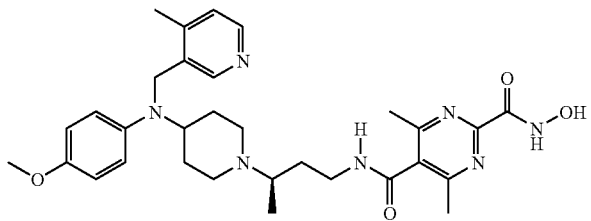<br>N'-Hydroxy-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.99(d+m, 4H), 1.11(m, 1H), 1.55(m, 1H), 1.67(m, 2H), 1.81(m, 1H), 2.10(br t, 1H), 2.18(s, 3H), 2.23(s, 6H), 2.44(br t, 1H), 2.71-2.99(m, 4H), 3.30(m, 1H), 3.70(s, 3H), 3.80 (m, 1H), 4.01(s, 2H), 6.71(s, 4H), 6.96(d, 1H, J=3.0 Hz), 7.36(s, 2H), 8.25(d, 1H, J=6.0 Hz), 8.32 (s, 1H), 8.61(br s, 1H). $^{13}$C NMR(CDCl$_3$) δ 13.4, 19.0, 19.5, 30.7, 31.6, 39.6, 44.0, 50.2, 51.5, 55.8, 59.9, 60.5, 114.7, 123.7, 125.6, 126.4, 128.1, 131.5, 134.8, 141.6, 143.4, 145.8, 147.2, 148.9, 155.5, 165.7, 169.9. ES-MS m/z 574(M+H). Anal. Calcd. for C$_{33}$H$_{43}$N$_5$O$_4$•0.9 CH$_2$Cl$_2$: C, 62.63; H, 6.94; N, 10.77. Found: C, 62.77; H, 6.80; N, 10.55. |
| 81 | 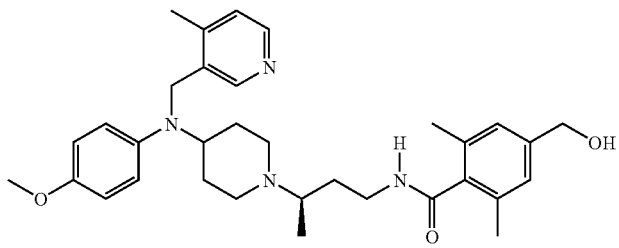<br>4-Hydroxymethyl-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d+m, 4H), 1.08(m, 1H), 1.52(m, 1H), 1.73(m, 3H), 2.06(br t, 1H), 2.15(s, 3H), 2.33(s, 6H), 2.45(br t, 1H), 2.68(m, 1H), 2.82(m, 2H), 2.95(m, 1H), 3.26(m, 1H), 3.72(s, 3H), 3.88(m, 1H), 3.95(s, 2H), 4.57(s, 2H), 4.92 (br s, 1H), 6.70(s, 4H), 6.95(d, 1H, J=6.0 Hz), 7.06(s, 2H), 8.26(d, 1H, J=6.0 Hz), 8.27(s, 1H), 8.38(br s, 1H). $^{13}$C NMR(CDCl$_3$) δ 13.6, 19.0, 19.6, 31.3, 31.5, 32.1, 40.2, 43.6, 49.4, 52.1, 55.8, 60.6, 60.9, 64.1, 114.5, 124.6, 125.2, 125.3, 134.3, 134.5, 142.9, 143.0, 145.5, 147.4, 149.9, 155.7. ES-MS m/z 545(M+H), 567(M+Na). Anal. Calcd. for C$_{33}$H$_{44}$N$_4$O$_3$•0.25 CH$_2$Cl$_2$: C, 70.57; H, 7.93; N, 9.90. Found: C, 70.60; H, 7.92; N, 9.71. |
| 82 | 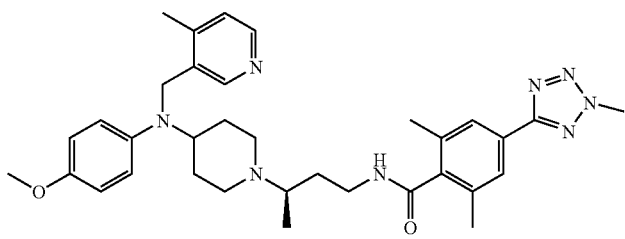<br>N-((R)-3-{4-[(4-Methoxy-phenyl)-(4-methyl-pyridin-3-ylmethyl)-amino]-piperidin-1-yl}-butyl)-2,6-dimethyl-4-(2-methyl-2H-tetrazol-5-yl)-benzamide | $^1$H NMR(CDCl$_3$) δ 0.97(d, 3H, J=6 Hz), 1.10(m, 1H), 1.27(m, 1H), 1.54(m, 1H), 1.77(m, 4H), 2.06(t, 1H, J=11Hz), 2.18(s, 3H), 2.42(s+m, 7H), 2.74(m, 1H), 2.86(m, 2H), 3.09(m, 1H), 3.32(m, 1H), 3.63(d, 1H, J=5 Hz), 3.67(s, 3H), 3.89(m, 1H), 4.29(s, 3H), 6.61(m, 4H), 6.82(d, 1H, J=5 Hz), 7.78(s, 2H), 7.97(s, 1H), 8.14(d, 1H, J=5 Hz), 8.42(br d, 1H). $^{13}$C NMR(CDCl$_3$) δ 13.8, 19.1, 19.6, 29.6, 30.4, 31.5, 39.8, 40.2, 44.1, 46.5, 52.5, 55.8, 60.7, 61.5, 114.5, 122.0, 125.4, 125.9, 135.4, 148.1, 150.3. ES-MS m/z 597 (M+H). Anal. Calcd. For C$_{34}$H$_{44}$N$_8$O$_2$•0.9 CH$_2$Cl$_2$: C, 68.43; H, 7.43; N, 18.78. Found: C, 62.57; H, 6.88; N, 16.67. |

| Ex. # | Structure/Name | Characterization Data |
|---|---|---|
| 83 | 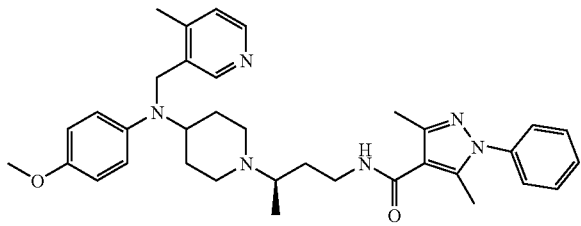

3,5-Dimethyl-1-phenyl-1H-pyrazole-4-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.99(d, 3H, J=6.6 Hz), 1.43-1.69(m, 2H), 1.69-1.76(m, 1H), 1.86-1.98(m, 2H), 2.15-2.22(m, 1H), 2.33(s, 3H), 2.46-2.52(m, 1H), 2.46(s, 3H), 2.77-2.84(ni, 3H), 3.35-3.59(m, 3H), 3.72(s, 3H), 4.23(s, 2H), 6.33-6.35(m, 1H), 6.67-6.76(m, 4H), 7.01(d, 1H, J=4.5 Hz), 7.31-7.46(m, 5H), 8.33(d, 1H, J=4.5 Hz), 8.34(s, 1H). $^{13}$C NMR(CDCl$_3$) δ 11.87, 13.20, 13.73, 18.40, 29.42, 29.99, 32.87, 37.65, 44.64, 47.22, 50.99, 53.17, 55.33, 57.65, 58.16, 114.21, 115.18, 119.00, 124.70, 125.10, 127.92, 128.89, 133.07, 138.64, 141.28, 142.38, 144.66, 146.38, 147.66, 148.67, 152.94, 164.47. ES-MS m/z 581(M+H). Anal. Calcd. for C$_{35}$H$_{44}$N$_6$O$_2$•0.1 H$_2$O•0.6 CH$_2$Cl$_2$: C, 67.49; H, 7.22; N, 13.27. Found: C, 67.64; H, 7.23; N, 13.33. |
| 84 | 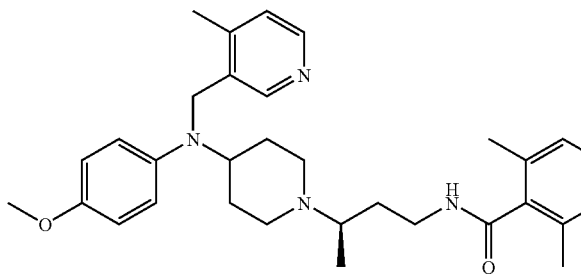

6-Amino-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.12(m, 1H), 1.28(m, 1H), 1.58(m, 1H), 1.78(m, 3H), 2.13(t, 1H, J=11.2 Hz), 2.20(s, 3H), 2.34(s, 3H), 2.37(s,3H), 2.48(t, 1H, J=11.2 Hz), 2.65-2.90(m, 3H), 3.25(m, 2H), 3.71(s, 3H), 3.75(m, 1H), 3.97 (s, 2H), 4.20(s, 2H), 6.65-6.75(m, 4H), 7.00(d, 2H, J=4.8 Hz), 7.84(br, 1H), 8.29(d, 1H, J=5.4 Hz), 8.33(s, 1H). $^{13}$C NMR(CDCl$_3$) δ 13.76, 19.23, 19.43, 22.50, 29.88, 30.78, 31.96, 39.94, 44.34, 47.36, 52.24, 55.91, 60.18(2C), 106.60, 114.69(2C), 121.00(2C), 125.10, 125.41, 133.73, 143.01, 145.72, 146.25, 148.29, 150.01, 153.33, 154.18, 157.95, 169.62. ES-MS m/z 531(M+H). |
| 85 | 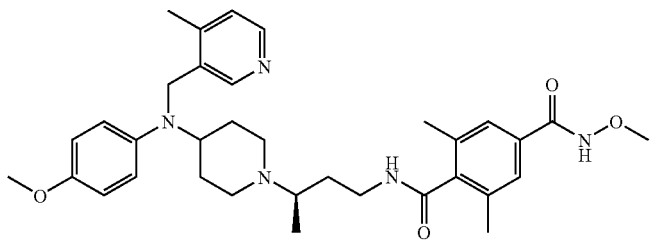

N′-Methoxy-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.80(m, 1H), 0.95(d+m, 4H), 1.53(m, 1H), 1.60-1.74(m, 3H), 2.05(br t, 1H), 2.21(s, 3H), 2.29(s, 6H), 2.43(br t, 1H), 2.66(m, 1H), 2.77(m, 2H), 2.95(m, 1H), 3.26(m, 1H), 3.73(s, 3H), 3.80(s, 3H), 3.88(m, 1H), 4.02(s, 2H), 6.72(m, 4H), 7.03(d, 1H, J=6.0 Hz), 7.54(s, 2H), 8.34(s, 1H), 8.35(d, 1H, J=6.0 Hz), 8.46(br s, 1H). $^{13}$C NMR(CDCl$_3$) δ 13.4, 13.6, 24.8, 25.9, 32.0, 32.5, 39.0, 44.1,44.6,47.3, 51.6, 52.1, 57.6, 57.8, 59.0, 59.4, 117.7, 122.7, 137.5, 157.9, 158.5, 160.2, 163.4, 167.0. ES-MS m/z 588 (M+H), 610(M+Na). Anal. Calcd. for C$_{34}$H$_{45}$N$_5$O$_4$•0.2 CH$_2$Cl$_2$: C, 67.93; H, 7.57; N, 11.58. Found: C, 67.87; H, 7.57; N, 11.60. |
| 86 | 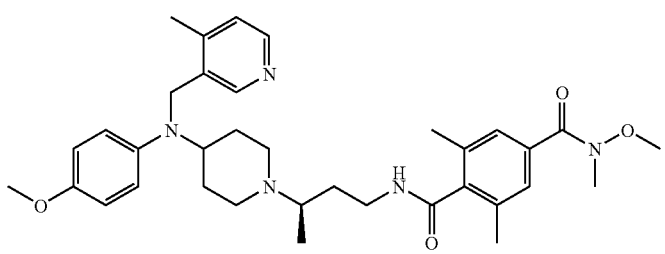

N′-Methoxy-N-((R)-3-{4-[(4-methoxy-phenyl)-(4-methyl-pyridin-3-ylmethyl)-amino]-piperidin-1-yl}-butyl)-2,6,N′-trimethyl-terephthalamide | $^1$H NMR(CDCl$_3$) δ 1.00(d, 3H, J=6.0 Hz), 1.18-1.38(m, 2H), 1.59(m, 1H), 1.80(m, 3H), 2.13(br t, 1H), 2.31(s, 3H), 2.34(s, 6H), 2.50(br t, 1H), 2.68-2.86(m, 3H), 3.28(s+m, 4H), 3.39(m, 1H), 3.53(s, 3H), 3.71(s+m, 4H), 4.04(s, 2H), 6.64(d, 2H, J=9.0 Hz), 6.71(d, 2H, J=9.0 Hz), 7.00(d, 1H, J=6.0 Hz), 7.29(s, 3H), 8.28(s+d, 2H). $^{13}$C NMR(CDCl$_3$) δ 13.7, 19.1, 19.6, 29.6, 30.6, 32.6, 34.1, 39.1, 44.7, 47.5, 51.9, 55.9, 58.8, 59.3, 61.5, 114.8, 119.5, 125.4, 127.2, 127.6, 133.7, 134.4, 134.7, 140.5, 142.9, 145.5, 148.3, 149.5, 153.6, 169.6, 169.9. ES-MS m/z 602(M+H), 624 (M+Na). Anal. Calcd. for C$_{35}$H$_{47}$N$_5$O$_4$•0.2 CH$_2$Cl$_2$: C, 68.33; H, 7.72; N, 11.32. Found: C, 68.40; H, 7.78; N, 11.33. |

| Ex. # | Structure/Name | Characterization Data |
|---|---|---|
| 87 | 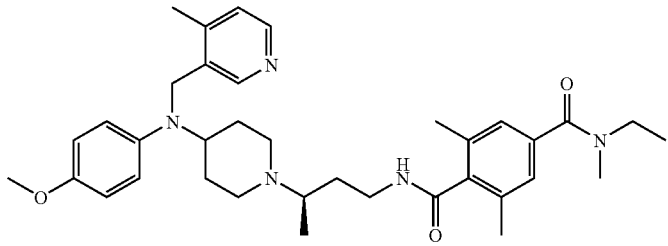<br>N'-Methoxy-N-((R)-3-{4-[(4-methoxy-phenyl)-(4-methyl-pyridin-3-ylmethyl)-amino]-piperidin-1-yl}-butyl)-2,6,N'-trimethyl-terephthalamide | $^1$H NMR(CDCl$_3$) δ 0.98(d, 3H, J=6.0 Hz), 1.05 (br t, 3H) 1.19-1.42(m, 2H), 1.61(m, 1H), 1.80 (m, 3H), 2.15(br t, 1H), 2.30(s, 3H), 2.31(s, 6H), 2.47(br t, 1H), 2.75-2.86(m, 3H), 3.02(m, 2H), 3.21-3.51(m, 4H), 3.65(m, 1H), 3.72(s, 3H), 4.12 (s, 2H), 6.66(d, 2H, J=9.0 Hz), 6.73(d, 2H, J=9.0 Hz), 6.83(br s, 1H), 7.03(s+d, 3H), 8.28 (s+d, 2H). $^{13}$C NMR(CDCl$_3$) δ 13.7, 19.2, 19.5, 29.8, 30.6, 32.9, 38.8, 44.9, 46.2, 47.6, 51.8, 56.0, 58.8, 114.8, 119.3, 125.3,125.8,126.2, 126.4, 133.8, 134.8, 137.6, 143.0, 145.4, 148.3, 149.5. ES-MS m/z 600(M+H), 622(M+Na). Anal. Calcd. for C$_{36}$H$_{49}$N$_5$O$_3$•0.2 CH$_2$Cl$_2$: C, 70.49; H, 8.07; N, 11.35. Found: C, 70.23; H, 8.07; N, 11.42. |
| 88 | 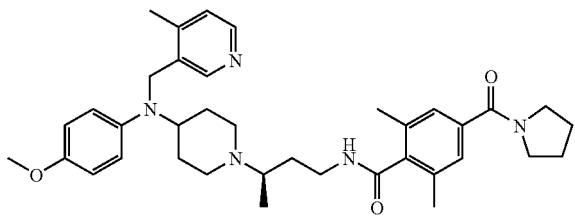<br>N-((R)-3-{4-[(4-Methoxy-phenyl)-(4-methyl-pyridin-3-ylmethyl)-amino]-piperidin-1-yl}-butyl)-2,6-dimethyl-4-(pyrrolidine-1-carbonyl)-benzamide | $^1$H NMR(CDCl$_3$) 50.98(d, 3H, J=6.0 Hz), 1.05 (br t, 3H) 1.19-1.42(m, 2H), 1.61(m, 1H), 1.80 (m, 3H), 2.15(br t, 1H), 2.30(s, 3H), 2.31(s, 6H), 2.47(br t, 1H), 2.75-2.86(m, 3H), 3.02(m, 2H), 3.21-3.51(m, 4H), 3.65(m, 1H), 3.72(s, 3H), 4.12 (s, 2H), 6.66(d, 2H, J=9.0 Hz), 6.73(d, 2H, J=9.0 Hz), 6.83(br s, 1H), 7.03(s+d, 3H), 8.28 (s+d, 2H). $^{13}$C NMR(CDCl$_3$) δ 13.7, 19.2, 19.5, 29.8, 30.6, 32.9, 38.8, 44.9, 46.2, 47.6, 51.8, 56.0, 58.8, 114.8, 119.3, 125.3, 125.8, 126.2, 126.4, 133.8, 134.8, 137.6, 143.0, 145.4, 148.3, 149.5. ES-MS m/z 600(M+H), 622(M+Na). Anal. Calcd. for C$_{36}$H$_{49}$N$_5$O$_3$•0.2 CH$_2$Cl$_2$: C, 70.49; H, 8.07; N, 11.35. Found: C, 70.23; H, 8.07; N, 11.42. |
| 89 | 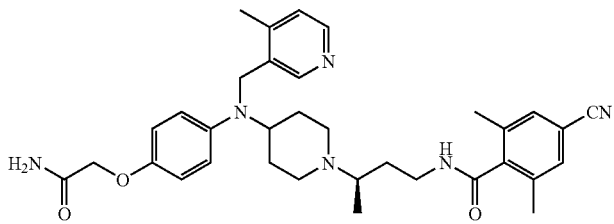<br>N-((R)-3-{4-[(4-Carbamoylmethoxy-phenyl)-(4-methyl-pyridin-3-ylmethyl)-amino]-piperidin-1-yl}-butyl)-4-cyano-2,6-dimethyl-benzamide | $^1$H NMR(CDCl$_3$) δ 1.00(d, 3H, J=6.6 Hz), 1.08-1.29(m, 2H), 1.53-1.60(m, 1H), 1.69-1.83(m, 2H), 2.11-2.19(m, 1H), 2.31(s, 3H), 2.33(s, 6H), 2.45-2.54(m, 1H), 2.71-2.85(m, 3H), 3.30-3.37 (m, 2H), 3.58-3.63(m, 1H), 3.74-3.79(m, 1H), 4.00(s, 2H), 4.40(s, 2H), 5.71(br s, 1H), 6.50-6.60(br s, 1H), 6.61(d, 2H, J=9 Hz), 6.75(d, 2H, J=9 Hz), 7.07(d, 1H, J=4.8 Hz), 7.26(s, 2H), 7.67-7.72(m, 1H), 8.23(s, 1H), 8.32(d, 1H, J=4.8 Hz). $^{13}$C NMR(CDCl$_3$) δ 13.35, 18.61, 18.92, 29.55, 30.29, 31.66, 39.02, 44.10, 46.88, 51.52, 58.07, 59.21, 67.69, 112.07, 115.39, 118.32, 118.46, 125.10, 130.72, 132.71, 135.63, 142.48, 143.47, 144.67, 148.01, 148.61, 150.65, 167.96, 171.30. ES-MS m/z 605(M+Na). Anal. Calcd. for C$_{34}$H$_{42}$N$_6$O$_3$•0.1H$_2$O•1.1CH$_2$Cl$_2$: C, 62.18; H, 6.60; N, 12.40. Found: C, 62.25; H, 6.47; N, 12.38. |
| 90 | 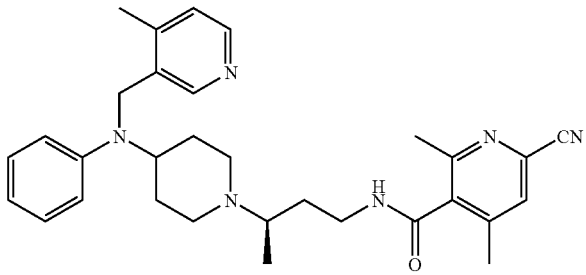<br>6-Cyano-2,4-dimethyl-N-((R)-3-{4-[(4-methyl-pyridin-3-ylmethyl)-phenyl-amino]-piperidin-1-yl}-butyl)-nicotinamide | $^1$H NMR(CDCl$_3$) δ 1.04(d, 3H, J=9.0 Hz), 1.20 (m, 1H), 1.51-1.99(m, 5H), 2.34(s, 3H), 2.42(s, 3H), 2.59(s, 3H), 2.70-2.89(m, 6H), 3.30-3.46(m, 1H), 3.48(s, 2H), 3.55-3.72(m, 1H), 3.72-3.87(m, 1H), 4.11(s, 2H), 6.73(t, 1H, J=6 Hz), 7.10(d, 1H, J=9 Hz), 7.17(t, 1H, J=9 Hz), 7.30(s, 1H), 7.89(br s, 1H), 8.25(s, 1H), 8.34(d, 1H, J=3). $^{13}$C NMR(CDCl$_3$) δ 13.79, 19.09, 19.15, 22.74, 29.81, 30.74, 31.96, 39.74, 44.49, 46.01, 52.28, 56.56, 59.86, 113.64, 114.52, 117.31, 118.34, 125.51, 127.80, 129.7, 133.17, 144.76, 145.93, 148.47, 148.61, 156.98. ES-MS m/z 511(M+H). Anal. Calcd. for C$_{31}$H$_{38}$N$_6$O•0.2CH$_2$Cl$_2$: C, 71.02; H, 7.33; N, 15.93. Found: C, 70.82; H, 7.46; N, 16.04 |

| Ex. # | Structure/Name | Characterization Data |
|---|---|---|
| 91 | 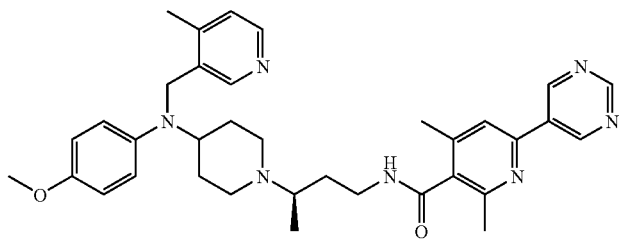<br>N-((R)-3-{4-[(4-Methoxy-phenyl)-(4-methyl-pyridin-3-ylmethyl)-amino]-piperidin-1-yl}-butyl)-2,4-dimethyl-6-pyrimidin-5-yl-nicotinamide | $^1$H NMR(CDCl$_3$) δ1.02(br d, 3H), 1.61(br m, 2H), 1.82(br m, 4H), 2.16(s, 4H), 2.40(s, 3H), 2.53(br m, 1H), 2.62(s, 3H), 2.78(br m, 1H), 2.87 (br m, 2H), 3.22(br m, 1H), 3.41(br m, 1H), 3.68 (s, 3H), 3.83(br m, 3H), 6.62(m, 4H), 6.85(d, 1H, J=5 Hz), 7.38(s, 1H), 8.02(s, 1H), 8.18(m, 2H), 9.20(s, 3H). $^{13}$C NMR(CDCl$_3$) δ 13.7, 19.0, 19.6, 23.0, 29.8, 30.6, 32.0, 39.8, 44.4, 47.5, 52.2, 55.9, 60.0, 114.7, 119.4, 120.9, 125.3, 132.0, 133.2, 142.7, 145.3, 145.6, 148.4, 149.6, 151.2, 154.3, 155.3, 155.7, 158.9, 168.4. ES-MS m/z 594 (M+H). Anal. Calcd. For C$_{35}$H$_{43}$N$_7$O$_2$•1.1 CH$_2$Cl$_2$: C, 70.80; H, 7.30; N, 16.51. Found: C, 62.87; H, 6.59; N, 14.24. |
| 92 | 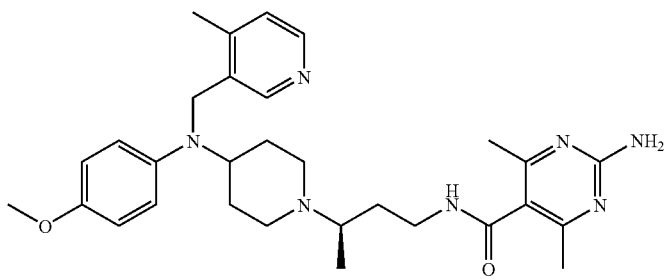<br>2-Amino-4,6-dimethyl-pyrimidine-5-carboxylic acid (R)-(3-{4-[(4-methoxy-phenyl)-(4-methyl-pyridin-3-ylmethyl)-amino]-piperidin-1-yl}-butyl)-amide | $^1$H NMR(CDCl$_3$) δ 0.98(d, 3H, J=6.6 Hz), 1.14-1.34(m, 2H), 1.50-1.56(m, 1H), 1.63-1.86(m, 3H), 2.07-2.15(m, 1H), 2.35(s, 9H), 2.41-2.52(m, 1H), 2.72-2.86(m, 3H), 3.22-3.32(m, 2H), 3.72(s, 3H), 3.72-3.8 1(m, 1H), 4.00(s, 2H), 4.84(s, 2H), 6.66-6.74(m, 4H), 7.00(d, 1H, J=5.0 Hz), 7.97 (br s, 1H), 8.33(d, 1H, J=5.0 Hz), 8.31(s, 1H). $^{13}$C NMR(CDCl$_3$) δ 13.37, 18.83, 21.96, 29.58, 30.49, 31.43, 39.73, 43.93, 47.10, 51.85, 55.53, 59.68, 59.77, 114.31, 120.75, 121.82, 125.03, 133.20, 142.48, 145.43, 147.93, 149.61, 153.91, 161.60, 164.61, 167.88. ES-MS m/z 532(M+H). Anal. Calcd. for C$_{30}$H$_{41}$N$_7$O$_2$•1.0 CH$_2$Cl$_2$: C, 60.38; H, 7.03; N, 15.90. Found: C, 60.71; H, 7.02; N, 16.02. |
| 93 | 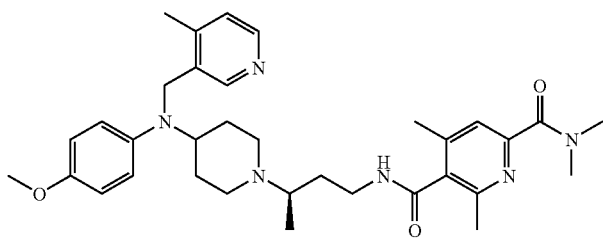<br>4,6-Dimethyl-pyridine-2,5-dicarboxylic acid 2-dimethylamide 5-[(R)-(3-{4-[(4-methoxy-phenyl)-(4-methyl-pyridin-3-ylmethyl)-amino]-piperidin-1-yl}-butyl)-amide] | $^1$H NMR(CDCl$_3$) δ 0.99(d, 3H, J=6.6 Hz), 1.25 (m, 1H), 1.35(m, 1H), 1.60(m, 1H), 1.78(m, 3H), 2.14(t, 1H, J=11.2 Hz), 2.32(s, 3H), 2.34(s, 3H), 2.48(t, 1H, J 11.2 Hz), 2.54(s, 3H), 2.65-2.85 (m, 3H), 3.01(s, 3H), 3.08(s, 3H), 3.30(m, 1H), 3.42(m, 1H), 3.69(m, 1H), 3.73(s, 3H), 4.08(s, 2H), 6.62-6.80(m, 4H), 7.01(d, 1H, J=5.4 Hz), 7.24(br, 1H), 7.28(s, 1H), 8.29(d, 1H, J=4.8 Hz), 8.30(s, 1H). ES-MS m/z 587(M+H). |
| 94 | 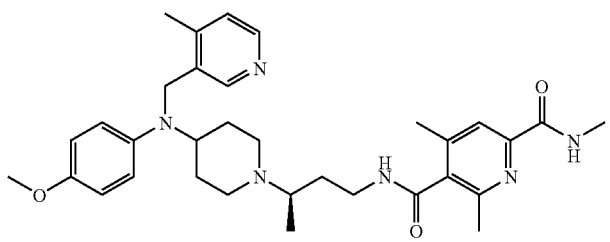<br>4,6-Dimethyl-pyridine-2,5-dicarboxylic acid 5-[(R)-(3-{4-[(4-methoxy-phenyl)-(4-methyl-pyridin-3-ylmethyl)-amino]-piperidin-1-yl}-butyl)-amide] 2-methylamide | $^1$H NMR(CDCl$_3$) δ0.99(d, 3H, J=6.6 Hz), 1.06 (m, 1H), 1.21(m, 1H), 1.56(m, 1H), 1.78(m, 3H), 2.14(t, 1H, J=11.2 Hz), 2.35(s, 3H), 2.38(s, 3H), 2.47(t, 1H, J=11.2 Hz), 2.54(s, 3H), 2.65-2.85 (m, 3H), 2.91(s, 3H), 2.92(s, 3H), 3.18(m, 1H), 3.36(m, 1H), 3.71(s, 3H), 3.78(m, 1H), 3.87(s, 2H), 6.58-6.75(m, 4H), 7.00(d, 1H, J=4.8 Hz), 7.87(s, 1H), 7.93(m, 1H), 7.99(br, 1H), 8.23(s, 1H), 8.27(d, 1H, J=4.8 Hz). ES-MS m/z 573 (M+H). |

| Ex. # | Structure/Name | Characterization Data |
|---|---|---|
| 95 | 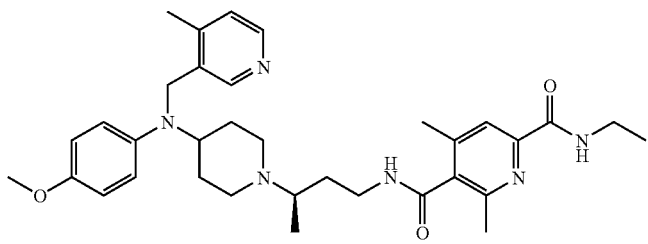<br>4,6-Dimethyl-pyridine-2,5-dicarboxylic acid 2-ethylamide 5-[(R)-(3-{4-[(4-methoxy-phenyl)-(4-methyl-pyridin-3-ylmethyl)-amino]-piperidin-1-yl}-butyl)-amide] | $^1$H NMR(CDCl$_3$) 80.99(d, 3H, J=6.6 Hz), 1.07 (m, 1H), 1.24(t, 3H, J=7.2 Hz), 1.28(m, 1H), 1.58(m, 1H), 1.78(m, 3H), 2.11(t, 1H, J=11.2 Hz), 2.26(s, 3H), 2.37(s, 3H), 2.47(t, 1H, J=11.2 Hz), 2.54(s, 3H), 2.65-2.85(m, 3H), 3.19(m, 1H), 3.36(m, 1H), 3.41(m, 2H), 3.72(s, 3H), 3.80(m, 1H), 3.91(s, 2H), 6.60-6.80(m, 4H), 7.00(d, 1H, J=5.4 Hz), 7.87(br, 2H), 7.95(t, 1H, J=6.0 Hz), 8.23(s, 1H), 8.28(d, 1H, J=4.8 Hz). ES-MS m/z 587(M+H). |
| 96 | 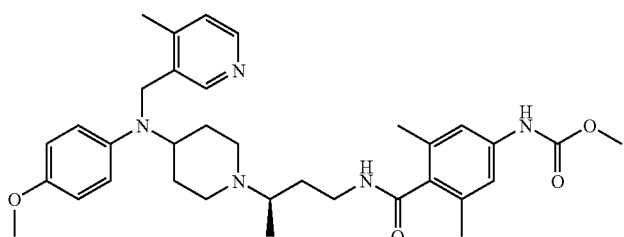<br>[4-(R)-(3-{4-[(4-Methoxy-phenyl)-(4-methyl-pyridin-3-ylmethyl)-amino]-piperidin-1-yl}-butylcarbamoyl)-3,5-dimethyl-phenyl]-carbamic acid methyl ester | $^1$H NMR(CDCl$_3$) δ 0.96(d, 3H, J=6.6 Hz), 1.04-1.25(m, 2H), 1.48-1.54(m, 1H), 1.72-1.78(m, 3H), 2.03-2.11(m, 1H), 2.26(s, 3H), 2.30(s, 6H), 2.39-2.51(m, 1H), 2.70-2.86(m, 3H), 3.09-3.15 (m, 1H), 3.24-3.33(m, 1H), 3.70(s, 3H), 3.71(s, 3H), 3.80-3.87(m, 3H), 6.65-6.72(m, 5H), 6.97(d, 1H, J=4.8 Hz), 7.03(s, 2H), 8.03(br. s, 1H), 8.26-8.29(m, 2H). $^{13}$C NMR(CDCl$_3$) δ 15.22, 20.60, 21.24, 31.37, 32.18, 33.27, 41.29, 45.73, 48.94, 53.62, 53.97, 57.35, 61.72, 61.98, 116.08, 118.85, 123.12, 126.85, 135.27, 135.35, 136.95, 139.98, 144.56, 147.20, 149.51, 151.32, 155.64, 155.86, 171.76. ES-MS m/z 588(M+1)$^+$. Anal. Calcd. for C$_{34}$H$_{45}$N$_5$O$_4$•0.1CH$_2$Cl$_2$: C, 62.49; H, 7.04; N, 10.41. Found: C, 62.56; H, 6.97; N, 10.45. |
| 97 | 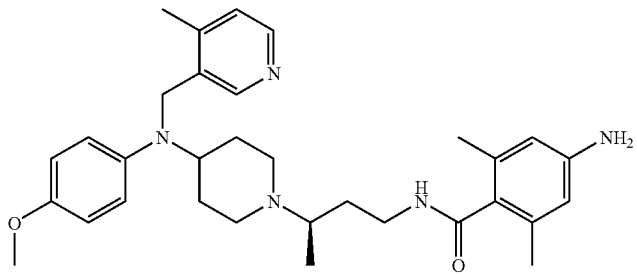<br>4-Amino-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d, 3H, J=6 Hz), 1.23-1.48(m, 3H), 1.47-1.55(m, 1H), 1.67-1.75(m, 3H), 2.08-2.11(m, 1H), 2.22(s, 6H), 2.33(s, 3H), 2.41-2.46(m, 1H), 2.71-2.83(m, 3H), 3.20-3.38 (m, 4H), 3.71(s, 3H), 3.71-3.74(m, 1H), 3.96(s, 2H), 6.23(s, 2H), 6.66-6.73(m, 4H), 7.00(d, 1H, J=5.1 Hz), 7.57(br m, 1H), 8.28(d, 1H, J=5.1 Hz), 8.33(s, 1H). ES-MS m/z 530(M + H). Anal. Calcd. for C$_{32}$H$_{43}$N$_5$O$_2$•0.7H$_2$O: C, 70.87; H, 8.25; N, 12.91. Found: C, 71.07; H, 8.20; N, 12.55. |
| 98 | 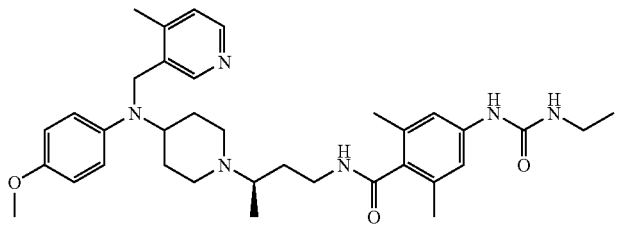<br>4-(3-Ethyl-ureido)-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.96(d, 3H, J=6 Hz), 1.08(t, 3H, J=6 Hz), 1.10-1.55(m, 2H), 1.69-1.75(m, 3H), 2.02-2.13(m, 2H), 2.15(s, 6H), 2.25(s, 3H), 2.35-2.42(m, 1H), 2.71-2.83(m, 3H), 3.08-3.28 (m, 4H), 3.70(s, 3H), 3.71-3.73(m, 1H), 3.96(s, 2H), 5.45(br m, 1H), 6.70-6.74(m, 4H), 6.79(s, 2H), 6.98(d, 1H, J=5.1 Hz), 7.48(s, 1H), 8.02(br m, 1H), 8.25(d, 1H, J=5.1 Hz), 8.32(s, 1H). ES-MS m/z 601(M+H). |

-continued

| Ex. # | Structure/Name | Characterization Data |
|---|---|---|
| 99 | 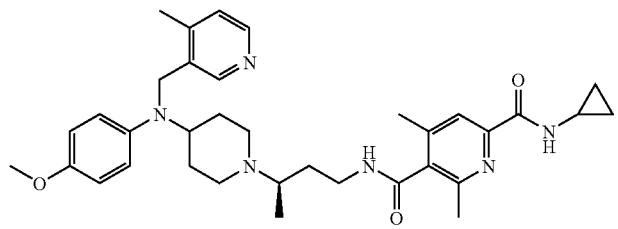<br>4,6-Dimethyl-pyridine-2,5-dicarboxylic acid 2-cyclopropylamide 5-[(R)-(3-{4-[(4-methoxy-phenyl)-(4-methyl-pyridin-3-ylmethyl)-amino]-piperidin-1-yl}-butyl)-amide] | $^1$H NMR(CDCl$_3$) δ 0.60(q, 2H, J=4.5 Hz), 0.84 (q, 2H, J=6.3 Hz), 0.99(d, 3H, J=6.6 Hz), 1.00 (m, 1H), 1.17(m, 1H), 1.57(m, 1H), 1.78(m, 3H), 2.12(t, 1H, J=11.2 Hz), 2.26(s, 3H), 2.37(s, 3H), 2.48(t, 1H, J=11.2 Hz), 2.52(s, 3H), 2.65-2.90 (m, 4H), 3.18(m, 1H), 3.32(m, 1H), 3.72(s, 3H), 3.77(m, 1H), 3.92(s, 2H), 6.60(d, 2H, J= 9.0 Hz), 6.72(d, 2H, J=9.0 Hz), 7.01(d, 1H, J=5.4 Hz), 7.85(br, 1H), 7.87(s, 1H), 7.99(d, 1H, J=4.8 Hz), 8.23(s, 1H), 8.29(d, 1H, J=5.4 Hz). ES-MS m/z 599(M+H). |
| 100 | 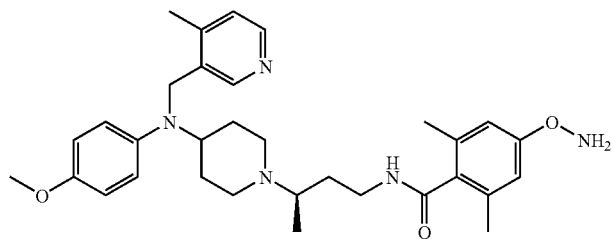<br>4-Aminooxy-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.84(br m, 1H), 1.00(br m, 3H), 1.25(s, 1H), 1.31(br m, 2H), 1.69(br m, 9H), 2.30(s, 6H), 2.32(s, 3H), 2.51(br m, 1H), 2.86(br m, 3H), 3.27(br m, 3H), 3.70(s, 3H), 3.85(br m, 3H), 5.55(br m, 2H), 6.70(s, 4H), 6.72(s, 2H), 7.00(d, 1H, J=5 Hz), 8.28(d, 1H, J=5 Hz), 8.30 (s, 1H). $^{13}$C NMR(CDCl$_3$) δ 13.6, 19.3, 19.9, 30.1, 31.9, 46.9, 52.3, 55.9, 60.4, 112.1, 114.7, 121.7, 125.5, 135.9, 146.0, 148.2, 150.2, 161.3. ES-MS m/z 546(M+H). |
| 101 | 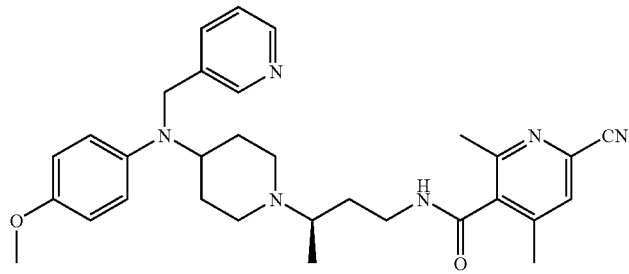<br>6-Cyano-N-((R)-3-{4-[(4-methoxy-phenyl)-pyridin-3-ylmethyl-amino]-piperidin-1-yl}-butyl)-2,4-dimethyl-nicotinamide | $^1$H NMR(CDCl$_3$) δ 0.95-1.05(m, 1H), 1.00(d, 3H, J=6 Hz), 1.51-1.82(m, 5H), 2.09-2.13(m, 1H), 2.34(s, 6H), 2.49-2.54(m, 1H), 2.71-2.87(m, 2H), 3.29-3.37(m, 3H), 3.71(s, 3H), 3.84-3.88(m, 1H), 3.88(s, 2H), 6.62(d, 2H, J=9 Hz), 6.75(d, 2H, J=9 Hz), 7.20-7.29(m, 3H), 7.54(d, 1H, J= 5.1 Hz), 8.45(br m, 3H). ES-MS m/z 527(M+H). |
| 102 | 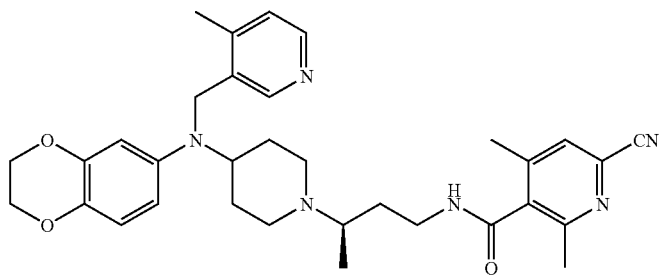<br>6-Cyano-N-((R)-3-{4-[(2,3-dihydro-benzo[1,4]dioxin-6-yl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 0.99-1.22(m, 2H), 1.52-1.59(m, 1H), 1.69-1.85(m, 3H), 2.11-2.19(m, 2H), 2.35(s, 6H), 2.47-2.56(m, 1H), 2.56(s, 3H), 2.70-2.88(m, 3H), 3.30-3.41(m, 2H), 3.74-3.83(m, 1H), 3.97(s, 2H), 4.10-4.30(m, 4H), 6.12-6.25(m, 2H), 6.66(d, 1H, J=8.7 Hz), 7.07(d, 1H, J=5.0 Hz), 7.32(s, 1H), 7.95(br s, 1H), 8.26(s, 1H), 8.32(d, 1H, J=5.1 Hz). $^{13}$C NMR(CDCl$_3$) δ 13.23, 18.55, 22.14, 29.51, 30.30, 31.30, 32.18, 39.22, 43.91, 46.56, 51.49, 57.61, 59.20, 64.01, 64.46, 105.48, 110.03, 116.72, 117.18, 124.98, 127.21, 132.44, 132.78, 136.44, 136.68, 143.03, 143.52, 144.65, 145.31, 147.80, 148.38, 156.43, 166.28. ES-MS m/z 569(M+H). Anal. Calcd. for C$_{33}$H$_{40}$N$_6$O$_3$•0.4 H$_2$O•0.9 CH$_2$Cl$_2$: C, 62.42; H, 6.58; N, 12.88. Found: C, 62.40; H, 6.27; N, 12.62. |

| Ex. # | Structure/Name | Characterization Data |
|---|---|---|
| 103 | 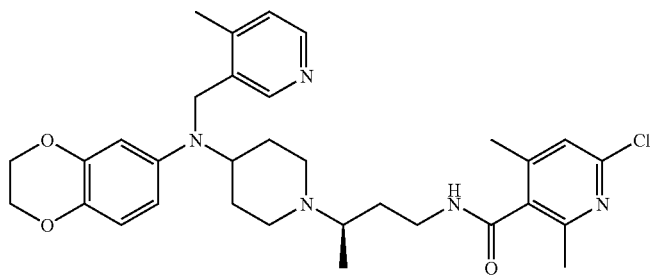<br>6-Cyano-N-((R)-3-{4-[(2,3-dihydro-benzo[1,4]dioxin-6-yl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 0.99-1.25(m, 2H), 1.57-1.61(m, 1H), 1.71-1.85(m, 3H), 2.11-2.18(m, 1H), 2.29(s, 3H), 2.36(s, 3H), 2.47-2.58(m, 1H), 2.51(s, 3H), 2.70-2.84(m, 3H), 3.30-3.40(m, 2H), 3.74-3.83(m, 1H), 3.98(s, 2H), 4.10-4.30(m, 4H), 6.14-6.25(m, 2H), 6.65(d, 1H, J=8.7 Hz), 6.98(s, 1H), 7.03(d, 1H, J=5.0 Hz), 7.88(br s, 1H), 8.27(s, 1H), 8.30(d, 1H, J=5.1 Hz). $^{13}$C NMR(CDCl$_3$) δ 13.80, 19.14, 22.49, 29.86, 30.78, 31.94, 39.77, 44.49, 46.78, 52.09, 58.47, 59.81, 64.56, 65.01, 105.99, 110.54, 117.70, 122.83, 125.43, 132.87, 133.43, 137.13, 143.73, 144.06, 145.30, 147.70, 148.24, 149.08, 150.54, 155.54, 167.71. ES-MS m/z 578(M+H). Anal. Calcd. for C$_{32}$H$_{40}$ClN$_5$O$_3$•0.5 H$_2$O•1.2 CH$_2$Cl$_2$: C, 57.87; H, 6.35; N, 10.16. Found: C, 58.01; H, 6.00; N, 10.30. |
| 104 | 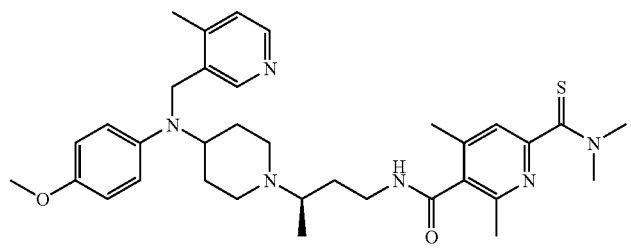<br>4-Dimethylthiocarbamoyl-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.98(d, 3H, J=6.0 Hz), 1.25-1.48(m, 2H), 1.59(m, 1H), 1.75-1.88(m, 4H), 2.15(br t, 1H), 2.30(s, 6H), 2.34(s, 3H), 2.46(br t, 1H), 2.70-2.81(m, 3H), 3.13(s, 3H), 3.35-3.46(m, 2H), 3.56(s+m, 4H), 3.72(s, 3H), 4.19(s, 2H), 6.61(m, 1H), 6.67-6.76(m, 4H), 6.93(s, 2H), 7.01(d, 1H, J=6.0 Hz), 8.29(d, 1H, J=6.0 Hz), 8.32(s, 1H). ES-MS m/z 602(M+H), 624(M+Na). |
| 105 | 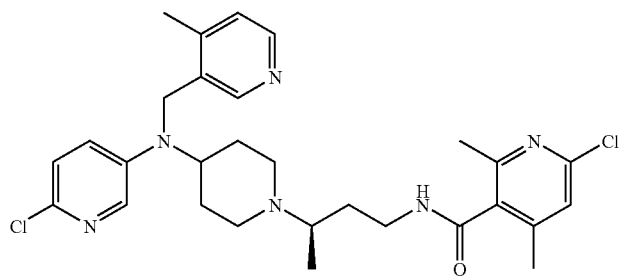<br>6-Chloro-N-((R)-3-{4-[(6-chloro-pyridin-3-yl)-(4-methyl-pyridin-3-ylmethyl)-amino]-piperidin-1-yl}-butyl)-2,4-dimethyl-nicotinamide | $^1$H NMR(CDCl$_3$) δ 1.02(d, 3H, J=6.0 Hz), 1.21(m, 1H), 1.37(m, 1H), 1.62(m, 1H), 1.75(m, 1H), 1.87(m, 2H), 2.23(br t, 1H), 230(s, 3H), 2.38(s, 3H), 2.51(s, 3H), 2.57(br t, 1H), 2.76-2.85(m, 3H), 3.39(m, 1H), 3.60(m, 1H), 3.75(m, 1H), 4.13(s, 2H), 6.81(d, 1H, J=9.0 Hz), 6.99(s, 1H), 7.11(m, 2H), 7.51(m, 1H), 7.74(d, 1H, J=3.0 Hz), 8.21(s, 1H), 8.36(d, 1H, J=3.0 Hz), ES-MS m/z 556(M+H). |
| 106 | 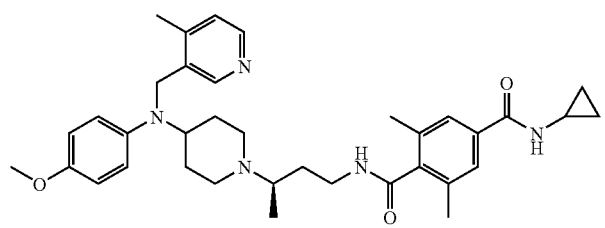<br>N'-Cyclopropyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.53(m, 2H), 0.78(m, 2H), 0.96(d+m, 4H), 1.09(m, 1H), 1.54(m, 1H), 1.73(m, 3H), 2.07(br t, 1H), 2.25(s, 3H), 2.29(s, 6H), 2.41(br t, 1H), 2.66(m, 1H), 2.84(m, 2H), 3.10(m, 1H), 3.29(m, 1H), 3.72(s, 3H), 3.77(m, 1H), 3.97(s, 2H), 6.63(d, 2H, J=9.0 Hz), 6.74(d, 2H, J=9.0 Hz), 7.01(d, 1H, J=6.0 Hz), 7.06(s, m 1H), 7.44(s, 2H), 8.01(br s, 1H), 8.30(s+d, 2H). ES-MS m/z 598(M+H), 620(M+Na). |

| Ex. # | Structure/Name | Characterization Data |
|---|---|---|
| 107 | 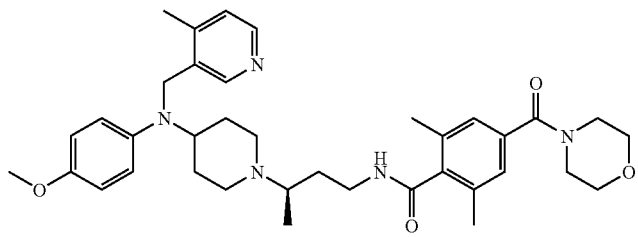<br>N-((R)-3-{4-[(4-Methoxy-phenyl)-(4-methyl-pyridin-3-ylmethyl)-amino]-piperidin-1-yl}-butyl)-2,6-dimethyl-4-(morpholine-4-carbonyl)-benzamide | $^1$H NMR(CDCl$_3$) δ 0.98(d, 3H, J=6.0 Hz), 1.21-1.46(m, 2H), 1.59(m, 1H), 1.73(m, 3H), 2.14(br t, 1H), 2.31(s, 3H), 2.33(s, 6H), 2.46(br t, 1H), 2.74-2.79(m, 3H), 3.25-3.48(m, 4H), 3.55-3.68 (m, 7H), 3.72(s, 3H), 4.09(s, 2H), 6.66(d, 2H, J=9.0 Hz), 6.73(d, 2H, J=9.0 Hz), 7.02(s+d, 4H), 8.30(s+d, 2H). ES-MS m/z 628(M+H), 650 (M+Na). |
| 108 | 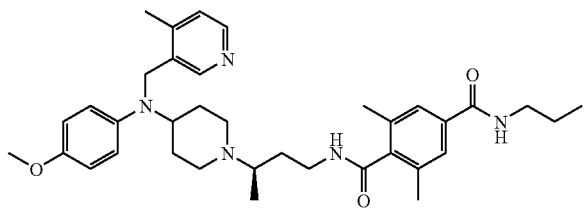<br>N-((R)-3-{4-[(4-Methoxy-phenyl)-(4-methyl-pyridin-3-ylmethyl)-amino]-piperidin-1-yl}-butyl)-2,6-dimethyl-N'-propyl-terephthalamide | $^1$H NMR(CDCl$_3$) δ 0.95(m, 7H), 1.20(m, 1H), 1.57(m, 3H), 1.73(m, 3H), 2.07(br t, 1H), 2.25(s, 3H), 2.31(s, 6H), 2.44(br t, 1H), 2.67(m, 1H), 2.81(m, 2H), 3.13(m, 1H), 3.32(m,3H), 3.71(s, 3H), 3.78(m, 1H), 3.96(s, 2H), 6.63-6.77(m, 5H), 7.00(d, 1H, J=3.0 Hz), 7.45(s, 2H), 7.91(br s, 1H), 8.28(s+d, 2H). ES-MS m/z 600(M+H), 622 (M+Na). |
| 109 | 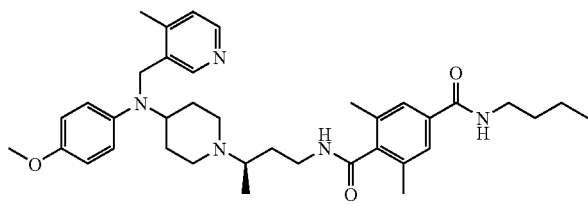<br>N'-Butyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.87-0.97(m, 6H), 0.98-1.25 (m, 2H), 1.35(m, 2H), 1.53(m, 3H), 1.73(m, 3H), 2.07(br t, 1H), 2.25(s, 3H), 2.30(s, 6H), 2.43(br t, 1H), 2.67(m, 1H), 2.81(m, 2H), 3.13(m, 1H), 3.36(m, 3H), 3.71(s, 3H), 3.78(m, 1H), 3.97(s, 2H), 6.63-6.77(m, 5H), 7.00(d, 1H, J=3.0 Hz), 7.43(s, 2H), 7.91(br s, 1H), 8.28(s+d, 2H). ES-MS m/z 614(M+H), 636(M+Na). |
| 110 | 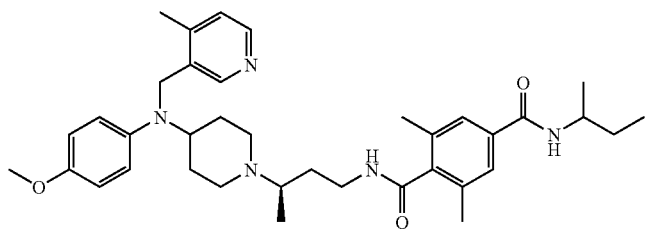<br>N'-sec-Butyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.88-0.98(m, 7H), 1.15(d+m, 4H), 1.52(m, 3H), 1.70(m, 3H), 2.08(br t, 1H), 2.26(s, 3H), 2.31(s, 6H), 2.44(br t, 1H), 2.77(m, 1H), 2.85(m, 2H), 3.13(m, 1H), 3.31(m, 1H), 3.72(s, 3H), 3.74(m, 1H), 4.01(s, 2H), 4.07(m, 1H), 6.51(d, 1H, J=9.0 Hz), 6.65(d, 2H, J= 9.0 Hz), 6.73(d, 2H, J=9.0 Hz), 7.01(d, 1H, J=3.0 Hz), 7.46(s, 2H), 7.75(br s, 1 H), 8.29(s+d, 2H). ES-MS m/z 614(M+H), 636(M+Na). |
| 111 | 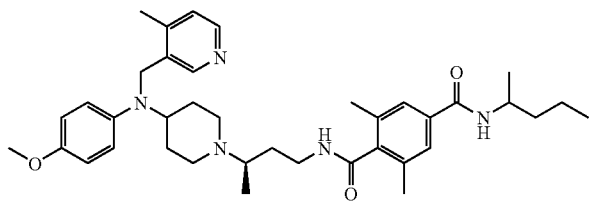<br>N-((R)-3-{4-[(4-Methoxy-phenyl)-(4-methyl-pyridin-3-ylmethyl)-amino]-piperidin-1-yl}-butyl)-2,6-dimethyl-N'-(1-methyl-butyl)-terephthalamide | $^1$H NMR(CDCl$_3$) δ 0.87(t, 3H, J=9.0 Hz), 0.96 (d+m, 4H), 1.15 (d+m, 4H), 1.26-1.54(m, 5H), 1.72(m, 3H), 2.07(br t, 1H), 2.25(s, 3H), 2.30(s, 6H), 2.43(br t, 1H), 2.76(m, 1H), 2.85(m, 2H), 3.13(m, 1H), 3.29(m, 1H), 3.72(s, 3H), 3.74(m, 1H), 4.01(s, 2H), 4.13(m, 1H), 6.53(d, 1H, J= 9.0 Hz), 6.65(d, 2H, J=9.0 Hz), 6.73(d, 2H, J= 9.0 Hz), 7.00(d, 1H, J=3.0 Hz), 7.46(s, 2H), 7.78 (br s, 1H), 8.30(s+d, 2H). ES-MS m/z 628(M+H), 650(M+Na). |

| Ex. # | Structure/Name | Characterization Data |
|---|---|---|
| 112 | 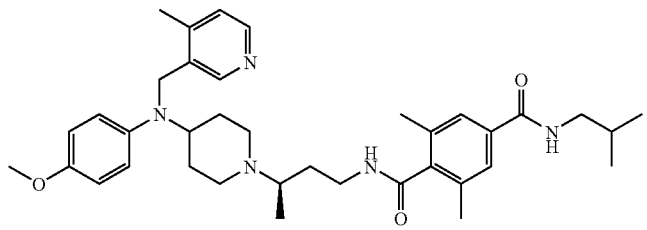<br>N'-Isobutyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.92(d, 6H, J=6.0 Hz), 0.98 (d+m, 4H), 1.16(m, 1H), 1.54(m, 1H), 1.70-1.86 (m, 5H), 2.08(br t, 1H), 2.25(s, 3H), 2.32(s, 6H), 2.44(br t, 1H), 2.67(m, 1H), 2.81(m, 2H), 3.15 (m, 3H), 3.21(m, 1H), 3.72(s, 3H), 3.76(m, 1H), 3.97(s, 2H), 6.64(d, 2H, J=9.0 Hz), 6.74(d, 2H, J=9.0 Hz), 6.76(s, 1H), 7.00(d, 1H, J=3.0 Hz), 7.46(s, 2H), 7.85(br s, 1H), 8.29(s+d, 2H). ES-MS m/z 614(M+H), 636(M+Na). |
| 113 | 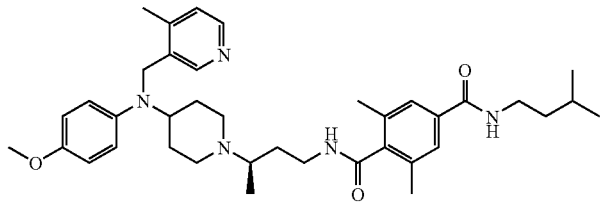<br>N-((R)-3-{4-[(4-Methoxy-phenyl)-(4-methyl-pyridin-3-ylmethyl)-amino]-piperidin-1-yl}-butyl)-2,6-dimethyl-N'-(3-methyl-butyl)-terephthalamide | $^1$H NMR(CDCl$_3$) δ 0.90(d, 6H, J=6.0 Hz), 0.96 (d+m, 4H), 1.14(m, 1H), 1.42(q, 2H, J=7.5 Hz), 1.52(m, 2H), 1.72(m, 3H), 2.07(br t, 1H), 2.25(s, 3H), 2.31(s, 6I-I), 2.43(br t, 1H), 2.72(m, 1H), 2.79(m, 2H), 3.10(m, 1H), 3.38(m, 3H), 3.72(s, 3H), 3.78(m, 1H), 3.96(s, 2H), 6.64(d, 2H, J= 9.0 Hz), 6.74(s+d, 3H, J=9.0 Hz), 7.00(d, 1H, J=3.0 Hz), 7.45(s, 2H), 7.91(br s, 1H), 8.29(s+d, 2H). ES-MS m/z 628(M+H), 650(M+Na). |
| 114 | 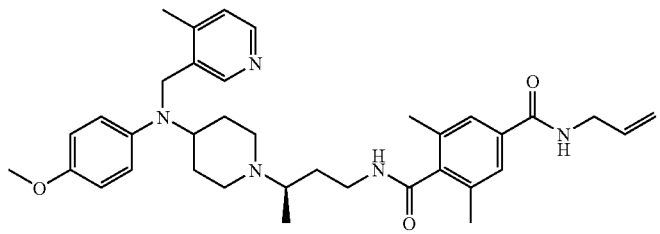<br>N'-Allyl-N-((R)-3-{4-[(4-methoxy-phenyl)-(4-methyl-pyridin-3-ylmethyl)-amino]-piperidin-1-yl}-butyl)-2,6-dimethyl-terephthalamide | $^1$H NMR(CDCl$_3$) δ 0.96(d+m, 4H), 1.14(m, 1H), 1.53(m, 1H), 1.73(m, 3H), 2.07(br t, 1H), 2.24(s, 3H), 2.32(s, 6H), 2.44(br t, 1H), 2.67(m, 1H), 2.80(m, 2H), 3.11(m, 1H), 3.28(m, 1H), 3.72(s, 3H), 3.78(m, 1H), 3.98(s+m, 4H), 5.13(t, 2H, J= 9.0 Hz), 5.83(m, 1H), 6.65(d, 2H, J=9.0 Hz), 6.72(d, 3H, J=9.0 Hz), 6.91(br t, 1H), 6.99(d, 1H, J=3.0 Hz), 7.48(s, 2H), 7.97(br s, 1H), 8.28 (s+d, 2H). ES-MS m/z 598(M+H), 620(M+Na). |
| 115 | 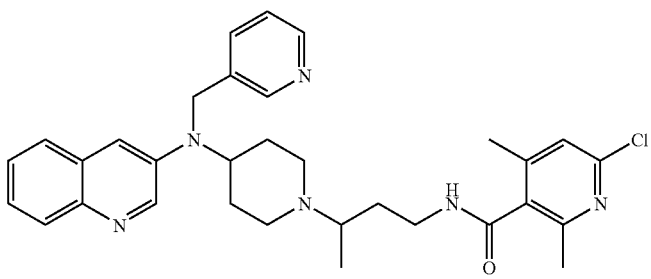<br>6-Chloro-2,4-dimethyl-N-{3-[4-(pyridin-3-ylmethyl-quinolin-3-yl-amino)-piperidin-1-yl]-butyl}-nicotinamide | $^1$H NMR(CDCl$_3$) δ 0.77-0.99(m, 1H), 1.00-1.18 (m, 1H), 1.04(d, 3H, J=6.7 Hz), 1.20-1.41(m, 2H), 1.69-1.94(m, 2H), 2.17-2.29(m, 1H), 2.32(s, 3H), 2.53(s, 3H), 2.57-2.70(m, 1H), 2.76-2.98(m, 3H), 3.26-3.40(m, 1H), 3.74-3.92(m, 2H), 4.11(s, 2H), 7.02(s, 1H), 7.07(d, 1H, J=2.6 Hz), 7.21-7.29(m, 2H), 7.36-7.47(m, 2H), 7.50-7.57(m, 1H), 7.66(d, 1H, J=8.3 Hz), 7.91(dd, 1H, J= 2.2, 8.2 Hz), 8.42-8.53(m, 2H), 8.59(s, 2I-I). $^{13}$C NMR(CDCl$_3$) δ 13.84, 19.18, 22.54, 29.70, 30.93, 31.29, 40.36, 43.97, 46.36, 52.40, 57.46, 60.73, 115.62, 122.89, 123.94, 126.22, 126.61, 127.41, 129.18, 134.75, 141.92, 142.47, 148.85, 149.01, 155.74. ES-MS m/z 579(M+Na). Anal. Calcd. For C$_{32}$H$_{37}$N$_6$ClO•0.3CH$_2$Cl$_2$•0.9CH$_4$O: C, 65.48; H, 6.80; N, 13.83. Found: C, 65.53; H, 6.68; N, 13.68 |

-continued

| Ex. # | Structure/Name | Characterization Data |
|---|---|---|
| 116 | 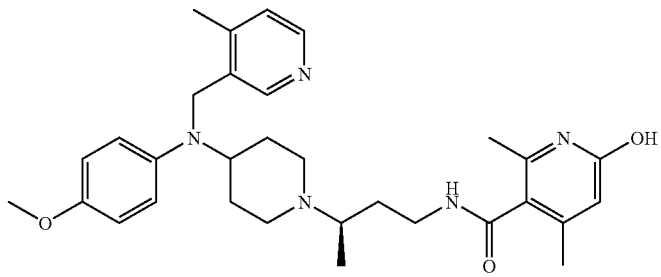<br>6-Hydroxy-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.3 Hz), 1.25-1.43(m, 2H), 1.50-1.58(m, 1H), 1.70-1.89(m, 3H), 2.05-2.16(m, 1H), 2.20(s, 3H), 2.27(s, 3H), 2.33(s, 3H), 2.39-2.49(m, 1H), 2.70-2.85(m, 3H), 3.13-3.21(m, 1H), 3.25-3.35(m, 1H), 3.64-3.74 (m, 4H), 4.05(s, 2H), 6.21(s, 1H), 6.71(s, 4H), 6.94(d, 1H, J=4.8 Hz), 7.99(s, 1H), 8.18(d, 1H, J=4.8 Hz), 8.36(br. s, 1H). $^{13}$C NMR(CDCl$_3$) δ 13.65, 17.33, 18.96, 20.08, 29.59, 30.49, 32.14, 39.34, 44.60, 47.40, 51.74, 55.68, 59.30, 60.56, 114.39, 116.39, 119.21, 121.78, 125.35, 133.49, 142.49, 142.55, 146.04, 147.81, 149.46, 151.37, 154.34, 164.98, 166.92. ES-MS m/z 532(M+H). Anal. Calcd. for C$_{31}$H$_{41}$N$_5$O$_3$•0.4CH$_2$Cl$_2$: C, 66.67; H, 7.45; N, 12.38. Found: C, 66.60; H, 7.62; N, 12.28. |
| 117 | 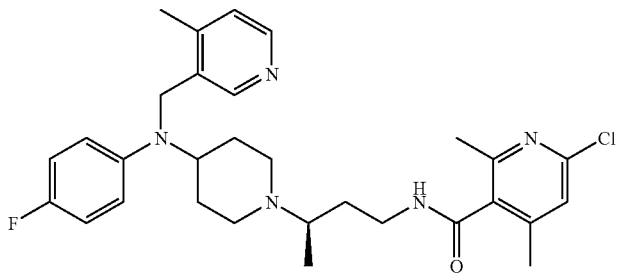<br>6-Chloro-N-((R)-3-{4-[(4-fluoro-phenyl)-(4-methyl-pyridin-3-ylmethyl)-amino]-piperidin-1-yl}-butyl)-2,4-dimethyl-nicotinamide | $^1$H NMR(CDCl$_3$) δ 0.94(d, 3H, J=6.3 Hz), 0.98-1.09(m, 1H), 1.23-1.28(m, 1H), 1.53-1.61(m, 1H), 1.71-1.85(m, 3H), 2.11-2.19(m, 1H), 2.29(s, 3H), 2.36(s, 3H), 2.47-2.56(m, 4H), 2.72-2.86(m, 3H), 3.29-3.42(m, 2H), 3.72-3.80(m, 1H), 4.03(s, 2H), 6.56-6.62(m, 2H), 6.81-6.89(m, 2H), 6.98(s, 1H), 7.05(d, 1H, J=4.8 Hz), 7.85(br. s, 1H), 8.25 (s, 1H), 8.31(d, 1H, J=4.8 Hz). $^{13}$C NMR (CDCl$_3$) δ 13.57, 18.95, 22.30, 29.63, 30.55, 31.76, 39.57, 44.21, 46.76, 51.92, 58.30, 59.68, 115.73(d, J=22.0 Hz), 118.04(d, J=7.2 Hz), 122.63, 125.30, 132.66, 132.83, 144.94, 145.14, 147.52, 148.28, 148.87, 150.35, 155.34, 156.82(d, J=238 Hz), 167.48. ES-MS m/z 538(M+H). Anal. Calcd. for C$_{30}$H$_{37}$N$_5$ClFO•0.45CH$_2$Cl$_2$: C, 63.46; H, 6.63; N, 12.15; Cl, 11.69. Found: C, 63.37; 11, 6.60; N, 12.08; Cl, 11.51. |
| 118 | 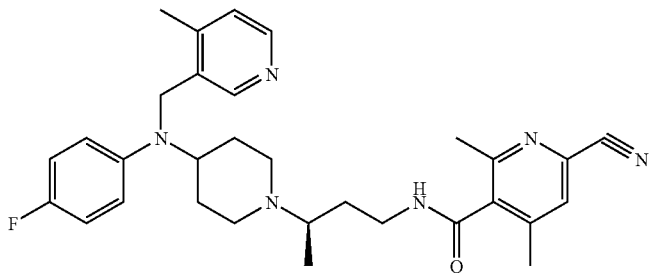<br>6-Cyano-N-((R)-3-{4-[(4-fluoro-phenyl)-(4-methyl-pyridin-3-ylmethyl)-amino]-piperidin-1-yl}-butyl)-2,4-dimethyl-nicotinamide | $^1$H NMR(CDCl$_3$) δ 0.96-1.07(m, 4H), 1.18-1.24 (m, 1H), 1.53-1.60(m, 1H), 1.72-1.85(m, 3H), 2.72-2.85(m, 3H), 3.33-3.43(m, 2.13-2.20(1H, 1H), 2.34(s, 3H), 2.36(s, 3H), 2.47-2H), 3.73-3.80(m, 1H), 4.04(s, 2H), 6.54-6.61(m, 2H), 6.81-6.89(m, 2H), 7.07(d, 1H, J=4.8 Hz), 7.31(s, 1H), 7.85(br. s, 1H), 8.21(s, 1H), 8.31(d, 1H, J=4.8 Hz). $^{13}$C NMR(CDCl$_3$) δ 13.61, 18.93, 22.50, 29.85, 30.61, 31.77, 39.40, 44.26, 46.96, 51.83, 57.95, 59.48, 115.79(d, J=22.0 Hz), 117.11, 117.82(d, J=7.2 Hz), 125.40, 127.57, 132.80, 136.77, 144.88, 145.04, 145.71, 148.32, 148.63, 156.79, 156.80(d, J=238 Hz), 166.64. ES-MS m/z 529(M+H). Anal. Calcd. for C$_{31}$H$_{37}$N$_6$IFO•0.6CH$_2$Cl$_2$: C, 65.48; H, 6.64; N, 14.50. Found: C, 65.31; H, 6.69; N, 14.45. |
| 119 | 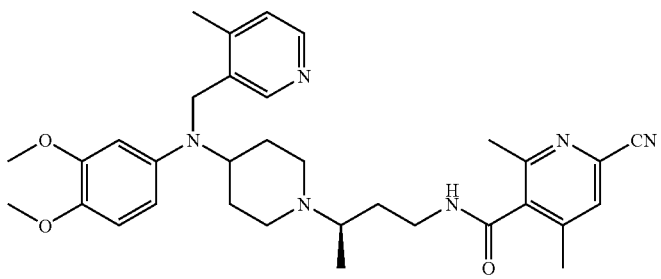<br>6-Cyano-N-((R)-3-{4-[(3,4-dimethoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 0.96-1.21(m, 2H), 1.54-1.60(m, 1H), 1.72-1.86(m, 2H), 2.10-2.18(m, 1H), 2.35(s, 6H), 2.47-2.54(m, 1H), 2.57(s, 3H), 2.74-2.84(m, 4H), 3.19-3.38(m, 2H), 3.74(s, 3H) 3.79(s, 3H), 3.73-3.83(m, 1H), 3.98(s, 2H), 6.23-6.26(m, 2H), 6.69(d, 1H, J= 8.4 Hz), 7.05(d, 1H, J=5.1 Hz), 7.33(s, 1H), 8.18(br s, 1H), 8.24(s, 1H), 8.30(d, 1H, J=5.1 Hz). $^{13}$C NMR(CDCl$_3$) δ 13.77, 19.14, 19.19, 22.71, 30.38, 31.18, 31.58, 40.05, 44.24, 48.03, 52.07, 56.33, 56.72, 59.14, 60.13, 104.89, 111.21, 112.59, 117.31, 125.57, 127.76, 133.31, 143.23, 145.46, 145.86, 148.52, 149.59, 156.99, 166.80. ES-MS m/z 571(M+H). Anal. Calcd. for C$_{33}$H$_{42}$N$_6$O$_3$•0.1 C$_3$H$_7$NO•0.7 H$_2$O: C, 67.72; H, 7.53; N, 14.47. Found: C, 67.64; H, 7.68; N, 14.67. |

| Ex. # | Structure/Name | Characterization Data |
|---|---|---|
| 120 | 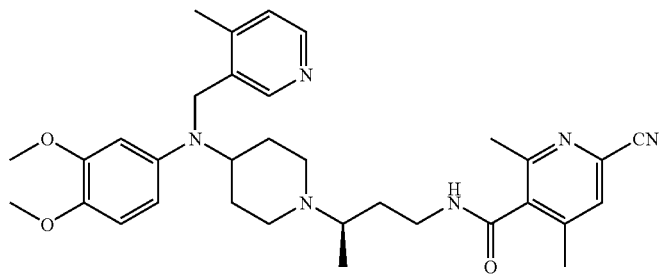<br>6-Chloro-N-((R)-3-{4-[(3,4-dimethoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 0.96-1.25(m, 2H), 1.52-1.60(m, 1H), 1.72-1.86(m, 3H), 2.09-2.16(m, 1H), 2.30(s, 3H), 2.35(s, 3H), 2.47-2.54(m, 1H), 2.51(s, 3H), 2.74-2.84(m, 4H), 3.24-3.33(m, 2H), 3.74(s, 3H) 3.79(s, 3H), 3.73-3.83(m, 1H), 3.97(s, 2H), 6.23-6.29(m, 2H), 6.69 (d, 1H, J=8.4 Hz), 6.98(s, 1H), 7.02(d, 1H, J= 5.1 Hz), 8.04(br s, 1H), 8.27(s, 1H), 8.29(d, 1H, J=5.1 Hz). $^{13}$CNMR(CDCl$_3$) δ 13.80, 19.15, 19.25, 22.49, 30.12, 31.00, 31.84, 39.86, 44.40, 47.51, 52.05, 53.85, 56.30, 56.69, 59.59, 104.72, 111.04, 112.59, 122.80, 125.48, 132.95, 133.46, 143.42, 143.75, 145.61, 147.72, 148.31, 149.66, 150.50, 155.57, 167.69. ES-MS m/z 580(M+H). Anal. Calcd. for C$_{33}$H$_{42}$N$_5$ClO$_3$•0.2 CH$_2$Cl$_2$: C, 62.69; H, 6.96; N, 11.25. Found: C, 62.88; H, 6.80; N, 11.23. |
| 121 | 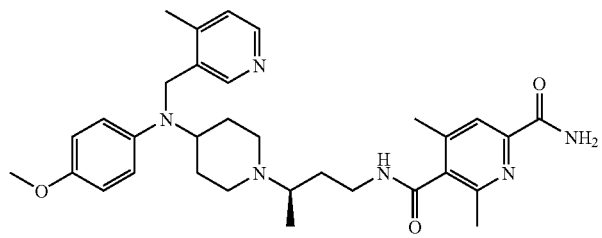<br>4,6-Dimethyl-pyridine-2,5-dicarboxylic acid 2-amide 5-[((R)-3-{4-[(4-methoxy-phenyl)-(4-methyl-pyridin-3-ylmethyl)-amino]-piperidin-1-yl}-butyl)-amide] | $^1$H NMR(CDCl$_3$) δ 0.99(d, 3H, J=6.6 Hz), 1.02 (m, 1H), 1.20(m, 1H), 1.56(m, 1H), 1.76(m, 3H), 2.11(t, 1H, J=11.2 Hz), 2.32(s, 3H), 2.38(s, 3H), 2.48(t, 1H, J=11.2 Hz), 2.55(s, 3H), 2.65-2.85 (m, 3H), 3.16(m, 1H), 3.35(m, 1H), 3.71(s, 3H), 3.74(m, 1H), 3.89(s, 2H), 5.41(br, 1H), 6.58-6.80 (m, 4H), 7.00(d, 1H, J=4.8 Hz), 7.75(br, 1H), 7.87(s, 1H), 7.98(br, 1H), 8.24(s, 1H), 8.28(d, 1H, J=4.8 Hz). ES-MS In/z 559(M+H). Anal. Calcd. for C$_{32}$H$_{42}$N$_6$O$_3$•0.2CH$_2$Cl$_2$: C, 67.18; H, 7.42; N, 14.60. Found: C, 67.04; H, 7.53; N, 14.59 |
| 122 | 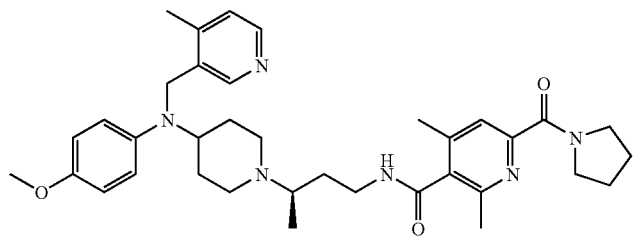<br>N-((R)-3-{4-[(4-Methoxy-phenyl)-(4-methyl-pyridin-3-ylmethyl)-amino]-piperidin-1-yl}-butyl)-2,4-dimethyl-6-(pyrrolidine-1-carbonyl)-nicotinamide | $^1$H NMR(CDCl$_3$) δ 0.99(d, 3H, J=6.6 Hz), 1.17 (m, 1H), 1.30(m, 1H), 1.59(m, 1H), 1.70-1.95(m, 7H), 2.14(t, 1H, J=11.2 Hz), 2.32(s, 3H), 2.37(s, 3H), 2.48(t, 1H, J=11.2 Hz), 2.54(s, 3H), 2.65-2.85(m, 3H), 3.25(m, 1H), 3.37(m, 1H), 3.61(t, 2H, J=6.9 Hz), 3.64(t, 2H, J=6.9 Hz), 3.72(s, 3H), 3.73(m, 1H), 4.01(s, 2H), 6.63(m, 2H), 6.72 (m, 2H), 7.01(d, 1H, J=5.4 Hz), 7.45(br, 1H), 7.51(s, 1H), 8.27(s, 1H), 8.28(d, 1H, J=5.4 Hz). ES-MS m/z 613(M+H). |
| 123 | 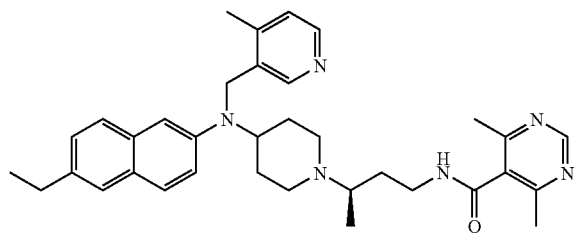<br>4,6-Dimethyl-pyrimidine-5-carboxylic acid (3-{4-[(6-methoxy-naphthalen-2-yl)-(4-methyl-pyridin-3-ylmethyl)-amino]-piperidin-1-yl}-butyl)-amide | $^1$H NMR(CDCl$_3$) δ 0.77-0.95(m, 1H), 0.98-1.17 (m, 1H), 1.04(d, 3H, J=6.5 Hz), l.21-1.44(m, 2H), 1.69-1.99(m, 2H), 2.16-2.29(m, 1H), 2.43(s, 3H), 2.52(s, 6H), 2.54-2.67(m, 1H), 2.69-2.95(m, 3H), 3.29-3.45(m, 1H), 3.55-3.70(m, 1H), 3.74-3.84(m, 1H), 3.86(s, 3H), 4.08(s, 2H), 6.81-7.11 (m, 5H), 7.42-7.56(m, 2H), 8.10(br s, 1H), 8.29-8.37(m, 2H), 8.77(s, 1H). $^{13}$C NMR(CDCl$_3$) δ 12.40, 17.81, 20.98, 23.46, 28.49, 29.40, 30.27, 38.69, 42.99, 44.86, 50.98, 54.28, 56.85, 58.75, 104.59, 109.97, 117.83, 117.93, 124.05, 126.71, 126.92, 127.54, 128.88, 131.85, 143.58, 147.11, 147.66, 154.70, 156.51, 161.96, 165.45. ES-MS m/z 567(M+H). Anal. Calcd. For C$_{34}$H$_{42}$N$_6$O$_2$•0.4CH$_2$Cl$_2$•1.7CH$_4$O: C, 66.40; H, 7.64; N, 12.89. Found: C, 66.53; H, 7.34; N, 12.48. |

| Ex. # | Structure/Name | Characterization Data |
|---|---|---|
| 124 | 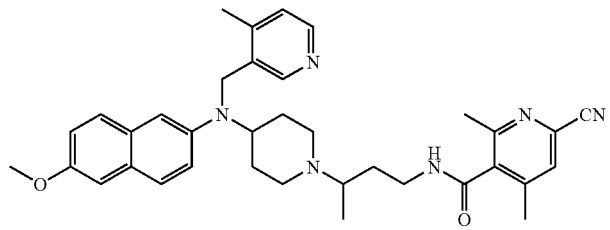<br>6-Cyano-N-(3-{4-[(6-methoxy-naphthalen-2-yl)-(4-methyl-pyridin-3-ylmethyl)-amino]-piperidin-1-yl}-butyl)-2,4-dimethyl-nicotinamide | $^1$H NMR(CDCl$_3$) δ 0.94-1.33(m, 2H), 1.03(d, 3H, J=6.6 Hz), 1.50-1.97(m, 4H), 2.15-2.29(m, 1H), 2.32(s, 3H), 2.41(s, 3H), 2.51-2.64(m, 1H), 2.57 (s, 3H), 2.70-2.9 1(m, 3H), 3.29-3.45(m, 1H), 3.51-3.67(m, 1H), 3.72-3.89(m, 1H), 3.88(s, 3H), 4.15(s, 2H), 6.86-6.97(m, 2H), 7.00-7.12(m, 3H), 7.22-7.28(m, 1H), 7.46-7.58(m, 2H), 7.94(br s, 1H), 8.30-8.35(m, 2H). $^{13}$C NMR(CDCl$_3$) δ 13.72, 19.21, 22.77, 31.89, 44.55, 46.77, 52.35, 55.71, 59.89, 106.02, 119.47, 125.59, 127.79, 128.22, 128.35, 130.28, 148.57. ES-MS m/z 591 (M+H). |
| 125 | 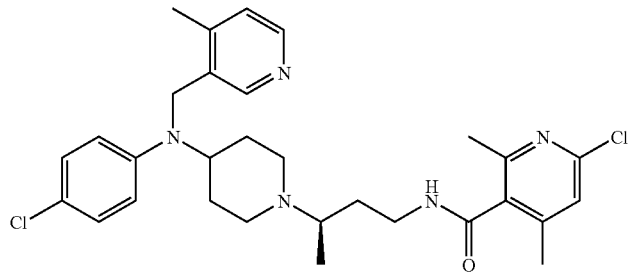<br>6-Chloro-N-((R)-3-{4-[(4-chloro-phenyl)-(4-methyl-pyridin-3-ylmethyl)-amino]-piperidin-1-yl}-butyl)-2,4-dimethyl-nicotinamide | $^1$H NMR(CDCl$_3$) δ 1.01(d, 3H, J=6.3 Hz), 1.06-1.15(m, 1H), 1.25-1.35(m, 1H), 1.53-1.87(m, 4H), 2.16-2.24(m, 1H), 2.30(s, 3H), 2.37(s, 3H), 250-2.59(m, 4H), 2.74-2.88(m, 3H), 3.31-3.39 (m, 1H), 3.50-3.61(m, 1H), 3.74-3.81(m, 1H), 4.09(s, 2H), 6.48-6.53(m, 2H), 6.98(s, 1H), 7.07-7.11(m, 3H), 7.66(br. s, 1H), 8.24(s, 1H), 8.34(d, 1H, J=4.8 Hz). $^{13}$C NMR(CDCl$_3$) δ 13.61, 18.93, 18.96, 22.34, 29.46, 30.45, 31.93, 39.46, 44.26, 45.60, 51.96, 56.99, 59.56, 115.56, 122.67, 122.84, 125.29, 129.24, 132.52, 132.64, 144.67, 147.07, 147.58, 148.20, 148.35, 150.38, 155.33, 167.49. ES-MS m/z 554(M+H). Anal. Calcd. for C$_{30}$H$_{37}$N$_5$Cl$_2$O·0.2CH$_2$Cl$_2$: C, 63.46; H, 6.60; N, 12.25; Cl, 14.89. Found: C, 63.51; H, 6.66; N, 12.25; Cl, 14.57. |
| 126 | 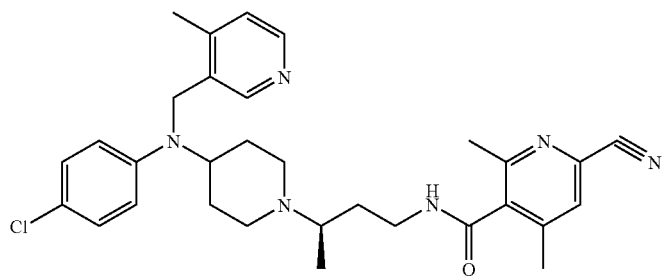<br>N-((R)-3-{4-[(4-Chloro-phenyl)-(4-methyl-pyridin-3-ylmethyl)-amino]-piperidin-1-yl}-butyl)-6-cyano-2,4-dimethyl-nicotinamide | $^1$H NMR(CDCl$_3$) δ 0.96-1.10(m, 4H), 1.19-1.30 (m, 1H), 1.53-1.89(m, 4H), 2.17-2.26(m, 1H), 2.35(s, 3H), 2.38(s, 3H), 2.52-2.60(m, 4H), 2.74-2.88(m, 3H), 3.32-3.41(m, 1H), 3.54-3.62(m, 1H), 3.74-3.80(m, 1H), 4.09(s, 2H), 6.48-6.52(m, 2H), 7.08-7.11(m, 3H), 7.32(s, 1H), 7.74(br. s, 1H), 8.22(s, 1H), 8.35(d, 1H, J=4.8 Hz). $^{13}$C NMR(CDCl$_3$) δ 13.63, 18.87, 18.95, 22.53, 29.61, 30.39, 31.98, 39.31, 44.34, 45.72, 51.85, 56.75, 59.28, 115.41, 117.12, 122.85, 125.40, 127.59, 129.28, 132.49, 132.75, 136.74, 144.64, 145.78, 147.00, 147.95, 148.33, 156.78, 166.66. ES-MS m/z 545(M+H). Anal. Calcd. for C$_{31}$H$_{37}$N$_6$ClO·0.3CH$_2$Cl$_2$: C, 65.89; H, 6.64; N, 14.73; Cl, 9.94. Found: C, 65.96; H, 6.50; N, 14.79; Cl, 10.08. |
| 127 | 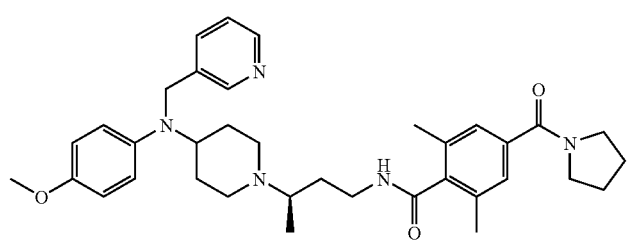<br>N-((R)-3-{4-[(4-Methoxy-phenyl)-pyridin-3-ylmethyl-amino]-piperidin-1-yl}-butyl)-2,6-dimethyl-4-(pyrrolidine-1-carbonyl)-benzamide | $^1$H NMR(CDCl$_3$) δ 1.03(br s, 3H), 1.24(br m, 2H), 1.57(m, 2H), 1.80(m, 5H), 1.93(m, 3H), 2.18(br m, 1H), 2.31(s, 6H), 2.55(m, 1H), 2.78 (m, 1H), 2.88(m, 2H), 3.33(t, 2H, J=6 Hz), 3.44 (m, 2H)'3.60(t, 2H, J=6 Hz), 3.69(s, 3H), 3.79 (m, 1H), 3.95(s, 2H), 6.67(m, 4H), 7.15(m, 3H), 7.61(d, 1H, J=8 Hz), 8.17(br s, 1H), 8.40(d, 1H, J=5 Hz), 8.49(s, 1H). $^{13}$C NMR(CDCl$_3$) δ 13.7, 19.6, 24.9, 26.7, 29.4, 30.6, 31.6, 39.7, 44.4, 46.5, 47.6, 50.0, 52.3, 56.0, 57.9, 60.4, 115.0, 117.2, 123.6, 126.5, 134.7, 135.2, 136.6, 138.0, 143.0, 148.2, 149.3, 169.5, 169.9. ES-MS m/z 598 (M+H), 621(M+Na). Anal. Calcd. For C$_{36}$H$_{47}$N$_5$O$_3$·0.6 CH$_2$Cl$_2$: C, 72.33; H, 7.92; N, 11.72. Found: C, 67.95; H, 7.45; N, 10.80. |

| Ex. # | Structure/Name | Characterization Data |
|---|---|---|
| 128 | 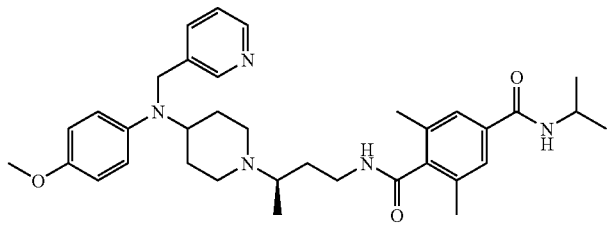<br>N'-Isopropyl-N-((R)-3-{4-[(4-methoxy-phenyl)-pyridin-3-ylmethyl-amino]-piperidin-1-yl}-butyl)-2,6-dimethyl-terephthalamide | $^1$H NMR(CDCl$_3$) δ 1.02(br d, 3H), 1.23(d, 6H, J=7 Hz), 1.56(m, 1H), 1.74(m, 2H), 2.16(m, 1H), 2.29(s, 6H), 2.54(m, 1H), 2.78(m, 1H), 2.88(m, 2H), 3.34(m, 2H), 3.70(s, 3H), 3.80(m, 1H), 3.87 (m, 2H), 4.26(sept, 1H, J=7 Hz), 6.33(d, 1H, J=8 Hz), 6.61(m, 2H), 6.72(m, 2H), 7.18(dd, 1H, J=5 Hz, 8 Hz), 7.40(s, 2H), 7.54(d, 1H, J=8 Hz), 8.28(br s, 1H), 8.41(m, 2H). $^{13}$C NMR(CDCl$_3$) δ 11.2, 17.1, 20.7, 27.1, 27.6, 28.3, 29.1, 37.3, 39.9, 41.9, 45.8, 49.8, 51.4, 53.6, 55.8, 58.2, 112.5, 115.6, 121.2, 124.0, 132.5, 132.7, 132.9, 133.9, 138.9, 140.5, 145.8, 146.7, 164.2, 167.2. ES-MS m/z 586(M+H), 609(M+Na). Anal. Calcd. For C$_{35}$H$_{47}$N$_5$O$_3$•0.5 CH$_2$Cl$_2$: C, 71.76; H, 8.09; N, 11.96. Found: C, 68.05; H, 7.75; N, 11.11. |
| 129 | 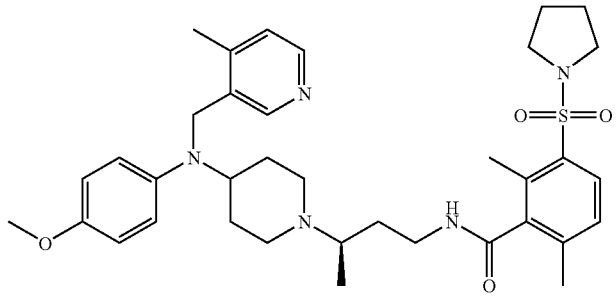<br>N-((R)-3-{4-[(4-Methoxy-phenyl)-(4-methyl-pyridin-3-ylmethyl)-amino]-piperidin-1-yl}-butyl)-2,6-dimethyl-3-(pyrrolidine-1-sulfonyl)-benzamide | $^1$H NMR(CDCl$_3$) δ 0.99(d, 3H, J=6.6 Hz), 1.07-1.28(m, 2H), 1.53-1.59(m, 1H), 1.79-1.91(m, 8H), 2.08-2.15(m, 1H), 2.31(s, 3H), 2.36(s, 3H), 2.47-2.55(m, 1H), 2.58(s, 3H), 2.73-2.87(m, 3H), 3.19-3.39(m, 5H), 3.70(s, 3H), 3.71-3.78(m, 1H), 3.93 (br s, 2H), 6.65(d, 2H, J=9 Hz), 6.71(d, 2H, J=9 Hz), 7.00(d, 1H, J=4.8 Hz), 7.03(d, 1H, J=8.1 Hz), 7.70(d, 1H, J=8.1 Hz), 7.91(br s, 1H), 8.26(s, 1H), 8.27(d, 1H, J=4.8 Hz). $^{13}$C NMR (CDCl$_3$) δ 11.43, 14.78, 16.88, 17.53, 23.52, 27.36, 28.09, 29.56, 37.05, 42.36, 42.92, 45.05, 45.17, 49.53, 53.53, 57.32, 112.34, 118.01, 123.09, 125.41, 127.87, 131.17, 132.26, 133.39, 137.59, 138.99, 140.47, 143.35, 145.85, 146.65, 151.60, 166.87. ES-MS m/z 648(M+H). Anal. Calcd. for C$_{36}$H$_{49}$N$_5$O$_4$S•1.5H$_2$O: C, 64.07; H, 7.77; N, 10.38. Found: C, 64.06; H, 7.61; N, 10.47. |
| 131 | 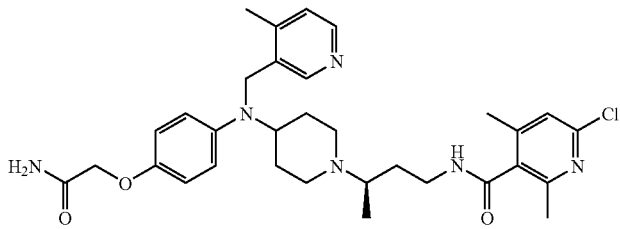<br>N-((R)-3-{4-[(4-Carbamoylmethoxy-phenyl)-(4-methyl-pyridin-3-ylmethyl)-amino]-piperidin-1-yl}-butyl)-6-chloro-2,4-dimethyl-nicotinamide | $^1$H NMR(CDCl$_3$) δ 1.00(d, 3H, J=9 Hz), 1.10(m, 1H), 1.31(m, 1H), 1.51-1.56(m, 1H), 1.71-1.77 (m, 1H), 1.83(d, 2H, J=12 Hz), 2.19(t, 1H, J=9 Hz), 2.30(s, 3H), 2.36(s, 3H), 2.50(s, 3H), 2.71-2.89(m, 3H), 3.29-3.44(m, 2H), 3.75-3.90(m, 1H), 4.01(s, 2H), 4.40(s, 2H), 5.58(br s, 1H), 6.54(br s, 1H), 6.62(d, 2H, J=9 Hz), 6.75(d, 2H, J=9 Hz), 6.98(s, 1H), 7.05(d, 1H, J=6 Hz), 7.92 (br s, 1H), 8.24(s, 1H), 8.31(d, 1H, J=6 Hz). $^{13}$C NMR(CDCl$_3$) δ 13.38, 18.81, 22.14, 29.57, 30.54, 31.46, 39.61, 43.93, 46.73, 51.89, 58.39, 59.78, 67.80, 115.44, 118.77, 122.48, 125.13, 132.75, 145.06, 148.17, 148.98. ES-MS m/z 593(M+H). Anal. Calcd. for C$_{32}$H$_{41}$N$_6$ClO$_3$•0.5CH$_2$Cl$_2$: C, 61.41; 11, 6.66; N, 13.22. Found: C, 61.07; H, 6.55; N, 13.00. |
| 132 | 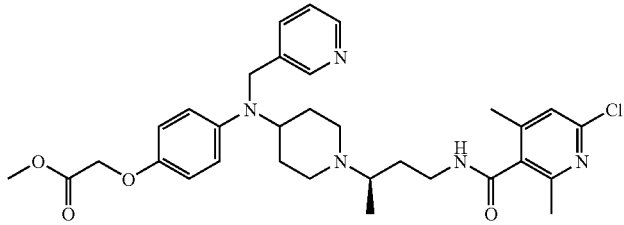<br>{4-[(1-{(R)-3-[(6-Chloro-2,4-dimethyl-pyridine-3-carbonyl)-amino]-1-methyl-propyl}-piperidin-4-yl)-pyridin-3-ylmethyl-amino]-phenoxy}-acetic acid methyl ester | $^1$H NMR(CDCl$_3$) δ 0.99(d, 3H, J=6 Hz), 1.48-1.56(m, 1H), 1.71-1.81(m, 3H), 2.11-2.23(m, 1H), 2.29(s, 3H), 2.50(s, 3H), 2.53(m, 1H), 2.71-2.92(m, 3H), 3.25-3.33(m, 1H), 3.37-3.51(m, 1H), 3.77(s, 3H), 3.90(s, 2H), 4.52(s, 2H), 6.58 (d, 2H, J=12 Hz), 6.75(d, 2H, J=12 Hz), 7.00(s, 1H), 7.22(m, 1H), 7.59(d, 1H, J=9 Hz), 8.44(d, 1H, J=3 Hz), 8.45(s, 1H), 8.58(br s, 1H). $^{13}$C NMR(CDCl$_3$) δ 13.76, 19.14, 22.48, 29.63, 31.12, 40.46, 43.97, 47.49, 52.50, 57.86, 60.85, 66.55, 116.21, 117.01, 122.85, 123.71, 133.14, 134.99, 135.98, 143.84, 147.86, 148.56, 149.09, 150.58, 151.12, 155.71, 167.51. ES-MS m/z 594(M+H). Anal. Calcd. for C$_{32}$H$_{40}$N$_5$ClO$_4$•0.22CH$_2$Cl$_2$: C, 63.15; H, 6.65; N, 11.43. Found: C, 63.15; H, 6.64; N, 11.03. |

| Ex. # | Structure/Name | Characterization Data |
|---|---|---|
| 135 | 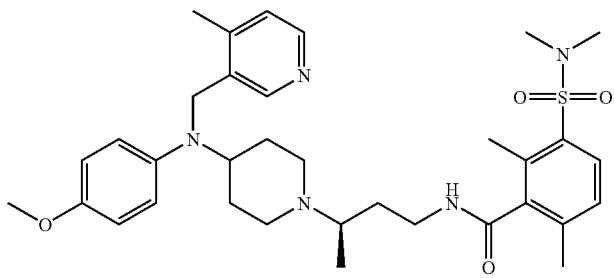<br>3-Dimethylsulfamoyl-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.99(d, 3H, J=6.6 Hz), 1.02-1.29(m, 2H), 1.56-1.63(m, 1H), 1.76-1.85(m, 3H), 2.00-2.11(m, 1H), 2.30(s, 3H), 2.36(s, 3H), 2.46-2.54(m, 1H), 2.56(s, 3H), 2.72-2.87(m, 3H), 2.73(s, 6H), 3.16-3.40(m, 2H), 3.70(s, 3H), 3.71-3.78(m, 1H), 3.90(br s, 2H), 6.65(d, 2H, J=9.3 Hz), 6.71(d, 2H, J=9 Hz), 7.00(d, 1H, J=5.1 Hz), 7.04(d, 1H, J=8.1 Hz), 7.68(d, 1H, J=8.1 Hz), 7.88(br s, 1H), 8.26(s, 1H), 8.27(d, 1H, J=4.8 Hz). $^{13}$C NMR(CDCl$_3$) δ 13.79, 17.16, 19.27, 19.92, 29.90, 30.66, 31.91, 37.24, 39.62, 44.59, 45.39, 47.48, 52.02, 55.90, 59.81, 114.70, 120.66, 125.48, 127.78, 130.80, 133.52, 134.55, 134.79, 140.17, 141.55, 142.85, 145.75, 148.27, 149.80, 154.06, 169.12. ES-MS m/z 622(M+H). Anal. Calcd. for C$_{34}$H$_{47}$N$_5$O$_4$S•1.0H$_2$O: C, 63.82; H, 7.72; N, 10.95. Found: C, 63.68; H, 7.45; N, 10.87. |
| 136 | 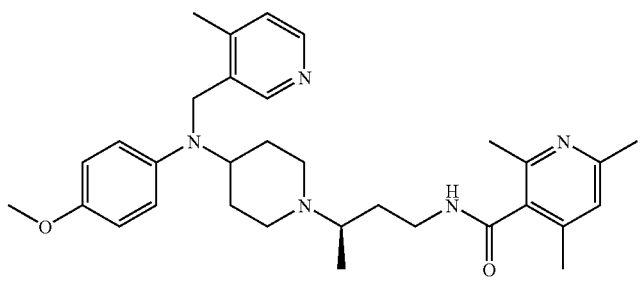<br>N-((R)-3-{4-[(4-Methoxy-phenyl)-(4-methyl-pyridin-3-ylmethyl)-amino]-piperidin-1-yl}-butyl)-2,4,6-trimethyl-nicotinamide | $^1$H NMR(CDCl$_3$) δ 0.98(d, 3H, J=6.6 Hz), 1.09-1.30(m, 2H), 1.53-1.60(m, 1H), 1.71-1.82(m, 3H), 2.07-2.14(m, 1H), 2.28(s, 6H), 2.33(s, 3H), 2.43-2.57(m, 4H), 2.71-2.85(m, 3H), 3.32-3.40 (m, 2H), 3.71(s, 3H), 3.75-3.81(m, 1H), 3.90(s, 2H), 6.63-6.73(m, 4H), 6.77(s, 1H), 7.01(d, 1H, J=4.8 Hz), 7.82(br. s, 1H), 8.27(s, 1H), 8.29(d, 1H, J=4.8 Hz). $^{13}$C NMR(CDCl$_3$) δ 13.56, 18.95, 19.01, 22.51, 24.28, 29.67, 30.51, 31.78, 39.65, 44.20, 47.08, 51.98, 55.72, 59.84, 114.50, 120.51, 122.03, 125.26, 131.08, 133.28, 142.71, 144.17, 145.43, 148.24, 149.71, 153.65, 153.95, 157.79, 168.93. ES-MS m/z 530(M+H). Anal. Calcd. for C$_{32}$H$_{43}$N$_5$O$_2$•0.2CH$_2$Cl$_2$: C, 70.74; H, 8.00; N, 12.81. Found: C, 70.98; H, 8.05; N, 12.70. |
| 139 | 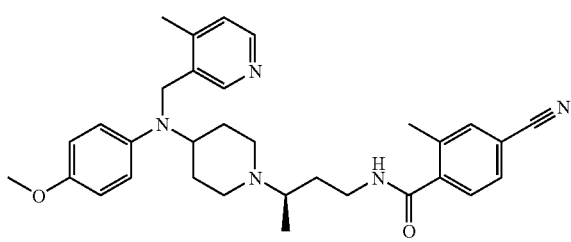<br>4-Cyano-N-((R)-3-{4-[(4-methoxy-phenyl)-(4-methyl-pyridin-3-ylmethyl)-amino]-piperidin-1-yl}-butyl)-2-methyl-benzamide | $^1$H NMR(CDCl$_3$) δ 1.00(d, 3H, J=6.0 Hz), 1.13 (m, 1H), 1.28(m, 1H), 1.53(m, 1H), 1.74(m, 1H), 1.84(m, 2H), 2.14(br t, 1H), 2.29(s, 3H), 2.45(s, 6H), 2.50(br t, 1H), 2.78(m, 3H), 3.28(m, 2H), 373(s+m, 4H), 4.02(s, 2H), 6.65(d, 2H, J=9.0 Hz), 6.72(d, 3H, J=9.0 Hz), 7.03(d, 1H, J=6.0 Hz), 7.39(s, 2H), 7.47(s, 1H), 7.79(br s, 1H), 8.27 (s, 1H), 8.32(d, 1H, J=3.0 Hz). ES-MS m/z 526 (M+H), 548(M+Na). |
| 140 | 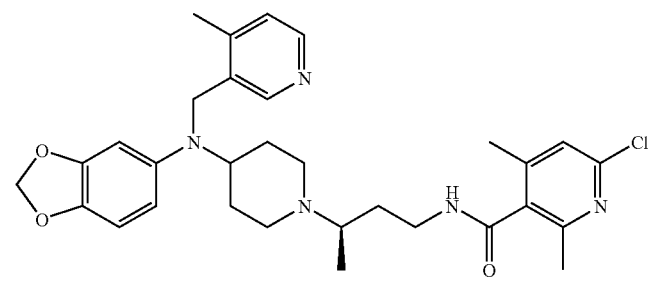<br>N-((R)-3-{4-[Benzo[1,3]dioxol-5-yl-(4-methyl-pyridin-3-ylmethyl)-amino]-piperidin-1-yl}-butyl)-6-chloro-2,4-dimethyl-nicotinamide | $^1$H NMR(CDCl$_3$) δ 0.97(d, 3H, J=6.6 Hz), 1.02 (m, 1H), 1.21(m, 1H), 1.54(m, 1H), 1.73(m, 1H), 1.82(br d, 2H, 11.7 Hz), 2. 12(t, 1H, 11.2 Hz), 2.30(s, 3H), 2.35(s, 3H), 2.49(t, 1H, J=11.2 Hz), 2.51(s, 3H), 2.65-2.85(m, 3H), 3.21(m, 1H), 3.33(m, 1H), 3.79(m, 1H), 3.96(s, 3H), 5.85(s, 2H), 6.11(d, 1H, J=8.4 Hz), 6.32(br, 1H), 6.60 (d, 1H, J=8.1 Hz), 6.98(s, 1H), 7.02(d, 1H, J=3.3 Hz), 7.96(br, 1H), 8.25(s, 1H), 8.30(d, 1H, J=5.4 Hz). $^{13}$C NMR(CDCl$_3$) δ 13.80, 19.18(2C), 22.51, 30.07, 30.93, 31.87, 39.85, 44.41, 47.78, 52.03, 59.53, 59.92, 101.21, 101.28, 108.56, 111.51, 122.84, 125.51, 132.91, 133.24, 141.78, 144.34, 145.66, 147.70, 148.39, 148.47, 149.54, 150.55, 155.57, 167.71. ES-MS m/z 564(M+H). Anal. Calcd. for C$_{31}$H$_{38}$N$_5$O$_3$•0.3CH$_2$Cl$_2$: C, 63.76; H, 6.60; N, 11.88. Found: C, 63.91; H, 6.59; N, 11.87. |

| Ex. # | Structure/Name | Characterization Data |
|---|---|---|
| 141 | 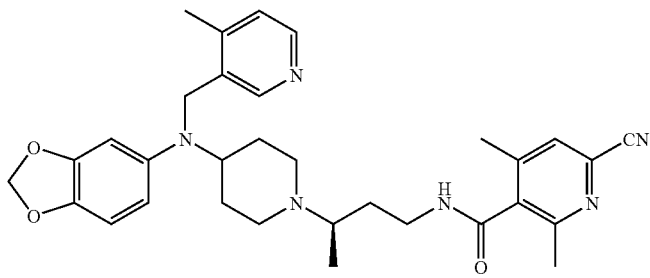<br>N-((R)-3-{4-[Benzo[1,3]dioxol-5-yl-(4-methyl-pyridin-3-ylmethyl)-amino]-piperidin-1-yl}-butyl)-6-cyano-2,4-dimethyl-nicotinamide | $^1$H NMR(CDCl$_3$) δ 0.99(d, 3H, J=6.6 Hz), 1.00 (m, 1H), 1.15(m, 1H), 1.56(m, 1H), 1.73(m, 1H), 1.82(brd, 2H, J 11.7 Hz), 2.13(t, 1H, J= 11.2 Hz), 2.35(s, 6H) 2.49(t, 1H, J=11.2 Hz), 2.57(s, 3H), 2.65-2.85(m, 3H), 3.18(m, 1H), 3.35(m, 1H), 3.78(m, 1H), 3.97(s, 3H), 5.86(s, 2H), 6.10 (dd, 1H, J=8.5, 2.3 Hz), 6.30(d, 1H, J=2.1 Hz), 6.60(d, 1H, J=8.4 Hz), 7.06(d, 1H, J=5.1 Hz), 7.33(s, 1H), 8.03(br, 1H), 8.23(s, 1H), 8.31(d, 1H, J=5.4 Hz). $^{13}$C NMR(CDCl$_3$) δ 13.84, 19.13 (2C), 22.69, 30.27, 30.95, 31.94, 39.68, 44.52, 48.17, 51.87, 59.15, 59.59, 101.13, 101.25, 108.61, 111.38, 117.34, 125.61, 127.78, 132.92, 133.25, 137.03, 141.80, 144.24, 145.59, 145.87, 148.38, 148.55, 149.24, 157.02, 166.89. ES-MS m/z 555 (M+H). Anal. Calcd. for C$_{32}$H$_{38}$N$_6$O$_3$•0.2CH$_2$Cl$_2$: C, 67.65; H, 6.77; N, 14.70. Found: C, 67.54; H, 6.87; N, 14.59. |
| 142 | 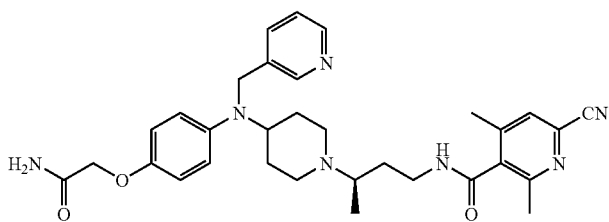<br>N-((R)-3-{4-[(4-Carbamoylmethoxy-phenyl)-pyridin-3-ylmethyl-amino]-piperidin-1-yl}-butyl)-6-chloro-2,4-dimethyl-nicotinamide | $^1$H NMR(CDCl$_3$) δ 0.99(d, 3H, J=9 Hz), 1.01-1.22(m, 1H), 1.49-1.55(m, 1H), 1.75-1.82(m, 4H), 2.16(t, 1H, J=12 Hz), 2.29(s, 3H), 2.50(s, 3H), 2.51-2.61(t, 1H, J=12 Hz), 2.73-2.89(m, 3H), 3.26(t, 1H, J=12 Hz), 3.48(t, 1H, J=12 Hz), 3.90(m, 1H), 4.38(s, 2H), 5.74(br s, 1H), 6.58(d, 2H, J=6 Hz), 6.75(d, 2H, J=6 Hz), 7.00(s, 1H), 7.21-7.24(m, 1H), 7.60(d, 1H, J=9 Hz), 8.45(d, 1H, J=6 Hz), 8.50(s, 1H), 8.63(br s, 1H). $^{13}$C NMR(CDCl$_3$) δ 13.79, 19.15, 22.48, 29.67, 31.01, 31.12, 40.48, 43.96, 47.40, 52.50, 57.92, 60.87, 68.27, 116.04, 117.08, 122.84, 123.74, 133.17, 134.97, 135.82, 144.03, 147.90, 148.61, 149.06, 150.42, 155.72, 167.47, 171.66. ES-MS m/z 580 (M+H). Anal. Calcd. for C$_{31}$H$_{39}$N$_6$ClO$_3$•0.2CH$_2$Cl$_2$: C, 62.86; H, 6.66; N, 14.10. Found: C, 62.77; H, 6.75; N, 13.84. |
| 143 | 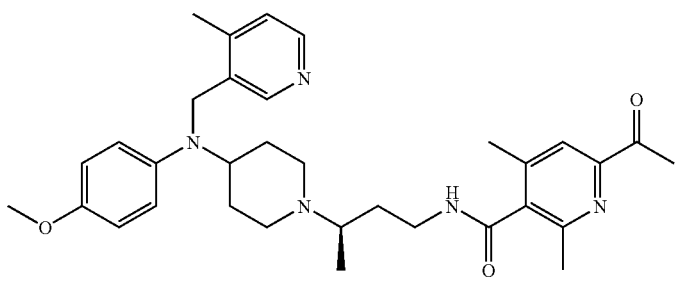<br>6-Acetyl-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.03 (m, 1H), 1.20(m, 1H), 1.57(m, 1H), 1.75(m, 1H), 1.80(br d, 2H, J=11.7 Hz), 2.10(t, 1H, J= 11.2 Hz), 2.25(s, 3H), 2.37(s, 3H), 2.47(t, 1H, J= 11.2 Hz), 2.53(s, 3H), 2.59(s, 3H), 2.65-2.85(m, 3H), 3.17(m, 1H), 3.35(m, 1H), 3.71(m, 1H), 3.82(m, 1H), 3.85(s, 3H), 6.59(m, 2H), 6.71(m, 2H), 6.99 (d, 1H, J=4.8 Hz), 7.69(s, 1H), 7.97(br, 1H), 8.21(s, 1H), 8.28(d, 1H, J=5.1 Hz). $^{13}$C NMR (CDCl$_3$) δ 13.78, 19.09, 19.33, 22.75, 25.98, 30.09, 30.86, 31.91, 39.82, 44.40, 47.72, 52.05, 55.91, 59.70, 59.92, 114.69(2C), 120.79, 120.97(2C), 125.49, 133.33, 136.88, 142.73, 145.10, 145.60, 148.42, 149.79, 152.70, 154.30, 150.50, 168.23, 200.34. ES-MS m/z 558(M+H). Anal. Calcd. for C$_{33}$H$_{43}$N$_5$O$_3$•0.1CH$_2$Cl$_2$: C, 70.21; H, 7.69; N, 12.37. Found: C, 70.03; H, 7.82; N, 12.13. |
| 144 | 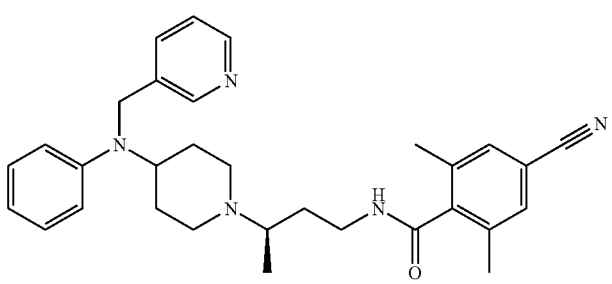<br>4-Cyano-2,6-dimethyl-N-{(R)-3-[4-(phenyl-pyridin-3-ylmethyl-amino)-piperidin-1-yl]-butyl}-benzamide | $^1$H NMR(CDCl$_3$) δ 1.02(d+m, 4H), 1.13(m, 1H), 1.53(m, 1H), 1.80(m, 3H), 2.19(br t, 1H), 2.34(s, 6H), 2.57(br t, 1H), 2.75(m, 1H), 2.84(m, 2H), 3.17(m, 1H), 3.27(m, 1H), 3.64(m, 1H), 3.85(m, 1H), 3.93(s, 2H), 6.60(d, 2H, J=9.0 Hz), 6.71(t, 1H, J=6.0 Hz), 7.13(t, 2H, J=6.0 Hz), 7.26(m, 1H), 7.30(s, 2H), 7.54(d, 1H, J=9.0 Hz), 8.32(br s, 1H), 8.49(s+d, 2H). ES-MS m/z 496(M+H). |

-continued

| Ex. # | Structure/Name | Characterization Data |
|---|---|---|
| 145 | 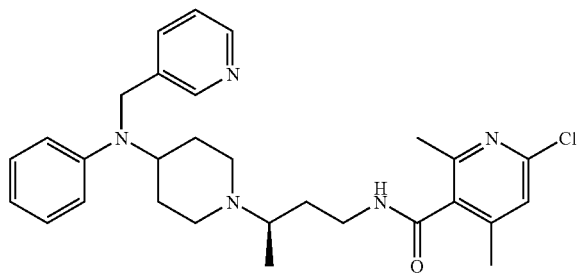<br>6-Chloro-2,4-dimethyl-N-{(R)-3-[4-(phenyl-pyridin-3-ylmethyl-amino)-piperidin-1-yl]-butyl}-nicotinamide | $^1$H NMR(CDCl$_3$) δ 0.94(m, 1H), 0.98(d, 3H, J=6.0 Hz), 1.12(m, 1H), 1.56(m, 1H), 1.79(m, 3H), 2.20(br t, 1H), 2.30(s, 3H), 2.51(s, 3H), 2.57(br t, 1H), 2.74(m, 1H), 2.84(m, 2H), 3.29(m, 1H), 3.65(m, 1H), 3.86(m, 1H), 3.96(s, 2H), 6.59(d, 2H, J=9.0 Hz), 6.71(t, 1H, J=6.0 Hz), 7.02(s, 1H), 7.17(t, 1H, J=6.0 Hz), 7.24(m, 1H), 7.62(d, 1H, J=9.0 Hz), 8.47(d, 1H, J=3.0 Hz), 8.53(s, 1H), 8.64(s, 1H). ES-MS m/z 506(M+H), 528 (M+Na). |
| 146 | 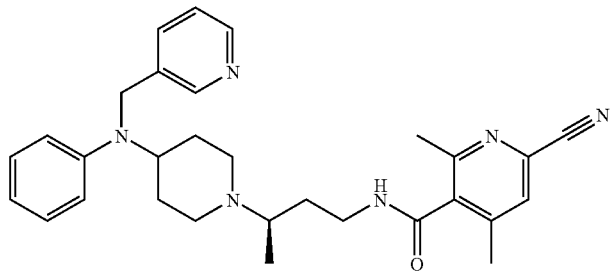<br>6-Cyano-2,4-dimethyl-N-{(R)-3-[4-(phenyl-pyridin-3-ylmethyl-amino)-piperidin-1-yl]-butyl}-nicotinamide | $^1$H NMR(CDCl$_3$) δ 0.94(m, 1H), 0.99(d, 3H, J=6.0 Hz), 1.14(m, 1H), 1.59(m, 1H), 1.79(m, 3H), 2.19(br t, 1H), 2.35(s, 3H), 2.57(s+br t, 4H), 2.73 (m, 1H), 2.84(m, 2H), 3.34(m, 1H), 3.64(m, 1H), 3.84(m, 1H), 3.98(s, 2H), 6.61(d, 2H, J=9.0 Hz), 6.72(t, 1H, J=6.0 Hz), 7.17(t, 1H, J=6.0 Hz), 7.25(m, 1H), 7.35(s, 1H), 7.61(d, 1H, J=9.0 Hz), 8.51(s+d, 2H). ES-MS m/z 497(M+H), 519(M+Na). |
| 147 | 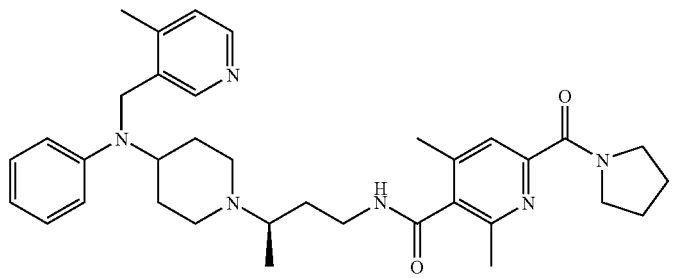<br>2,4-Dimethyl-N-((R)-3-{4-[(4-methyl-pyridin-3-ylmethyl)-phenyl-amino]-piperidin-1-yl}-butyl)-6-(pyrrolidine-1-carbonyl)-nicotinamide | $^1$H NMR(CDCl$_3$) δ 1.02(d, 3H, J=9 Hz), 1.25(m, 1H), 1.39(m, 1H), 1.61(m, 1H), 1.86(m, 8H), 2.24(m, 1H), 2.33(s, 6H), 2.52(s, 3H), 2.59(m, 1H), 2.81(m, 3H), 3.41(m, 1H), 3.66(m, 6H), 4.15(s, 2H), 6.59(d, 2H, J=8 Hz), 6.69(t, 1H, J=8 Hz), 7.04(d, 1H, J=5 Hz), 7.15(t, 2H, J=8 Hz), 7.45(m, 2H), 8.27(s, 1H), 8.31(d, 1H, J=5 Hz). ES-MS m/z 583(M+H). |
| 148 | 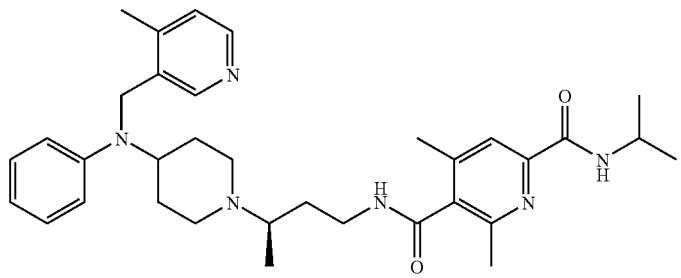<br>4,6-Dimethyl-pyridine-2,5-dicarboxylic acid 2-isopropylamide 5-[(R)-(3-{4-[(4-methyl-pyridin-3-ylmethyl)-phenyl-amino]-piperidin-1-yl}-butyl)-amide] | $^1$H NMR(CDCl$_3$) δ 1.02(d, 3H, J=6 Hz), 1.25(d, 6H, J=7 Hz), 1.30(m, 1H), 1.61(m, 1H), 1.82(m, 5H), 2.27(s, 3H), 2.36(s, 3H), 2.53(s, 3H), 2.80 (m, 3H), 3.38,(m, 1H), 3.62(m, 1H), 3.75(m, 1H), 4.08(s, 2H), 4.19(m, 1H), 6.58(d, 2H, J=8 Hz), 6.71(t, 1H, J=7 Hz), 7.05(d, 1H, J=5 Hz), 7.15 (t, 2H, J=8 Hz), 7.49(m, 1H), 7.79(s, 1H), 7.81 (s, 1H), 8.27(s, 1H), 8.32(d, 1H, J=5 Hz). ES-MS m/z 571(M+H), 594(M+Na). |

| Ex. # | Structure/Name | Characterization Data |
|---|---|---|
| 149 | 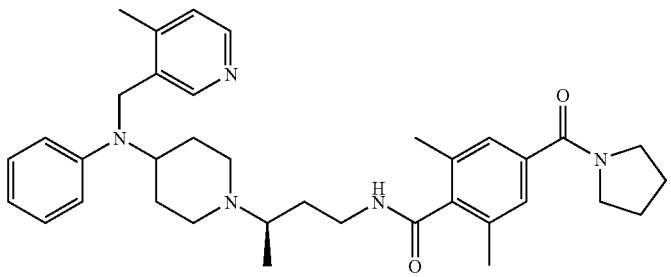<br>2,4-Dimethyl-N-((R)-3-{4-[(4-methyl-pyridin-3-ylmethyl)-phenyl-amino]-piperidin-1-yl}-butyl)-4-(pyrrolidine-1-carbonyl)-benzamide | $^1$H NMR(CDCl$_3$) δ 1.01(d, 3H, J=6 Hz), 1.27(m, 1H), 1.41(m,1H), 1.59(m, 1), 1.87(m, 10H), 2.29 (m, 1H), 2.33(s, 9H), 2.54(m, 1H), 2.80(m, 3H), 3.33(t, 2H, J 7 Hz), 3.40(m, 1H), 3.58(t, 2H, J= 7 Hz), 3.68(m, 2H), 4.18(s, 2H), 6.60(d, 2H, J= 9 Hz), 6.69(t, 1H, J=8 Hz), 7.04(m, 2H), 7.14(m, 4H), 8.29(s, 1H), 8.32(d, 1H, J=5 Hz). ES-MS m/z 604(M+Na). |
| 150 | 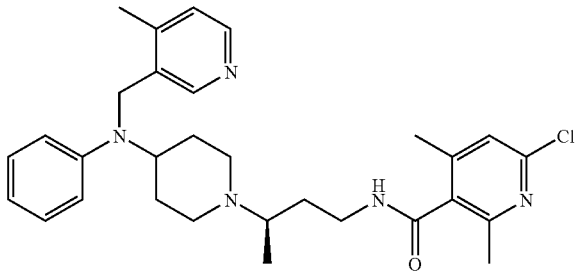<br>6-Chloro-2,4-dimethyl-N-((R)-3-{4-[(4-methyl-pyridin-3-ylmethyl)-phenyl-amino]-piperidin-1-yl}-butyl)-nicotinamide | $^1$H NMR(CDCl$_3$) δ 1.02(d, 3H, J=6 Hz), 1.11(m, 1H), 1.29(m, 2H), 1.68(m, 4H), 1.88(d, 2H, J= 12 Hz), 2.21(m, 1H), 2.30(s, 3H), 2.37(s, 3H), 2.51(s, 3H), 2.58(m, 1H), 2.80(m, 3H), 2.88(s, 1H), 2.95(s, 1H), 3.34(m, 1H), 3.48(s, 1H), 3.64 (m, 1H), 3.77(m, 1H), 4.11(s, 2H), 6.60(d, 2H, J=8 Hz), 6.73(t, 1H, J=8 Hz), 6.98(s, 1H), 7.07(d, 1H, J=5 Hz), 7.16(t, 2H, J=8 Hz), 7.75(br s, 1H), 8.29(s, 1H), 8.33(d, 1H, J=5 Hz). ES-MS m/z 520(M+H), 543(M+Na). |
| 151 | 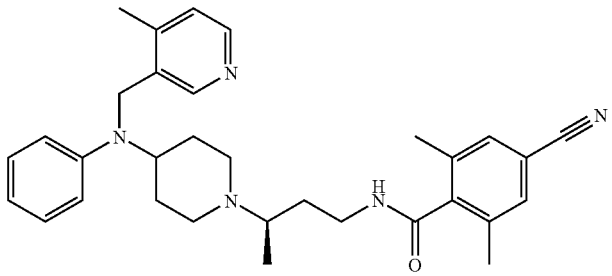<br>4-Cyano-2,6-dimethyl-N-((R)-3-{4-[(4-methyl-pyridin-3-ylmethyl)-phenyl-amino]-piperidin-1-yl}-butyl)-benzamide | $^1$H NMR(CDCl$_3$) δ 1.03(d, 3H, J=5 Hz); 1.17(m, 1H), 1.32(m, 1H), 1.60(m, 1H), 1.75(m, 1H), 1.87(m, 2H), 2.23(m, 1H), 2.33(s, 9H), 2.58(m, 1H), 2.82(m, 3H), 2.87(s, 1H), 2.95(s, 1H), 3.37 (m, 1H), 3.47(s, 1H), 3.65(m, 1H), 3.76(m, 1H), 4.09(s, 2H), 6.59(d, 2H, J=8 Hz), 6.73(t, 1H, J=7 Hz), 7.09(d, 1H, J=5 Hz), 7.16(t, 2H, J=8 Hz), 7.53(m, 1H), 8.27(s, 1H), 8.34(d, 1H, J=5H). ES-MS m/z 510(M+H), 533(M+Na). |
| 152 | 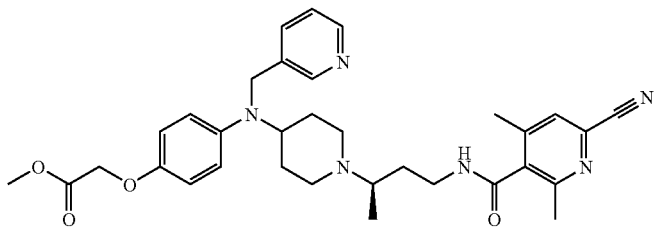<br>{4-[(1-{(R)-3-[(6-Cyano-2,4-dimethyl-pyridine-3-carbonyl)-amino]-1-methyl-propyl}-piperidin-4-yl)-pyridin-3-ylmethyl-amino]-phenoxy}-acetic acid methyl ester | $^1$H NMR(CDCl$_3$) δ 0.99(d, 3H, J=9 Hz), 1.51-1.63(m, 1H), 1.69-1.81(m, 4H), 2.16(t, 1H, J=12 Hz), 2.35(s, 3H), 2.56(s, 3H), 2.73-2.88(m, 3H), 3.27-3.43(m, 2H), 3.78(s, 3H), 3.80-3.89(m, 1H), 3.91(s, 2H), 4.53(s, 2H), 6.60(d, 2H, J= 9 Hz), 6.76(d, 2H, J=9 Hz), 7.22-7.24(m, 1H), 7.35(s, 1H), 7.59(d, 1H, J=6 Hz), 8.44-8.47(m, 2H), 8.55(br s, 1H). $^{13}$C NMR(CDCl$_3$) δ 12.28, 12.55, 17.88, 21.43, 28.68, 29.64, 30.20, 31.83, 38.77, 41.63, 42.96, 46.87, 50.93, 51.32, 52.63, 56.68, 58.37, 58.91, 65.25, 114.45, 114.93, 115.80, 116.16, 116.27, 122.60, 126.56, 131.69, 133.86, 134.63, 135.94, 142.48, 144.78, 147.29, 147.66, 150.07, 155.86, 165.51, 168.89. ES-MS m/z 585 (M+H). Anal. Calcd. for C$_{33}$H$_{40}$N$_6$O$_4$•0.8CH$_2$Cl$_2$: C, 62.20; H, 6.42; N, 12.88. Found: C, 61.85; H, 6.43; N, 12.70. |

| Ex. # | Structure/Name | Characterization Data |
|---|---|---|
| 153 | 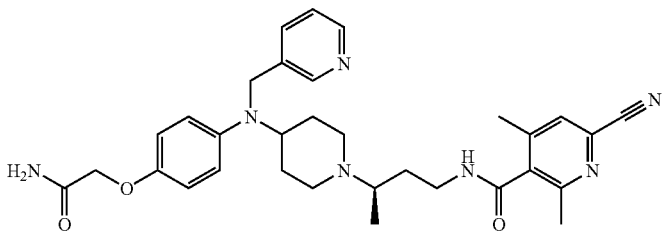<br>N-((R)-3-{4-[(4-Carbamoylmethoxy-phenyl)-pyridin-3-ylmethyl-amino]-piperidin-1-yl}-butyl)-6-cyano-2,4-dimethyl-nicotinamide | $^1$H NMR(CDCl$_3$) δ 1.02(d, 3H, J=9 Hz), 0.98-1.10(m, 1H), 1.51-1.58(m, 1H), 1.71-1.79(m, 5H), 2.12-2.20(m, 1H), 2.35(s, 3H), 2.56(s, 3H), 2.75-2.91(m, 3H), 3.26-3.45(m, 3H), 3.79-3.84 (m, 1H), 3.93(s, 2H), 4.39(s, 2H), 5.67(br s, 1H), 6.62(d, 2H, J=9 Hz), 6.76(d, 2H, J=9 Hz), 7.24 (s, 2H), 7.60(d, 1H, J=6 Hz), 8.47(s, 1H), 8.51 (br s, 1H). $^{13}$C NMR(CDCl$_3$) δ 13.72, 19.17, 22.69, 29.66, 30.56, 31.44, 39.83, 44.29, 48.19, 52.17, 57.85, 60.20, 68.19, 116.02, 117.42, 117.88, 123.87, 127.80, 132.97, 135.12, 135.64, 137.11, 143.80, 146.03, 148.63, 148.94, 150.81, 157.12, 166.83, 171.76. ES-MS m/z 570(M+H). Anal. Calcd. for C$_{32}$H$_{39}$N$_7$O$_3$•1.0CH$_2$Cl$_2$: C, 57.52; H, 5.85; N, 14.23. Found: C, 57.51; H, 6.05; N, 14.06. |
| 154 | 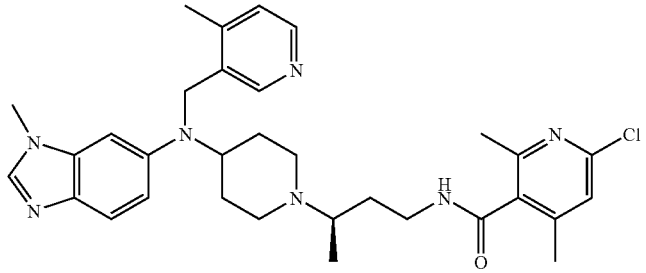<br>6-Chloro-2,4-dimethyl-N-((R)-3-{4-[(3-methyl-3H-benzoimidazol-5-yl)-(4-methyl-pyridin-3-ylmethyl)-amino]-piperidin-1-yl}-butyl)-nicotinamide | $^1$H NMR(CDCl$_3$) δ 1.00(d, 3H, J=6.6 Hz), 1.07-1.12(m, 1H), 1.23-1.30(m, 1H), 1.52-1.60(m, 1H), 1.71-1.78(m, 1H), 1.84-1.89(m, 2H), 2.12-2.20(m, 1H), 2.30(s, 3H), 2.38(s, 3H), 2.47-2.57 (m, 4H), 2.72-2.87(m, 3H), 3.32-3.45(m, 2H), 3.69(s, 3H), 3.76-3.84(m, 1H), 4.10(s, 2H), 6.57 (d, 1H, J=2.1 Hz), 6.79(dd, 1H, J=2.1, 8.7 Hz), 6.97(s, 1H), 7.03(d, 1H, J=5.1 Hz), 7.56(d, 1H, J=7.8 Hz), 7.67(s, 1H), 8.09(br. s, 1H), 8.28(d, 1H, J=5.1 Hz),8.31(s, 1H). $^{13}$CNMR(CDCl$_3$) δ 13.61, 18.95, 19.08, 22.29, 29.86, 30.78, 31.07, 31.63, 39.64, 44.20, 47.31, 51.90, 59.53, 59.73, 98.48, 114.60, 120.48, 122.61, 125.31, 132.74, 133.12, 135.48, 138.17, 142.74, 145.33, 145.62, 147.54, 148.18, 149.35, 150.28, 155.35, 167.48. ES-MS m/z 574(M+H). Anal. Calcd. for C$_{32}$H$_{40}$N$_7$ClO•1.3CH$_2$Cl$_2$•0.7H$_2$O: C, 57.37; H, 6.36; N, 14.06; Cl, 18.31. Found: C, 57.52; H, 6.15; N, 14.20; Cl, 18.03. |
| 155 | 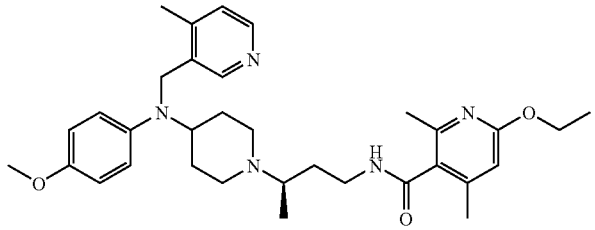<br>6-Ethoxy-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 1.21 (t, 3H, J=7.2 Hz), 1.26-1.43(m, 2H), 1.52-1.58 (m, 1H), 1.65-1.75(m, 1H), 1.84-1.88(m, 2H), 2.12(s, 3H), 2.15-2.20(m, 1H), 2.33(s, 3H), 2.35 (s, 3H), 2.45-2.53(m, 1H), 2.71-2.84(m, 3H), 3.25-3.34(m, 2H), 3.61-3.68(m, 1H), 3.72(s, 3H), 3.99(q, 2H, J=7.2 Hz), 4.13(s, 2H), 6.23(s, 1H), 6.65-6.75(m, 4H), 7.03(d, 1H, J=4.8 Hz), 7.41 (br. s, 1H), 8.28-8.31(m, 3H). $^{13}$C NMR(CDCl$_3$) δ 13.68, 13.80, 17.46, 18.84, 19.61, 29.99, 30.63, 32.41, 39.07, 39.49, 44.80, 47.85, 51.40, 55.76, 58.68, 114.61, 117.27, 119.52, 119.65, 125.24, 133.48, 142.29, 142.67, 145.32, 147.26, 148.08, 149.20, 153.66, 162.28, 167.73. ES-MS m/z 560 (M+H). Anal. Calcd. for C$_{33}$H$_{45}$N$_5$O$_3$•0.3CH$_2$Cl$_2$: C, 68.34; H, 7.85; N, 11.97. Found: C, 68.57; H, 7.97; N, 12.08. |
| 156 | 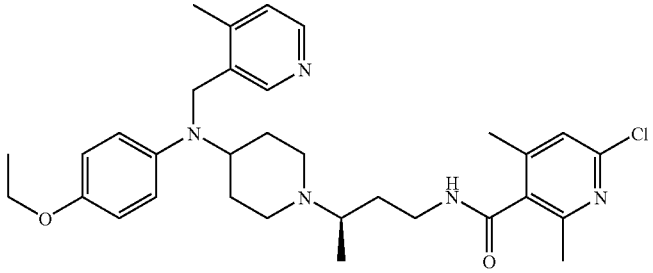<br>6-Chloro-N-((R)-3-{4-[(4-ethoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.00 (m, 1H), 1.18(m, 1H), 1.35(t, 3H, J=7.2 Hz), 1.57(m, 1H), 1.73(m, 1H), 1.81(d, 2H, J= 12.0 Hz), 211(t, 1H, J=11.2 Hz), 2.29(s, 3H), 2.34(s, 3H), 2.49(t, 1H, J=11.2 Hz), 2.51(s,3H), 2.65-2.90(m, 3H), 3.21(m, 1H), 3.32(m, 1H), 3.78(m, 1H), 3.92(q, 2H, J 7.2 Hz), 3.97(s, 2H), 6.62 (m, 2H), 6.74(m, 2H), 6.98(s, 1H), 7.02(d, 1H, J=5.1 Hz), 8.04(br, 1H), 8.26(s, 1H), 8.28(d, 1H, J=4.8 Hz). $^{13}$C NMR(CDCl$_3$) δ 13.76, 15.35, 19.17, 19.22, 22.51, 30.07, 30.97, 31.78, 39.96, 44.36, 47.85, 52.13, 59.33, 60.08, 64.15, 114.45 (2C), 120.60(2C), 122.85, 125.48, 125.48, 132.91, 133.52, 142.65, 145.75, 147.68, 148.34, 149.70, 150.57, 153.52, 155.58, 167.71. ES-MS m/z 564 (M+H). Anal. Calcd. for C$_{32}$H$_{42}$N$_5$ClO$_2$•0.1CH$_2$Cl$_2$: C, 67.33; H, 7.43; N, 12.23. Found: C, 67.37; H, 7.43; N, 12.22. |

| Ex. # | Structure/Name | Characterization Data |
|---|---|---|
| 157 | 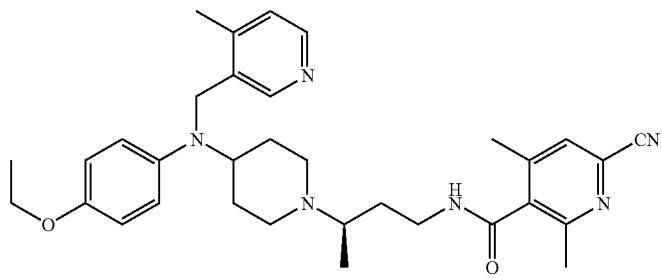<br>6-Cyano-N-((R)-3-{4-[(4-ethoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(m, 1H), 0.99(d, 3H, J= 6.6 Hz), 1.14(m, 1H), 1.36(t, 3H, J=7.2 Hz), 1.58(m, 1H), 1.74(m, 1H), 1.81(d, 2H, J= 12.0 Hz), 2.12(t, 1H, J 11.2 Hz), 2.33(s,3H), 2.34(s, 3H), 2.49(t, 1H, J=11.2 Hz), 2.56(s,3H), 2.65-2.90(m, 3H), 3.20(m, 1H), 3.34(m, 1H), 3.78(m, 1H), 3.92(q, 2H, J=7.2 Hz), 3.98(s, 2H), 6.62 (m, 2H), 6.73(m, 2H), 7.05(d, 1H, J=4.8 Hz), 7.32(s, 1H), 8.14(br, 1H), 8.24(s, 1H), 8.30(d, 1H, J=5.1 Hz). $^{13}$CNMR(CDCl$_3$)δ 13.79, 15.35, 19.15(2C), 22.70, 30.28, 31.01, 31.77, 39.84, 44.42, 48.26, 51.97, 58.87, 59.83, 64.21, 115.52 (2C), 117.35, 120.49(2C), 125.58, 127.80, 132.95, 133.51, 137.02, 142.54, 145.67, 145.84, 148.34, 149.41, 153.57, 157.02, 166.89. ES-MS m/z 555 (M+H). Anal. Calcd. for C$_{33}$H$_{42}$N$_6$O$_2$•0.1CH$_2$Cl$_2$: C, 70.59; H, 7.55; N, 14.92. Found: C, 70.53; H, 7.60; N, 14.84. |
| 158 | 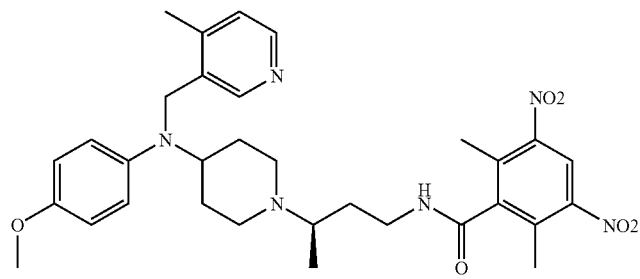<br>Methoxy-phenyl)-(4-methyl-phenyl)-(4-methyl-pyridin-3-ylmethyl)-amino]-piperidin-1-yl}-butyl)-2,6-dimethyl-3,5-dinitro-benzamide | $^1$H NMR(CDCl$_3$) δ 0.85-1.08(m, 5H), 1.48-1.54 (m, 1H), 1.76-1.83(m, 3H), 2.06-2.14(m, 1H), 2.24(s, 3H), 2.40-2.51(m, 1H), 2.55(s, 6H), 2.70-2.82(m, 3H), 2.96-3.03(m, 1H), 3.32-3.38(m, 1H), 3.72(s, 3H), 3.80-3.85(m, 1H), 3.93(s, 2H), 6.65-6.72(m, 4H), 6.99(d, 1H, J=5.1 Hz), 8.19 (s, 1H), 8.28(s, 2H, J=4.5 Hz), 8.53(br. s, 1H). $^{13}$C NMR(CDCl$_3$) δ 13.78, 17.39, 19.01, 30.20, 30.90, 31.34, 40.16, 44.35, 49.23, 52.10, 55.85, 59.64, 60.16, 114.52, 120.97, 122.69, 125.59, 133.25, 134.88, 142.15, 144.28, 146.05, 147.92, 148.46, 149.76, 154.97, 166.23. ES-MS m/z 605 (M+1)$^+$. Anal. Calcd. for C$_{32}$H$_{40}$N$_6$O$_6$: C, 63.56; H, 6.67; N, 13.90. Found: C, 63.45; H, 6.67; N, 13.67. |
| 159 | 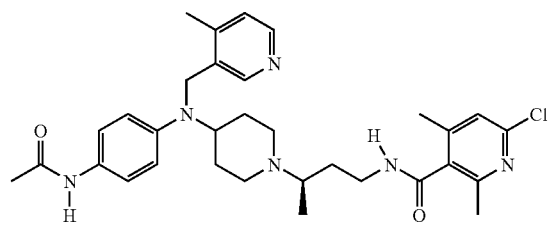<br>N-((R)-3-{4-[(4-Acetylamino-phenyl)-(4-methyl-pyridin-3-ylmethyl)-amino]-piperidin-1-yl}-butyl)-6-chloro-2,4-dimethyl-nicotinamide | $^1$H NMR(CDCl$_3$) δ 0.98(d, 3H, J=6.6 Hz), 0.99-1.01(m, 1H), 1.16(s, 1H), 1.47-1.64(m, 1H), 1.63-1.79(m, 1H), 1.79-1.95(m, 2H), 2.12(s, 3H), 2.14-2.22(m, 1H), 2.29(s, 3H), 2.36(s, 3H), 2.50 (s, 3H), 2.51-2.60(m, 1H), 2.70-2.90(m, 3H), 3.32-3.35(m, 1H), 3.48-3.50(m, 1H), 3.60-3.75 (m, 1H), 4.05(s, 2H), 6.57(d, 2H, J=9.2 Hz), 6.98(s, 1H), 7.06(d, 1H, J=5.1 Hz), 7.15(s, 1H), 7.23(d, 2H, J=9.2 Hz), 7.84-7.83(br s, 1H), 8.26 (s, 1H), 8.30(d, 1H, J=5.1 Hz). $^{13}$C NMR (CDCl$_3$) δ 13.87, 19.17, 22.51, 24.37, 29.75, 30.73, 32.02, 39.75, 44.52, 46.37, 57.78, 59.83, 116.06, 122.06, 122.66, 125.33, 129.59, 132.66, 133.13, 145.10, 145.46, 147.60, 148.05, 148.52, 150.30, 155.32, 167.52, 168.54. ES-MS m/z 578(M+H). Anal. Calcd. for C$_{32}$H$_{41}$N$_6$ClO$_2$•0.9H$_2$O•0.3CH$_2$Cl$_2$: C, 62.69; H, 7.07; N, 13.58. Found: C, 62.70; H, 7.10; N, 13.51. |
| 160 | 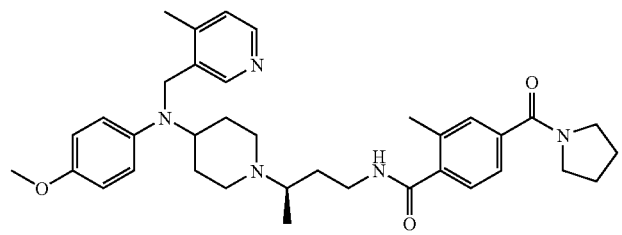<br>N-((R)-3-{4-[(4-Methoxy-phenyl)-(4-methyl-pyridin-3-ylmethyl)-amino]-piperidin-1-yl}-butyl)-2-methyl-4-(pyrrolidine-1-carbonyl)-benzamide | $^1$H NMR(CDCl$_3$) δ 0.99(d, 3H, J=6.0 Hz), 1.19-1.40(m, 2H), 1.59(m, 1H), 1.75-1.88(m, 5H), 1.93(m, 2H), 2.16(br t, 1H), 2.28(s, 3H), 2.45(s, 3H), 2.47(br t, 1H), 2.74-2.83(m, 3H), 3.32-3.44 (m, 4H), 3.58(m, 3H), 3.72(s, 3H), 4.11(s, 2H), 6.65(d, 2H, J=9.0 Hz), 6.73(d, 2H, J=9.0 Hz), 7.01(d, 1H, J=6.0 Hz), 7.21(br s, 1H), 7.35(d, 2H, J=6.0 Hz), 8.31(s+d, 2H). ES-MS m/z 598 (M+H). |

| Ex. # | Structure/Name | Characterization Data |
|---|---|---|
| 161 | 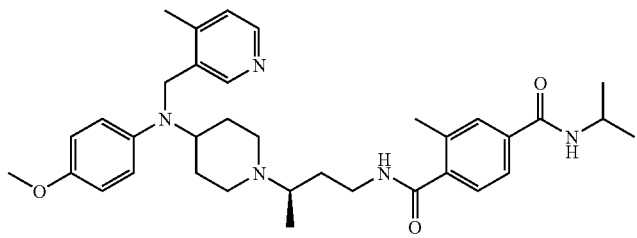<br>N4-Isopropyl-N1-((R)-3-{4-[(4-methoxy-phenyl)-(4-methyl-pyridin-3-ylmethyl)-amino]-piperidin-1-yl}-butyl)-2-methyl-terephthalamide | $^1$H NMR(CDCl$_3$) δ 0.98(d, 3H, J=6.0 Hz), 1.11 (m, 1H), 1.23(d+m, 7H), 1.56(m, 1H), 1.74(m, 3H), 2.10(br t, 1H), 2.24(s, 6H), 2.45(s+m, 4H), 2.72-2.84(m, 3H), 3.17(m, 1H), 3.29(m, 1H), 3.73(s, 3H), 3.77(m, 1H), 4.05(s, 2H), 4.27(m, 1H), 6.66(d, 1H, J=6.0 Hz), 6.71(d, 2H, J=9.0 Hz), 6.74(d, 2H, J=9.0 Hz), 7.01(d, 1H, J=3.0 Hz), 7.35(d, 1H, J=6.0 Hz), 7.63(d, 1H, J=6.0 Hz), 7.68(s, 1H), 7.77(br s, 1H), 8.31(d, 1H, J=6.0 Hz), 8.34(s, 1H). ES-MS m/z 586(M+H). |
| 162 | 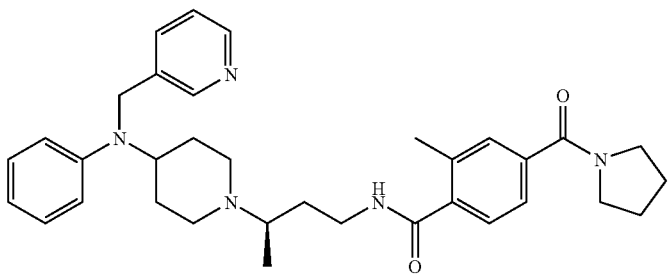<br>2,6-Dimethyl-N-{(R)-3-[(4-(phenyl-pyridin-3-ylmethyl-amino)-piperidin-1-yl]-butyl}-4-(pyrrolidine-1-carbonyl)-benzamide | $^1$H NMR(CDCl$_3$) δ 1.00(d+m, 4H), 1.22(m, 1H), 1.56(m, 1H), 1.75-1.88(m, 5H), 1.93(m, 2H), 2.17(br t, 1H), 2.33(s, 3H), 2.55(br t, 1H), 2.73-2.85(m, 3H), 3.37(m, 3H), 3.62(m, 3H), 3.90(m, 1H), 3.97(d, 2H, J=9.0 Hz), 6.60(d, 2H, J=9.0 Hz), 6.66(d, 2H, J=9.0 Hz), 7.10-7.19(m, 5H), 7.61(br s, 1H), 8.31(m, 1H), 8.42(d, 2H, J=3.0 Hz), 8.51(s, 1H). ES-MS m/z 568(M+H). |
| 163 | 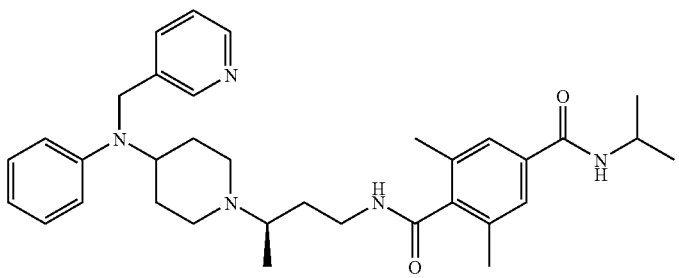<br>N'-Isopropyl-2,6-dimethyl-N-{(R)-3-[4-(phenyl-pyridin-3-ylmethyl-amino)-piperidin-1-yl]-butyl}-terephthalamide | $^1$H NMR(CDCl$_3$) δ 0.98(d+m, 4H), 1.16(m, 1H), 1.26(d, 6H, J=6.0 Hz), 1.56(m, 1H), 1.76(m, 3H), 2.14(br t, 1H), 2.33(s, 6H), 2.57(br t, 1H), 2.74-2.88(m, 3H), 3.28(m, 1H), 3.62(m, 1H), 3.91(s+m, 3H), 4.29(m, 1H), 6.17(d, J=9.0 Hz), 6.57(d, 1H, J=6.0 Hz), 6.69(t, 1H, J=7.5 Hz), 7.11-7.22(m, 3H), 7.42(s, 2H), 8.33(d, 1H, J=6.0 Hz), 8.38(s, 1H), 8.46(d, 1H, J=3.0 Hz). ES-MS m/z 556(M+H). |
| 164 | 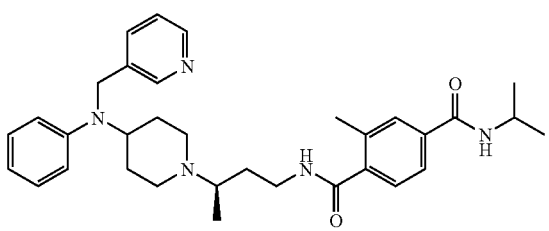<br>N4-Isopropyl-2-methyl-N1-{(R)-3-[4-(phenyl-pyridin-3-ylmethyl-amino)-piperidin-1-yl]-butyl}-terephthalamide | $^1$H NMR(CDCl$_3$) δ 1.01(d, 3H, J=6.0 Hz), 1.14 (m, 1H), 1.28(d+m, 7H), 1.56(m, 1H), 1.78(m, 3H), 2.17(br t, 1H), 2.44(s, 3H), 2.56(br t, 1H), 2.78-2.88(m, 3H), 3.28(m, 1H), 3.64(m, 1H), 3.82(m, 1H), 4.02(s, 1H), 4.30(m, 1H), 6.32(d, J=9.0 Hz), 6.60(d, 1H, J=6.0 Hz), 6.70(t, 1H, J=7.5 Hz), 7.12-7.22(m, 3H), 7.38(d, 1H, J=9.0 Hz), 7.63(m, 3H), 8.12(br d, 1H), 8.36(s, 1H), 8.44(d, 1H, J=3.0 Hz). ES-MS m/z 542(M+H). |

| Ex. # | Structure/Name | Characterization Data |
|---|---|---|
| 165 | 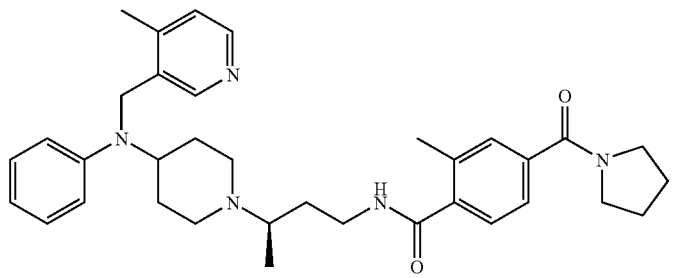<br>2-Methyl-N-((R)-3-{4-[(4-methyl-pyridin-3-ylmethyl)-phenyl-amino]-piperidin-1-yl}-butyl)-4-(pyrrolidine-1-carbonyl)-benzamide | $^1$H NMR(CDCl$_3$) δ 1.02(d, 3H, J=6.0 Hz), 1.37-1.53(m, 3H), 1.83-1.97(m, 7H), 2.23(br t, 1H), 2.27(s, 3H), 2.46(s, 3H), 2.55(br t, 1H), 2.78-2.88 (m, 3H), 3.35(m, 3H), 3.59-3.71(m, 4H), 4.20(s, 2H), 6.61(d, 2H, J=9.0 Hz), 6.70(d, 2H, J= 9.0 Hz), 7.05(d, 1H, J=3.0 Hz), 7.13-7.22(m, 4H), 7.34(s=d, 2H), 8.34(s=d, 2H). ES-MS m/z 568 (M+H). |
| 166 | 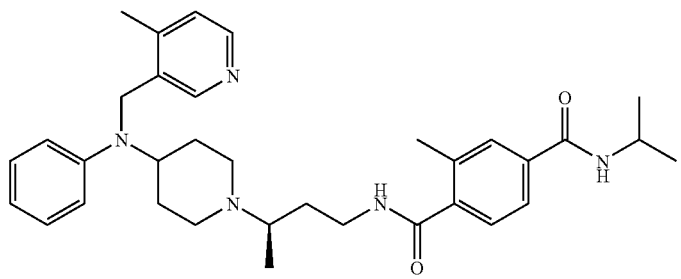<br>N4-Isopropyl-2-methyl-N1-{(R)-3-{4-[(4-methyl-pyridin-3-ylmethyl)-phenyl-amino]-piperidin-1-yl}-butyl)-terephthalamide | $^1$H NMR(CDCl$_3$) δ 1.02(d, 3H, J=6.0 Hz), 1.26 (d+m, 7H), 1.42(m, 1H), 1.59(m, 1H), 1.83(m, 3H), 2.24(s+m, 4H), 2.46(s, 3H), 2.55(br t, 1H), 2.78-2.88(m, 3H), 3.30(m, 1H), 3.67(m, 1H), 3.72(m, 1H), 4.15(s, 1H), 4.26(m, 1H), 6.17(d, 1H, J= 9.0 Hz), 6.60(d, 1H, J=6.0 Hz), 6.72(t, 1H, J= 7.5 Hz), 7.04(d, 1H, J=3.0 Hz), 7.14(t, 1H, J= 7.5 Hz), 7.38(d, 1H, J=6.0 Hz), 7.43(s, 1H), 7.55 (d, 1H, J=6.0 Hz), 7.60(s, 1H), 8.30(s, 1H), 8.33 (d, 1H, J=6.0 Hz). ES-MS m/z 556(M+H). |
| 167 | 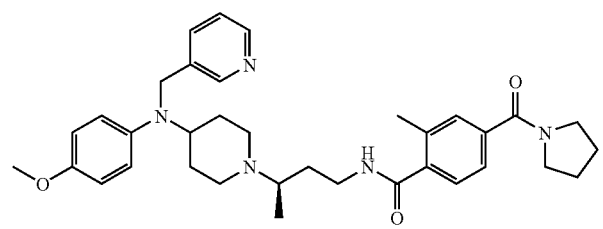<br>N-((R)-3-{4-[(4-Methoxy-phenyl)-pyridin-3-ylmethyl-amino]-piperidin-1-yl}-butyl)-2-methyl-4-(pyrrolidine-1-carbonyl)-benzamide | $^1$H NMR(CDCl$_3$) δ 1.00(d, 3H, J=6.0 Hz), 1.17 (m, 1H), 1.35(m, 1H), 1.53(m, 1H), 1.75-1.87(m, 5H), 1.97(m, 2H), 2.14(brt, 1H), 2.44(s, 3H), 2.52(br t, 1H), 2.76-2.88(m, 3H), 3.34(m, 3H), 3.44(m, 1H), 3.64(m, 2H), 3.70(s, 1H), 3.75(m, 1H), 4.01(s, 2H), 6.61(d, 2H, J=9.0 Hz), 6.72(d, 2H, J=9.0 Hz), 7.13(m, 1H), 7.29(s, 1H), 7.36 (s=d, 2H), 7.58(d, 1H, J=6.0 Hz), 8.08(s, 1H), 8.40(d, 1H, J=1Hz), 8.49(s, 1H). ES-MS m/z 584 (M+H). |
| 168 | 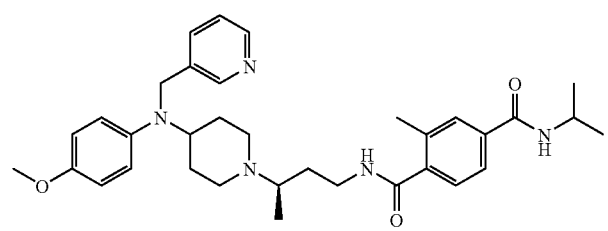<br>N4-Isopropyl-N1-((R)-3-{4-[(4-methoxy-phenyl)-pyridin-3-ylmethyl-amino]-piperidin-1-yl}-butyl)-2-methyl-terephthalamide | $^1$H NMR(CDCl$_3$) δ 0.99(d, 3H, J=6.0 Hz), 1.06 (m, 1H), 1.28(d+m, 7H), 1.51(m, 1H), 1.83(m, 3H), 2.11(br t, 1H), 2.43(s, 1H), 2.50(br t, 1H), 2.75-2.88(m, 3H), 3.27-3.37(m, 2H), 3.71(s, 3H), 3.80(m, 1H), 3.95(s, 2H), 4.29(m, 1H), 6.39(d, J=9.0 Hz), 6.61(d, 1H, J=6.0 Hz), 6.72(t, 1H, J=7.5 Hz), 7.19(m, 1H), 7.36(d, 1H, J=9.0 Hz), 7.52(d, 1H, J=6.0 Hz), 7.61(s=d, 2H), 8.18(s, 1H), 8.39(s, 1H), 8.41(d, 1H, J 3.0 Hz). ES-MS m/z 572(M+H). |

| Ex. # | Structure/Name | Characterization Data |
|---|---|---|
| 169 | 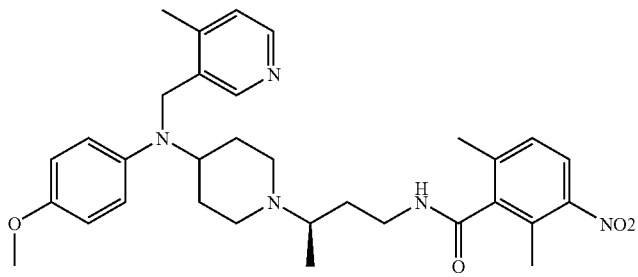<br>N-((R)-3-{4-[(4-Methoxy-phenyl)-(4-methyl-pyridin-3-ylmethyl)-amino]-piperidin-1-yl}-butyl)-2,6-dimethyl-3-nitro-benzamide | $^1$H NMR(CDCl$_3$) δ 0.99(d, 3H, J=6.3 Hz), 1.16-1.29(m, 2H), 1.53-1.64(m, 2H), 1.79-1.83(m, 3H), 2.02-2.18(m, 1H), 2.26(s, 3H), 2.38(s, 3H), 2.49(s, 3H), 2.72-2.82(m, 3H), 3.12-3.18(m, 1H), 3.34-3.45(m, 1H), 3.71(s, 3H), 3.80-3.92(m, 3H), 6.62(d, 2H, J=9.0 Hz), 6.69(d, 2H, J=9.0 Hz), 7.00(d, 1H, J=4.8 Hz), 7.05(d, 1H, J=8.4 Hz), 7.58(d, 1H, J=8.4 Hz), 8.21(br. s, 1H), 8.23(s, 1H), 8.29(d, 1H, J=4.8 Hz). $^{13}$C NMR(CDCl$_3$) δ 13.77, 16.94, 19.10, 19.97, 30.04, 30.74, 31.64, 39.93, 44.38, 47.77, 52.16, 55.90, 59.86, 60.21, 114.67(2 carbons), 121.13, 124.75, 125.51, 128.64, 129.97, 133.40, 140.48, 141.26, 142.65, 145.68, 148.38, 149.79, 154.34, 168.22. ES-MS m/z 560(M+1)$^+$. Anal. Calcd. for C$_{32}$H$_{41}$N$_5$O$_4$•0.6H$_2$O: C, 67.37; H, 7.46; N, 12.28. Found: C, 67.37; H, 7.24; N, 12.15. |
| 170 | 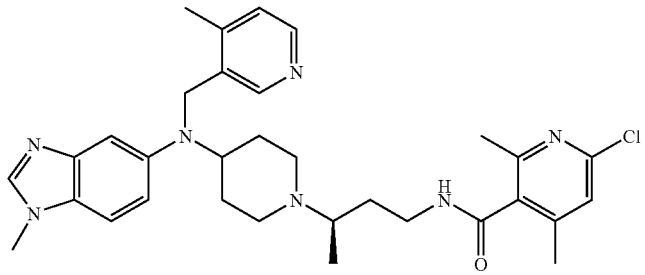<br>6-Chloro-2,4-dimethyl-N-((R)-3-{4-[(1-methyl-1H-benzoimidazol-5-yl)-(4-methyl-pyridin-3-ylmethyl)-amino]-piperidin-1-yl}-butyl)-nicotinamide | $^1$H NMR(CDCl$_3$) δ 0.98(d, 3H, J=6.6 Hz), 1.05-1.14(m, 2H), 1.51-1.58(m, 1H), 1.70-1.89(m, 3H), 2.10-2.17(m, 1H), 2.27(s, 3H), 2.38(s, 3H), 2.47-2.54(m, 4H), 2.70-2.84(m, 3H), 3.30-3.37(m, 2H), 3.69-3.81(m, 4H), 4.08(s, 2H), 6.72(dd, 1H, J=2.1, 8.7 Hz), 6.96(s, 1H), 7.01(d, 1H, J=4.8 Hz), 7.14(d, 1H, J=7.8 Hz), 7.19(d, 1H, J=2.1 Hz), 7.73(s, 1H), 8.08(br. s, 1H), 8.23-8.26 (m 2H). $^{13}$C NMR(CDCl$_3$) δ 13.52, 18.96, 19.04, 22.28, 29.69, 30.51, 31.24, 31.57, 39.52, 44.26, 48.06, 51.77, 59.44, 59.75, 109.53, 109.88, 117.04, 122.62, 125.28, 129.85, 132.65, 133.27, 143.82, 144.70, 145.67, 147.50, 148.07, 149.41, 150.30, 155.37, 167.58. ES-MS m/z 574(M+H). Anal. Calcd. for C$_{32}$H$_{40}$N$_7$ClO•0.5CH$_2$Cl$_2$: C, 63.31; H, 6.70; N, 15.90. Found: C, 63.32; H, 6.98; N, 15.78. |
| 171 | 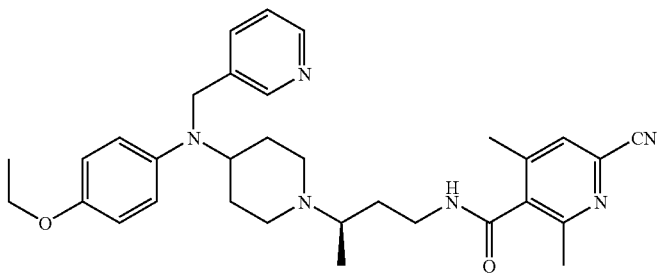<br>6-Cyano-N-((R)-3-{4-[(4-ethoxy-phenyl)-pyridin-3-ylmethyl-amino]-piperidin-1-yl}-butyl)-2,4-dimethyl-nicotinamide | $^1$H NMR(CDCl$_3$) δ 0.92(m, 1H), 0.99(d, 3H, J=6.6 Hz), 1.08(m, 1H), 1.35(t, 3H, J=7.2 Hz), 1.58(m, 2H), 1.78(d, 2H, J=12.0 Hz), 2.13(t, 1H, J=11.2 Hz), 2.35(s, 3H), 2.52(t, 1H, J=11.2 Hz), 2.57(s, 3H), 2.72(m, 1H), 2.83(m, 2H), 3.33 (m, 2H), 3.84(m, 1H), 3.89(s, 2H), 3.92(q, 2H, J= 7.2 Hz), 6.62(m, 2H), 6.73(m, 2H), 7.23(m, 1H), 7.35(s, 1H), 7.59(d, 1H, J=7.8 Hz), 8.45(d, 1H, J=5.7 Hz), 8.47(s, 1H), 8.62(br, 1H). $^{13}$C NMR(CDCl$_3$) δ 13.78, 15.34, 19.12, 22.66, 30.08, 31.07, 31.29, 40.19, 44.11, 48.57, 52.20, 58.41, 60.32, 64.21, 115.67(2C), 116.20, 117.38, 118.71 (2C), 123.80, 127.77, 133.00, 135.28, 135.99, 142.66, 145.96, 148.50, 149.13, 152.84, 157.11, 166.74. ES-MS m/z 541(M+H). Anal. Calcd. for C$_{32}$H$_{40}$N$_6$O$_2$•0.2CH$_2$Cl$_2$: C, 69.35; H, 7.30; N, 15.07. Found: C, 68.98; 11, 7.46; N, 15.11. |
| 172 | 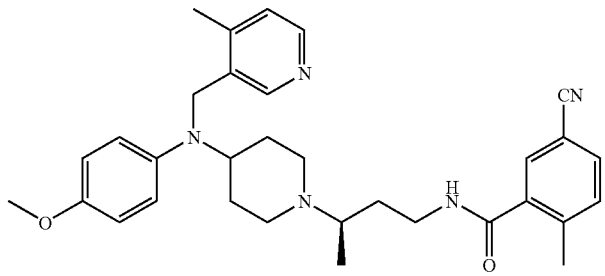<br>5-Cyano-N-((R)-3-{4-[(4-methoxy-phenyl)-(4-methyl-pyridin-3-ylmethyl)-amino]-piperidin-1-yl}-butyl)-2-methyl-benzamide | $^1$H NMR(CDCl$_3$) δ 1.00(d, 3H, J=6.6 Hz), 1.10-1.59(m, 3H), 1.72-1.86(m, 3H), 2.10-2.16(m, 1H), 2.30(s, 3H), 2.45-2.53(m, 1H), 2.46(s, 3H), 2.77-2.87(m, 3H), 3.20-3.34(m, 2H), 3.71(s, 3H), 3.71-3.75(m, 1H), 3.94-4.03(m, 2H), 6.66(d, 2H, J=9.3 Hz), 6.71(d, 2H, J=9.3 Hz), 7.02(d, 1H, J= 4.8 Hz), 7.23(d, 1H, J=7.8 Hz), 7.40(dd, 1H, J= 7.8, 1.5 Hz), 7.60(d, 1H, J=1.5 Hz), 7.95(br m, 1H), 8.25(s, 1H), 8.28(d, 1H, J=4.8 Hz). $^{13}$C NMR(CDCl$_3$) δ 13.30, 18.63, 19.89, 29.55, 30.12, 31.42, 39.30, 44.13, 47.46, 51.36, 55.36, 58.91, 59.24, 109.35, 114.17, 118.07, 120.20, 124.94, 130.10, 131.45, 132.46, 133.02, 138.28, 141.52, 142.15, 145.06, 147.76, 149.07, 153.61, 167.55. ES-MS m/z 571(M+H). Anal. Calcd. for C$_{32}$H$_{39}$N$_5$O$_2$•1.0H$_2$O: C, 70.69; H, 7.60; N, 12.88. Found: C, 70.58; H, 7.44; N, 12.73. |

| Ex. # | Structure/Name | Characterization Data |
|---|---|---|
| 173 | 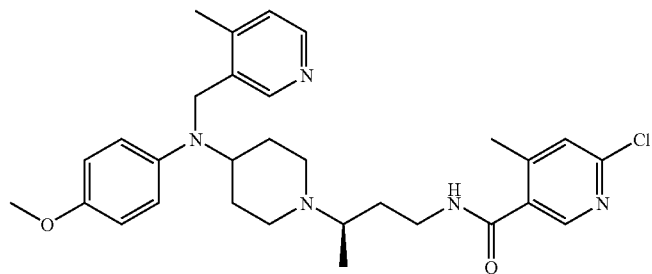<br>6-Chloro-N-((R)-3-{4-[(4-methoxy-phenyl)-(4-methyl-pyridin-3-ylmethyl)-amino]-piperidin-1-yl}-butyl)-4-methyl-nicotinamide | $^1$H NMR(CDCl$_3$) δ 1.00(d, 3H, J=5 Hz), 1.21(m, 1H), 1.39(m, 1H), 1.58(s, 3H), 1.77(m, 1H), 1.87(m, 2H), 2.15(m, 1H), 2.36(s, 3H), 2.47(s, 3H), 2.53(m, 1H), 2.81(m, 3H), 3.31(m, 2H), 3.71(s, 3H), 3.77(m, 1H), 4.10(s, 2H), 6.70(dd, 4H, J= 10 Hz, 22 Hz), 7.02(d, 1H, J=5 Hz), 7.18(s, 1H), 8.30(m, 2H), 8.39(s, 1H). ES-MS m/z 536(M+H). |
| 174 | 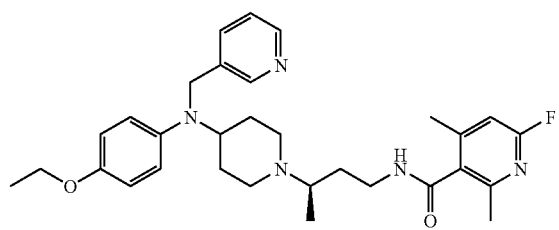<br>N-((R)-3-{4-[(4-Ethoxy-phenyl)-pyridin-3-ylmethyl-amino]-piperidin-1-yl}-butyl)-6-fluoro-2,4-dimethyl-nicotinamide | $^1$H NMR(CDCl$_3$) δ 0.93(m, 1H), 0.99(d, 3H, J= 6.6 Hz), 1.12(m, 1H), 1.35(t, 3H, J=7.2 Hz), 1.54(m, 1H), 1.78(m, 3H), 2.12(t, 1H, J= 11.2 Hz), 2.33(s, 3H), 2.48(s, 3H), 2.52(t, 1H, J= 11.2 Hz), 2.74(m, 1H), 2.87(m, 2H), 3.33(m, 2H), 3.84(m, 1H), 3.85(s, 2H), 3.92(q, 2H, J=7.2 Hz), 6.54(s, 1H), 6.60(m, 2H), 6.73(m, 2H), 7.20(m, 1H), 7.57(d, 1H, J=4.5 Hz), 8.44(d, 1H, J= 4.8 Hz), 8.48(s, 1H), 8.64(br, 1H). $^{13}$C NMR (CDCl$_3$) δ 13.79, 15.34, 19.51, 22.27, 29.80, 31.02, 31.16, 40.49, 44.03, 48.03, 52.44, 58.56, 60.79, 64.21, 107.67(d, 1C, J=146 Hz), 115.66(2C), 116.17, 118.33(2C), 123.67, 132.30, 135.16, 136.03, 142.73, 148.46, 149.17, 150.71, 152.64, 162.71(d, 1C, 950 Hz), 164.29. ES-MS m/z 534 (M+H). Anal. Calcd. for C$_{31}$H$_{40}$N$_5$FO$_2$•0.2CH$_2$Cl$_2$: C, 68.05; H, 7.39; N, 12.72. Found: C, 68.07; H, 7.51; N, 12.74. |
| 175 | 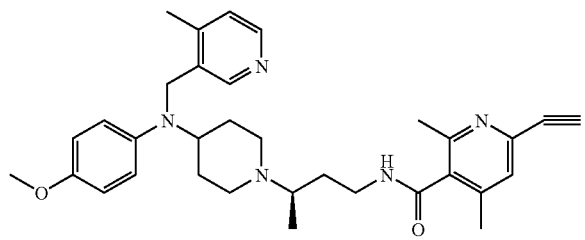<br>6-Ethynyl-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.95-1.07(m, 4H), 1.21-1.29(m, 1H), 1.50-1.60(m, 1H), 1.70-1.83(m, 3H), 2.08-2.17(m, 1H), 2.29(s, 3H), 2.35(s, 3H), 2.45-2.55(m, 4H), 2.71-2.84(m, 3H), 3.24-3.34(m, 2H), 3.49(s, 1H), 3.71(s, 3H), 3.75-3.82(m, 1H), 3.97(s, 2H), 6.62-6.75(m, 4H), 7.03(d, 1H, J= 4.8 Hz), 7.19(s, 1H), 7.99(br. s, 1H), 8.21(s, 1H), 8.27(d, 1H, J=4.8 Hz). ES-MS m/z 540(M+H). |
| 176 | 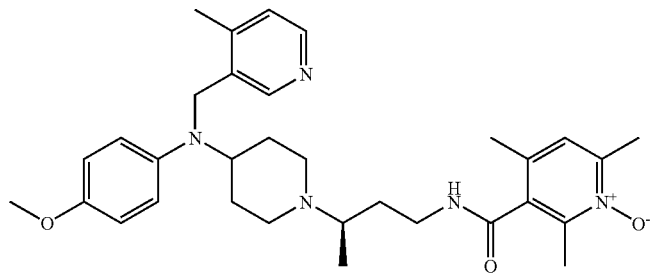<br>N-((R)-3-{4-[(4-Methoxy-phenyl)-(4-methyl-pyridin-3-ylmethyl)-amino]-piperidin-1-yl}-butyl)-2,4,6-trimethyl-1-oxy-nicotinamide | $^1$H NMR(CDCl$_3$) δ 0.99(d, 3H, J=6.6 Hz), 1.24(m, 1H), 1.33(m, 1H), 1.58(m, 1H), 1.77(m, 1H), 1.83(d, 2H, J=12.0 Hz), 2.13(t, 1H, J=11.2 Hz), 2.26(s, 3H), 2.32(s, 3H), 2.34(s, 3H), 2.48(t, 1H, J=11.2 Hz), 2.48(s, 3H), 2.77(m, 3H), 3.21(m, 1H), 3.38(m, 1H), 3.69(m, 1H), 3.73(s, 3H), 4.02(s, 2H), 6.71(m, 4H), 6.91(s, 1H), 7.01(d, 1H, J= 5.1 Hz), 7.79(br, 1H), 8.29(s, 1H), 8.29(d, 1H, J= 4.8 Hz). ES-MS m/z 546(M+H). |

| Ex. # | Structure/Name | Characterization Data |
|---|---|---|
| 177 | 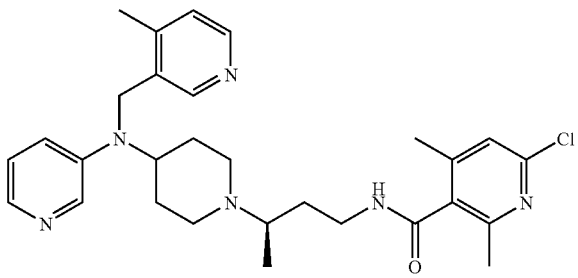<br>6-Chloro-2,4-dimethyl-N-((R)-3-{4-[(4-methyl-pyridin-3-ylmethyl)-pyridin-3-yl-amino]-piperidin-1-yl}-butyl)-nicotinamide | $^1$H NMR(CDCl$_3$) δ 1.02(d, 3H, J=6.0 Hz), 1.18 (m, 1H), 1.35(m, 1H), 1.60(m, 1H), 1.75(m, 1H), 1.88(m, 2H), 2.22(br t, 1H), 2.29(s, 3H), 2.39(s, 3H), 2.51(s, 3H), 2.57(br t, 1H), 2.75-2.85(m, 3H), 3.37(m, 1H), 3.67-3.77(m, 2H), 4.14(s, 2H), 6.83(d, J=9.0 Hz), 6.98(s, 1H), 7.03-7.10(m, 2H), 7.63(m, 1H), 7.96(d, 1H, J 3.0 Hz), 8.02 (d, 1H, J=3.0 Hz), 8.24(s, 1H), 8.36(d, 1H, J= 3.0 Hz). ES-MS m/z 521(M+H). |
| 178 | 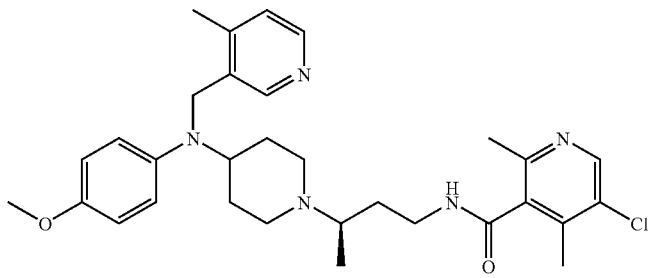<br>5-Chloro-N-((R)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.94-1.04(m, 4H), 1.15-1.25 (m, 1H), 1.51-1.57(m, 1H), 1.68-1.89(m, 3H), 2.06-2.14(m, 1H), 2.33(s, 6H), 2.40-2.50(m, 4H), 2.74-2.84(m, 3H), 3.15-3.23(m, 1H), 3.32-3.36 (m, 1H), 3.70(s, 3H), 3.78-3.86(m, 3H), 6.62-6.71 (m, 4H), 7.01(d, 1H, J=4.8 Hz), 8.17(s, 1H), 8.25(s, 1H), 8.28(d, 1H, J=4.8 Hz), 8.32(br. s, 1H). $^{13}$C NMR(CDCl$_3$) δ 13.57, 16.82, 19.05, 22.20, 29.76, 30.59, 31.28, 40.02,-44.02, 47.21, 52.08, 55.69, 59.83, 60.20, 114.49, 120.79, 125.30, 130.34, 133.09, 134.72, 141.74, 142.50, 145.56, 148.08, 148.25, 149.70, 152.71, 154.07, 167.31. ES-MS m/z 550(M+H). Anal. Calcd. for C$_{31}$H$_{40}$N$_5$ClO$_2$•0.4H$_2$O: C, 66.81; H, 7.38; N, 12.57; Cl, 6.36. Found: C, 66.49; H, 7.26; N, 12.48; Cl, 6.73. |
| 179 | 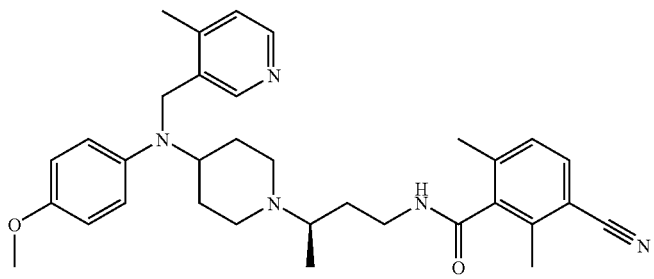<br>3-Cyano-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.98(d, 3H, J=6.3 Hz), 1.05-1.25(m, 2H), 1.52-1.58(m, 1H), 1.69-1.82(m, 3H), 2.06-2.14(m, 1H), 2.31(s, 3H), 2.37(s, 3H), 2.44-2.54(m, 1H), 2.51(s, 3H), 2.71-2.84(m, 3H), 3.11-3.19(m, 1H), 3.27-3.36(m, 1H), 3.72(s, 3H), 3.75-3.86(m, 3H), 6.40(d, 2H, J=9.0 Hz), 6.71 (d, 2H, J=9.0 Hz), 7.00-7.04(m, 2H), 7.24-7.26 (m, 1H), 8.12(br. s, 1H), 8.25(s, 1H), 8.31(d, 1H, J=4.8 Hz). ES-MS m/z 540(M+1)$^+$. |
| 180 | 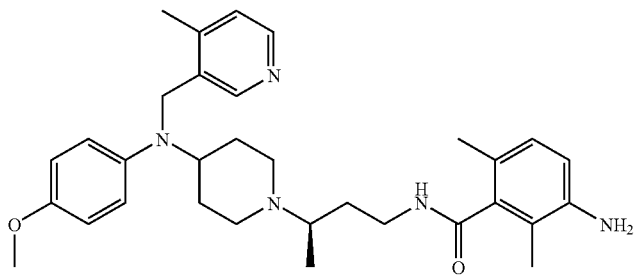<br>3-Amino-N-((R)-3-{4-[(4-methoxy-phenyl)-(4-methyl-pyridin-3-ylmethyl)-amino]-piperidin-1-yl}-butyl)-2,6-dimethyl-benzamide | $^1$H NMR(CDCl$_3$) δ 0.99(d, 3H, J=6.6 Hz), 1.12-1.32(m, 2H), 1.51-1.80(m, 4H), , 2.02-2.13(m, 1H), 2.10(s, 3H), 2.21(s, 3I-I), 2.32(s, 3H), 2.40-2.50(m, 1H), 2.72-2.86(m, 3H), 3.20-3.36(m, 4H), 3.73(s, 3H), 3.74-3.89(m, 3H), 6.21(d, 1H, J= 8.1 Hz), 6.63-6.76(m, 5H), 7.01(d, 1H, J= 4.8 Hz), 7.95(br. s, 1 H), 8.29-8.31(m, 2H). $^{13}$C NMR (CDCl$_3$) δ 13.76, 14.46, 18.91, 19.35, 29.63, 30.45, 31.95, 39.81, 44.33, 46.53, 52.36, 55.90, 60.35, 60.44, 114.68, 115.52, 118.66, 120.18, 123.84, 125.43, 128.33, 133.81, 139.43, 142.89, 143.16, 145.57, 148.26, 149.98, 153.80, 170.78. ES-MS m/z 530(M+1)$^+$. Anal. Calcd. for C$_{32}$H$_{43}$N$_5$O$_2$•0.9CH$_2$Cl$_2$: C, 65.19; H, 7.45; N, 11.55. Found: C, 65.43; H, 7.59; N, 11.58. |

-continued

| Ex. # | Structure/Name | Characterization Data |
|---|---|---|
| 181 | 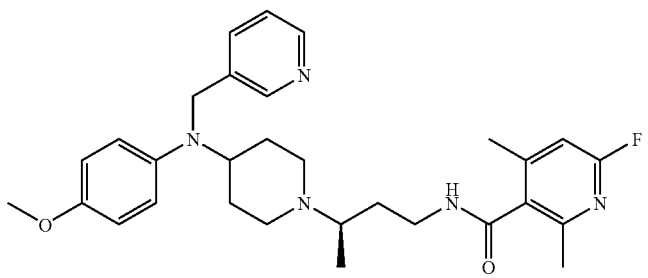<br>6-Fluoro-N-((R)-3-{4-[(4-methoxy-phenyl)-pyridin-3-ylmethyl-amino]-piperidin-1-yl}-butyl)-2,4-dimethyl-nicotinamide | $^1$H NMR(CDCl$_3$) δ 0.95(m, 1H), 0.99(d, 3H, J=6.6 Hz), 1.12(m, 1H), 1.53(m, 1H), 1.78(m, 3H), 2.14(t, 1H, J=11.2 Hz), 2.33(s, 3H), 2.48(s, 3H), 2.53(t, 1H, J=11.2 Hz), 2.74(m, 1H), 2.86(m, 2H), 3.33(m, 2H), 3.71(s, 3H), 3.85(m, 1H), 3.85 (s, 2H), 6.54(s, 1H), 6.62(m, 2H), 6.72(m, 2H), 7.21(m, 1H), 7.57(d, 1H, J=8.1 Hz), 8.44(dd, 1H, J=4.8, 1.5 Hz), 8.48(s, 1H), 8.62(br, 1H). $^{13}$C NMR(CDCl$_3$) δ 13.78, 19.51, 22.27, 29.76, 30.95, 31.20, 40.40, 44.06, 48.06, 52.41, 55.98, 58.60, 60.73, 107.67(d, 1H, J=146 Hz), 114.93 (2C), 118.44(2C), 123.68, 132.34, 135.17, 135.98, 142.77, 148.47, 149.18, 150.70(d, 1H, J=33 Hz), 153.36, 162.70(d, 1C, 950 Hz), 167.77. ES-MS m/z 520(M+H). Anal. Calcd. for C$_{30}$H$_{38}$N$_5$FO$_2$•0.3CH$_2$Cl$_2$: C, 66.76; H, 7.14; N, 12.85. Found: C, 66.98; H, 7.19; N, 12.69. |
| 182 | 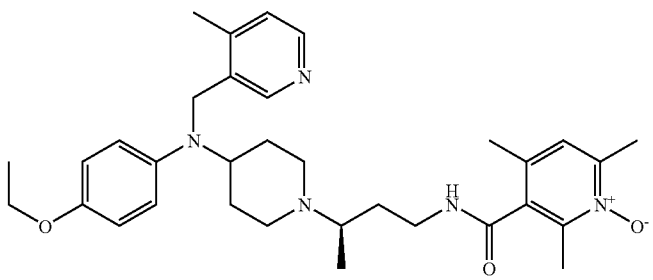<br>N-((R)-3-{4-[(4-Ethoxy-phenyl)-(4-methyl-pyridin-3-ylmethyl)-amino]-piperidin-1-yl}-butyl)-2,4,6-trimethyl-1-oxy-nicotinamide | $^1$H NMR(CDCl$_3$) δ 0.99(d, 3H, J=6.6 Hz), 1.25 (m, 2H), 1.35(t, 3H, J=7.2 Hz), 1.58(m, 1H), 1.80(m, 3H), 2.13(t, 1H, J=11.2 Hz), 2.26(s, 3H), 2.32(s, 3H), 2.33(s, 3H), 2.46(t, 1H, J=11.2 Hz), 2.46(s, 3H), 2.77(m, 3H), 3.22(m, 1H), 3.38 (m, 1H), 3.68(m, 1H), 3.92(q, 2H, J=7.2 Hz), 4.04(s, 2H), 6.70(m, 4H), 6.89(s, 1H), 7.01 (d, 1H, J=4.8 Hz), 7.87(br, 1H), 8.29(m, 2H). $^{13}$C NMR(CDCl$_3$) δ 14.02, 15.36, 16.01, 18.40, 18.87, 19.09, 30.18, 30.65, 32.77, 39.06, 45.26, 47.95, 51.48, 58.54, 59.23, 64.19, 115.51(2C), 120.02(2C), 125.41(2C), 133.16, 133.75, 134.90, 142.94, 145.47, 145.66, 148.17, 148.34, 149.59, 153.22, 166.28. ES-MS m/z 560(M+H). Anal. Calcd. for C$_{33}$H$_{45}$N$_5$O$_3$•0.4CH$_2$Cl$_2$: C, 67.57; H, 7.77; N, 11.80. Found: C, 67.51; H, 7.87; N, 11.76. |
| 183 | 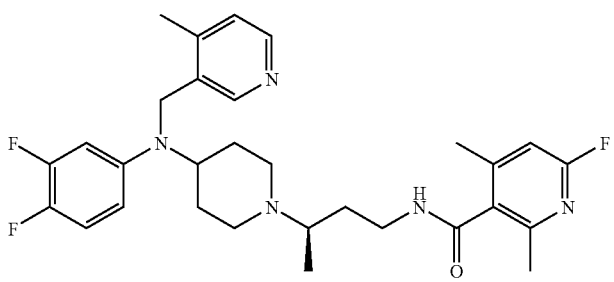<br>N-((R)-3-{4-[(3,4-Difluoro-phenyl)-(4-methyl-pyridin-3-ylmethyl)-amino]-piperidin-1-yl}-butyl)-6-fluoro-2,4-dimethyl-nicotinamide | $^1$H NMR(CDCl$_3$) δ 0.99(d, 3H, J=6.6 Hz), 1.09 (m, 1H), 1.29(m, 1H), 1.61(m, 1H), 1.76(m, 1H), 1.85(br d, 2H, J=11.7 Hz), 2.20(t, 1H, J=11.2 Hz), 2.33(s, 3H), 2.36(s, 3H), 2.48(s, 3H), 2.56 (t, 1H, J=11.2 Hz), 2.70-2.90(m, 3H), 3.33(m, 1H), 3.46(m, 1H), 3.77(m, 1H), 4.03(s, 2H), 6.20 (m, 1H), 6.37(m, 1H), 6.51(s, 1H), 6.92(m, 1H), 7.09(br s, 1H), 7.72(br s, 1H), 8.23(br, 1H), 8.35 (br s, 1H). $^{13}$C NMR(CDCl$_3$) δ 13.81, 19.00, 19.54, 22.32, 29.74, 30.62, 32.01, 39.78, 44.41, 46.04, 52.14, 57.67, 59.89, 103.78(d, 1C, J=83 Hz), 107.67(d, 1C, J=146 Hz), 110.06, 117.74(d, 1C, J=70 Hz), 125.62, 131.97, 132.41, 143.53 (dd, 1C, J=949, 50 Hz), 144.95, 145.68, 148.24, 148.64, 151.05(dd, 1C, J=973, 52 Hz), 150.70(d, 1C, 32 Hz), 153.96(d, 1C, J=61 Hz), 162.70(d, 1C, J=950 Hz), 167.88. ES-MS m/z 540(M+H). Anal. Calcd. for C$_{30}$H$_{36}$N$_5$FO$_3$•0.5CH$_2$C 12: C, 62.93; H, 6.41; N, 12.03. Found: C, 63.12; H, 6.21; N, 12.00. |

| Ex. # | Structure/Name | Characterization Data |
|---|---|---|
| 184 | 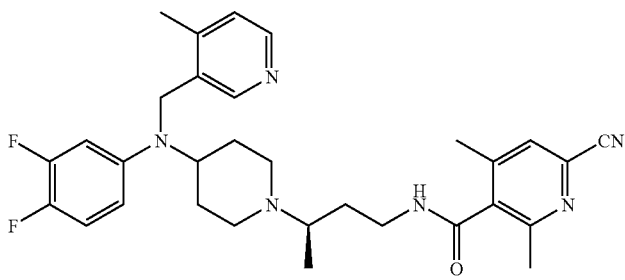<br>6-Cyano-N-((R)-3-{4-[(3,4-difluoro-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 1.05 (m, 1H), 1.26(m, 1H), 1.59(m, 1H), 1.77(m, 1H), 1.86(br d, 2H, J=11.7 Hz), 2.21(t, 1H, J= 11.2 Hz), 2.36(s, 3H), 2.38(s, 3H), 2.57(s, 3H), 2.57 (t, 1H, J=11.2 Hz), 2.70-2.90(m, 3H), 3.39(m, 1H), 3.45(m, 1H), 3.76(m, 1H), 4.07(s, 2H), 6.20 (m, 1H), 6.38(m, 1H), 6.92(m, 1H), 7.11(br s, 1H), 7.33(s, 1H), 7.68(br, 1H), 8.22(br s, 1H), 8.37(br, 1H). $^{13}$C NMR(CDCl$_3$) δ 13.81, 19.07, 19.16, 22.73, 29.77, 30.49, 32.21, 39.42, 43.88, 44.54, 46.24, 51.96, 57.42, 59.39, 103.65(d, 1C, J=83 Hz), 109.99, 117.32, 117.81(d, 1C, J=70 Hz), 125.75, 127.80, 132.47, 132.94, 136.91, 143.53(dd, 1C, J=950, 50 Hz), 144.95, 145.75(d, 1C, J=27 Hz), 146.00, 148.06, 148.61, 151.06 (dd, 1C, J=973, 52 Hz), 156.99, 166.90. ES-MS m/z 547(M+H). Anal. Calcd. for C$_{31}$H$_{36}$N$_6$FO$_2$•0.7CH$_2$Cl$_2$: C, 62.82; H, 6.22; N, 13.87. Found: C, 62.95; H, 6.28; N, 13.82. |
| 185 | 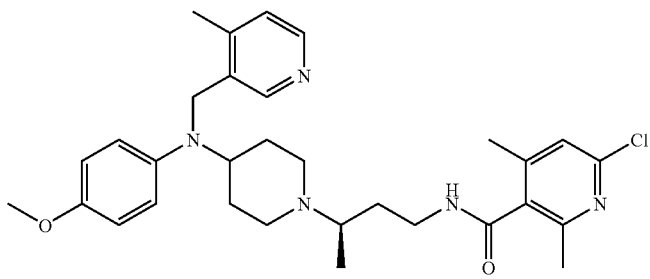<br>6-Chloro-N-((R)-3-{4-[(6-methoxy-pyridin-3-yl)-(4-methyl-pyridin-3-ylmethyl)-amino]-piperidin-1-yl}-butyl)-2,4-dimethyl-nicotinamide | $^1$H NMR(CDCl$_3$) δ 0.99(d+m, 4H), 1.25(m, 1H), 1.56(m, 1H), 1.74-1.85(m, 3H), 2.12(br t, 1H), 2.29(s, 3H), 2.35(s, 3H), 2.51(s+m, 4H), 2.73-2.86(m, 3H), 3.18(m, 1H), 3.33(m, 1H), 3.75(m, 1H), 3.83(s, 3H), 4.00(s, 2H), 6.58(d, J=9.0 Hz), 6.98(s, 1H), 7.05(m, 2H), 7.59(d, 1H, J= 3.0 Hz), 7.89(s, 1H), 8.23(s, 1H), 8.29(d, 1H, J= 3.0 Hz). $^{13}$C NMR(CDCl$_3$) δ 13.7, 19.2, 22.5, 29.9, 30.7, 31.8, 39.8, 44.2, 47.7, 52.0, 53.7, 59.6, 59.9, 111.0, 122.8, 125.6, 131.5, 132.7, 138.1, 139.3, 145.9, 147.7, 148.7, 149.5, 155.6. ES-MS m/z 551 (M+H). |
| 186 | 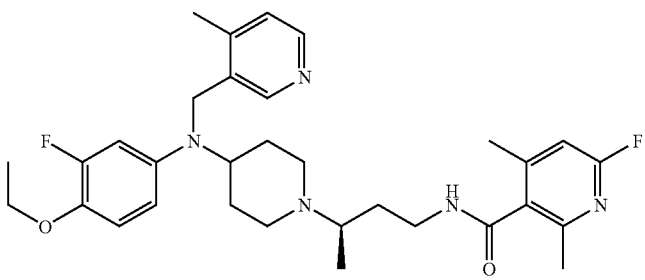<br>6-Fluoro-N-((R)-3-{4-[(3-fluoro-4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 1.01(d, 3H, J=6.6 Hz), 1.04 (m, 1H), 1.23(m, 1H), 1.57(m, 1H), 1.76(m, 1H), 1.84(brd, 2H, J=11.7 Hz), 2.18(t, 1H, J=11.2 Hz), 2.33(s, 3H), 2.35(s, 3H), 2.47(s, 3H), 2.54 (t, 1H, J=11.2 Hz), 2.70-2.90(m, 3H), 3.35(m, 2H), 3.79(m, 1H), 3.79(s, 3H), 3.99(s, 2H), 6.26 (d, 1H, J=9.0 Hz), 6.43(dd, 1H, J=14.1, 2.7 Hz), 6.51(s, 1H), 6.76(t, 1H, J=9.3 Hz), 7.07(d, 1H, J=5.1 Hz), 7.89(br s, 1H), 8.24(s, 1H), 8.34(d, 1H, J=6.3 Hz). $^{13}$C NMR(CDCl$_3$) δ 13.82, 19.03, 19.50, 22.29, 29.84, 30.67, 31.94, 39.79, 44.47, 46.65, 52.10, 57.55, 59.23, 59.89, 105.26(d, 1C, J=86 Hz), 107.66(d, 1C, J=146 Hz), 111.82, 115.53, 12556, 130.00, 132.92, 140.64, 143.57(d, 1C, J=33 Hz), 145.25, 148.44, 148.71, 150.62, 151.83, 153.97(d, 1C, 60 Hz), 155.06, 161.09, 164.26. ES-MS m/z 552(M+H). Anal. Calcd. for C$_{31}$H$_{39}$N$_5$F$_2$O$_2$•0.4CH$_2$Cl$_2$: C, 64.40; H, 6.85; N, 11.96. Found: C, 64.53; H, 6.95; N, 11.97. |

| Ex. # | Structure/Name | Characterization Data |
|---|---|---|
| 187 | 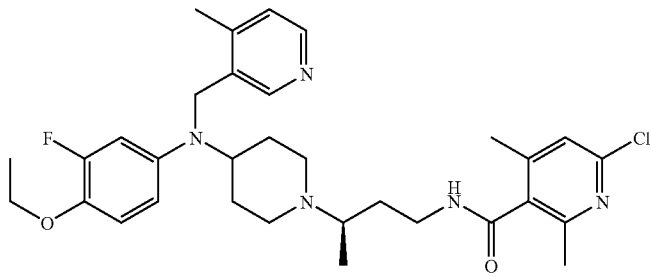<br>6-Chloro-N-((R)-3-{4-[(3-fluoro-4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 1.00(d, 3H, J=6.6 Hz), 1.03 (m, 1H), 1.24(m, 1H), 1.56(m, 1H), 1.74(m, 1H), 1.83(brd, 2H, J=11.7 Hz), 2.16(t, 1H, J=11.2 Hz), 2.30(s, 3H), 2.36(s, 3H), 2.51(s, 3H), 2.52 (t, 1H, J=11.2 Hz), 2.65-2.90(m, 3H), 3.34(br, 2H), 3.78(m, 1H), 3.79(s, 3H), 4.01(s, 2H), 6.28 (d, 1H, J=9.0 Hz), 6.45(dd, 1H, J=14.1, 2.7 Hz), 6.77(t, 1H, J=9.3 Hz), 6.98(s, 1H), 7.06(br d, 1H, J=4.2 Hz), 7.82(br s, 1H), 8.25(br s, 1H), 8.33(br, 1H). $^{13}$C NMR(CDCl$_3$) δ 13.80, 19.17 (2C), 22.53, 29.78, 30.66, 32.01, 39.70, 44.46, 46.69, 52.10; 57.56, 58.32, 59.83, 105.43(d, 1C, J=85 Hz), 112.03, 115.52, 122.86(2C), 125.53, 132.86, 132.90, 143.67(d, 1C, J=33 Hz), 145.29, 147.77, 148.47, 148.87, 150.57, 153.46(d, 1C, 969 Hz), 155.56, 167.74. ES-MS m/z 568(M+H). Anal. Calcd. for C3, H$_{39}$N$_5$ClFO$_2$•0.4CH$_2$Cl$_2$: C, 62.64; H, 6.66; N, 11.63. Found: C, 62.67; H, 6.76; N, 11.56. |
| 188 | 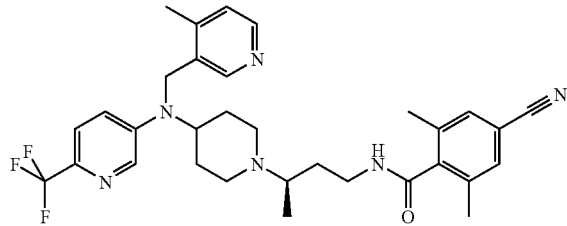<br>4-Cyano-2,6-dimethyl-N-((R)-3-{4-[(4-methyl-pyridin-3-ylmethyl)-(6-trifluoromethyl-pyridin-3-yl)-amino]-piperidin-1-yl}-butyl)-benzamide | $^1$H NMR(CDCl$_3$) δ 1.04(d, 3H, J=5 Hz), 1.32(m, 1H), 1.46(m, 1H), 1.61(m, 1H), 1.77(m, 1H), 1.91(m, 2H), 2.28(m, 1H), 2.34(s, 6H), 2.36(s, 3H), 2.59(m, 1H), 2.86(m, 3H), 3.43(m, 1H), 3.49(s, 1H), 3.75(m, 2H), 4.23(s, 2H), 6.85(d, 1H, J=9 Hz), 6.98(m, 1H), 7.15(d, 1H, J=4 Hz), 7.28(s, 1H), 7.42(d, 1H, J=9 Hz), 8.06(d, 1H, J=3 Hz), 8.19(s, 1H), 8.41(d, 1H, J=5 Hz). ES-MS m/z 579(M+H), 602(M+Na). |
| 189 | 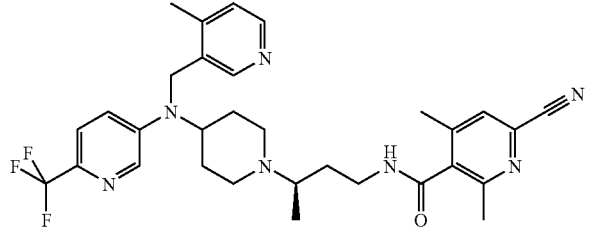<br>6-Cyano-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide | $^1$H NMR(CDCl$_3$) δ 1.06(m, 3H), 1.25(m, 1H), 1.40(m, 1H), 1.60(m, 5H), 1.76(m, 1H), 1.92(m, 2H), 2.27(m, 1H), 2.36(s, 3H), 2.42(s,.3H), 2.57 (s, 3H), 2.61(m, 1H), 2.84(m, 3H), 3.43(m, 1H), 3.48(s, 2H), 3.75(m, 2H), 4.25(s, 2H), 6.83(d, 1H, J=9 Hz), 7.15(d, 1H, J=5 Hz), 7.38(m, 3H), 8.06(m, 1H), 8.17(s, 1H), 8.40(d, 1H, J=6 Hz). ES-MS m/z 580(M+H). |
| 190 | 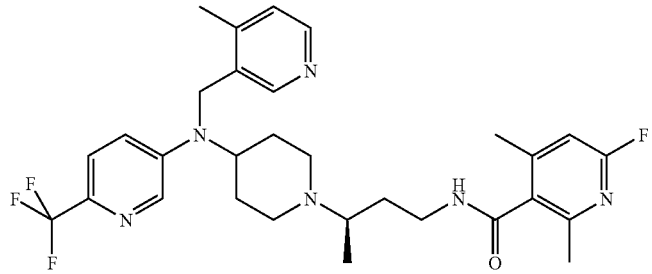<br>6-Fluoro-2,4-dimethyl-N-((R)-3-{4-[(4-methyl-pyridin-3-ylmethyl)-(6-trifluoromethyl-pyridin-3-yl)-amino]-piperidin-1-yl}-butyl)-nicotinamide | $^1$H NMR(CDCl$_3$) δ 1.04(d, 2H, J=5 Hz), 1.36(m, 1H), 1.58 9m, 2H), 1.79(m, 1H), 1.88(m, 2H), 2.10(m, 3H), 2.30(s+m, 4H), 2.37(s, 3H), 2.42 (s, 3H), 2.61(t, 1H, J=10 Hz), 2.86(m, 3H), 3.36 (m, 1H), 3.41(s, 6H), 3.65(m, 1H), 3.80(m, 1H,), 4.25(s, 2H), 6.49(s, 1H), 6.83(dd, 1H, J=3 Hz, 9 Hz), 7.11(d, 1H, 5 Hz), 7.39(d, 1H, J=9 Hz), 7.99(d, 1H, J=3 Hz), 8.33(d, 1H, J=5 Hz). ES-MS m/z 573(M+H), 596(M+Na). |

| Ex. # | Structure/Name | Characterization Data |
|---|---|---|
| 191 | 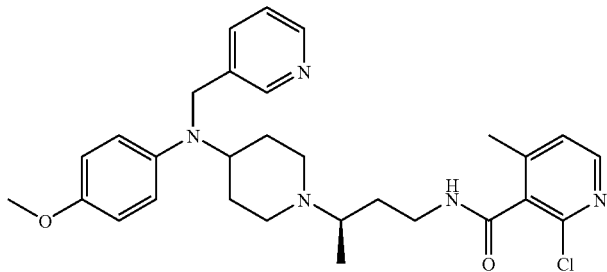<br>2-Chloro-N-((R)-3-{4-[(4-methoxy-phenyl)-pyridin-3-ylmethyl-amino]-piperidin-1-yl}-butyl)-4-methyl-nicotinamide | $^1$H NMR(CDCl$_3$) δ 1.00(d+m, 4H), 1.22(m, 1H), 1.56(m, 1H), 1.77-1.82(m, 3H), 2.14(br t, 1H), 2.36(s, 3H), 2.54(br t, 1H), 2.78-2.92(m, 3H), 3.32-3.37(m, 2H), 3.70(s, 3H), 3.82(s, 2H), 3.89 (m, 1H), 6.61(d, J=9.0 Hz), 6.71(d, J=9.0 Hz), 6.98(d, J=6.0 Hz), 7.21(m, 1H), 7.52(d, 1H, J= 6.0 Hz), 8.05(d, J=6.0 Hz), 8.44(s=d, 2H), 8.79 (s, 1 H). ES-MS m/z 522(M+H), 544(M+Na). |
| 192 | 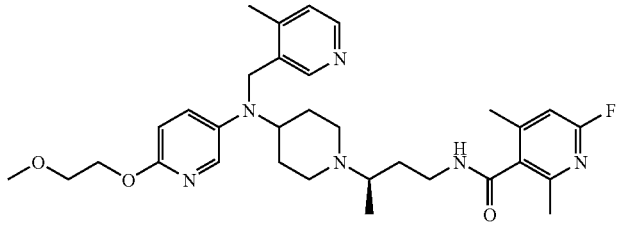<br>6-Fluoro-N-((R)-3-{4-[[4-(2-methoxy-ethoxy)-phenyl]-(4-methyl-pyridin-3-ylmethyl)-amino]-piperidin-1-yl}-butyl)-2,4-dimethyl-nicotinamide | $^1$H NMR(CDCl$_3$) δ 1.00(d, 3H, J=9 Hz), 1.19-1.28(m, 1H), 1.72-1.87(m, 3H), 2.13-2.22(m, 1H), 2.32(s, 3H), 2.33(s, 3H), 2.47(s, 3H), 2.48-2.56(m, 1H), 2.73-2.91(m, 3H), 3.23-3.32(m, 2H), 3.43(s, 3H), 3.68-3.71(m, 2H), 3.77-3.82(m, 1H), 3.97(s, 2H), 4.00-4.03(m, 2H), 6.51(s, 1H), 6.60(d, 2H, J=9 Hz), 6.75(d, 2H, J=9 Hz), 7.03 (d, 1H, J=3 Hz), 7.99-8.10(br s, 1H), 8.26(s, 1H), 8.30(d, 1H, J=6 Hz). $^{13}$C NMR(CDCl$_3$) δ 13.70, 19.09, 22.31, 31.67, 44.31, 52.24, 60.29, 68.05, 71.53, 107.95, 115.71, 119.90, 125.49, 148.41, 149.51. ES-MS m/z 578(M+H). Anal. Calcd. for C$_{33}$H$_{44}$N$_5$O$_3$F.0.4CH$_2$Cl$_2$: C, 65.58; H, 7.38; N, 11.45. Found: C, 65.28; H, 7.42; N, 11.39. |
| 193 | 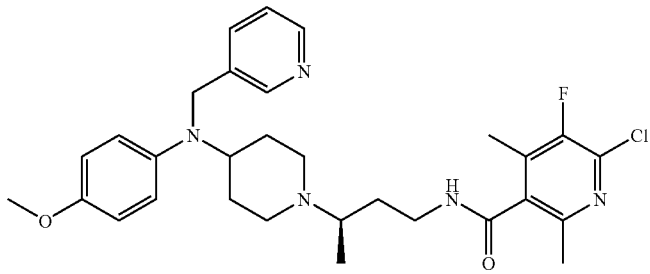<br>6-Chloro-5-fluoro-N-((R)-3-{4-[(4-methoxy-phenyl)-pyridin-3-ylmethyl-amino]-piperidin-1-yl}-butyl)-2,4-diemthyl-nicotinamide | $^1$H NMR(CDCl$_3$) δ 0.95(m, 1H), 0.99(d, 3H, J= 6.6 Hz), 1.15(m, 1H), 1.54(m, 1H), 1.74(m, 1H), 1.78(br d, 2H, J=11.7 Hz), 2.13(t, 1H, J=11.2 Hz), 2.28(s, 3H), 2.47(s, 3H), 2.53(t, 1H, J=11.2 Hz), 2.65-2.90(m, 3H), 3.33(m, 2H), 3.71(m, 1H), 3.80(m, 1H), 3.92(s, 2H), 6.62(m, 2H), 6.72 (m, 2H), 7.20(m, 1H), 7.57(d, 1H, J=7.8 Hz), 8.42(br, 1H), 8.47(s, 1H), 8.67(br, 1H). $^{13}$C NMR (CDCl$_3$) δ 12.46, 13.75, 22.08, 29.86, 31.15, 31.16, 40.39, 44.02, 48.20, 52.39, 55.99, 58.62, 60.67, 114.95(2C), 118.85(2C), 123.74, 134.75, 135.27, 136.21, 142.74, 148.47, 148.50, 149.30, 149.79, 153.84, 157.65, 160.12(d, 1C, J=950 Hz), 166.11. ES-MS m/z 554(M+H). Anal. Calcd. for C$_{30}$H$_{37}$N$_5$ClFO$_2$•0.3CH$_2$Cl$_2$: C, 62.79; H, 6.54; N, 12.08. Found: C, 62.48; H, 6.56; N, 11.94. |
| 194 | 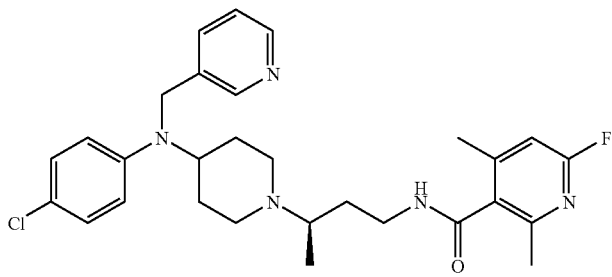<br>N-((R)-3-{4-[(4-Chloro-phenyl)-pyridin-3-ylmethyl-amino]-piperidin-1-yl}-butyl)-6-fluoro-2,4-dimethyl-nicotinamide | $^1$H NMR(CDCl$_3$) δ 0.95(m, 1H), 0.99(d, 3H, J= 6.6 Hz), 1.15(m, 1H), 1.54(m, 1H), 1.74(m, 1H), 1.78(brd, 2H, J=11.7 Hz), 2.18(t, 1H, J=11.2 Hz), 2.32(s, 3H), 2.47(s, 3H), 2.57(t, 1H, J=11.2 Hz), 2.70-2.90(m, 3H), 3.31(m, 2H), 3.58(m, 1H), 3.81(m, 1H), 3.93(s, 2H), 6.50(d, 2H, J= 8.1 Hz), 6.54(s, 1H), 7.07(d, 2H, J=8.7 Hz), 7.23 (m, 1H), 7.54(d, 1H, J=7.8 Hz), 8.46(br, 3H). $^{13}$C NMR(CDCl$_3$) δ 13.42, 19.14, 21.90, 29.16, 30.43, 30.83, 40.02, 43.60, 46.45, 52.07, 56.50, 60.37, 107.33(d, 1C, J=146 Hz), 114.95(2C), 122.50, 123.42, 129.08(2C), 131.83, 134.19, 134.84, 146.77, 148.26, 148.37, 150.44(d, 1C. J= 32 Hz), 153.72(d, 1C, J=60 Hz), 162.34(d, 1C, J= 949 Hz), 167.32. ES-MS m/z 524(M+H). Anal. Calcd. for C$_{29}$H$_{35}$N$_5$ClFO•0.2CH$_2$Cl$_2$: C, 64.82; H, 6.59; N, 12.94. Found: C, 64.81; H, 6.81; N, 12.71. |

| Ex. # | Structure/Name | Characterization Data |
|---|---|---|
| 195 | 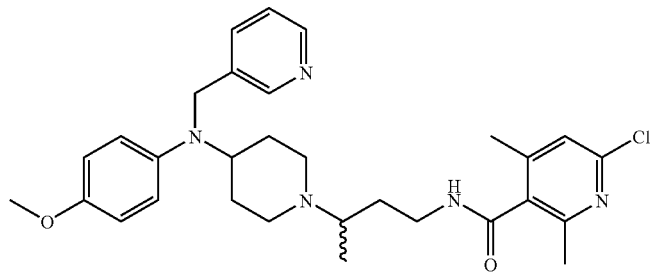<br>6-Chloro-N-(3-{4-[(4-methoxy-phenyl)-pyridin-3-ylmethyl-amino]-piperidin-1-yl}-butyl)-2,4-dimethyl-nicotinamide | $^1$H NMR(δ, CDCl$_3$): 8.66(1H, d, br, J=5.7 Hz), 8.51(1H, s), 8.44(1H, d, J=4.8 Hz), 7.61(1H, d, J=8.1Hz), 7.20(1H, dd, J=7.8, 4.8 Hz), 7.01 (1H, s), 6.73(2H, d, J=9.0 Hz), 6.62(2H, d, J= 9.0 Hz), 3.88(2 H, s, an overlapping 1H, m), 3.71 (3 H, s), 3.33(2 H, pentet, J=13.5 Hz), 2.80(3 H, m), 2.51(3 H, s, an overlapping 1H, m), 2.30(3 H, s), 2.12(1H, t, J=11.4 Hz), 1.82-1.66(3 H, m), 1.60-1.46(1H, m), 1.11(1H, qd, J=12.3, 3.6 Hz), 0.99(3 H, d, j =6.6 Hz), 0.92(1H, qd, J=12.0, 3.0 Hz); $^{13}$CNMR(δ,CDCl$_3$): 167.2, 155.4, 152.9, 150.2, 148.9, 148.1, 147.5, 142.5, 135.7, 134.8, 123.3, 122.5, 117.8, 114.6, 60.5, 58.1, 55.6, 52.1, 47.5, 43.6, 40.1, 30.7, 29.4, 22.1, 18.8, 13.4; ES-MS m/z 536.5(M+1). |
| 196 | 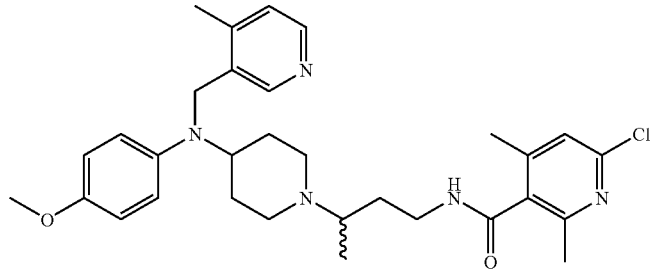<br>6-Chloro-N-(3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.00 (m, 1H), 1.19(m, 1H), 1.54(m, 1H), 1.71(m, 1H), 1.80(brd, 2H, J=12.6 Hz), 2.11(t, 1H, J= 11.2 Hz), 2.29(s, 3H), 2.35(s, 3H), 2.48(t, 1H, J= 11.2 Hz), 2.51(s, 3H), 2.65-2.85(m, 3H), 3.15-3.45(m, 2H), 3.72(s, 3H), 3.78(m, 1H), 3.97(s, 2H), 6.62-6.78(m, 4H), 6.98(s, 1H), 7.02(d, 1H, J=4.8 Hz), 8.05(br. 5, 1H), 8.25(s, 1H), 8.28(d, 1H, J= 5. 1Hz). $^{13}$C NMR(CDCl$_3$) δ 13.74, 19.16, 19.22, 22.51, 30.07, 31.01, 31.72, 40.04, 44.27, 47.85, 52.20, 55.93, 59.41, 60.20, 114.75(2C), 120.74 (2C), 122.85, 125.47, 132.90, 133.43, 142.69, 145.73, 147.66, 148.42, 149.78, 150.59, 154.22, 155.58, 167.68. ES-MS m/z 550(M+H). |
| 197 | 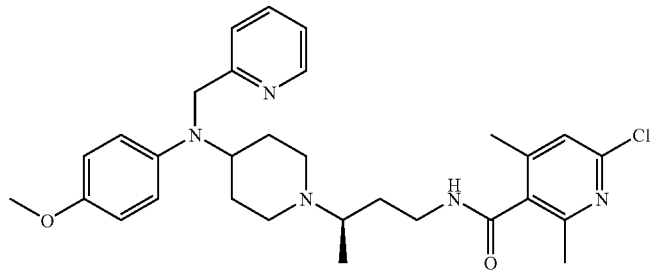<br>6-Chloro-N-((R)-3-{4-[(4-methoxy-phenyl)-pyridin-2-ylmethyl-amino]-piperidin-1-yl}-butyl)-2,4-dimethyl-nicotinamide | $^1$H NMR(CDCl$_3$) δ 0.99(d, 3H, J=6.6 Hz), 1.10 (m, 1H), 1.24(m, 1H), 1.54(m, 1H), 1.72(m, 1H), 1.78(brd, 2H, J=11.7 Hz), 2.13(t, 1H, J=11.2 Hz), 2.30(s, 3H), 2.50(s, 3H), 2.52(t, 1H, J=11.2 Hz), 2.65-2.85(m, 3H), 3.40(m, 2H), 3.71(s, 3H), 3.77(m, 1H), 4.11(s, 2H), 6.66(m, 2H), 6.75(m, 2H), 7.06(s, 1H), 7.11(m, 1H), 7.26(dt, 1H, J= 7.5, 1.5 Hz), 8.08(br, 1H), 8.54(d, 1H, J= 3.9 Hz). ES-MS m/z 536(M+H). |
| 198 | 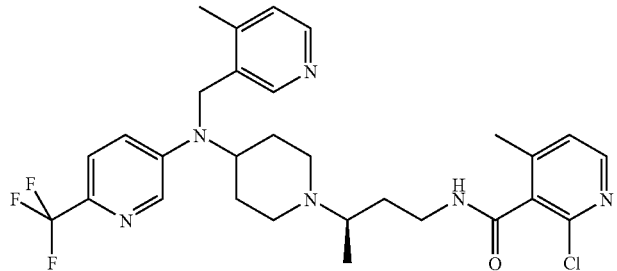<br>6-Chloro-4-methyl-N-((R)-3-{4-[(4-methyl-pyridin-3-ylmethyl)-(6-trifluoromethyl-pyridin-3-yl)-amino]-piperidin-1-yl}-butyl)-nicotinamide | $^1$H NMR(CDCl$_3$) δ 1.10(m, 3H), 1.67(m, 3H), 1.90 9m, 3H), 2.38(s, 3H), 2.43(s, 3H), 2.66(m, 1H), 2.93(m, 3H), 3.44(m, 1H), 3.48(s, 1H), 3.77 (m, 2H), 4.26(s, 2H), 6.85(dd, 1H, J=3 Hz, 9 Hz), 6.99(d, 1H, J=5 Hz), 7.40(d, 1H, J 9 Hz), 7.82(m, 1H), 8.03(m, 2H), 8.15(s, 1H), 8.38(d, 1H, J= 5 Hz). ES-MS m/z 575(M+H), 598(M+Na). |

| Ex. # | Structure/Name | Characterization Data |
|---|---|---|
| 199 | 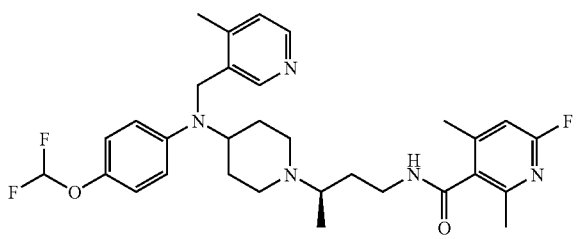<br>N-((R)-3-{4-[(4-Difluoromethoxy-phenyl)-(4-methyl-pyridin-3-ylmethyl)-amino]-piperidin-1-yl}-butyl)-6-fluoro-2,4-dimethyl-nicotinamide | $^1$H NMR(CDCl$_3$) δ 1.01(d, 3H, J=6.6 Hz), 1.10 (m, 1H), 1.29(m, 1H), 1.58(m, 1H), 1.76(m, 1H), 1.85(brd, 2H, J=11.7 Hz), 2.20(t, 1H, J=11.2 Hz), 2.32(s, 3H), 2.35(s, 3H), 2.46(s, 3H), 2.56 (t, 1H, J=11.2 Hz), 2.70-2.90(m, 3H), 3.37(m, 2H), 3.56(m, 1H), 3.76(m, 1H), 4.06(s, 2H), 6.35 (t, 1H, J=75 Hz), 6.50(s, 1H), 6.53(d, 2H, J=9.0 Hz), 6.92(d, 2H, J=9.0 Hz), 7.07(d, 1H, J=5.1 Hz), 7.83(br, 1H), 8.23(s, 1H), 8.32(d, 1H, J=5.1 Hz). $^{13}$C NMR(CDCl$_3$) δ 13.42, 18.64, 19.13, 21.95, 29.40, 30.33, 31.59, 39.47, 44.06, 45.65, 51.88, 57.09, 59.61, 107.30(d, 1C, J=146 Hz), 115.32(2C), 116.36(t, 1C, J=1030 Hz), 121.19(2C), 125.15, 132.38, 142.81, 144.57, 146.14, 148.07, 148.19, 150.30(d, 1C, J=33 Hz), 153.59(d, 1C, J=62 Hz), 162.32(d, 1C, J=950 Hz), 163.90. ES-MS m/z 570(M+H). Anal. Calcd. for C$_{31}$H$_{38}$N$_5$F$_3$O$_2$•0.3CH$_2$Cl$_2$: C, 63.17; H, 6.54; N, 11.77. Found: C, 63.30; H, 6.56; N, 11.77. |
| 200 | 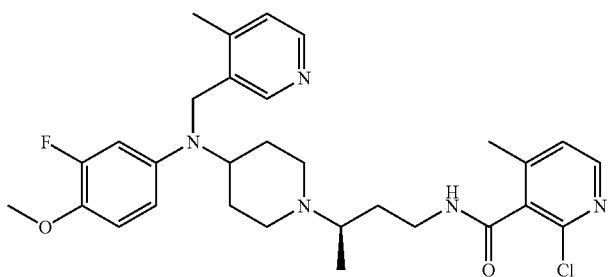<br>2-Chloro-N-((R)-3-{4-[(3-fluoro-4-methoxy-phenyl)-(4-methyl-pyridin-3-ylmethyl)-amino]-piperidin-1-yl}-butyl)-4-methyl-nicotinamide | $^1$H NMR(CDCl$_3$) δ 0.99(d, 3H, J=6.6 Hz), 1.10 (m, 1H), 1.28(m, 1H), 1.54(m, 1H), 1.74(m, 1H), 1.81(br d, 2H, J=11.7 Hz), 2.15(t, 1H, J=11.2 Hz), 2.35(s, 3H), 2.37(s, 3H), 2.52(t, 1H, J=11.2 Hz), 2.70-2.90(m, 3H), 3.35(m, 2H), 3.78(s, 3H), 3.79(m, 1H), 3.95(s, 2H), 6.27(br d, 1H, J=7.5 Hz), 6.41(dd, 1H, J=14.1, 2.7 Hz), 6.75(t, 1H, J=9.3 Hz), 6.95(d, 1H, J=5.1 Hz), 7.06(d, 1H, J=5.4 Hz), 7.98(d, 1H, J=5.1 Hz), 8.23(s, 1H), 8.25(br, 1H), 8.33(d, 1H, J=5.1 Hz). ES-MS m/z 554 (M+H). |
| 201 | 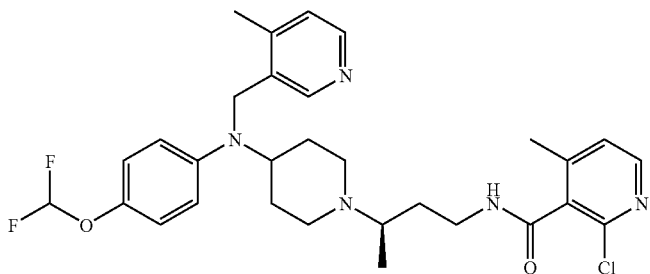<br>2-Chloro-N-((R)-3-{4-[(4-difluoromethoxy-phenyl)-(4-methyl-pyridin-3-ylmethyl)-amino]-piperidin-1-yl}-butyl)-4-methyl-nicotinamide | $^1$H NMR(CDCl$_3$) δ 1.01(d, 3H, J=6.6 Hz), 1.10 (m, 1H), 1.29(m, 1H), 1.58(m, 1H), 1.77(m, 1H), 1.83(br d, 2H, J=11.7 Hz), 2.18(t, 1H, J=11.2 Hz), 2.36(s, 3H), 2.39(s, 3H), 2.56(t, 1H, J=11.2 Hz), 2.75-2.95(m, 3H), 3.36(m, 1H), 3.54(m, 1H), 3.81(m, 1H), 4.02(s, 2H), 6.35(t, 1H, J=75 Hz), 6.52(d, 2H, J=9.0 Hz), 6.91(d, 2H, J=9.0 Hz), 6.96(d, 1H, J=5.1 Hz), 7.09(d, 1H, J=4.8 Hz), 7.98(d, 1H, J=5.1 Hz), 8.13(br, 1H), 8.24 (s, 1H), 8.35(d, 1H, J=5.1Hz). ES-MS m/z 572 (M+H) |
| 202 | 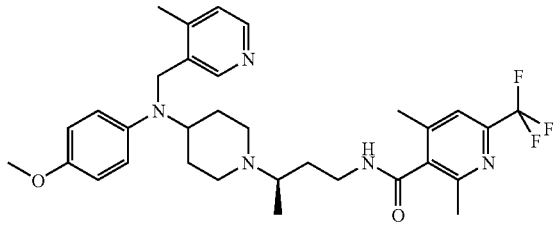<br>N-((R)-3-{4-[(4-Methoxy-phenyl)-(4-methyl-pyridin-3-ylmethyl)-amino]-piperidin-1-yl}-butyl)-2,4-dimethyl-6-trifluoromethyl-nicotinamide | $^1$H NMR(CDCl$_3$) δ 0.99(d, 3H, J=6.6 Hz), 1.21 (m, 2H), 1.62(m, 1H), 1.79(brd, 2H, J=11.7 Hz), 2.15(t, 1H, J=11.2 Hz), 2.30(s, 3H), 2.38(s, 3H), 2.i0(t, 1H, J=11.2 Hz), 2.60(s,3H), 2.65-2.90(m, 3H), 3.23(m, 1H), 3.38(m, 1H), 3.72(s, 3H), 3.77(m, 1H), 4.00(s, 2H), 6.62(d, 2H, J=9.0 Hz), 6.71(d, 2H, J=9.0 Hz), 7.01(d, 1H, J=4.8 Hz), 7.34(s, 1H), 7.78(s, 1H), 8.23(s, 1H), 8.29(d, 1H, J=5.4 Hz). $^{13}$C NMR(CDCl$_3$) δ 13.72, 19.02, 19.46, 22.68, 29.99, 30.72, 32.07, 39.49, 44.59, 48.15, 51.92, 55.93, 58.90, 59.61, 114.78(2C), 119.70, 120.48(2C), 125.45, 133.50, 136.41, 142.68, 145.64, 146.14, 148.33, 149.52, 154.20, 155.90, 167.61. ES-MS m/z 584(M+H). Anal. Calcd. for C$_{32}$H$_{40}$N$_5$F$_3$O$_2$•0.4CH$_2$Cl$_2$: C, 63.00; H, 6.66; N, 11.34. Found: C, 62.96; H, 6.65; N, 11.48. |

| Ex. # | Structure/Name | Characterization Data |
|---|---|---|
| 203 | 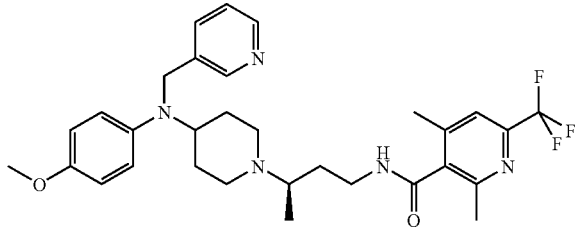<br>N-((R)-3-{4-[(4-Methoxy-phenyl)-pyridin-3-ylmethyl-amino]-piperidin-1-yl}-butyl)-2,4-dimethyl-6-trifluoromethyl-nicotinamide | $^1$H NMR(CDCl$_3$) δ 0.99(d, 3H, J=6.6 Hz), 0.90-1.20(m, 2H), 1.60(m, 1H), 1.77(br d, 2H, J=11.7 Hz), 2.15(t, 1H, J=11.2 Hz), 2.40(s, 3H), 2.55(t, 1H, J=11.2 Hz), 2.61(s, 3H), 2.65-2.95 (m, 3H), 3.36(m, 2H), 3.72(s, 3H), 3.85(m, 1H), 3.88 (s, 2H), 6.61(d, 2H, J=9.0 Hz), 6.72(d, 2H, J=9.0 Hz), 7.19(m, 1H), 7.37(s, 1H), 7.54(br d, 1H, J=7.8 Hz), 8.43(br, 3H). $^{13}$C NMR(CDCl$_3$) δ 13.70, 19.46, 22.67, 29.69, 30.74, 31.47, 39.93, 44.25, 48.35, 52.23, 55.98, 58.19, 60.30, 114.97 (2C), 118.36(2C), 119.69, 123.13, 123.66, 135.16, 136.09, 136.57, 142.81, 146.26, 147.78, 148.43, 149.12, 153.42, 155.96, 167.47. ES-MS m/z 570 (M+H). Anal. Calcd. for C$_{31}$H$_{38}$N$_5$N$_3$O$_2$•0.3CH$_2$Cl$_2$: C, 63.17; H, 6.54; N, 11.77. Found: C, 63.16; H, 6.63; N, 11.65. |
| 204 | 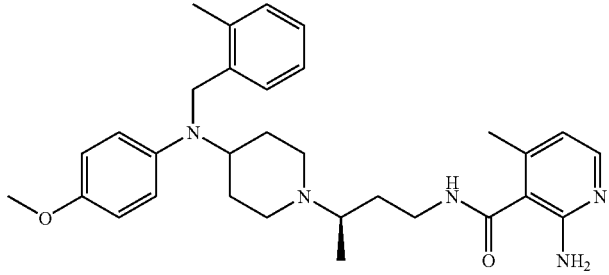<br>2-Amino-N-((R)-3-{4-[(4-methoxy-phenyl)-(4-methyl-pyridin-3-ylmethyl)-amino]-piperidin-1-yl}-butyl)-4-methyl-nicotinamide | $^1$H NMR(CDCl$_3$) δ 0.98(d, 3H, J=9.0 Hz), 1.17 (m, 1H), 1.31(m, 1H), 1.56(m, 1H), 1.74(m, 1H), 1.82(m, 2H), 2.12(br t, 1H), 2.26(s, 3H), 2.34(s, 3H), 2.49(br t, 1H), 2.74-2.83(m, 3H), 3.27-3.32 (m, 2H), 3.71(s, 3H), 3.75(m, 1H), 4.00(s, 2H), 6.35(d, 1H, J=6.0 Hz), 6.63(d, 2H, J=9.0 Hz), 6.72(d, 2H, J=9.0 Hz), 7.02(d, 1H, J 3.0 Hz), 7.74(d, 1H, J=6.0 Hz), 7.96(s, 1H), 8.30(s=d, 2H). ES-MS m/z 517(M+H), 539(M+Na). |
| 205 | 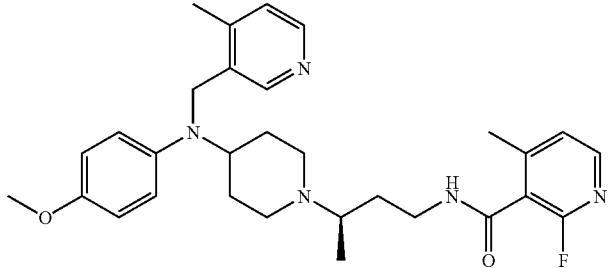<br>2-Fluoro-N-((R)-3-{4-[(4-methoxy-phenyl)-(4-methyl-pyridin-3-ylmethyl)-amino]-piperidin-1-yl}-butyl)-4-methyl-nicotinamide | $^1$H NMR(CDCl$_3$) 61.00(d, 3H, J=9.0 Hz), 1.18 (m, 1H), 1.33(m, 1H), 1.53(m, 1H), 1.74(m, 1H), 1.82(m, 2H), 2.16(br t, 1H), 2.35(s, 3H), 2.42(s, 3H), 2.53(br t, 1H), 2.78-2.87(m, 3H), 3.31-3.35 (m, 2H), 3.70(s, 3H), 3.75(m, 1H), 4.02(s, 2H), 6.63(d, 2H, J=9.0 Hz), 6.71(d, 2H, J=9.0 Hz), 6.95(d, 1H, J=6.0 Hz), 7.02(d, 1H, J=6.0 Hz), 7.85(d, 1H, J=6.0 Hz), 8.21(s, 1H), 8.29(s=d, 2H). ES-MS m/z 520(M+H), 542(M+Na). |
| 206 | 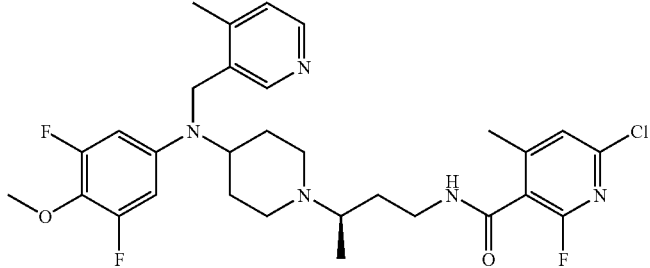<br>6-Chloro-N-((R)-3-{4-[(3,5-difluoro-4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 1.21 (m, 1H), 1.28(m, 1H), 1.57(m, 1H), 1.75(m, 1H), 1.83(brd, 2H, J=11.7 Hz), 2.21(t, 1H, J=11.2 Hz), 2.29(s, 3H), 2.37(s, 3H), 2.50(s, 3H), 2.56 (t, 1H, J=11.2 Hz), 2.70-2.90(m, 3H), 3.37(m, 1H), 3.49(m, 1H), 3.77(m, 1H), 3.83(s, 3H), 4.07 (s, 2H), 6.07(m, 2H), 6.98(s, 1H), 7.09(d, 1H, J=4.8 Hz), 7.56(br, 1H), 8.20(s, 1H), 8.35(d, 1H, J=5.4 Hz). ES-MS m/z 586(M+H). |

| Ex. # | Structure/Name | Characterization Data |
|---|---|---|
| 207 | 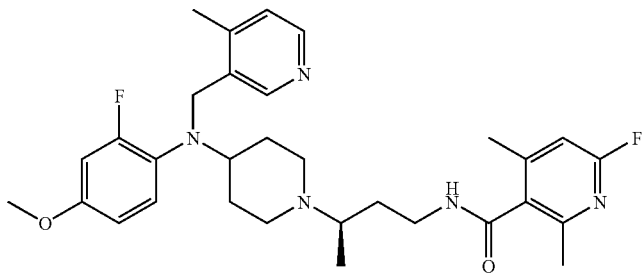<br>6-Fluoro-N-((R)-3-{4-[(2-fluoro-4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.99(d, 3H, J=6.6 Hz), 0.90-1.20(m, 2H), 1.62(m, 1H), 1.85(br d, 2H, J=11.7 Hz), 2.22(t, 1H, J=11.2 Hz), 2.33(s, 6H), 2.46(s, 3H), 2.49(t, 1H, J=11.2 Hz), 2.75-3.00 (m, 3H), 3.39(m, 2H), 3.71(s, 3H), 3.77(m, 1H), 4.01(s, 2H), 6.50(m, 2H), 6.55(s, 1H), 6.75(br, 1H), 6.98(br d, 1H, J=4.8 Hz), 8.22(br, 1H). $^{13}$C NMR(CDCl$_3$) δ 13.14, 18.67, 19.22, 21.93, 29.69 (br, 2C), 31.19, 39.01, 44.01, 49.76, 51.04, 55.52, 58.73, 58.96, 102.41(d, 1C, J=98 Hz), 107.34(d, 1C, J=146 Hz), 109.23, 125.24, 127.58(d, 1C, J=45 Hz), 129.73(d, 1C, J=18 Hz), 131.37, 132.51, 146.65, 148.33, 150.08(d, 1C, J=32 Hz), 150.36, 153.63(d, 1C, J=61 Hz), 158.03, 160.58 (d, 1C, J=983 Hz), 162.33(d, 1C, J=948 Hz), 167.89. ES-MS m/z 552(M+H). Anal. Calcd. for C$_{31}$H$_{39}$N$_5$F$_2$O$_2$•0.7CH$_2$Cl$_2$: C, 62.30; H, 6.66; N, 11.46. Found: C, 62.15; H, 6.77; N, 11.59. |
| 208 | 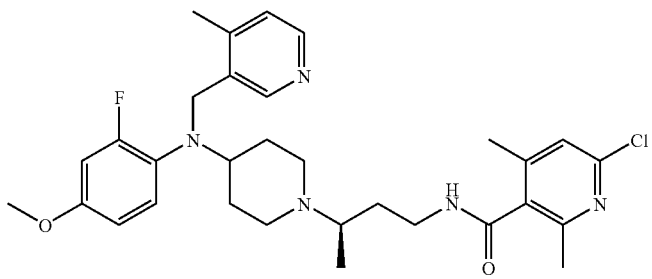<br>6-Chloro-N-((R)-3-{4-[(2-fluoro-4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.94(m, 1H), 0.97(d, 3H, J=6.6 Hz), 1.10(m, 1H), 1.55(m, 1H), 1.78(br d, 2H, J=11.7 Hz), 2.03(t, 1H, J=11.2 Hz), 2.30(s, 3H), 2.34(s, 3H), 2.45(t, 1H, J=11.2 Hz), 2.50(s, 3H), 2.67(m, 1H), 2.80(m, 2H), 3.30(m, 1H), 3.71(s, 3H), 3.80(m, 1H), 3.93(s, 2H), 6.50(m, 2H), 6.72(t, 1H, J=9.3 Hz), 6.97(d, 1H, J=4.8 Hz), 7.00(s, 1H), 8.19(s, 1H), 8.24(d, 1H, J=5.1 Hz), 8.40(br, 1H). $^{13}$C NMR(CDCl$_3$) δ 13.69, 19.15(2C), 22.45, 30.73, 31.31, 31.46, 40.28, 43.94, 49.73, 51.76, 55.91, 60.44, 61.09, 102.72(d, 1C, J=98 Hz), 109.37, 122.83, 125.61, 128.40(d, 1C, J=45 Hz), 130.26(d, 1C, J=20 Hz), 132.97, 133.05, 147.16, 147.55, 148.70, 150.54, 150.88, 155.60, 158.12(d, 1C, J=45 Hz), 160.99(d, 1C, J=983 Hz), 167.70. ES-MS m/z 568(M+H). Anal. Calcd. for C$_{31}$H$_{39}$N$_5$ClFO$_2$•0.5CH$_2$Cl$_2$: C, 64.77; H, 7.07; N, 11.99. Found: C, 64.81; H, 6.97; N, 11.67. |
| 209 | 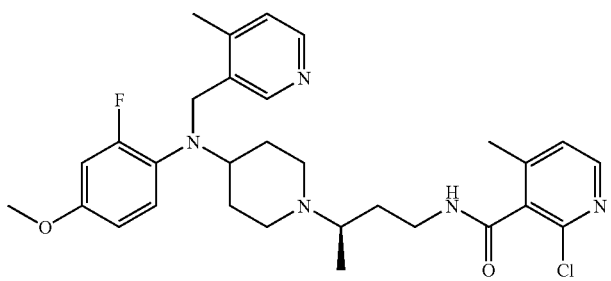<br>6-Chloro-N-((R)-3-{4-[(2-fluoro-4-methoxy-phenyl)-(4-methyl-pyridin-3-ylmethyl)-amino]-piperidin-1-yl}-butyl)-4-methyl-nicotinamide | $^1$H NMR(CDCl$_3$) δ 0.98(d, 3H, J=6.6 Hz), 1.00 (m, 1H), 1.18(m, 1H), 1.53(m, 1H), 1.79(m, 3H), 2.02(t, 1H, J=11.2 Hz), 2.33(s, 3H), 2.37(s, 3H), 2.41(t, 1H, J=11.2 Hz); 2.70-2.85(m, 4H), 3.32 (m, 1H), 3.70(s, 3H), 3.84(m, 1H), 3.84(s, 2H), 6.44(s, 1H), 6.44(dd, 1H, J=21.9, 3.0 Hz), 6.75 (t, 1H, J=9.0 Hz), 7.00(dd, 2H, J=13.2, 5.1 Hz), 8.07(d, 1H, J=5.1Hz), 8.19(s, 1H), 8.24(d, 1H, J=5.1 Hz), 8.71(br, 1H). $^{13}$C NMR(CDCl$_3$) δ 13.32, 18.80, 19.06, 30.31, 30.53, 30.80, 40.15, 43.52, 48.86, 51.43, 55.50, 60.15, 60.98, 102.40(d, 1C, J=98 Hz), 109.02, 124.14, 125.21, 128.27(d, 1C, J=44 Hz), 129.16(d, 1C, J=19 Hz), 132.64, 133.62, 146.70, 147.53, 147.65, 148.28, 149.06, 150.42, 157.46(d, 1G. J=42 Hz), 160.27(d, 1C, J=983 Hz), 165.15. ES-MS m/z 554(M + H). Anal. Calcd. for C$_{30}$H$_{37}$N$_5$ClFO$_2$•0.3CH$_2$Cl$_2$: C, 62.79; H, 6.54; N, 12.08. Found: C, 62.85; H, 6.73; N, 11.69. |

| Ex. # | Structure/Name | Characterization Data |
|---|---|---|
| 210 | 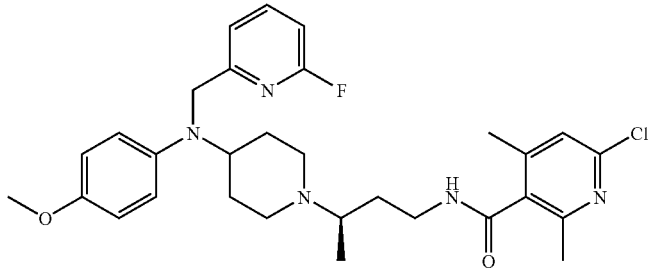<br>6-Chloro-N-((R)-3-{4-[(6-fluoro-pyridin-2-ylmethyl)-(4-methoxy-phenyl)-amino]-piperidin-1-yl}-butyl)-2,4-dimethyl-nicotinamide | $^1$H NMR(CDCl$_3$) 50.99(d, 3H, J=6.6 Hz), 1.00 (m, 1H), 1.15(m, 1H), 1.54(m, 1H), 1.78(m, 3H), 2.13(t, 1H, J=11.2 Hz), 2.33(s, 3H), 2.51(s, 3H), 2.54(t, 1H, J=11.2 Hz), 2.74(br, 1H), 2.86(m, 2H), 3.42(m, 2H), 3.72(s, 3H), 3.77(m, 1H), 4.01 (s, 2H), 6.66(d, 2H, J=9.0 Hz), 6.75(m, 3H), 7.11 (s, 1H), 7.13(d, 2H, J=8.4 Hz), 7.66(q, 1H, J=7.8 Hz), 8.19(br, 1H). $^{13}$C NMR(CDCl$_3$) δ 13.71, 19.15, 22.43, 29.74, 30.65, 31.64, 39.76, 44.28, 52.21(2C), 55.99, 58.05, 60.01, 107.50(d, 1C, J=147 Hz), 114.99(2C), 117.61(2C), 119.00, 123.31, 132.89, 141.78(d, 1C, J=30 Hz), 143.08, 147.56, 150.52, 153.14, 155.52, 160.56(d, 1C, J=49 Hz), 163.32(d, 1C, J=950 Hz), 167.85. ES-MS m/z 554(M+H). Anal. Calcd. for C$_{30}$H$_{37}$N$_6$ClFO$_2$•0.2CH$_2$Cl 12: C, 63.52; H, 6.60; N, 12.26. Found: C, 63.36; H, 6.66; N, 12.08. |
| 211 | 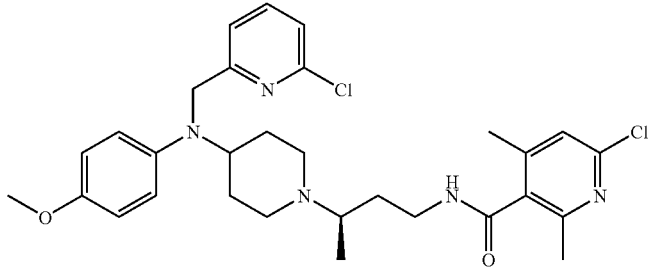<br>6-Chloro-N-((R)-3-{4-[(6-chloro-pyridin-2-ylmethyl)-(4-methoxy-phenyl)-amino]-piperidin-1-yl}-butyl)-2,4-dimethyl-nicotinamide | $^1$H NMR(CDC 13) δ 0.99(d, 3H, J=6.6 Hz), 1.05 (m,1H), 1.25(m, 1H), 1.57(m, 1H), 1.78(m, 3H), 2.17 (t, 1H, J=11.2 Hz), 2.33(s, 3H), 2.50(s, 3H), 2.55(t, 1H, J=11.2 Hz), 2.74(br, 1H), 2.86(m, 2H), 3.41(m, 2H), 3.73(s, 3H), 3.77(m, 1H), 4.07 (s, 2H), 6.66(d, 2H, J=9.0 Hz), 6.76(m, 2H), 7.15(m, 3H), 7.52(t, 1H, J=7.8 Hz), 8.12(br, 1H). $^{13}$C NMR(CDCl$_3$) δ 13.65, 19.21, 22.48, 29.66, 29.66, 30.59, 31.71, 39.70, 44.26, 52.21, 52.66, 56.02, 58.16, 60.00, 115.04(2C), 117.87(2C), 120.31, 122.51, 123.41, 132.86, 139.52, 143.02, 147.58, 150.61, 150.90, 153.31, 155.53, 162.46, 167.95. ES-MS m/z 570(M+H). Anal. Calcd. for C$_{30}$H$_{37}$N$_5$Cl$_2$O$_2$•0.5CH$_2$Cl$_2$: C, 59.76; H, 6.25; N, 11.42. Found: C, 59.50; H, 6.19; N, 11.39. |
| 212 | 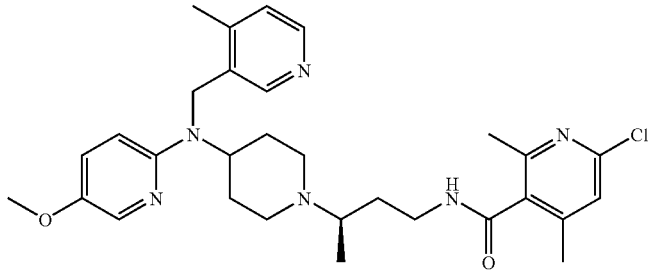<br>6-Chloro-N-((R)-3-{4-[(5-methoxy-pyridin-2-yl)-(4-methyl-pyridin-3-ylmethyl)-amino]-piperidin-1-yl}-butyl)-2,4-dimethyl-nicotinamide | $^1$H NMR(CDCl$_3$) δ 0.94(d, 3H, J=6.6 Hz), 1.20-1.38(m, 2H), 1.52-1.59(m, 1H), 1.75-1.84(m, 3H), 2.24-2.34(m, 4H), 2.34(s, 3H), 2.51(s, 3H), 2.60-2.83(m, 4H), 3.30-3.40(m, 1H), 3.74-3.82 (m, 4H), 4.18(s, 2H), 4.42-4.49(m, 1H), 6.13(d, 1H, J=9.0 Hz), 6.97(s, 1H), 7.01(dd, 1H, J=3.0, 9.0 Hz), 7.07(d, 1H, J=4.8 Hz), 7.86-7.88(m, 2H), 8.22(s, 1H), 8.32(d, 1H, J=4.8 Hz). $^{13}$C NMR(CDCl$_3$) δ 13.58, 18.94, 19.00, 22.34, 29.26, 30.08, 31.80, 39.22, 43.67, 44.46, 52.00, 53.31, 56.56, 59.68, 107.53, 122.65, 125.17, 125.43, 132.59, 132.94, 133.69, 144.65, 147.58, 147.71, 148.08, 148.63, 150.30, 153.15, 155.35, 167.61. ES-MS m/z 551(M+H). Anal. Calcd. for C$_{30}$H$_{39}$N$_6$ClO$_2$•0.15CH$_2$Cl$_2$•0.8CH$_3$OH: C, 63.06; H, 7.27; N, 14.26; Cl, 7.82. Found: C, 63.02; H, 7.18; N, 14.25; Cl, 7.66. |
| 213 | 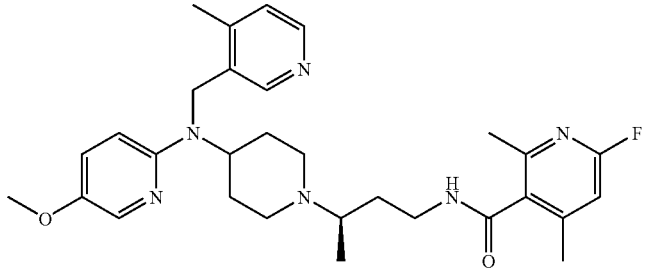<br>6-Fluoro-N-((R)-3-{4-[(5-methoxy-pyridin-2-yl)-(4-methyl-pyridin-3-ylmethyl)-amino]-piperidin-1-yl}-butyl)-2,4-dimethyl-nicotinamide | $^1$H NMR(CDCl$_3$) δ 0.93-1.08(m, 3H), 1.23-1.30 (m, 1H), 1.52-1.59(m, 1H), 1.74-1.83(m, 3H), 2.24-2.34(m, 4H), 2.38(s, 3H), 2.47(s, 3H), 2.60-2.83(m, 4H), 3.3 1-3.37(m, 1H), 3.74-3.84(m, 4H), 4.12(s, 2H), 4.42-4.49(m, 1H), 6.10(d, 1H, J=9.0 Hz), 6.48(s, 1H), 7.00(dd, 1H, J=3.0, 9.0 Hz), 7.08(d, 1H, J=5.1 Hz), 7.87(d, 1H, J=3.0 Hz), 8.00(br. s, 1H), 8.21(s, 1H), 8.32(d, 1H, J=5.1 Hz). $^{13}$C NMR(CDCl$_3$) δ 13.58, 18.81, 19.35, 22.13, 29.50, 30.20, 31.71, 39.50, 43.65, 44.40, 52.13, 53.60, 56.58, 59.89, 107.44(d, J=36.8 Hz), 107.57, 125.22, 125.41, 131.71, 132.89, 133.76, 144.64, 147.69, 148.12, 148.68, 150.47(d, J=8.2 Hz), 153.13, 153.80(d, J=15.4 Hz), 162.48(d, J=238.7 Hz), 167.79. ES-MS m/z 535(M+H). Anal. Calcd for C$_{30}$H$_{39}$N$_6$FO$_2$•0.3CH$_2$Cl$_2$: C, 64.97; H, 7.13; N, 15.00. Found: C, 64.73; H, 7.21; N, 14.82. |

| Ex. # | Structure/Name | Characterization Data |
|---|---|---|
| 214 | 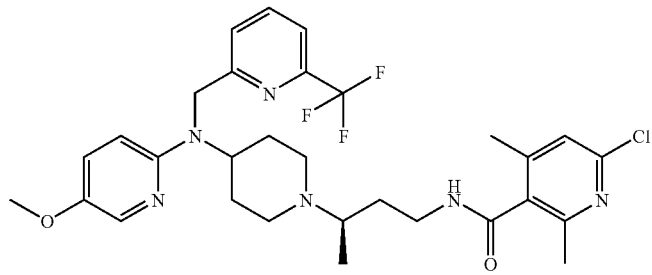<br>6-Chloro-N-((R)-3-{4-[(4-methoxy-phenyl)-(6-trifluoromethyl-pyridin-2-ylmethyl)-amino]-piperidin-1-yl}-butyl)-2,4-dimethyl-nicotinamide | $^1$H NMR(CDCl$_3$) δ 0.99(d, 3H, J=6.6 Hz), 1.04 (m, 1H), 1.15(m, 1H), 1.53(m, 1H), 1.76(m, 3H), 2.12(t, 1H, J=11.2 Hz), 2.32(s, 3H), 2.50(s, 3H), 2.51(t, 1H, J=11.2 Hz), 2.71(br, 1H), 2.82(m, 2H), 3.38(m, 2H), 3.73(s, 3H), 3.77(m, 1H), 4.09 (s, 2H), 6.66(d, 2H, J=9.0 Hz), 6.75(m, 2H, J= 9.0 Hz), 7.16(s, 1H), 7.47(dd, 2H, J=18.9, 7.8 Hz), 7.73(t, 1H, J 7.8 Hz), 8.34(br, 1H). $^{13}$C NMR(CDCl$_3$) δ 13.33, 18.66, 22.02, 29.37, 30.68, 31.03, 39.88, 43.54, 51.95, 52.09, 55.63, 58.09, 60.13, 114.66(2C), 117.32(2C), 118.30, 123.45, 124.25, 132.61, 137.73, 142.68, 147.14(2C), 147.64, 150.30, 152.86, 155.14, 162.11, 167.41. ES-MS m/z 604(M+H). Anal. Calcd. for C$_{31}$H$_{37}$N$_5$ClF$_3$O$_2$•0.2CH$_2$Cl$_2$: C, 60.34; 11, 6.07; N, 11.28. Found: C, 60.68; H, 6.20; N, 11.01. |
| 215 | 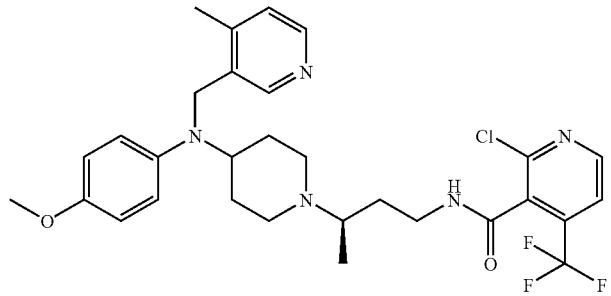<br>2-Chloro-N-((R)-3-{4-[(4-methoxy-phenyl)-(4-methyl-pyridin-3-ylmethyl)-amino]-piperidin-1-yl}-butyl)-4-trifluoromethyl-nicotinamide | $^1$H NMR(CDCl$_3$) δ 0.85-1.12(m, 5H), 1.52-1.64 (m, 2H), 1.74-1.83(m, 2H), 2.05-2.16(m, 1H), 2.33(s, 3H), 2.44-2.51(m, 1H), 2.71-2.86(m, 3H), 3.08-3.15(m, 1H), 3.30-3.37(m, 1H), 3.73(s, 3H), 3.78-3.90(m, 3H), 6.61-6.72(m, 4H), 7.03(d, 1H, J=5.1 Hz), 7.35(d, 1H, J=5.1Hz), 8.23(s, 1H), 8.30-8.33(m, 2H), 8.76(br. s, 1H). $^{13}$C NMR (CDCl$_3$) δ 13.48, 18.88, 29.76, 30.50, 30.65, 40.17, 43.96, 47.83, 51.82, 55.65, 59.22, 59.87, 114.46, 118.83, 120.95, 122.34(q, J=209.0 Hz), 125.26, 130.72, 133.15, 137.63(q, J=33.9 Hz), 142.23, 145.51, 148.14, 149.42, 149.94, 150.48, 154.10, 162.43. ES-MS m/z 590(M+H). |
| 216 | 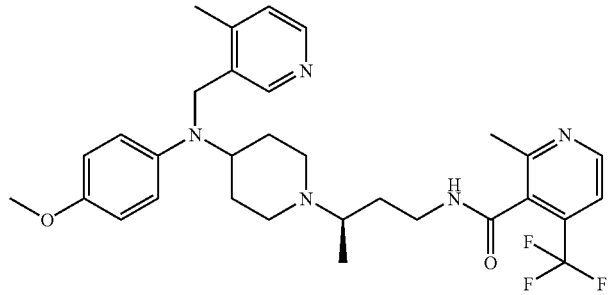<br>N-((R)-3-{4-[(4-Methoxy-phenyl)-(4-methyl-pyridin-3-ylmethyl)-amino]-piperidin-1-yl}-butyl)-2-methyl-4-trifluoromethyl-nicotinamide | $^1$H NMR(CDCl$_3$) δ 0.85-1.15(m, 5H), 1.51-1.57 (m, 1H), 1.68-1.81(m, 3H), 2.04-2.12(m, 1H), 2.33(s, 3H), 2.40-2.50(m, 1H), 2.64(s, 3H), 2.72-2.84(m, 3H), 3.11-3.20(m, 1H), 3.32-3.38(m, 1H), 3.72(s, 3H), 3.79-3.90(m, 3H), 6.60-6.71(m, 4H), 7.03(d, 1H, J=5.1Hz), 7.23(d, 1H, J=5.1 Hz), 8.24(s, 1H), 8.30(d, 1H, J=5.1Hz), 8.41 (br. s, 1H), 8.44(d, 1H, J=5.1 Hz). $^{13}$C NMR (CDCl$_3$) δ 13.52, 18.96, 22.55, 29.77, 30.52, 30.97, 40.22, 43.93, 47.56, 51.94, 55.69, 59.47, 60.00, 114.49, 117.03, 120.77, 122.79(q, J=275.1 Hz), 125.28, 129.90, 133.15, 134.83(q, J=32.8 Hz), 142.37, 145.44, 148.23, 149.57, 150.06, 154.05, 157.44, 165.44. ES-MS m/z 570(M+H). Anal. Calcd. for C$_{31}$H$_{38}$N$_5$F$_3$O$_2$•0.2CH$_2$Cl$_2$: C, 63.88; H, 6.60; N, 11.94. Found: C, 63.65; H, 6.68; N, 11.83. |
| 217 | 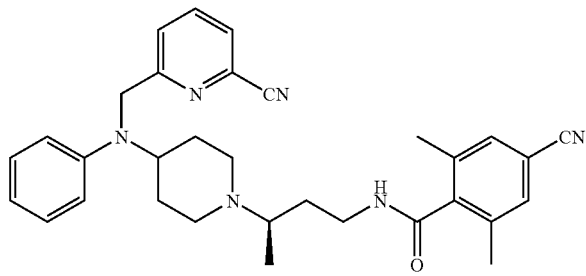<br>4-Cyano-N-((R)-3-{4-[(6-cyano-pyridin-2-ylmethyl)-phenyl-amino]-piperidin-1-yl}-butyl)-2,6-dimethyl-benzamide | $^1$H NMR(CDCl$_3$) 81.01(d+m, 4H), 1.18(m, 1H), 1.57(m, 1H), 1.66-1.77(m, 3H), 2.16(br t, 1H), 2.37(s, 6H), 2.55(br t, 1H), 2.74(m, 1H), 2.86(m, 2H), 3.31(m, 1H), 3.63(m, 1H), 3.84(m, 1H), 3.98(s, 2H), 6.62(d, 2H, J9.0Hz), 6.75(t, 1H, J= 9.0 Hz), 7.18(t, 2H, J=9.0 Hz), 7.40(s=d, 3H), 7.56(d, 1H, 1 6.0 Hz), 7.69(t, 1H, J=6.0 Hz), 8.41(br s, 1H). ES-MS m/z 521(M+H), 543 (M+Na). |

| Ex. # | Structure/Name | Characterization Data |
|---|---|---|
| 218 | 6-Chloro-N-((S)-3-{4-[(4-methoxy-phenyl)-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.00 (m, 1H), 1.19(m, 1H), 1.54(m, 1H), 1.71(m, 1H), 1.80(br d, 2H, J 12.6 Hz), 2.11(t, 1H, J=11.2 Hz), 2.29(s, 3H), 2.35(s, 3H), 2.48(t, 1H, J=11.2 Hz), 2.51(s, 3H), 2.65-2.85(m, 3H), 3.15-3.45(m, 2H), 3.72(s, 3H), 3.78(m, 1H), 3.97(s, 2H), 6.62-6.78(m, 4H), 6.98(s, 11), 7.02(d, 1H, J=4.8 Hz), 8.05 (br. s, 1H), 8.25(s, 1H), 8.28(d, 1H, J= 5.1 Hz). $^{13}$C NMR(CDCl$_3$) δ 13.74, 19.16, 19.22, 22.51, 30.07, 31.01, 31.72, 40.04, 44.27, 47.85, 52.20, 55.93, 59.41, 60.20, 114.75(2C), 120.74 (2C), 122.85, 125.47, 132.90, 133.43, 142.69, 145.73, 147.66, 148.42, 149.78, 150.59, 154.22, 155.58, 167.68. ES-MS m/z 550(M+H). |
| 219 | 6-Chloro-N-((R)-3-{4-[(4-hydroxy-phenyl)-(4-methyl-pyridin-3-ylmethyl)-amino]-piperidin-1-yl}-butyl)-2,4-dimethyl-nicotinamide | $^1$H NMR(CDCl$_3$) 61.01(d, 3H, J=6.0 Hz), 1.05-1.50(m, 2H), 1.52-1.60(m, 1H), 1.75-1.85(m, 3H), 2.10-2.20(m, 1H), 2.27(s, 3H), 2.36(s, 3H), 2.48-2.55(m, 4H), 2.69-2.84(m, 3H), 3.05-3.15 (m, 1H), 3.28-3.38(m, 1H), 3.71-3.80(m, 1H), 3.96(s, 2H), 6.51-6.60(m, 4H), 6.95(s, 1H), 7.05 (d, 1H, J=5.1 Hz), 8.15-8.25(m, 3H). ES-MS m/z 536(M+H). |
| 220 | 6-Chloro-N-((S)-3-{4-[[6-(2-methoxy-ethoxy)-pyridin-3-yl]-(4-methyl-pyridin-3-ylmethyl)-amino]-piperidin-1-yl}-butyl)-2,4-dimethyl-nicotinamide | $^1$H NMR(CDCl$_3$) 60.98(d, 3H, J=6.6 Hz), 1.10 (m, 1H), 1.22(m, 1H), 1.58(m, 1H), 1.73(m, 1H), 1.82(brd, 2H, J=12.6 Hz), 2.11(t, 1H, J=11.2 Hz), 2.29(s,3H), 2.35(s,3H), 2.48(t, LH, J=11.2 Hz), 2.51(s, 3H), 2.65-2.85(m, 3H), 3.20(m, 1H), 3.36(m, 1H), 3.41(s, 3H), 3.69(t, 2H, J=4.5 Hz), 3.74(m, 1H), 3.99(s, 2H), 4.35(t, 2H, J=4.5 Hz), 6.64(d, 1H, J=9.0 Hz), 6.99(s, 1H), 7.05(m, 2H), 7.54(d, 1H, J=2.7 Hz), 7.85(br. s, 1H); 8.24 (s, 1H), 8.29(d, 1H, J=4.8 Hz). $^{13}$C NMR (CDCl$_3$) δ 13.78, 19.14, 19.19, 22.49, 29.94, 30.71, 31.98, 39.69, 44.39, 47.59, 51.86, 59.43, 59.68, 65.21, 71.51, 111.45, 122.83, 125.63, 131.15, 132.76, 132.88, 137.56, 139.46, 145.86, 147.72, 148.58, 149.39, 150.53, 155.54, 158.55, 167.71. ES-MS m/z 595(M+H). Anal. Calcd. for C$_{32}$H$_{43}$N$_6$ClO$_3$•0.3CH$_2$Cl$_2$: C, 62.51; H, 7.08; N, 13.54. Found: C, 62.39; H, 7.22; N, 13.21. |
| 221 | 6-Fluoro-N-((R)-3-{4-[[6-(2-methoxy-ethoxy)-pyridin-3-yl]-(4-methyl-pyridin-3-ylmethyl)-amino]-piperidin-1-yl}-butyl)-2,4-dimethyl-nicotinamide | $^1$H NMR(CDCl$_3$) δ 0.98(d, 3H, J=6.6 Hz), 1.05 (m, 1H), 1.22(m, 1H), 1.56(m, 1H), 1.74(m, 1H), 1.82(br d, 2H, J 12.6 Hz), 2.12(t, 1H, J=11.2 Hz), 2.32(s, 3H), 2.34(s, 3H), 2.48(t, 1H, J=11.2 Hz), 2.48(s, 3H), 2.65-2.85(m, 3H), 3.20(m, 1H), 3.33(m, 1H), 3.41(s, 3H), 3.69(t, 2H, J=4.5 Hz), 3.75(m, 1H), 3.98(s, 2H), 4.35(t, 2H, J=4.5 Hz), 6.52(s, 1H), 6.63(d, 1H, J=9.0 Hz), 7.03(m, 2H), 7.52(br, 1H), 7.89(br. s, 1H), 8.24(s, 1H), 8.31(d, 1H, J=4.8 Hz). $^{13}$C NMR(CDCl$_3$) δ 13.77, 19.08, 19.49, 22.26, 29.96, 30.70, 31.88, 39.79, 44.35, 47.54, 51.89, 59.22, 59.42, 59.80, 65.19, 71.50, 107.63(d, 1C, J=146 Hz), 111.45, 125.63, 130.84, 131.93, 132.69, 137.20, 139.39, 145.77, 148.55, 149.21, 150.61(d, 1C, J=32 Hz), 153.93(d, 1C, J=60 Hz), 158.44, 162.65(d, 1C, J=950 Hz), 167.90. ES-MS m/z 579(M+H). Anal. Calcd. for C$_{32}$H$_{43}$N$_6$FO$_3$•0.6CH$_2$Cl$_2$: C, 62.18; H, 7.07; N, 13.35. Found:C, 62.31;H,7.13; N, 13.11. |

| Ex. # | Structure/Name | Characterization Data |
|---|---|---|
| 222 | 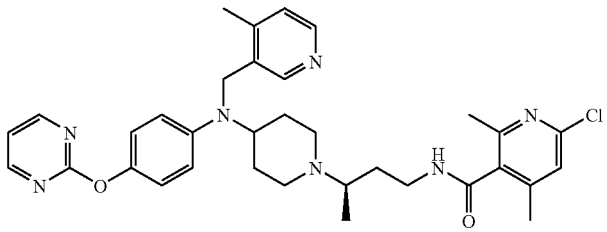<br>6-Chloro-2,4-dimethyl-N-[(R)-3-(4-{(4-methyl-pyridin-3-ylmethyl)-[4-(pyrimidin-2-yloxy)-phenyl]-amino}-piperidin-1-yl)-butyl]-nicotinamide | $^1$H NMR(CDCl$_3$) δ 1.01(d, 3H, J=6.0 Hz), 1.05-1.40(m, 2H), 1.52-1.63(m, 1H), 1.64-1.78(m, 1H), 1.85-1.92(m, 2H), 2.15-2.25(m, 1H), 2.30(s, 3H), 2.37(s, 3H), 2.48-2.60(m, 4H), 2.73-2.88(m, 3H), 3.32-3.39(m, 1H), 3.57-3.65(m, 1H), 3.74-3.82(m, 1H), 4.12(s, 2H), 6.58-6.65(m, 2H), 6.96-7.04(m, 4H), 7.08(d, 1H, J=4.8 Hz), 7.70 (br. s, 1H), 8.34(br. s, 2H), 8.53(d, 2H, J= 4.8 Hz). ES-MS m/z 614(M+H). |
| 223 | 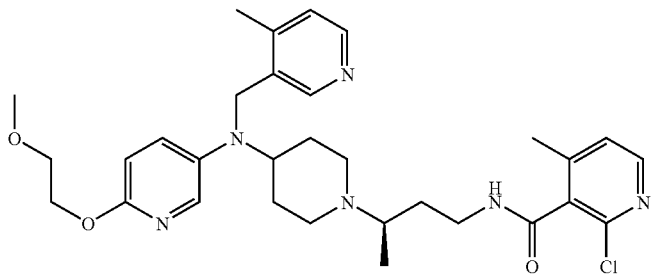<br>2-Chloro-N-((R)-3-{4-[[6-(2-methoxy-ethoxy)-pyridin-3-yl]-(4-methyl-pyridin-3-ylmethyl)-amino]-piperidin-1-yl}-butyl)-4-methyl-nicotinamide | $^1$H NMR(CDCl$_3$) δ 0.98(d, 3H, J=6.6 Hz), 1.10 (m, 1H), 1.25(m, 1H), 1.58(m, 1H), 1.73(m, 1H), 1.82(br d, 2H, J=12.6 Hz), 2.30(t, 1H, J=11.2 Hz), 2.35(s, 6H), 2.51(t, 1H, J=11.2 Hz), 2.65-2.85(m, 3H), 3.20(m, 1H), 3.36(m, 1H), 3.41(s, 3H), 3.69(t, 2H, J=4.5 Hz), 3.78(m, 1H), 3.95(s, 2H), 4.35(t, 2H, J=4.5 Hz), 6.62(d, 1H, J=9.0 Hz), 6.98(d, 1H, J=4.2 Hz), 7.03(m, 2H), 7.51 (d, 1H, J=2.7 Hz), 8.01(d, 1H, J=5.1Hz), 8.23 (br. s, 1H), 8.24(br, 1H), 8.32(d, 1H, J=4.8 Hz). ES-MS m/z 581(M+H). |
| 224 | 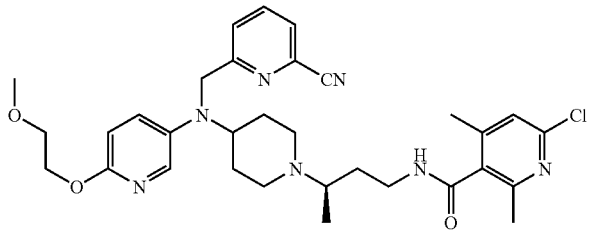<br>6-Chloro-N-((R)-3-(4-{(6-cyano-pyridin-2-ylmethyl)-[6-(2-methoxy-ethoxy)-pyridin-3-yl]-amino}-piperidin-1-yl)-butyl]-2,4-dimethyl-nicotinamide | $^1$H NMR(CDCl$_3$) δ 0.98(d, 3H, J=6.6 Hz), 1.99 (m, 1H), 1.18(m, 1H), 1.53(m, 1H), 1.75(m, 3H), 2.11(t, 1H, J=11.2 Hz), 2.34(s, 3H), 2.50(s, 3H), 2.50(t, 1H, J=11.2 Hz), 2.65-2.85(m, 3H), 3.31 (m, 1H), 3.42(s, 3H), 3.70(t, 2H, J=4.5 Hz), 3.78 (m, 1H), 4.05(s, 2H), 4.35(t, 2H, J=4.5 Hz), 6.66 (d, 1H, J=9.0 Hz), 7.05(dd, 1H, J=9.0, 3.0 Hz), 7.09(s, 1H), 7.47(d, 1H, J=8.1 Hz), 7.54(d, 1H, J=7.8 Hz), 7.58(d, 1H, J=3.0 Hz), 7.73(t, 1H, J= 7.8 Hz), 8.30(br. s, 1H). $^{13}$C NMR(CDCl$_3$) δ 13.75, 19.20, 22.46, 29.91, 30.92, 31.48, 40.12, 43.97, 52.18, 52.32, 59.11, 59.47, 60.33, 65.28, 71.53, 111.66, 117.71, 123.26, 125.53, 127.16, 129.45, 133.01, 133.49, 135.67, 137.96, 139.74, 147.74, 150.60, 155.56, 158.16, 162.80, 167.71. ES-MS m/z 606(M+H). Anal. Calcd. for C$_{32}$H$_{40}$N$_7$ClO$_3$•0.4CH$_2$Cl$_2$: C, 60.79; H, 6.42; N, 15.32. Found: C, 61.02; H, 6.49; N, 15.36. |
| 225 | 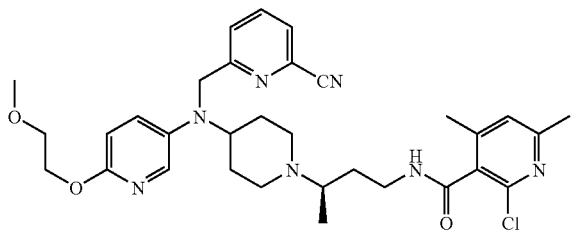<br>2-Chloro-N-[(R)-3-(4-{(6-cyano-pyridin-2-ylmethyl)-[6-(2-methoxy-ethoxy)-pyridin-3-yl]-amino}-piperidin-1-yl)-butyl]-4-methyl-nicotinamide | $^1$H NMR(CDCl$_3$) δ 0.99(d, 3H, J=6.6 Hz), 1.07 (m, 1H), 1.18(m, 1H), 1.53(m, 1H), 1.77(m, 3H), 2.11(t, 1H, J=11.2 Hz), 2.40(s, 3H), 2.51(t, 1H, J=11.2 Hz), 2.75-2.95(m, 3H), 3.33(m, 2H), 3.41(s, 3H), 3.69(t, 2H, J=4.5 Hz), 3.85(m, 1H), 3.90(s, 2H), 4.34(t, 2H, J=4.5 Hz), 6.64(d, 1H, J= 9.0 Hz), 7.01(dd, 1H, J=9.0, 3.3 Hz), 7.15(d, 1H, J=5.1Hz), 7.42(d, 1H, J=7.8 Hz), 7.51(d, 1H, J=3.0 Hz), 7.54(d, 1H, J=7.5 Hz), 7.71(t, 1H, J=7.8 Hz), 8.14(d, 1H, J=5.1Hz), 8.70(br. (s, 1H). ES-MS m/z 592(M+H). |

-continued

| Ex. # | Structure/Name | Characterization Data |
|---|---|---|
| 226 | N-((R)-3-{4-[(6-Cyano-pyridin-2-ylmethyl)-phenyl-amino]-piperidin-1-yl}-butyl)-N'-isopropyl-2,6-dimethyl-terephthalalmide | $^1$H NMR(CDCl$_3$) δ 0.75(m, 1H), 0.91(m, 1H), 0.99(d, 3H, J=6.0 Hz), 1.24(m, 6H), 1.48(m, 1H), 1.60-1.75(m, 3H), 2.13(br t, 1H), 2.32(s, 6H), 2.58(br t, 1H), 2.73(m, 1H), 2.86(m, 2H), 3.25(m, 1H), 3.63(m, 1H), 3.77(s, 2H), 3.90(m, 1H), 4.31(m, 1H), 6:43(d, 2H, J=9.0 Hz), 6.73(t, 1H, J=6.0 Hz), 7.17(t, 2H, J=9.0 Hz), 7.47(s=d, 2H), 7.61(s, 1H), 7.63(d, 1H, J=6.0 Hz), 7.75(t, 1H, J=6.0 Hz), 9.01(br s, 1H). ES-MS m/z 581 (M+H), 603(M+Na). |
| 227 | 2,6-Dichloro-N-((R)-3-{4-[(4-methoxy-phenyl)-(4-methyl-pyridin-3-ylmethyl)-amino]-piperidin-1-yl}-butyl)-4-methyl-nicotinamide | $^1$H NMR(CDCl$_3$) δ 0.98(d, 3H, J=6.0 Hz), 1.07 (m, 1H), 1.25(m, 1H), 1.56(m, 1H), 1.69-1.85(m, 3H), 2.11(br t, 1H), 2.33(s, 3H), 2.36(s, 3H), 2.50 (br t, 1H), 2.73-2.88(m, 3H), 3.05(m, 1H), 3.22 (m, 1H), 3.72(s, 3H), 3.77(m, 1H), 4.00(s, 2H), 6.64(d, 2H, J=9.0 Hz), 6.73(d, 2H, J=9.0 Hz), 7.02(d, 1H, J=6.0 Hz), 7.10(s, 1H), 8.25(s, 1H), 8.28(d, 1H, J=6.0 Hz), 8.34(br s, 1H). ES-MS m/z 570(M+H), 592(M+Na). |

EXAMPLE 28

Cell Fusion Assay

The assay measures the ability of a test compound to inhibit gp120 and CD4/CCR5-dependent cell-cell fusion. The assay uses two cell lines, 1) CHO-tat cell line that expresses the viral gp120 from a R5 using virus (JR-FL) and the HIV tat proteins, 2) P4-CCR5 cell line that expresses human CD4 and CCR5 on the surface and carries a β-galactosidase construct under the control of the retroviral promotor LTR. Once fusion of these two cell lines occurs, the tat protein from the CHO cell line trans-activates the reporter gene β-galactosidase in the P4-CCR5 cell line. In a 96 well format, 1×10$^4$ cells of each cell line are plated per well in the presence or absence of test compound. The cells are then incubated at 37° C., 5% CO$_2$ for 18-24 hours. The β-galactosidase activity in each well is measured by the addition of a luminescence substrate (Gal-Screen substrate, Applied Biosystems) and luminescence monitored with a Victor 2 plate reader (Wallac). The ability of test compounds to inhibit fusion is indicated by a decrease in β-galactosidase activity. Results are reported as the concentration of test compound required to inhibit 50% of the β-galactosidase activity in the test controls.

When tested in the assay described above, many compounds of the invention exhibited IC$_{50}$'s in the range of 0.01 nM to 100 nM.

EXAMPLE 29

Assay for Inhibition of RANTES Binding to HEK293F.CCR5 Cells

For the competition binding studies, a concentration range of antagonist was incubated for 45 minutes at room temperature in binding buffer (50 mM HEPES, 5 mM MgCl$_2$, 1 mM CaCl$_2$, 0.2% BSA pH 7.4) with 8 µg of HEK293F.CCR5 cell membrane and 50 pM $^{125}$I-RANTES (Perkin Elmer, 81400 GBq/mmol) in Milipore GF-B filter plates. Unbound $^{125}$I-RANTES was removed by washing with cold 50 mM HEPES, 0.5 M NaCl pH 7.4. Compounds were tested at a concentration range of 10000-0.6 nM. The 50% inhibitory concentration (IC$_{50}$ value) was defined as the concentration of test compound required to inhibit RANTES binding by 50% relative to untested controls.

When tested in the assay described above, many compounds of the invention exhibited $IC_{50}$'s in the range of 1 nM to 500 nM.

EXAMPLE 30

Assay for Inhibition of HIV-1 Using PBMC and R5

Performed as described in literature (Inhibition of T-tropic HIV strains by selective antagonization of the chemokine receptor CXCR4. 1997—D. Schols, S. Struyf, J. Van Damme, J. A. Esté, G. Henson & E. De Clercq. J. Exp. Med. 186, 1383-1388.)

The method were as follows:

PBMC from healthy donors were isolated by density gradient centrifugation and stimulated with PHA at 1 μg/ml (Sigma Chemical Co., Bornem, Belgium) for 3 days at 37° C. The activated cells (PHA-stimulated blasts) were washed three times with PBS, and viral infections were performed. The cells were seeded in 48-well plates ($5 \times 10^5$ cells per well in 200 uL culture medium) and pre-incubated for 15 min with compounds at different concentrations. Then 500 pg p24 viral Ag/well of CCR5-using viruses was added. The HIV-1 R5 strains BaL, SF-162, ADA, and JR-FL were all obtained through the Medical Research Council AIDS reagent project (Herts, UK).

HIV-infected or mock-infected PHA-stimulated blasts were then further cultured in the presence of 25 U/ml of IL-2 and supernatant was collected at days 8-10, and HIV-1 core antigen in the culture supernatant was analyzed by the p24 Ag ELISA kit from DuPont-Merck Pharmaceutical Co. (Wilmington, Del.).

When tested in the assay described above, many compounds of the invention exhibited $IC_{50}$'s in the range of 0.01 nM to 50 μM.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A compound or a pharmaceutically acceptable salt thereof, having the formula:

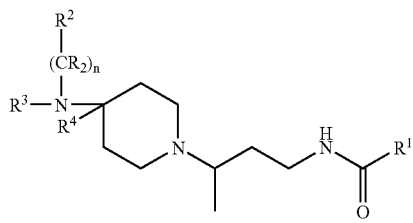

(2)

wherein $R^1$ is an optionally substituted aryl or heteroaryl;
$R^2$ is an optionally substituted pyridine;
$R^3$ is an optionally substituted aryl, heteroaryl, or a phenyl fused with a cyclic ring;
R and $R^4$ are independently hydrogen or $C_{1-6}$ alkyl; and
n is 0 or 1.

2. The compound of claim 1, where $R^1$ is an optionally substituted phenyl, pyrimidinyl, pyridine, pyridine N-oxide, thiophenyl, isoxazolyl, or pyrazolyl, each of which may be substituted with halo, alkoxy, trifluoromethyl, carboxyalkyl, cyano, amido, amine, heterocyclic ring, aryl, heteroaryl, or an alkyl which may be substituted with a heteroatom.

3. The compound of claim 2, wherein $R^1$ is pyridine.

4. The compound of claim 1, wherein $R^3$ is phenyl, pyridinyl, thiazolyl, oxazolyl, pyrimidinyl, indolyl, indolinyl, isoindolinyl, 1,3-benzodioxolyl, 1,4-benzodioxanyl, benzofuranyl, 2,3-dihydroxybenzofuranyl or phthalanyl, each of which is optionally linked to halo, alkoxy, trifluoromethyl, carboxyalkyl, cyano, amido, amine, heterocyclic ring, aryl, heteroaryl, an alkyl which may be substituted with a heteroatom, oxotrifluoromethyl, sulfanyl, $SO_2R^9$, where $R^9$ is alkyl, amine or amino alkyl; $C(O)R^{10}$, where $R^{10}$ is alkyl, amine, morpholine, $NMe_2$, N(OMe)Me, NPh, piperidine, NHMe, piperazine, $NHCH_2C(O)OMe$ or $PhC(O)OH$; $OR^{11}$, where $R^{11}$ is H, alkyl, $(CH_2)_2OMe$, $CH_2C(O)NH_2$, $CH_2C(O)NHNH_2$, $CH_2C(O)OCMe_3$, $CH_2C(O)OMe$, $CH_2C(O)OH$, PhC(O)OH, $PhC(O)NH_2$, $SO_2Me$, C(O)Me, C(O)OMe, $C(O)NEt_2$, $C(O)NMe_2$ or

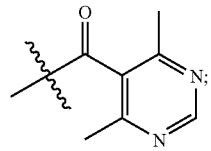

$NHR^{12}$, where $R^{12}$ is H, C(O)Me, $C(O)CF_3$, $SO_2Me$, $C(O)NH_2$, $C(O)NMe_2$ or

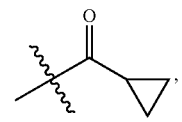

$NO_2$, $CH_2PhC(O)OH$, SOMe, $CH_2NHC(O)Me$, morpholine, CH=CHC(O)OMe, CH=CHC(O)OH,

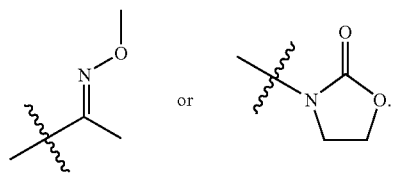

5. The compound of claim 4, wherein $R^3$ is phenyl.

6. The compound of claim 1, wherein each R and $R^4$ is hydrogen.

7. The compound of claim 1, wherein $R^1$ is pyridine and $R^3$ is phenyl, each of which may be substituted with halo, alkoxy, trifluoromethyl, carboxyalkyl, cyano, amido, amine, heterocyclic ring, aryl, heteroaryl, or an alkyl which may be substituted with a heteroatom.

8. A pharmaceutical composition comprising the compound of claim 1 and a pharmaceutically acceptable carrier.

9. The compound of claim 7, wherein said alkyl is unsubstituted.

10. The compound of claim 1, wherein $R^1$ is a 5-6 membered aryl or a heteroaryl containing a N, O or S.

11. The compound of claim 1, wherein $R^3$ is a phenyl fused with a 5-6 membered aryl heteroaryl, or heterocyclic ring.

12. The compound of claim 1, wherein n is 1.

* * * * *